US012516016B2

(12) United States Patent
Cao et al.

(10) Patent No.: US 12,516,016 B2
(45) Date of Patent: Jan. 6, 2026

(54) GPX4 INHIBITORS, PHARMACEUTICAL COMPOSITIONS THEREOF, AND THEIR USE FOR TREATING GPX4-MEDIATED DISEASES

(71) Applicants: EUBULUS BIOTHERAPEUTICS (HONG KONG) LIMITED, Hong Kong (HK); Sheldon Cao, San Diego, CA (US); Xiaolei Wang, Jiaxing (CN)

(72) Inventors: Sheldon Cao, San Diego, CA (US); Xiaolei Wang, Jiaxing (CN)

(73) Assignees: Sheldon Cao, San Diego, CA (US); Xiaolei Wang, Zhejiang (CN); EUBULUS BIOTHERAPEUTICS (HONG KONG) LIMITED, Hong Kong (HK)

( * ) Notice: Subject to any disclaimer, the term of this patent is extended or adjusted under 35 U.S.C. 154(b) by 412 days.

(21) Appl. No.: 17/929,597

(22) PCT Filed: Mar. 10, 2021

(86) PCT No.: PCT/US2021/021796
§ 371 (c)(1),
(2) Date: Sep. 2, 2022

(87) PCT Pub. No.: WO2021/183702
PCT Pub. Date: Sep. 16, 2021

(65) Prior Publication Data

US 2024/0246901 A1 Jul. 25, 2024

Related U.S. Application Data

(60) Provisional application No. 62/988,292, filed on Mar. 11, 2020.

(51) Int. Cl.

| | |
|---|---|
| ***C07C 237/22*** | (2006.01) |
| ***A61K 31/167*** | (2006.01) |
| ***A61K 31/18*** | (2006.01) |
| ***A61K 31/245*** | (2006.01) |
| ***A61K 31/277*** | (2006.01) |
| ***A61K 31/337*** | (2006.01) |
| ***A61K 31/351*** | (2006.01) |
| ***A61K 31/36*** | (2006.01) |
| ***A61K 31/365*** | (2006.01) |
| ***A61K 31/381*** | (2006.01) |
| ***A61K 31/404*** | (2006.01) |
| ***A61K 31/4155*** | (2006.01) |
| ***A61K 31/416*** | (2006.01) |
| ***A61K 31/4184*** | (2006.01) |
| ***A61K 31/4245*** | (2006.01) |
| ***A61K 31/428*** | (2006.01) |

(Continued)

(52) U.S. Cl.
CPC .......... *C07C 237/22* (2013.01); *A61K 31/167* (2013.01); *A61K 31/18* (2013.01); *A61K 31/245* (2013.01); *A61K 31/277* (2013.01); *A61K 31/337* (2013.01); *A61K 31/351* (2013.01); *A61K 31/36* (2013.01); *A61K 31/365* (2013.01); *A61K 31/381* (2013.01); *A61K 31/404* (2013.01); *A61K 31/4155* (2013.01); *A61K 31/416* (2013.01); *A61K 31/4184* (2013.01); *A61K 31/4245* (2013.01); *A61K 31/428* (2013.01); *A61K 31/433* (2013.01); *A61K 31/437* (2013.01); *A61K 31/44* (2013.01); *A61K 31/4412* (2013.01); *A61K 31/5377* (2013.01); *A61P 35/00* (2018.01); *C07C 255/60* (2013.01); *C07C 311/08* (2013.01); *C07C 311/16* (2013.01); *C07C 317/40* (2013.01); *C07D 213/56* (2013.01); *C07D 213/64* (2013.01); *C07D 213/89* (2013.01); *C07D 231/56* (2013.01); *C07D 249/18* (2013.01); *C07D 271/12* (2013.01); *C07D 277/64* (2013.01); *C07D 285/14* (2013.01); *C07D 303/04* (2013.01); *C07D 305/06* (2013.01); *C07D 309/06* (2013.01); *C07D 309/14* (2013.01); *C07D 317/66* (2013.01); *C07D 333/24* (2013.01); *C07D 405/12* (2013.01); *C07D 407/12* (2013.01); *C07C 2601/02* (2017.05); *C07C 2601/14* (2017.05)

(58) Field of Classification Search
CPC ...... C07C 237/22; A61P 35/00; A61K 31/167
See application file for complete search history.

(56) References Cited

PUBLICATIONS

Weiwer et al, 2012, Development of small-molecule probes that selectively kill cells induced to express mutant RAS, Bioorg. Med. Chem. Lett., vol. 22, p. 1822-1826 (Year: 2012).*

(Continued)

*Primary Examiner* — Adam C Milligan
*Assistant Examiner* — Karen Cheng
(74) *Attorney, Agent, or Firm* — NKL Law; Bin Lu; Allen Xue

(57) ABSTRACT

Provided herein are GPX4 inhibitors, e.g., a compound of Formula (I), and pharmaceutical compositions thereof. Also provided herein are methods of their use for treating, preventing, or ameliorating one or more symptoms of a GPX4-mediated disorder, disease, or condition.

(I)

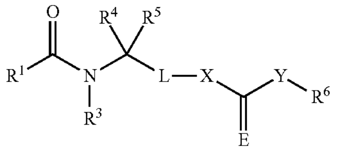

11 Claims, No Drawings

(51) Int. Cl.
*A61K 31/433* (2006.01)
*A61K 31/437* (2006.01)
*A61K 31/44* (2006.01)
*A61K 31/4412* (2006.01)
*A61K 31/5377* (2006.01)
*A61P 35/00* (2006.01)
*C07C 255/60* (2006.01)
*C07C 311/08* (2006.01)
*C07C 311/16* (2006.01)
*C07C 317/40* (2006.01)
*C07D 213/56* (2006.01)
*C07D 213/64* (2006.01)
*C07D 213/89* (2006.01)
*C07D 231/56* (2006.01)
*C07D 249/18* (2006.01)
*C07D 271/12* (2006.01)
*C07D 277/64* (2006.01)
*C07D 285/14* (2006.01)
*C07D 303/04* (2006.01)
*C07D 305/06* (2006.01)
*C07D 309/06* (2006.01)
*C07D 309/14* (2006.01)
*C07D 317/66* (2006.01)
*C07D 333/24* (2006.01)
*C07D 405/12* (2006.01)
*C07D 407/12* (2006.01)

(56) References Cited

PUBLICATIONS

CA Reg No. 345216-25-3, entered into Registry on Jul. 10, 2001 (Year: 2001).*
CA Reg No. 934710-45-9, entered into Registry on May 14, 2007 (Year: 2007).*

* cited by examiner

GPX4 INHIBITORS, PHARMACEUTICAL COMPOSITIONS THEREOF, AND THEIR USE FOR TREATING GPX4-MEDIATED DISEASES

CROSS REFERENCE TO RELATED APPLICATION

This application is a National Stage of International Application No. PCT/US2021/021796, filed Mar. 10, 2021; which claims the benefit of U.S. Provisional Application No. 62/988,292, filed Mar. 11, 2020; the disclosure of each of which is incorporated herein by reference in its entirety.

FIELD

Provided herein are GPX4 inhibitors and pharmaceutical compositions thereof. Also provided herein are methods of their use for treating, preventing, or ameliorating one or more symptoms of a GPX4-mediated disorder, disease, or condition.

BACKGROUND

Regulated cell death is essential for the survival of a multicellular organism. Dixon et al., *Cell* 2012, 149, 1060-72; Fearnhead et al., *Cell Death Differ.* 2017, 24, 1991-8; Gudipaty et al., *Annu. Rev. Cell Dev. Biol.* 2018, 34, 311-32; Mou et al., *J. Hematol. Oncol.* 2019, 12, 34. Ferroptosis is one type of regulated cell death characterized by loss of glutathione peroxidase 4 (GPX4) activity and accumulation of lipid peroxides. Dixon et al., *Cell* 2012, 149, 1060-72; Yang et al., *Cell* 2014, 156, 317-31. Ferroptosis dysfunction has been observed in many types of cancer, including breast cancer, colorectal cancer, diffuse large B-cell lymphoma, gastric cancer, hepatocellular carcinoma, lung cancer, and ovarian cancer. Mou et al., *J. Hematol. Oncol.* 2019, 12, 34.

GPX4, a selenoenzyme, is a negative regulator of ferroptosis. Yang et al., *Cell* 2014, 156, 317-31; Seibt et al., *Free Radic. Biol. Med.* 2019, 133, 144-52. GPX4 catalyzes the reduction of lipid peroxides and prevents ferroptosis. Brigelius-Flohe and Maiorino, *Biochim. Biophys. Acta* 2013, 1830, 3289-303; Cao and Dixon, *Cell. Mol. Life Sci.* 2016, 73, 2195-209. Small molecule GPX4 inhibitors (e.g., RSL3 and ML162) have been shown to be able to induce ferroptosis and suppress tumor growth in xenograft models. Yang et al., *Cell* 2014, 156, 317-31; Lei et al., *Front. Physiol.* 2019, 10, 139; Bi et al., *Cell Death Disease* 2019, 10, 682.

Despite the advances in cancer treatment, cancer remains a major worldwide public health problem. It was estimated that there will be 1,762,450 new cancer cases diagnosed and 606,880 cancer deaths in the US alone in 2019. *Cancer Facts & Figures.* 2019. Therefore, there is a need for an effective therapy for cancer treatment.

SUMMARY OF THE DISCLOSURE

Provided herein is a compound of Formula (I):

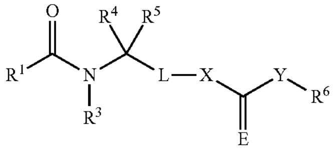

(I)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

E is O, S, $NR^{1a}$, or $NOR^{1a}$;

L is a bond, $C_{1-6}$ alkylene, $C_{2-6}$ alkenylene, $C_{2-6}$ alkynylene, $C_{3-10}$ cycloalkylene, $C_{6-14}$ arylene, $C_{7-15}$ aralkylene, heteroarylene, or heterocyclylene;

X and Y are: (i) X is a bond, —$NR^X$—, or —O—; and Y is —$NR^Y$—, —$NR^YO$—, or —O—; or (ii) X is —$NR^X$— or —O—; and Y is a bond; wherein each $R^X$ and $R^Y$ is independently hydrogen, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl;

$R^1$ is

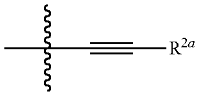

or —$CH_2$—$R^{2b}$, wherein $R^{2a}$ is hydrogen, deuterium, or $C_{1-6}$ alkyl; and $R^{2b}$ is halo, —$OS(O)_2R^{1a}$, or —$OS(O)_2OR^{1a}$; $R^3$ is $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl;

$R^4$ and $R^5$ are each independently hydrogen, deuterium, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or $R^4$ and $R^5$ together with the carbon atom to which they are attached form $C_{3-10}$ cycloalkyl or heterocyclyl;

$R^6$ is hydrogen, deuterium, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; and each $R^{1a}$ is independently hydrogen, deuterium, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl;

wherein each alkyl, alkylene, alkenyl, alkenylene, alkynyl, alkynylene, cycloalkyl, cycloalkylene, aryl, arylene, aralkyl, aralkylene, heteroaryl, heteroarylene, heterocyclyl, and heterocyclylene is optionally substituted with one or more, in one embodiment, one, two, three, or four, substituents Q, wherein each Q is independently selected from: (a) deuterium, cyano, halo, nitro, and oxo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —$C(O)R^a$, —$C(O)OR^a$, —$C(O)NR^bR^c$, —$C(O)SR^a$, —$C(NR^a)NR^bR^c$, —$C(S)R^a$, —$C(S)OR^a$, —$C(S)NR^bR^c$, —$OR^a$, —$OC(O)R^a$, —$OC(O)OR^a$, —$OC(O)NR^bR^c$, —$OC(O)SR^a$, —$OC(NR^a)NR^bR^c$, —$OC(S)R^a$, —$OC(S)OR^a$, —$OC(S)NR^bR^c$, —$OS(O)R^a$, —$OS(O)_2R^a$, —$OS(O)NR^bR^c$, —$OS(O)_2NR^bR^c$, —$NR^bR^c$, —$NR^aC(O)R^d$, —$NR^aC(O)OR^d$, —$NR^aC(O)NR^bR^c$, —$NR^aC(O)SR^d$, —$NR^aC(NR^d)NR^bR^c$, —$NR^aC(S)R^d$, —$NR^aC(S)OR^d$, —$NR^aC(S)NR^bR^c$, —$NR^aS(O)R^d$, —$NR^aS(O)_2R^d$, —$NR^aS(O)NR^bR^c$, —$NR^aS(O)_2NR^bR^c$, —$SR^a$, —$S(O)R^a$, —$S(O)_2R^a$, —$S(O)NR^bR^c$, and —$S(O)_2NR^bR^c$, wherein each $R^a$, $R^b$, $R^c$, and $R^d$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heterocyclyl optionally substituted with one or more, in one embodiment, one, two, three, or four, substituents $Q^a$;

wherein each $Q^a$ is independently selected from: (a) deuterium, cyano, halo, nitro, and oxo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) $—C(O)R^e$, $—C(O)OR^e$, $—C(O)NR^fR^g$, $—C(O)SR^e$, $—C(NR^e)NR^fR^g$, $—C(S)R^e$, $—C(S)OR^e$, $—C(S)NR^fR^g$, $—OR^e$, $—OC(O)R^e$, $—OC(O)OR^e$, $—OC(O)NR^fR^g$, $—OC(O)SR^e$, $—OC(NR^e)NR^fR^g$, $—OC(S)R^e$, $—OC(S)OR^e$, $—OC(S)NR^fR^g$, $—OS(O)R^e$, $—OS(O)_2R^e$, $—OS(O)NR^fR^g$, $—OS(O)_2NR^fR^g$, $—NR^fR^g$, $—NR^eC(O)R^h$, $—NR^eC(O)OR^f$, $—NR^eC(O)NR^fR^g$, $—NR^eC(O)SR^f$, $—NR^eC(NR^h)NR^fR^g$, $—NR^eC(S)R^h$, $—NR^eC(S)OR^f$, $—NR^eC(S)NR^fR^g$, $—NR^eS(O)R^h$, $—NR^eS(O)_2R^h$, $—NR^eS(O)NR^fR^g$, $—NR^eS(O)_2NR^fR^g$, $—SR^e$, $—S(O)R^e$, $—S(O)_2R^e$, $—S(O)NR^fR^g$, and $—S(O)_2NR^fR^g$; wherein each $R^e$, $R^f$, $R^g$, and $R^h$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

Also provided herein is a pharmaceutical composition comprising a compound of Formula (I), or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; and a pharmaceutically acceptable excipient.

Additionally provided herein is a method of treating, preventing, or ameliorating one or more symptoms of a disorder, disease, or condition mediated by a glutathione peroxidase 4 (GPX4) in a subject, comprising administering to the subject a compound of Formula (I), or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

Furthermore, provided herein is a method of treating, preventing, or ameliorating one or more symptoms of a proliferative disease in a subject, comprising administering to the subject a compound of Formula (I), or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

Provided herein is a method of inhibiting the growth of a cell, comprising contacting the cell with a compound of Formula (I), or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

Provided herein is a method of inducing ferroptosis in a cell, comprising contacting the cell with a compound of Formula (I), or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

Provided herein is a method of inhibiting the activity of a GPX4, comprising contacting the GPX4 with a compound of Formula (I), or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

DETAILED DESCRIPTION

To facilitate understanding of the disclosure set forth herein, a number of terms are defined below.

Generally, the nomenclature used herein and the laboratory procedures in organic chemistry, medicinal chemistry, biochemistry, biology, and pharmacology described herein are those well-known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject. In one embodiment, the subject is a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The terms "alleviate" and "alleviating" refer to easing or reducing one or more symptoms (e.g., pain) of a disorder, disease, or condition. The terms can also refer to reducing adverse effects associated with an active ingredient. Sometimes, the beneficial effects that a subject derives from a prophylactic or therapeutic agent do not result in a cure of the disorder, disease, or condition.

The term "contacting" or "contact" is meant to refer to bringing together of a therapeutic agent and cell or tissue such that a physiological and/or chemical effect takes place as a result of such contact. Contacting can take place in vitro, ex vivo, or in vivo. In one embodiment, a therapeutic agent is contacted with a cell in cell culture (in vitro) to determine the effect of the therapeutic agent on the cell. In another embodiment, the contacting of a therapeutic agent with a cell or tissue includes the administration of a therapeutic agent to a subject having the cell or tissue to be contacted.

The term "therapeutically effective amount" or "effective amount" is meant to include the amount of a compound that, when administered, is sufficient to prevent development of, or alleviate to some extent, one or more of the symptoms of the disorder, disease, or condition being treated. The term "therapeutically effective amount" or "effective amount" also refers to the amount of a compound that is sufficient to elicit a biological or medical response of a biological molecule (e.g., a protein, enzyme, RNA, or DNA), cell, tissue, system, animal, or human, which is being sought by a researcher, veterinarian, medical doctor, or clinician.

The term "$IC_{50}$" or "$EC_{50}$" refers to an amount, concentration, or dosage of a compound that is required for 50% inhibition of a maximal response in an assay that measures such a response.

The term "pharmaceutically acceptable carrier," "pharmaceutically acceptable excipient," "physiologically acceptable carrier," or "physiologically acceptable excipient" refers to a pharmaceutically acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of a subject (e.g., a human or an animal) without excessive toxicity, irritation, allergic response, immunogenicity, or other problems or complications, and commensurate with a reasonable benefit/risk ratio. See, e.g., *Remington: The Science and Practice of Pharmacy,* 22nd ed.; Allen Ed.; Pharmaceutical Press: London, 2012*; Handbook of Pharmaceutical Excipients,* 8th ed.; Sheskey et al., Eds.; Pharmaceutical Press: London, 2017*; Handbook of Pharmaceutical Additives,* 3rd ed.; Ash and Ash Eds.; Synapse Information Resources: 2007*; Pharmaceutical Preformulation and Formulation,* 2nd ed.; Gibson Ed.; Drugs and the Pharmaceutical Sciences 199; Informa Healthcare: New York, NY, 2009.

The term "about" or "approximately" means an acceptable error for a particular value as determined by one of ordinary skill in the art, which depends in part on how the value is measured or determined. In certain embodiments, the term "about" or "approximately" means within 1, 2, or 3 standard deviations. In certain embodiments, the term "about" or "approximately" means within 25%, 20%, 15%, 10%, 9%, 8%, 7%, 6%, 5%, 4%, 3%, 2%, 1%, 0.5%, or 0.05% of a given value or range.

The term "alkyl" refers to a linear or branched saturated monovalent hydrocarbon radical, wherein the alkyl is optionally substituted with one or more substituents Q as described herein. For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms, e.g., n-propyl and isopropyl), butyl (including all isomeric forms, e.g., n-butyl, isobutyl, sec-butyl, and t-butyl), pentyl (including all isomeric forms, e.g., n-pentyl, isopentyl, sec-pentyl, neopentyl, and tert-pentyl), and hexyl (including all isomeric forms, e.g., n-hexyl, isohexyl, and sec-hexyl).

The term "alkylene" refers to a linear or branched saturated divalent hydrocarbon radical, wherein the alkylene is optionally be substituted with one or more substituents Q as described herein. For example, $C_{1-6}$ alkylene refers to a linear saturated divalent hydrocarbon radical of 1 to 6 carbon atoms or a branched saturated divalent hydrocarbon radical of 3 to 6 carbon atoms. In certain embodiments, the alkylene is a linear saturated divalent hydrocarbon radical that has 1 to 30 ($C_{1-30}$), 1 to 20 ($C_{1-20}$), 1 to 15 ($C_{1-15}$), 1 to 10 ($C_{1-10}$), or 1 to 6 ($C_{1-6}$) carbon atoms, or branched saturated divalent hydrocarbon radical of 3 to 30 ($C_{3-30}$), 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkylene groups are also referred as "lower alkylene." Examples of alkylene groups include, but are not limited to, methylene, ethylene (including all isomeric forms, e.g., ethan-1,1-diyl and ethan-1,2-diyl), propylene (including all isomeric forms, e.g., propan-1,1-diyl, propan-1,2-diyl, and propan-1,3-diyl), butylene (including all isomeric forms, e.g., butan-1,1-diyl, butan-1,2-diyl, butan-1,3-diyl, and butan-1,4-diyl), pentylene (including all isomeric forms, e.g., pentan-1,1-diyl, pentan-1,2-diyl, pentan-1,3-diyl, and pentan-1,5-diyl), and hexylene (including all isomeric forms, e.g., hexan-1,1-diyl, hexan-1,2-diyl, hexan-1,3-diyl, and hexan-1,6-diyl).

The term "heteroalkylene" refers to a linear or branched saturated divalent hydrocarbon radical that contains one or more heteroatoms, each independently selected from O, S, and N in the hydrocarbon chain. The heteroalkylene is optionally substituted with one or more substituents Q as described herein. For example, $C_{1-6}$ heteroalkylene refers to a linear saturated divalent hydrocarbon radical of 1 to 6 carbon atoms or a branched saturated divalent hydrocarbon radical of 3 to 6 carbon atoms. In certain embodiments, the heteroalkylene is a linear saturated divalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ heteroalkylene groups are also referred as "lower heteroalkylene." Examples of heteroalkylene groups include, but are not limited to, $-CH_2O-$, $-CH_2OCH_2-$, $-CH_2CH_2O-$, $-CH_2NH-$, $-CH_2NHCH_2-$, $-CH_2CH_2NH-$, $-CH_2S-$, $-CH_2SCH_2-$, and $-CH_2CH_2S-$.

The term "alkenyl" refers to a linear or branched monovalent hydrocarbon radical, which contains one or more, in one embodiment, one, two, three, or four, in another embodiment, one, carbon-carbon double bond(s). The alkenyl is optionally substituted with one or more substituents Q as described herein. The term "alkenyl" embraces radicals having a "cis" or "trans" configuration or a mixture thereof, or alternatively, a "Z" or "E" configuration or a mixture thereof, as appreciated by those of ordinary skill in the art. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propenyl (including all isomeric forms, e.g., propen-1-yl, propen-2-yl, and allyl), and butenyl (including all isomeric forms, e.g., buten-1-yl, buten-2-yl, buten-3-yl, and 2-buten-1-yl).

The term "alkenylene" refers to a linear or branched divalent hydrocarbon radical, which contains one or more, in one embodiment, one, two, three, or four, in another embodiment, one, carbon-carbon double bond(s). The alkenylene is optionally substituted with one or more substituents Q as described herein. The term "alkenylene" embraces radicals having a "cis" or "trans" configuration or a mixture thereof, or alternatively, a "Z" or "E" configuration or a mixture thereof, as appreciated by those of ordinary skill in the art.

For example, $C_{2-6}$ alkenylene refers to a linear unsaturated divalent hydrocarbon radical of 2 to 6 carbon atoms or a branched unsaturated divalent hydrocarbon radical of 3 to 6 carbon atoms. In certain embodiments, the alkenylene is a linear divalent hydrocarbon radical of 2 to 30 ($C_{2-30}$), 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 3 to 30 ($C_{3-30}$), 3 to 20 ($C_{3-20}$), 3 to 15 ($C_{3-15}$), 3 to 10 ($C_{3-10}$), or 3 to 6 ($C_{3-6}$) carbon atoms. Examples of alkenylene groups include, but are not limited to, ethenylene (including all isomeric forms, e.g., ethen-1,1-diyl or ethen-1,2-diyl), propenylene (including all isomeric forms, e.g., 1-propen-1,1-diyl, 1-propen-1,2-diyl, and 1-propen-1,3-diyl), butenylene (including all isomeric forms, e.g., 1-buten-1,1-diyl, 1-buten-1,2-diyl, and 1-buten-1,4-diyl), pentenylene (including all isomeric forms, e.g., 1-penten-1,1-diyl, 1-penten-1,2-diyl, and 1-penten-1,5-diyl), and hexenylene (including all isomeric forms, e.g., 1-hexen-1,1-diyl, 1-hexen-1,2-diyl, and 1-hexen-1,6-diyl).

The term "heteroalkenylene" refers to a linear or branched divalent hydrocarbon radical, which contains one or more, in one embodiment, one, two, three, or four, in another embodiment, one, carbon-carbon double bond(s), and which contains one or more heteroatoms each independently selected from O, S, and N in the hydrocarbon chain. The heteroalkenylene is optionally substituted with one or more substituents Q as described herein. The term "heteroalkenylene" embraces radicals having a "cis" or "trans" configuration or a mixture thereof, or alternatively, a "Z" or "E" configuration or a mixture thereof, as appreciated by those of ordinary skill in the art. For example, $C_{2-6}$ heteroalkenylene refers to a linear unsaturated divalent hydrocarbon radical of 2 to 6 carbon atoms or a branched unsaturated divalent hydrocarbon radical of 3 to 6 carbon atoms. In certain embodiments, the heteroalkenylene is a linear divalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of heteroalkenylene groups include, but are not limited to, $—CH{=}CHO—$, $—CH{=}CHOCH_2—$, $—CH{=}CHCH_2O—$, $—CH{=}CHS—$, $—CH{=}CHSCH_2—$, $—CH{=}CHCH_2S—$, or $—CH{=}CHCH_2NH—$.

The term "alkynyl" refers to a linear or branched monovalent hydrocarbon radical, which contains one or more, in one embodiment, one, two, three, or four, in another embodiment, one, carbon-carbon triple bond(s). The alkynyl is optionally substituted with one or more substituents Q as described herein. For example, $C_{2-6}$ alkynyl refers to a linear unsaturated monovalent hydrocarbon radical of 2 to 6 carbon atoms or a branched unsaturated monovalent hydrocarbon radical of 4 to 6 carbon atoms. In certain embodiments, the alkynyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 4 to 20 ($C_{4-20}$), 4 to 15 ($C_{4-15}$), 4 to 10 ($C_{4-10}$), or 4 to 6 ($C_{4-6}$) carbon atoms. Examples of alkynyl groups include, but are not limited to, ethynyl ($—C{\equiv}CH$), propynyl (including all isomeric forms, e.g., 1-propynyl ($—C{\equiv}CCH_3$) and propargyl ($—CH_2C{\equiv}CH$)), butynyl (including all isomeric forms, e.g., 1-butyn-1-yl and 2-butyn-1-yl), pentynyl (including all isomeric forms, e.g., 1-pentyn-1-yl and 1-methyl-2-butyn-1-yl), and hexynyl (including all isomeric forms, e.g., 1-hexyn-1-yl and 2-hexyn-1-yl).

The term "alkynylene" refers to a linear or branched divalent hydrocarbon radical, which contains one or more, in one embodiment, one, two, three, or four, in another embodiment, one, carbon-carbon triple bond(s). The alkynylene is optionally substituted with one or more substituents Q as described herein. For example, $C_{2-6}$ alkynylene refers to a linear unsaturated divalent hydrocarbon radical of 2 to 6 carbon atoms or a branched unsaturated divalent hydrocarbon radical of 4 to 6 carbon atoms. In certain embodiments, the alkynylene is a linear divalent hydrocarbon radical of 2 to 30 ($C_{2-30}$), 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 4 to 30 ($C_{4-30}$), 4 to 20 ($C_{4-20}$), 4 to 15 ($C_{4-15}$), 4 to 10 ($C_{4-10}$), or 4 to 6 ($C_{4-6}$) carbon atoms. Examples of alkynylene groups include, but are not limited to, ethynylene, propynylene (including all isomeric forms, e.g., 1-propyn-1,3-diyl and 1-propyn-3,3-diyl), butynylene (including all isomeric forms, e.g., 1-butyn-1,3-diyl, 1-butyn-1,4-diyl, and 2-butyn-1,1-diyl), pentynylene (including all isomeric forms, e.g., 1-pentyn-1,3-diyl, 1-pentyn-1,4-diyl, and 2-pentyn-1,1-diyl), and hexynylene (including all isomeric forms, e.g., 1-hexyn-1,3-diyl, 1-hexyn-1,4-diyl, and 2-hexyn-1,1-diyl).

The term "cycloalkyl" refers to a cyclic monovalent hydrocarbon radical, which is optionally substituted with one or more substituents Q as described herein. In one embodiment, the cycloalkyl is a saturated or unsaturated but non-aromatic, and/or bridged or non-bridged, and/or fused bicyclic group. In certain embodiments, the cycloalkyl has from 3 to 20 ($C_{3-20}$), from 3 to 15 ($C_{3-15}$), from 3 to 10 ($C_{3-10}$), or from 3 to 7 ($C_{3-7}$) carbon atoms. In one embodiment, the cycloalkyl is monocyclic. In another embodiment, the cycloalkyl is bicyclic. In yet another embodiment, the cycloalkyl is tricyclic. In still another embodiment, the cycloalkyl is polycyclic. Examples of cycloalkyl groups include, but are not limited to, cyclopropyl, cyclobutyl, cyclopentyl, cyclopentenyl, cyclohexyl, cyclohexenyl, cyclohexadienyl, cycloheptyl, cycloheptenyl, bicyclo[1.1.1]pentyl, bicyclo[2.1.1]hexyl, bicyclo[2.2.1]heptyl, bicyclo[2.2.2]octyl, decalinyl, and adamantyl.

The term "cycloalkylene" refers to a cyclic divalent hydrocarbon radical, which may be optionally substituted with one or more substituents Q as described herein. In one embodiment, cycloalkyl groups may be saturated or unsaturated but non-aromatic, and/or bridged, and/or non-bridged, and/or fused bicyclic groups. In certain embodiments, the cycloalkylene has from 3 to 30 ($C_3\_30$), 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkylene groups include, but are not limited to, cyclopropylene (including all isomeric forms, e.g., cycloprop-1,1-diyl and cycloprop-1,2-diyl), cyclobutylene (including all isomeric forms, e.g., cyclobut-1,1-diyl, cyclobut-1,2-diyl, and cyclobut-1,3-diyl), cyclopentylene (including all isomeric forms, e.g., cyclopent-1,1-diyl, cyclopent-1,2-diyl, and cyclopent-1,3-diyl), cyclohexylene (including all isomeric forms, e.g., cyclohex-1,1-diyl, cyclohex-1,2-diyl, cyclohex-1,3-diyl, and cyclohex-1,4-diyl), cycloheptylene (including all isomeric forms, e.g., cyclohept-1,1-diyl, cyclohept-1,2-diyl, cyclohept-1,3-diyl, and cyclohept-1,4-diyl), decalinylene (including all isomeric forms, e.g., decalin-1,1-diyl, decalin-1,2-diyl, and decalin-1,8-diyl), and adamantylene (including all isomeric forms, e.g., adamant-1,2-diyl, adamant-1,3-diyl, and adamant-1,8-diyl).

The term "aryl" refers to a monovalent monocyclic aromatic hydrocarbon radical and/or monovalent polycyclic aromatic hydrocarbon radical that contain at least one aromatic carbon ring. In certain embodiments, the aryl has from 6 to 20 ($C_{6-20}$), from 6 to 15 ($C_{6-15}$), or from 6 to 10 ($C_{6-10}$) ring carbon atoms. Examples of aryl groups include, but are not limited to, phenyl, naphthyl, fluorenyl, azulenyl, anthryl, phenanthryl, pyrenyl, biphenyl, and terphenyl. The aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In one embodiment, the aryl is monocyclic. In another embodiment, the aryl is bicyclic. In yet another embodiment, the aryl is tricyclic. In still another embodiment, the aryl is polycyclic. In certain embodiments, the aryl is optionally substituted with one or more substituents Q as described herein.

The term "arylene" refers to a divalent monocyclic aromatic hydrocarbon radical or divalent polycyclic aromatic hydrocarbon radical that contains at least one aromatic hydrocarbon ring. In certain embodiments, the arylene has from 6 to 20 ($C_{6-20}$), from 6 to 15 ($C_{6-15}$), or from 6 to 10 ($C_{6-10}$) ring atoms. Examples of arylene groups include, but are not limited to, phenylene (including all isomeric forms, e.g., phen-1,2-diyl, phen-1,3-diyl, and phen-1,4-diyl), naphthylene (including all isomeric forms, e.g., naphth-1,2-diyl, naphth-1,3-diyl, and naphth-1,8-diyl), fluorenylene (including all isomeric forms, e.g., fluoren-1,2-diyl, fluoren-1,3-diyl, and fluoren-1,8-diyl), azulenylene (including all isomeric forms, e.g., azulen-1,2-diyl, azulen-1,3-diyl, and azulen-1,8-diyl), anthrylene (including all isomeric forms, e.g., anthr-1,2-diyl, anthr-1,3-diyl, and anthr-1,8-diyl), phenanthrylene (including all isomeric forms, e.g., phenanthr-1,2-diyl, phenanthr-1,3-diyl, and phenanthr-1,8-diyl), pyrenylene (including all isomeric forms, e.g., pyren-1,2-diyl, pyren-1,3-diyl, and pyren-1,8-diyl), biphenylene (including all isomeric forms, e.g., biphen-2,3-diyl, biphen-3,4'-diyl, and biphen-4,4'-diyl), and terphenylene (including all isomeric forms, e.g., terphen-2,3-diyl, terphen-3,4'-diyl, and terphen-4,4'-diyl). Arylene also refers to bicyclic or tricyclic carbon rings, where one of the rings is aromatic and the others of which may be saturated, partially unsaturated, or aromatic, for example, dihydronaphthylene (including all isomeric forms, e.g., dihydronaphth-1,2-diyl or dihydronaphth-1,8-diyl), indenylene (including all isomeric forms, e.g., inden-1,2-diyl, inden-1,5-diyl, or inden-1,7-diyl), indanylene (including all isomeric forms, e.g., indan-1,2-diyl, indan-1,5-diyl, or indan-1,7-diyl), or tetrahydronaphthylene (tetralinylene) (including all isomeric forms, e.g., tetrahydronaphth-1,2-diyl, tetrahydronaphth-1,5-diyl, or tetrahydronaphth-1,8-diyl). In certain embodiments, arylene is optionally substituted with one or more substituents Q as described herein.

The term "aralkyl" or "arylalkyl" refers to a monovalent alkyl group substituted with one or more aryl groups. In certain embodiments, the aralkyl has from 7 to 30 ($C_{7-30}$), from 7 to 20 ($C_{7-20}$), or from 7 to 16 ($C_{7-16}$) carbon atoms. Examples of aralkyl groups include, but are not limited to, benzyl, phenylethyl (including all isomeric forms, e.g., 1-phenylethyl and 2-phenylethyl), and phenylpropyl (including all isomeric forms, e.g., 1-phenylpropyl, 2-phenylpropyl, and 3-phenylpropyl). In certain embodiments, the aralkyl is optionally substituted with one or more substituents Q as described herein.

The term "aralkylene" or "arylalkylene" refers to a divalent alkyl group substituted with one or more aryl groups. In certain embodiments, the aralkylene has from 7 to 30 ($C_{7-30}$), from 7 to 20 ($C_{7-20}$), or from 7 to 16 ($C_{7-16}$) carbon atoms. Examples of aralkylene groups include, but are not limited to, benzylene (including all isomeric forms, e.g., phenylmethdiyl), phenylethylene (including all isomeric forms, e.g., 2-phenyl-ethan-1,1-diyl and 2-phenyl-ethan-1,2-diyl), and phenylpropylene (including all isomeric forms, e.g., 3-phenyl-propan-1,1-diyl, 3-phenyl-propan-1,2-diyl, and 3-phenyl-propan-1,3-diyl). In certain embodiments, the aralkylene is optionally substituted with one or more substituents Q as described herein.

The term "heteroaryl" refers to a monovalent monocyclic aromatic group or monovalent polycyclic aromatic group that contain at least one aromatic ring, wherein at least one aromatic ring contains one or more heteroatoms, each independently selected from O, S, and N, in the ring. The heteroaryl is bonded to the rest of a molecule through the aromatic ring. Each ring of a heteroaryl group can contain one or two O atoms, one or two S atoms, and/or one to four N atoms; provided that the total number of heteroatoms in each ring is four or less and each ring contains at least one carbon atom. In certain embodiments, the heteroaryl has from 5 to 20, from 5 to 15, or from 5 to 10 ring atoms. In one embodiment, the heteroaryl is monocyclic. Examples of monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. In another embodiment, the heteroaryl is bicyclic. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. In yet another embodiment, the heteroaryl is tricyclic. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, the heteroaryl is optionally substituted with one or more substituents Q as described herein.

The term "heteroarylene" refers to a divalent monocyclic aromatic group or divalent polycyclic aromatic group that contains at least one aromatic ring, wherein at least one aromatic ring contains one or more heteroatoms in the ring, each of which is independently selected from O, S, and N. A heteroarylene group has at least one linkage to the rest of a molecule via its aromatic ring(s). Each ring of a heteroarylene group can contain one or two O atoms, one or two S atoms, and/or one to four N atoms, provided that the total number of heteroatoms in each ring is four or less and each ring contains at least one carbon atom. In certain embodiments, the heteroarylene has from 5 to 20, from 5 to 15, or from 5 to 10 ring atoms. Examples of monocyclic heteroarylene groups include, but are not limited to, furanylene, imidazolylene, isothiazolylene, isoxazolylene, oxadiazolylene, oxadiazolylene, oxazolylene, pyrazinylene, pyrazolylene, pyridazinylene, pyridylene, pyrimidinylene, pyrrolylene, thiadiazolylene, thiazolylene, thienylene, tetrazolylene, triazinylene, and triazolylene. Examples of bicyclic heteroarylene groups include, but are not limited to, benzofuranylene, benzimidazolylene, benzoisoxazolylene, benzopyranylene, benzothiadiazolylene, benzothiazolylene, benzothienylene, benzotriazolylene, benzoxazolylene, furopyridylene, imidazopyridinylene, imidazothiazolylene, indolizinylene, indolylene, indazolylene, isobenzofuranylene, isobenzothienylene, isoindolylene, isoquinolinylene, isothiazolylene, naphthyridinylene, oxazolopyridinylene, phthalazinylene, pteridinylene, purinylene, pyridopyridylene, pyrrolopyridylene, quinolinylene, quinoxalinylene, quinazolinylene, thiadiazolopyrimidylene, and thienopyridylene. Examples of tricyclic heteroarylene groups include, but are not limited to, acridinylene, benzindolylene, carbazolylene, dibenzofuranylene, perimidinylene, phenanthrolinylene, phenanthridinylene, phenarsazinylene, phenazinylene, phenothiazinylene, phenoxazinylene, and xanthenylene. In certain embodiments, heteroarylene is optionally substituted with one or more substituents Q as described herein.

The term "heterocyclyl" or "heterocyclic" refers to a monovalent monocyclic non-aromatic ring system or monovalent polycyclic ring system that contains at least one non-aromatic ring, wherein one or more of the non-aromatic ring atoms are heteroatoms, each independently selected from O, S, and N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. The heterocyclyl is bonded to the rest of a molecule through the non-aromatic ring. In certain embodiments, the heterocyclyl is a monocyclic, bicyclic, tricyclic, or tetracyclic ring system, which may be fused or bridged, and in which nitrogen or sulfur atoms may be optionally oxidized, nitrogen atoms may be optionally quaternized, and some rings may be partially or fully saturated, or aromatic. The heterocyclyl may be attached to the main structure at any heteroatom or carbon atom which results in the creation of a stable compound. Examples of heterocyclyls and heterocyclic groups include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, the heterocyclyl is optionally substituted with one or more substituents Q as described herein.

The term "heterocyclylene" refers to a divalent monocyclic non-aromatic ring system or divalent polycyclic ring system that contains at least one non-aromatic ring, wherein one or more of the non-aromatic ring atoms are heteroatoms independently selected from O, S, and N; and the remaining ring atoms are carbon atoms. Heterocyclylene groups are bonded to the rest of a molecule through the non-aromatic ring. In certain embodiments, the heterocyclylene group has from 3 to 20, from 3 to 15, from 3 to 10, from 3 to 8, from 4 to 7, or from 5 to 6 ring atoms. In certain embodiments, the heterocyclylene is a monocyclic, bicyclic, tricyclic, or tetracyclic ring system, which may be fused or bridged, and in which nitrogen or sulfur atoms may be optionally oxidized, nitrogen atoms may be optionally quaternized, and some rings may be partially or fully saturated, or aromatic. The heterocyclylene may be attached to the main structure at any heteroatom or carbon atom which results in the creation of a stable compound. Examples of such heterocyclylene groups include, but are not limited to, azepinylene, benzodioxanylene, benzodioxolylene, benzofuranonylene, benzopyranonylene, benzopyranylene, benzotetrahydrofuranylene, benzotetrahydrothienylene, benzothiopyranylene, benzoxazinylene, β-carbolinylene, chromanylene, chromonylene, cinnolinylene, coumarinylene, decahydroisoquinolinylene, dihydrobenzisothiazinylene, dihydrobenzisoxazinylene, dihydrofurylene, dihydroisoindolylene, dihydropyranylene, dihydropyrazolylene, dihydropyrazinylene, dihydropyridinylene, dihydropyrimidinylene, dihydropyrrolylene, dioxolanylene, 1,4-dithianylene, furanonylene, imidazolidinylene, imidazolinylene, indolinylene, isobenzotetrahydrofuranylene, isobenzotetrahydrothienylene, isochromanylene, isocoumarinylene, isoindolinylene, isothiazolidinylene, isoxazolidinylene, morpholinylene, octahydroindolylene, octahydroisoindolylene, oxazolidinonylene, oxazolidinylene, oxiranylene, piperazinylene, piperidinylene, 4-piperidonylene, pyrazolidinylene, pyrazolinylene, pyrrolidinylene, pyrrolinylene, quinuclidinylene, tetrahydrofurylene, tetrahydroisoquinolinylene, tetrahydropyranylene, tetrahydrothienylene, thiamorpholinylene, thiazolidinylene, tetrahydroquinolinylene, and 1,3,5-trithianylene. In certain embodiments, the heterocyclylene is optionally substituted with one or more substituents Q as described herein.

The term "halogen", "halide," or "halo" refers to fluorine, chlorine, bromine, and/or iodine.

The term "optionally substituted" is intended to mean that a group or substituent, such as an alkyl, alkylene, heteroalkylene, alkenyl, alkenylene, heteroalkenylene, alkynyl, alkynylene, cycloalkyl, cycloalkylene, aryl, arylene, aralkyl, aralkylene, heteroaryl, heteroarylene, heterocyclyl, or heterocyclylene group, may be substituted with one or more, in one embodiment, one, two, three, or four, substituents Q, each of which is independently selected from, e.g., (a) deuterium (-D), cyano (—CN), halo, nitro (—$NO_2$), and oxo (═O); (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)N$R^bR^c$, —C(O)S$R^a$, —C(N$R^a$)N$R^bR^c$, —C(S)$R^a$, —C(S)O$R^a$, —C(S)N$R^bR^c$, —O$R^a$, —OC(O)$R^a$, —OC(O)O$R^a$, —OC(O)N$R^bR^c$, —OC(O)S$R^a$, —OC(N$R^a$)N$R^bR^c$, —OC(S)$R^a$, —OC(S)O$R^a$, —OC(S)N$R^bR^c$, —OS(O)$R^a$, —OS$(O)_2R^a$, —OS(O)N$R^bR^c$, —OS$(O)_2$N$R^bR^c$, —N$R^bR^c$, —N$R^a$C(O)$R^d$, —N$R^a$C(O)O$R^d$, —N$R^a$C(O)N$R^bR^c$, —N$R^a$C(O)S$R^d$, —N$R^a$C(N$R^d$)N$R^bR^c$, —N$R^a$C(S)$R^d$, —N$R^a$C(S)O$R^d$, —N$R^a$C(S)N$R^bR^c$, —N$R^a$S(O)$R^d$, —N$R^a$S$(O)_2R^d$, —N$R^a$S(O)N$R^bR^c$, —N$R^a$S$(O)_2$N$R^bR^c$, —S$R^a$, —S(O)$R^a$, —S$(O)_2R^a$, —S(O)N$R^bR^c$, and —S$(O)_2$N$R^bR^c$, wherein each $R^a$, $R^b$, $R^c$, and $R^d$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heterocyclyl optionally substituted with one or more, in one embodiment, one, two, three, or four, substituents $Q^a$. As used herein, all groups that can be substituted are "optionally substituted."

In one embodiment, each $Q^a$ is independently selected from: (a) deuterium, cyano, halo, nitro, and oxo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —C(O)

$R^e$, —C(O)$OR^e$, —C(O)$NR^fR^g$, —C(O)$SR^e$, —C($NR^e$)$NR^fR^g$, —C(S)$R^e$, —C(S)$OR^e$, —C(S)$NR^fR^g$, —$OR^e$, —OC(O)$R^e$, —OC(O)$OR^e$, —OC(O)$NR^fR^g$, —OC(O)$SR^e$, —OC($NR^e$)$NR^fR^g$, —OC(S)$R^e$, —OC(S)$OR^e$, —OC(S)$NR^fR^g$, —OS(O)$R^e$, —$OS(O)_2R^e$, —OS(O)$NR^fR^g$, —$OS(O)_2NR^fR^g$, —$NR^fR^g$, —$NR^eC(O)R^h$, —$NR^eC(O)OR^f$, —$NR^eC(O)NR^fR^g$, —$NR^eC(O)SR^f$, —$NR^eC(NR^h)NR^fR^g$, —$NR^eC(S)R^h$, —$NR^eC(S)OR^f$, —$NR^eC(S)NR^fR^g$, —$NR^eS(O)R^h$, —$NR^eS(O)_2R^h$, —$NR^fNR^g$, —$NR^eS(O)_2NR^fR^g$, —$SR^e$, —S(O)$R^e$, —$S(O)_2R^e$, —S(O)$NR^fR^g$, and —$S(O)_2NR^fR^g$; wherein each $R^e$, $R^f$, $R^g$, and $R^h$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

In certain embodiments, "optically active" and "enantiomerically active" refer to a collection of molecules, which has an enantiomeric excess of no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, an optically active compound comprises about 95% or more of one enantiomer and about 5% or less of the other enantiomer based on the total weight of the enantiomeric mixture in question. In certain embodiments, an optically active compound comprises about 98% or more of one enantiomer and about 2% or less of the other enantiomer based on the total weight of the enantiomeric mixture in question. In certain embodiments, an optically active compound comprises about 99% or more of one enantiomer and about 1% or less of the other enantiomer based on the total weight of the enantiomeric mixture in question.

In describing an optically active compound, the prefixes R and S are used to denote the absolute configuration of the compound about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the compound, R and S.

The term "isotopically enriched" refers to a compound that contains an unnatural proportion of an isotope at one or more of the atoms that constitute such a compound. In certain embodiments, an isotopically enriched compound contains unnatural proportions of one or more isotopes, including, but not limited to, hydrogen ($^1H$), deuterium ($^2H$), tritium ($^3H$), carbon-11 ($^{11}C$), carbon-12 ($^{12}C$), carbon-13 ($^{13}C$), carbon-14 ($^{14}C$), nitrogen-13 ($^{13}N$), nitrogen-14 ($^{14}N$), nitrogen-15 ($^{15}N$), oxygen-14 ($^{14}O$), oxygen-15 ($^{15}O$), oxygen-16 ($^{16}O$), oxygen-17 ($^{17}O$), oxygen-18 ($^{18}O$), fluorine-17 ($^{17}F$), fluorine-18 ($^{18}F$), phosphorus-31 ($^{31}P$), phosphorus-32 ($^{32}P$), phosphorus-33 ($^{33}P$), sulfur-32 ($^{32}S$), sulfur-33 ($^{33}S$), sulfur-34 ($^{34}S$), sulfur-35 ($^{35}S$), sulfur-36 ($^{36}S$), chlorine-35 ($^{35}Cl$), chlorine-36 ($^{36}Cl$), chlorine-37 ($^{37}Cl$), bromine-79 ($^{79}Br$), bromine-81 ($^{81}Br$), iodine-123 ($^{123}I$), iodine-125 ($^{125}I$), iodine-127 ($^{127}I$), iodine-129 ($^{129}I$), and iodine-131 ($^{131}I$). In certain embodiments, an isotopically enriched compound is in a stable form, that is, non-radioactive. In certain embodiments, an isotopically enriched compound contains unnatural proportions of one or more isotopes, including, but not limited to, hydrogen ($^1H$), deuterium ($^2H$), carbon-12 ($^{12}C$), carbon-13 ($^{13}C$), nitrogen-14 ($^{14}N$), nitrogen-15 ($^{15}N$), oxygen-16 ($^{16}O$), oxygen-17 ($^{17}O$), oxygen-18 ($^{18}O$), fluorine-17 ($^{17}F$), phosphorus-31 ($^{31}P$), sulfur-32 ($^{32}S$), sulfur-33 ($^{33}S$), sulfur-34 ($^{34}S$), sulfur-36 ($^{36}S$), chlorine-35 ($^{35}Cl$), chlorine-37 ($^{37}Cl$), bromine-79 ($^{79}Br$), bromine-81 ($^{81}Br$), and iodine-127 ($^{127}I$). In certain embodiments, an isotopically enriched compound is in an unstable form, that is, radioactive. In certain embodiments, an isotopically enriched compound contains unnatural proportions of one or more isotopes, including, but not limited to, tritium ($^3H$), carbon-11 ($^{11}C$), carbon-14 ($^{14}C$), nitrogen-13 ($^{13}N$), oxygen-14 ($^{14}O$), oxygen-15 ($^{15}O$), fluorine-18 ($^{18}F$), phosphorus-32 ($^{32}P$), phosphorus-33 ($^{33}P$), sulfur-35 ($^{35}S$), chlorine-36 ($^{36}Cl$), iodine-123 ($^{123}I$), iodine-125 ($^{125}I$), iodine-129 ($^{129}I$), and iodine-131 ($^{131}I$). It will be understood that, in a compound as provided herein, any hydrogen can be $^2H$, as example, or any carbon can be $^{13}C$, as example, or any nitrogen can be $^{15}N$, as example, or any oxygen can be $^{18}O$, as example, where feasible according to the judgment of one of ordinary skill in the art.

The term "isotopic enrichment" refers to the percentage of incorporation of a less prevalent isotope (e.g., D for deuterium or hydrogen-2) of an element at a given position in a molecule in the place of a more prevalent isotope (e.g., $^1H$ for protium or hydrogen-1) of the element. As used herein, when an atom at a particular position in a molecule is designated as a particular less prevalent isotope, it is understood that the abundance of that isotope at that position is substantially greater than its natural abundance.

The term "isotopic enrichment factor" refers the ratio between the isotopic abundance in an isotopically enriched compound and the natural abundance of a specific isotope.

The term "hydrogen" or the symbol "H" refers to the composition of naturally occurring hydrogen isotopes, which include protium ($^1H$), deuterium ($^2H$ or D), and tritium ($^3H$), in their natural abundances. Protium is the most common hydrogen isotope having a natural abundance of more than 99.98%. Deuterium is a less prevalent hydrogen isotope having a natural abundance of about 0.0156%.

The term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156% on average, deuterium enrichment at any position in a compound synthesized using non-enriched starting materials is about 0.0156% on average. As used herein, when a particular position in an isotopically enriched compound is designated as having deuterium, it is understood that the abundance of deuterium at that position in the compound is substantially greater than its natural abundance (0.0156%).

The term "carbon" or the symbol "C" refers to the composition of naturally occurring carbon isotopes, which include carbon-12 ($^{12}C$) and carbon-13 ($^{13}C$) in their natural abundances. Carbon-12 is the most common carbon isotope having a natural abundance of more than 98.89%. Carbon-13 is a less prevalent carbon isotope having a natural abundance of about 1.11%.

The term "carbon-13 enrichment" or "$^{13}C$ enrichment" refers to the percentage of incorporation of carbon-13 at a given position in a molecule in the place of carbon. For example, carbon-13 enrichment of 10% at a given position means that 10% of molecules in a given sample contain carbon-13 at the specified position. Because the naturally occurring distribution of carbon-13 is about 1.11% on average, carbon-13 enrichment at any position in a compound synthesized using non-enriched starting materials is about 1.11% on average. As used herein, when a particular position in an isotopically enriched compound is designated as having carbon-13, it is understood that the abundance of carbon-13 at that position in the compound is substantially greater than its natural abundance (1.11%).

The terms "substantially pure" and "substantially homogeneous" mean sufficiently homogeneous to appear free of readily detectable impurities as determined by standard analytical methods used by one of ordinary skill in the art, including, but not limited to, thin layer chromatography (TLC), gel electrophoresis, high performance liquid chromatography (HPLC), gas chromatography (GC), nuclear magnetic resonance (NMR), and mass spectrometry (MS); or sufficiently pure such that further purification would not detectably alter the physical, chemical, biological, and/or pharmacological properties, such as enzymatic and biological activities, of the substance. In certain embodiments, "substantially pure" or "substantially homogeneous" refers to a collection of molecules, wherein at least about 95%, at least about 96%, at least about 97%, at least about 98%, at least about 99%, or at least about 99.5% by weight of the molecules are a single compound, including a single enantiomer, a racemic mixture, or a mixture of enantiomers, as determined by standard analytical methods. As used herein, when an atom at a particular position in an isotopically enriched molecule is designated as a particular less prevalent isotope, a molecule that contains other than the designated isotope at the specified position is an impurity with respect to the isotopically enriched compound. Thus, for a deuterated compound that has an atom at a particular position designated as deuterium, a compound that contains a protium at the same position is an impurity.

The term "solvate" refers to a complex or aggregate formed by one or more molecules of a solute, e.g., a compound provided herein, and one or more molecules of a solvent, which are present in stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The phrase "an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof" has the same meaning as the phrase "(i) an enantiomer, a mixture of enantiomers, a mixture of two or more diastereomers, a tautomer, a mixture of two or more tautomers, or an isotopic variant of the compound referenced therein; (ii) a pharmaceutically acceptable salt, solvate, hydrate, or prodrug of the compound referenced therein; or (iii) a pharmaceutically acceptable salt, solvate, hydrate, or prodrug of an enantiomer, a mixture of enantiomers, a mixture of two or more diastereomers, a tautomer, a mixture of two or more tautomers, or an isotopic variant of the compound referenced therein."

Compounds

In one embodiment, provided herein is a compound of Formula (I):

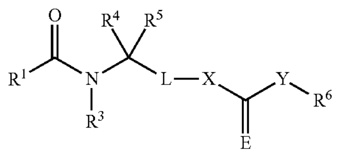

(I)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

E is O, S, $NR^{1a}$, or $NOR^{1a}$;

L is a bond, $C_{1-6}$ alkylene, $C_{2-6}$ alkenylene, $C_{2-6}$ alkynylene, $C_{3-10}$ cycloalkylene, $C_{6-14}$ arylene, $C_{7-15}$ aralkylene, heteroarylene, or heterocyclylene;

X and Y are: (i) X is a bond, $—NR^X—$, or —O—; and Y is $—NR^Y—$, $—NR^YO—$, or —O—; or (ii) X is $—NR^X—$ or —O—; and Y is a bond; wherein each $R^X$ and $R^Y$ is independently hydrogen, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl;

$R^1$ is

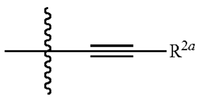

or $—CH_2—R^{2b}$, wherein $R^{2a}$ is hydrogen, deuterium, or $C_{1-6}$ alkyl; and $R^{2b}$ is halo, $—OS(O)_2R^{1a}$, or $—OS(O)_2OR^{1a}$;

$R^3$ is $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl;

$R^4$ and $R^5$ are each independently hydrogen, deuterium, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or $R^4$ and $R^5$ together with the carbon atom to which they are attached form $C_{3-10}$ cycloalkyl or heterocyclyl;

$R^6$ is hydrogen, deuterium, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; and each $R^{1a}$ is independently hydrogen, deuterium, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl;

wherein each alkyl, alkylene, alkenyl, alkenylene, alkynyl, alkynylene, cycloalkyl, cycloalkylene, aryl, arylene, aralkyl, aralkylene, heteroaryl, heteroarylene, heterocyclyl, and heterocyclylene is optionally substituted with one or more, in one embodiment, one, two, three, or four, substituents Q, wherein each Q is independently selected from: (a) deuterium, cyano, halo, nitro, and oxo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) $—C(O)R^a$, $—C(O)OR^a$, $—C(O)NR^bR^c$, $—C(O)SR^a$, $—C(NR^a)NR^bR^c$, —$C(S)R^a$, —$C(S)OR^a$, —$C(S)NR^bR^c$, —$OR^a$, —$OC(O)R^a$, —$OC(O)OR^a$, —$OC(O)NR^bR^c$, —$OC(O)SR^a$, —$OC(NR^a)NR^bR^c$, —$OC(S)R^a$, —$OC(S)OR^a$, —$OC(S)NR^bR^c$, —$OS(O)R^a$, —$OS(O)_2R^a$, —$OS(O)NR^bR^c$, —$OS(O)_2NR^bR^c$, —$NR^bR^c$, —$NR^aC(O)R^d$, —$NR^aC(O)OR^d$, —$NR^aC(O)NR^bR^c$, —$NR^aC(O)SR^d$, —$NR^aC(NR^d)NR^bR^c$, —$NR^aC(S)R^d$, —$NR^aC(S)OR^d$, —$NR^aC(S)NR^bR^c$, —$NR^aS(O)R^d$, —$NR^aS(O)_2R^d$, —$NR^aS(O)NR^bR^c$, —$NR^aS(O)_2NR^bR^c$, —$SR^a$, —$S(O)R^a$, —$S(O)_2R^a$, —$S(O)NR^bR^c$, and —$S(O)_2NR^bR^c$, wherein each $R^a$, $R^b$, $R^c$, and $R^d$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heterocyclyl optionally substituted with one or more, in one embodiment, one, two, three, or four, substituents $Q^a$;

wherein each $Q^a$ is independently selected from: (a) deuterium, cyano, halo, nitro, and oxo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —$C(O)R^e$, —$C(O)OR^e$, —$C(O)NR^fR^g$, —$C(O)SR^e$, —$C(NR^e)NR^fR^g$, —$C(S)R^e$, —$C(S)OR^e$, —$C(S)NR^fR^g$, —$OR^e$, —$OC(O)R^e$, —$OC(O)OR^e$, —$OC(O)NR^fR^g$, —$OC(O)SR^e$, —$OC(NR^e)NR^fR^g$, —$OC(S)R^e$, —$OC(S)OR^e$, —$OC(S)NR^fR^g$, —$OS(O)R^e$, —$OS(O)_2R^e$, —$OS(O)NR^fR^g$, —$OS(O)_2NR^fR^g$, —$NR^fR^g$, —$NR^eC(O)R^h$, —$NR^eC(O)OR^f$, —$NR^eC(O)NR^fR^g$, —$NR^eC(O)SR^f$, —$NR^eC(NR^h)NR^fR^g$, —$NR^eC(S)R^h$, —$NR^eC(S)OR^f$, —$NR^eC(S)NR^fR^g$, —$NR^eS(O)R^h$, —$NR^eS(O)_2R^h$, —$NR^eS(O)NR^fR^g$, —$NR^eS(O)_2NR^fR^g$, —$SR^e$, —$S(O)R^e$, —$S(O)_2R^e$, —$S(O)NR^fR^g$, and —$S(O)_2NR^fR^g$; wherein each $R^e$, $R^f$, $R^g$, and $R^h$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

In another embodiment, provided herein is a compound of Formula (Ia):

(Ia)

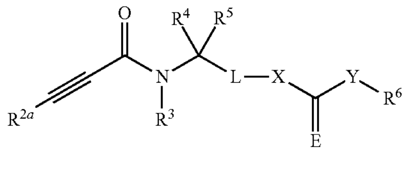

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^3$, $R^4$, $R^5$, $R^6$, $R^{2a}$, E, L, X, and Y are each as defined herein.

In yet another embodiment, provided herein is a compound of Formula (Ib):

(Ib)

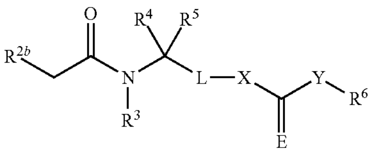

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^3$, $R^4$, $R^5$, $R^6$, $R^{2b}$, E, L, X, and Y are each as defined herein.

In yet another embodiment, provided herein is a compound of Formula (II):

(II)

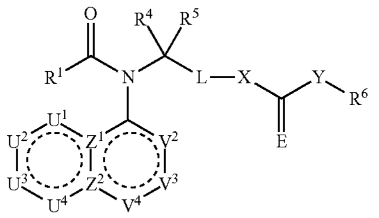

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

$U^1$, $U^2$, $U^3$, $U^4$, $V^2$, $V^3$, and $V^4$ are each independently —$CR^{3a}$═, —$CR^{3a}R^{3b}$—, —N═, —$NR^{3c}$—, —O—, or —S—;

$Z^1$ and $Z^2$ are each independently C, $CR^{3a}$, or N;

each $R^{3a}$ and $R^{3b}$ is independently (a) hydrogen, deuterium, cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —$C(O)R^{1a}$, —$C(O)OR^{1a}$, —$C(O)NR^{1b}R^{1c}$, —$C(NR^{1a})NR^{1b}R^{1c}$, —$OR^{1a}$, —$OC(O)R^{1a}$, —$OC(O)OR^{1a}$, —$OC(O)NR^{1b}R^{1c}$, —$OC(NR^{1a})NR^{1b}R^{1c}$, —$OS(O)R^{1a}$, —$OS(O)_2R^{1a}$, —$OS(O)NR^{1b}R^{1c}$, —$OS(O)_2NR^{1b}R^{1c}$, —$NR^{1b}R^{1c}$, —$NR^{1a}C(O)R^{1d}$, —$NR^{1a}C(O)OR^{1d}$, —$NR^{1a}C(O)NR^{1b}R^{1c}$, —$NR^{1a}C(NR^{1d})NR^{1b}R^{1c}$, —$NR^{1a}S(O)R^{1d}$, —$NR^{1a}S(O)_2R^{1d}$, —$NR^{1a}S(O)NR^{1b}R^{1c}$, —$NR^{1a}S(O)_2NR^{1b}R^{1c}$, —$SR^{1a}$, —$S(O)R^{1a}$, —$S(O)_2R^{1a}$, —$S(O)NR^{1b}R^{1c}$, or —$S(O)_2NR^{1b}R^{1c}$; or $R^{3a}$ and $R^{3b}$ together with the carbon atom to which they are attached form carbonyl, $C_{3-10}$ cycloalkyl, or heterocyclyl;

each $R^{3c}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl;

each $R^{1a}$, $R^{1b}$, $R^{1c}$, and $R^{1d}$ is independently hydrogen, deuterium, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl; and $R^1$, $R^4$, $R^5$, $R^6$, E, L, X, and Y are each as defined herein;

wherein each alkyl, alkenyl, alkynyl, cycloalkyl, aryl, aralkyl, heteroaryl, and heterocyclyl is optionally substituted with one or more, in one embodiment, one, two, three, or four, substituents Q as described herein.

In yet another embodiment, provided herein is a compound of Formula (IIa):

(IIa)

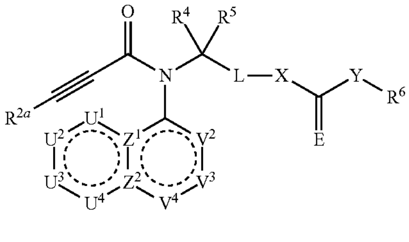

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^4$, $R^5$, $R^6$, $R^{2a}$, E, L, $U^1$, $U^2$, $U^3$, $U^4$, $V^2$, $V^3$, $V^4$, X, Y, $Z^1$, and $Z^2$ are each as defined herein.

In yet another embodiment, provided herein is a compound of Formula (IIb):

(IIb)

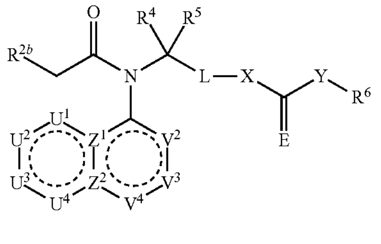

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^4$, $R^5$, $R^6$, $R^{2b}$, E, L, $U^1$, $U^2$, $U^3$, $U^4$, $V^2$, $V^3$, $V^4$, X, Y, $Z^1$, and $Z^2$ are each as defined herein.

In yet another embodiment, provided herein is a compound of Formula (III):

(III)

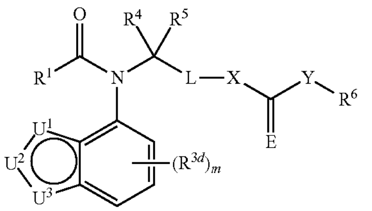

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

each $R^{3d}$ is independently (a) deuterium, cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) $-C(O)R^{1a}$, $-C(O)OR^{1a}$, $-C(O)NR^{1b}R^{1c}$, $-C(NR^{1a})NR^{1b}R^{1c}$, $-OR^{1a}$, $-OC(O)R^{1a}$, $-OC(O)OR^{1a}$, $-OC(O)NR^{1b}R^{1c}$, $-OC(NR^{1a})NR^{1b}R^{1c}$, $-OS(O)R^{1a}$, $-OS(O)_2R^{1a}$, $-OS(O)NR^{1b}R^{1c}$, $-OS(O)_2NR^{1b}R^{1c}$, $-NR^{1b}R^{1c}$, $-NR^{1a}C(O)R^{1d}$, $-NR^{1a}C(O)OR^{1d}$, $-NR^{1a}C(O)NR^{1b}R^{1c}$, $-NR^{1a}C(NR^{1d})NR^{1b}R^{1c}$, $-NR^{1a}S(O)R^{1d}$, $-NR^{1a}S(O)_2R^{1d}$, $-NR^{1a}S(O)NR^{1b}R^{1c}$, $-NR^{1a}S(O)_2NR^{1b}R^{1c}$, $-SR^{1a}$, $-S(O)R^{1a}$, $-S(O)_2R^{1a}$, $-S(O)NR^{1b}R^{1c}$ or $-S(O)_2NR^{1b}R^{1c}$;

$U^1$, $U^2$, and $U^3$ are each independently $-CR^{3a}=$, $-N=$, $-NR^{3c}-$, $-O-$, or $-S-$;

m is an integer of 0, 1, 2, or 3; and $R^1$, $R^4$, $R^5$, $R^6$, $R^{1a}$, $R^{1b}$, $R^{1c}$, $R^{1d}$, $R^{3a}$, $R^{3c}$, E, L, X, and Y are each as defined herein;

wherein each alkyl, alkenyl, alkynyl, cycloalkyl, aryl, aralkyl, heteroaryl, and heterocyclyl is optionally substituted with one or more, in one embodiment, one, two, three, or four, substituents Q as described herein.

In yet another embodiment, provided herein is a compound of Formula (IIIa):

(IIIa)

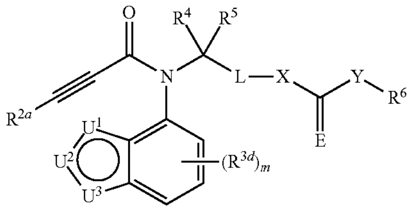

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $U^1$, $U^2$, and $U^3$ are each independently $-CR^{3a}=$, $-N=$, $-NR^{3c}-$, $-O-$, or $-S-$; and $R^4$, $R^5$, $R^6$, $R^{2a}$, $R^{3a}$, $R^{3c}$, $R^{3d}$, E, L, X, Y, and m are each as defined herein.

In yet another embodiment, provided herein is a compound of Formula (IIIb):

(IIIb)

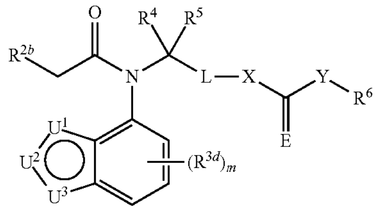

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $U^1$, $U^2$, and $U^3$ are each independently —$CR^{3a}$=, —N=, —$NR^{3c}$—, —O—, or —S—; and $R^4$, $R^5$, $R^6$, $R^{2b}$, $R^{3a}$, $R^{3c}$, $R^{3d}$, E, L, X, Y, and m are each as defined herein.

In yet another embodiment, provided herein is a compound of Formula (IV):

(IV)

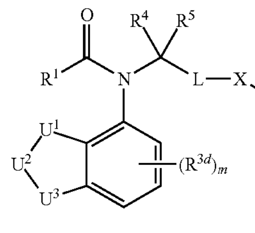

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $U^1$, $U^2$, and $U^3$ are each independently —$CR^{3a}R^{3b}$—, —$NR^{3c}$—, —O—, or —S—; and $R^1$, $R^4$, $R^5$, $R^6$, $R^{3a}$, $R^{3b}$, $R^{3c}$, $R^{3d}$, E, L, X, Y, and m are each as defined herein.

In yet another embodiment, provided herein is a compound of Formula (IVa):

(IVa)

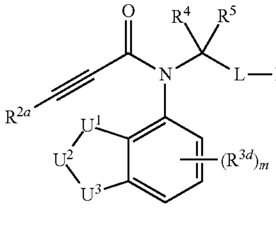

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $U^1$, $U^2$, and $U^3$ are each independently —$CR^{3a}R^{3b}$—, —$NR^{3c}$—, —O—, or —S—; and $R^4$, $R^5$, $R^6$, $R^{2a}$, $R^{3a}$, $R^{3b}$, $R^{3c}$, $R^{3d}$, E, L, X, Y, and m are each as defined herein.

In yet another embodiment, provided herein is a compound of Formula (IVb):

(IVb)

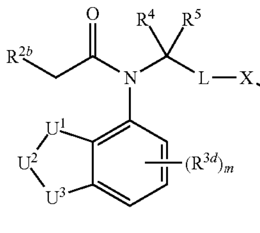

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $U^1$, $U^2$, and $U^3$ are each independently —$CR^{3a}R^{3b}$—, —$NR^{3c}$—, —O—, or —S—; and $R^4$, $R^5$, $R^6$, $R^{2b}$, $R^{3a}$, $R^{3b}$, $R^{3c}$, $R^{3d}$, E, L, X, Y, and m are each as defined herein.

In yet another embodiment, provided herein is a compound of Formula (V):

(V)

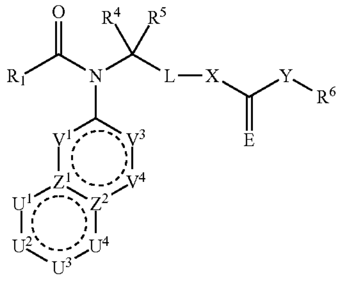

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $V^1$ is —$CR^{3a}$=, —$CR^{3a}R^{3b}$—, —N=, —$NR^{3c}$—, —O—, or —S—; and $R^1$, $R^4$, $R^5$, $R^6$, $R^{3a}$, $R^{3b}$, $R^{3c}$, E, L, $U^1$, $U^2$, $U^3$, $U^4$, $V^3$, $V^4$, X, Y, $Z^1$, and $Z^2$ are each as defined herein.

In yet another embodiment, provided herein is a compound of Formula (Va):

(Va)

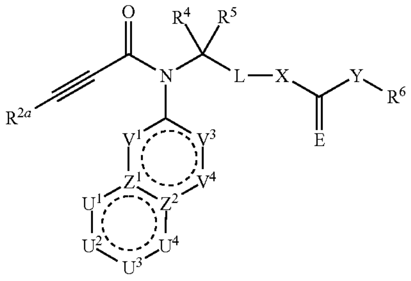

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^4$, $R^5$, $R^6$, $R^{2a}$, E, L, $U^1$, $U^2$, $U^3$, $U^4$, $V^1$, $V^3$, $V^4$, X, Y, $Z^1$, and $Z^2$ are each as defined herein.

In yet another embodiment, provided herein is a compound of Formula (Vb):

(Vb)

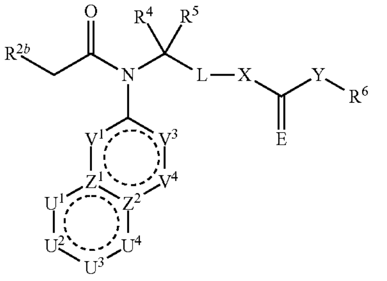

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^4$, $R^5$, $R^6$, $R^{2b}$, E, L, $U^1$, $U^2$, $U^3$, $U^4$, $V^1$, $V^3$, $V^4$, X, Y, $Z^1$, and $Z^2$ are each as defined herein.

In yet another embodiment, provided herein is a compound of Formula (VI):

(VI)

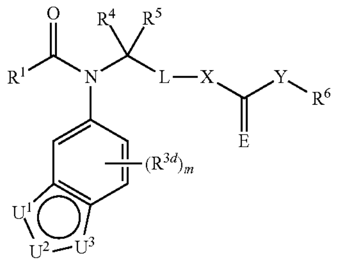

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $U^1$, $U^2$, and $U^3$ are each independently —$CR^{3a}$═, —N═, —$NR^{3c}$—, —O—, or —S—; and $R^1$, $R^4$, $R^5$, $R^6$, $R^{3a}$, $R^{3c}$, $R^{3d}$, E, L, X, Y, and m are each as defined herein.

In yet another embodiment, provided herein is a compound of Formula (VIa):

(VIa)

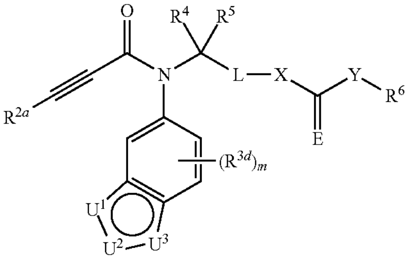

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $U^1$, $U^2$, and $U^3$ are each independently —$CR^{3a}$═, —N═, —$NR^{3c}$—, —O—, or —S—; and $R^4$, $R^5$, $R^6$, $R^{2a}$, $R^{3a}$, $R^{3c}$, $R^{3d}$, E, L, X, Y, and m are each as defined herein.

In yet another embodiment, provided herein is a compound of Formula (VIb):

(VIb)

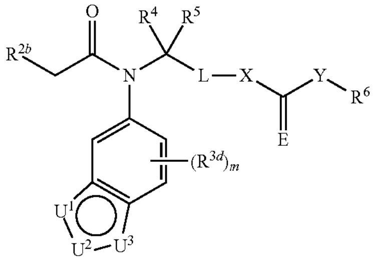

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $U^1$, $U^2$, and $U^3$ are each independently —$CR^{3a}$═, —N═, —$NR^{3c}$—, —O—, or —S—; and $R^4$, $R^5$, $R^6$, $R^{2b}$, $R^{3a}$, $R^{3c}$, $R^{3d}$, E, L, X, Y, and m are each as defined herein.

In yet another embodiment, provided herein is a compound of Formula (VII):

(VII)

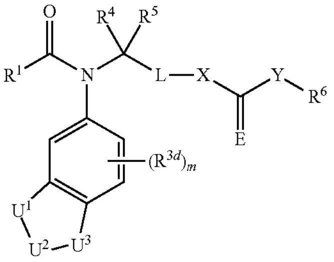

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $U^1$, $U^2$, and $U^3$ are each independently —$CR^{3a}R^{3b}$—, —$NR^{3c}$—, —O—, or —S—; and $R^1$, $R^4$, $R^5$, $R^6$, $R^{3a}$, $R^{3b}$, $R^{3c}$, $R^{3d}$, E, L, X, Y, and m are each as defined herein.

In yet another embodiment, provided herein is a compound of Formula (VIIa):

(VIIa)

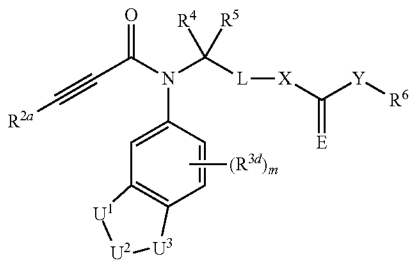

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $U^1$, $U^2$, and $U^3$ are each independently —$CR^{3a}R^{3b}$—, —$NR^{3c}$—, —O—, or —S—; and $R^4$, $R^5$, $R^6$, $R^{2a}$, $R^{3a}$, $R^{3b}$, $R^{3c}$, $R^{3d}$, E, L, X, Y, and m are each as defined herein.

In yet another embodiment, provided herein is a compound of Formula (VIIb):

(VIIb)

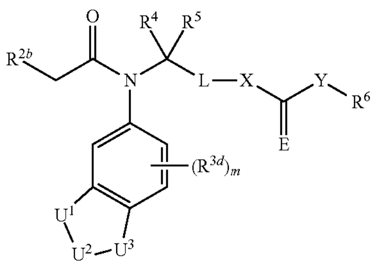

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $U^1$, $U^2$, and $U^3$ are each independently —$CR^{3a}R^{3b}$—, —$NR^{3c}$—, —O—, or —S—; and $R^4$, $R^5$, $R^6$, $R^{2b}$, $R^{3a}$, $R^{3b}$, $R^{3c}$, $R^{3d}$, E, L, X, Y, and m are each as defined herein.

In yet another embodiment, provided herein is a compound of Formula (VIII):

(VIII)

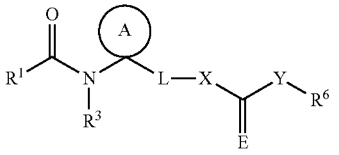

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein ring A is $C_{3-10}$ cycloalkyl or heterocyclyl, each optionally substituted with one or more, in one embodiment, one, two, three, or four, substituents Q as described herein; and $R^1$, $R^3$, $R^6$, E, L, X, and Y are each as defined herein.

In yet another embodiment, provided herein is a compound of Formula (VIIIa):

(VIIIa)

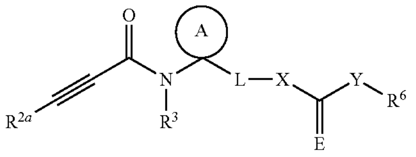

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein ring A, $R^3$, $R^6$, $R^{2a}$, E, L, X, and Y are each as defined herein.

In yet another embodiment, provided herein is a compound of Formula (VIIIb):

(VIIIb)

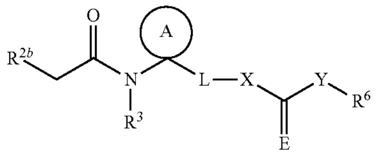

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein ring A, $R^3$, $R^6$, $R^{2b}$, E, L, X, and Y are each as defined herein.

In yet another embodiment, provided herein is a compound of Formula (IX):

(IX)

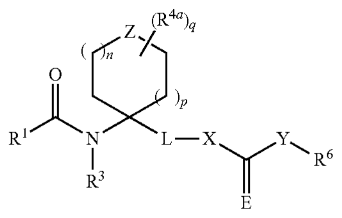

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

Z is a bond, —NH—, —$NR^{4a}$—, —O—, —S—, —S(O)—, or —$S(O)_2$—;

n and p are each independently an integer of 0, 1, 2, or 3;

q is an integer of 0, 1, 2, 3, 4, 5, or 6;

each $R^{4a}$ is independently (a) deuterium, cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$ or —S(O)$_2$N$R^{1b}R^{1c}$; or when q is an integer of 2, 3, 4, 5, or 6, two $R^{4a}$ are linked together to form a bond, —N$R^{1a}$—, —O—, —S—, —S(O)—, —S(O)$_2$—, $C_{1-6}$ alkylene, $C_{1-6}$ heteroalkylene, $C_{2-6}$ alkenylene, or $C_{2-6}$ heteroalkenylene; and $R^1$, $R^3$, $R^6$, $R^{1a}$, $R^{1b}$, $R^{1c}$, $R^{1d}$, E, L, X, and Y are each as defined herein;

wherein each alkyl, alkylene, heteroalkylene, alkenyl, alkenylene, heteroalkenylene, alkynyl, cycloalkyl, aryl, aralkyl, heteroaryl, and heterocyclyl is optionally substituted with one or more, in one embodiment, one, two, three, or four, substituents Q as described herein.

In yet another embodiment, provided herein is a compound of Formula (IXa):

(IXa)

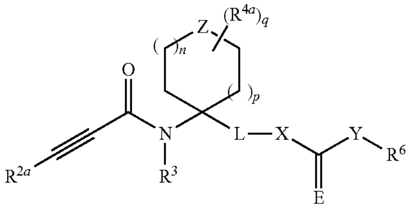

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^3$, $R^6$, $R^{2a}$, $R^{4a}$, E, L, X, Y, Z, n, p, and q are each as defined herein.

In yet another embodiment, provided herein is a compound of Formula (IXb):

(IXb)

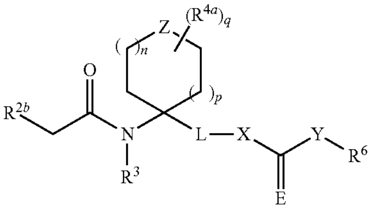

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^3$, $R^6$, $R^{2b}$, $R^{4a}$, E, L, X, Y, Z, n, p, and q are each as defined herein.

In any one of Formulae (I) to (IX), (Ia) to (IXa), and (Tb) to (IXb), in one embodiment, L and X are each a bond, and Y is —N$R^Y$—; in another embodiment, L and X are each a bond, and Y is —O—; in yet another embodiment, L is $C_{1-6}$ alkylene, X is —O— or —N$R^X$—, and Y is —O— or —N$R^Y$—; in yet another embodiment, L is $C_{1-6}$ alkylene, X and Y are each —O—; in yet another embodiment, L is $C_{1-6}$ alkylene, X is —O—, and Y is —N$R^Y$—; in yet another embodiment, L is $C_{1-6}$ alkylene, X is —N$R^X$—, and Y is —O—; in still another embodiment, L is $C_{1-6}$ alkylene, X is —N$R^X$—, and Y is —N$R^Y$—; wherein each $R^X$ and $R^Y$ is as defined herein and each alkylene is optionally substituted with one or more, in one embodiment, one, two, three, or four, substituents Q as described herein.

In any one of Formulae (I) to (IX), (Ia) to (IXa), and (Tb) to (IXb), in one embodiment, E is O, L and X are each a bond, and Y is —N$R^Y$—; in another embodiment, E is O, L and X are each a bond, and Y is —O—; in yet another embodiment, E is O, L is $C_{1-6}$ alkylene, X is —O— or —N$R^X$—, and Y is —O— or —N$R^Y$—; in yet another embodiment, E is O, L is $C_{1-6}$ alkylene, X and Y are each —O—; in yet another embodiment, E is O, L is $C_{1-6}$ alkylene, X is —O—, and Y is —N$R^Y$—; in yet another embodiment, E is O, L is $C_{1-6}$ alkylene, X is —N$R^X$—, and Y is —O—; in still another embodiment, E is O, L is $C_{1-6}$ alkylene, X is —N$R^X$—, and Y is —N$R^Y$—; wherein each $R^X$ and $R^Y$ is as defined herein and each alkylene is optionally substituted with one or more, in one embodiment, one, two, three, or four, substituents Q as described herein.

In yet another embodiment, provided herein is a compound of Formula (X):

(X)

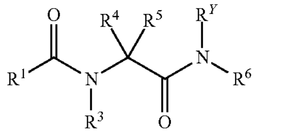

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^4$, $R^5$, $R^6$, and $R^Y$ are each as defined herein.

In yet another embodiment, provided herein is a compound of Formula (Xa):

(Xa)

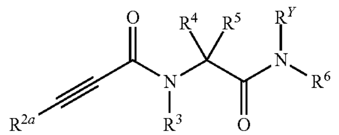

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^3$, $R^4$, $R^5$, $R^6$, $R^{2a}$, and $R^Y$ are each as defined herein.

In yet another embodiment, provided herein is a compound of Formula (Xb):

(Xb)

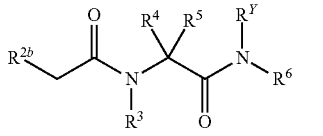

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^3$, $R^4$, $R^5$, $R^6$, $R^{2b}$, and $R^Y$ are each as defined herein.

In yet another embodiment, provided herein is a compound of Formula (XI):

(XI)

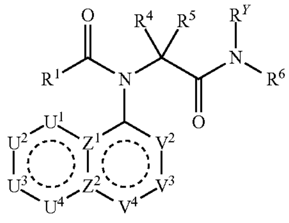

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^4$, $R^5$, $R^6$, $R^Y$, $U^1$, $U^2$, $U^3$, $U^4$, $V^2$, $V^3$, $V^4$, $Z^1$, and $Z^2$ are each as defined herein.

In yet another embodiment, provided herein is a compound of Formula (XIa):

(XIa)

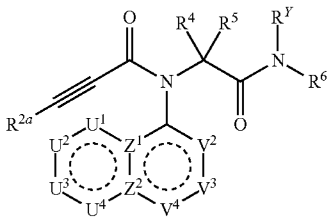

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^4$, $R^5$, $R^6$, $R^{2a}$, $R^Y$, $U^1$, $U^2$, $U^3$, $U^4$, $V^2$, $V^3$, $V^4$, $Z^1$, and $Z^2$ are each as defined herein.

In yet another embodiment, provided herein is a compound of Formula (XIb):

(XIb)

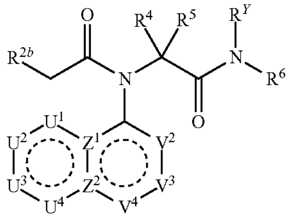

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^4$, $R^5$, $R^6$, $R^{2b}$, $R^Y$, $U^1$, $U^2$, $U^3$, $U^4$, $V^2$, $V^3$, $V^4$, $Z^1$, and $Z^2$ are each as defined herein.

In yet another embodiment, provided herein is a compound of Formula (XII):

(XII)

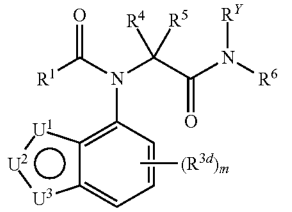

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $U^1$, $U^2$, and $U^3$ are each independently —$CR^{3a}$═, —N═, —$NR^{3c}$—, —O—, or —S—; and $R^1$, $R^4$, $R^5$, $R^6$, $R^{3a}$, $R^{3c}$, $R^{3d}$, $R^Y$ and m are each as defined herein.

In yet another embodiment, provided herein is a compound of Formula (XIIa):

(XIIa)

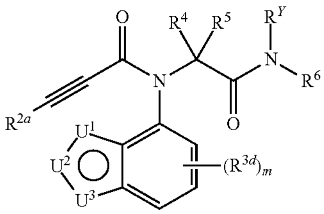

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $U^1$, $U^2$, and $U^3$ are each independently —$CR^{3a}$═, —N═, —$NR^{3c}$—, —O—, or —S—; and $R^4$, $R^5$, $R^6$, $R^{2a}$, $R^{3a}$, $R^{3c}$, $R^{3d}$, $R^Y$, and m are each as defined herein.

In yet another embodiment, provided herein is a compound of Formula (XIIb):

(XIIb)

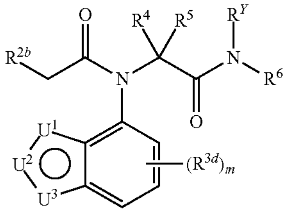

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $U^1$, $U^2$, and $U^3$ are each independently —$CR^{3a}$═, —N═, —$NR^{3c}$—, —O—, or —S—; and $R^4$, $R^5$, $R^6$, $R^{2b}$, $R^{3a}$, $R^{3c}$, $R^{3d}$, $R^Y$, and m are each as defined herein.

In yet another embodiment, provided herein is a compound of Formula (XIII):

(XIII)

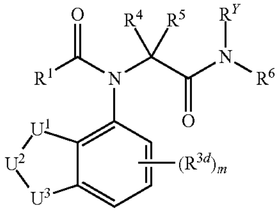

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $U^1$, $U^2$, and $U^3$ are each independently —$CR^{3a}R^{3b}$—, —$NR^{3c}$—, —O—, or —S—; and $R^1$, $R^4$, $R^5$, $R^6$, $R^{3a}$, $R^{3b}$, $R^{3c}$, $R^{3d}$, $R^Y$, and m are each as defined herein.

In yet another embodiment, provided herein is a compound of Formula (XIIIa):

(XIIIa)

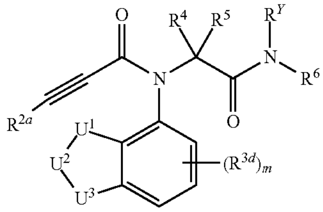

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $U^1$, $U^2$, and $U^3$ are each independently —$CR^{3a}R^{3b}$—, —$NR^{3c}$—, —O—, or —S—; and $R^4$, $R^5$, $R^6$, $R^{2a}$, $R^{3a}$, $R^{3b}$, $R^{3c}$, $R^{3d}$, $R^Y$, and m are each as defined herein.

In yet another embodiment, provided herein is a compound of Formula (XIIIb):

(XIIb)

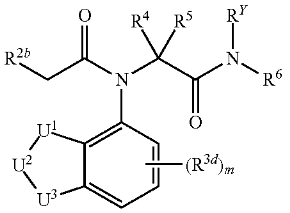

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $U^1$, $U^2$, and $U^3$ are each independently —$CR^{3a}R^{3b}$—, —$NR^{3c}$—, —O—, or —S—; and $R^4$, $R^5$, $R^6$, $R^{2b}$, $R^{3a}$, $R^{3b}$, $R^{3c}$, $R^{3d}$, $R^Y$, and m are each as defined herein.

In yet another embodiment, provided herein is a compound of Formula (XIV):

(XIV)

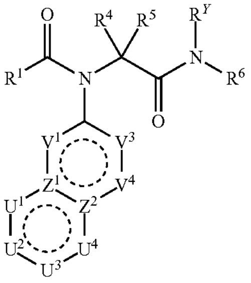

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^4$, $R^5$, $R^6$, $R^Y$, $U^1$, $U^2$, $U^3$, $U^4$, $V^1$, $V^3$, $V^4$, $Z^1$, and $Z^2$ are each as defined herein.

In yet another embodiment, provided herein is a compound of Formula (XIVa):

(XIVa)

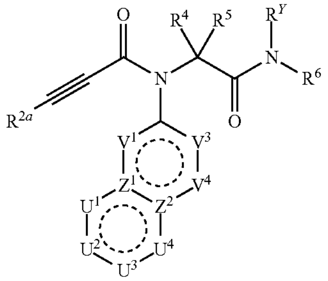

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^4$, $R^5$, $R^6$, $R^{2a}$, $R^Y$, $U^1$, $U^2$, $U^3$, $U^4$, $V^1$, $V^3$, $V^4$, $Z^1$, and $Z^2$ are each as defined herein.

In yet another embodiment, provided herein is a compound of Formula (XIVb):

(XIVb)

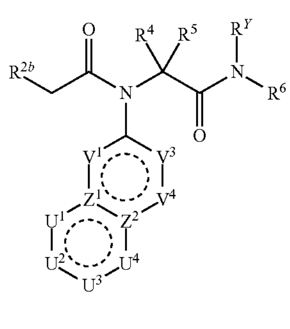

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^4$, $R^5$, $R^6$, $R^{2b}$, $R^Y$, $U^1$, $U^2$, $U^3$, $U^4$, $V^1$, $V^3$, $V^4$, $Z^1$, and $Z^2$ are each as defined herein.

In yet another embodiment, provided herein is a compound of Formula (XV):

(XV)

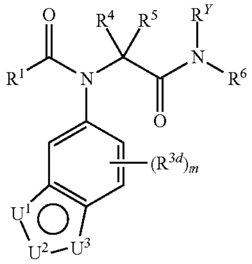

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $U^1$, $U^2$, and $U^3$ are each independently —$CR^{3a}$═, —N═, —$NR^{3c}$—, —O—, or —S—; and $R^1$, $R^4$, $R^5$, $R^6$, $R^{3a}$, $R^{3c}$, $R^{3d}$, $R^Y$ and m are each as defined herein.

In yet another embodiment, provided herein is a compound of Formula (XVa):

(XVa)

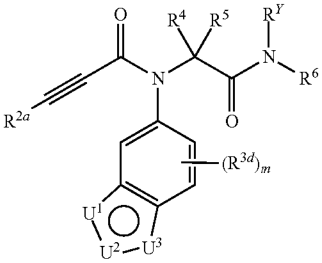

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $U^1$, $U^2$, and $U^3$ are each independently —$CR^{3a}$═, —N═, —$NR^{3c}$—, —O—, or —S—; and $R^4$, $R^5$, $R^6$, $R^{2a}$, $R^{3a}$, $R^{3c}$, $R^{3d}$, $R^Y$, and m are each as defined herein.

In yet another embodiment, provided herein is a compound of Formula (XVb):

(XVb)

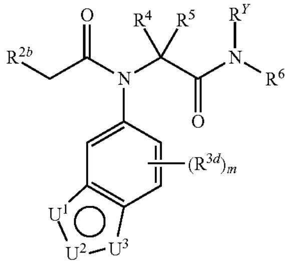

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $U^1$, $U^2$, and $U^3$ are each independently —$CR^{3a}$═, —N═, —$NR^{3c}$—, —O—, or —S—; and $R^4$, $R^5$, $R^6$, $R^{2b}$, $R^{3a}$, $R^{3c}$, $R^{3d}$, $R^Y$, and m are each as defined herein.

In yet another embodiment, provided herein is a compound of Formula (XVI):

(XVI)

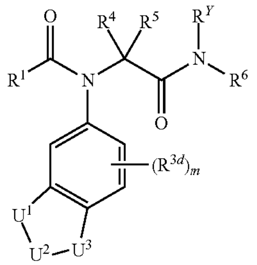

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $U^1$, $U^2$, and $U^3$ are each independently —$CR^{3a}R^{3b}$—, —$NR^{3c}$—, —O—, or —S—; and $R^1$, $R^4$, $R^5$, $R^6$, $R^{3a}$, $R^{3b}$, $R^{3c}$, $R^{3d}$, $R^Y$, and m are each as defined herein.

In yet another embodiment, provided herein is a compound of Formula (XVIa):

(XVIa)

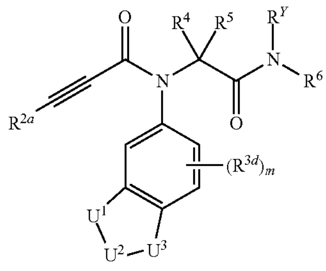

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $U^1$, $U^2$, and $U^3$ are each independently —$CR^{3a}R^{3b}$—, —$NR^{3c}$—, —O—, or —S—; and $R^4$, $R^5$, $R^6$, $R^{2a}$, $R^{3a}$, $R^{3b}$, $R^{3c}$, $R^{3d}$, $R^Y$, and m are each as defined herein.

In yet another embodiment, provided herein is a compound of Formula (XVIb):

(XVIb)

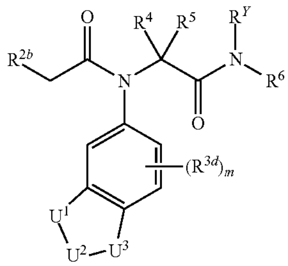

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $U^1$, $U^2$, and $U^3$ are each independently —$CR^{3a}R^{3b}$—, —$NR^{3c}$—, —O—, or —S—; and $R^4$, $R^5$, $R^6$, $R^{2b}$, $R^{3a}$, $R^{3b}$, $R^{3c}$, $R^{3d}$, $R^Y$, and m are each as defined herein.

In yet another embodiment, provided herein is a compound of Formula (XVII):

(XVII)

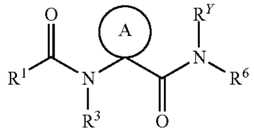

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein ring A, $R^1$, $R^3$, $R^6$, and $R^Y$ are each as defined herein.

In yet another embodiment, provided herein is a compound of Formula (XVIIa):

(XVIIa)

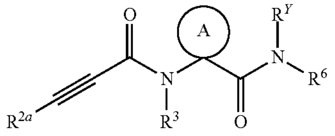

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein ring A, $R^3$, $R^6$, $R^{2a}$, and $R^Y$ are each as defined herein.

In yet another embodiment, provided herein is a compound of Formula (XVIIb):

(XVIIb)

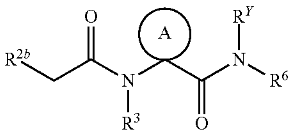

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein ring A, $R^3$, $R^6$, $R^{2b}$, and $R^Y$ are each as defined herein.

In yet another embodiment, provided herein is a compound of Formula (XVIII):

(XVIII)

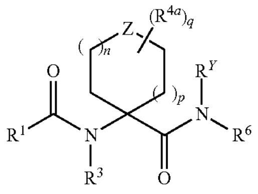

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^6$, $R^{4a}$, $R^Y$, Z, n, p, and q are each as defined herein.

In yet another embodiment, provided herein is a compound of Formula (XVIIIa):

(XVIIIa)

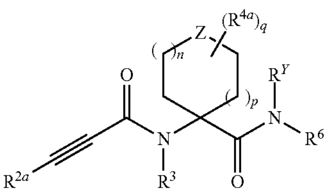

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^3$, $R^6$, $R^{2a}$, $R^{4a}$, $R^Y$, Z, n, p, and q are each as defined herein.

In still another embodiment, provided herein is a compound of Formula (XVIIIb):

(XVIIIb)

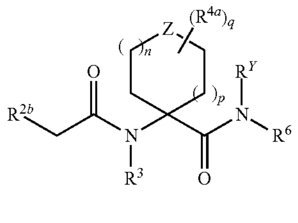

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^3$, $R^6$, $R^{2b}$, $R^{4a}$, $R^Y$, Z, n, p, and q are each as defined herein.

In any one of Formulae (I) to (XVIII), in one embodiment, $R^1$ is

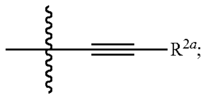

and in one embodiment, $R^{2a}$ is hydrogen or methyl optionally substituted with one substituent Q selected from heterocyclyl, —$OR^a$, and —$NR^bR^c$, wherein $R^a$, $R^b$, and $R^c$ are each as defined herein; in another embodiment, $R^{2a}$ is hydrogen, methyl, hydroxylmethyl, methoxymethyl, aminomethyl, dimethylaminomethyl, or pyrrolidinylmethyl; in yet another embodiment, $R^{2a}$ is hydrogen, methyl, hydroxylmethyl, methoxymethyl, aminomethyl, dimethylaminomethyl, or pyrrolidin-1-ylmethyl; in still another embodiment, $R^{2a}$ is hydrogen.

In any one of Formulae (I) to (XVIII), in one embodiment, $R^1$ is —$CH_2$—$R^{2b}$; and in one embodiment, $R^{2b}$ is chloro, fluoro, bromo, iodo, methylsulfonyloxy, or methoxysulfonyloxy; in another embodiment, $R^{2b}$ is chloro or methylsulfonyloxy; in yet another embodiment, $R^{2b}$ is chloro.

In any one of Formulae (Ia) to (XVIIIa), in one embodiment, $R^{2a}$ is hydrogen or methyl optionally substituted with one substituent Q selected from heterocyclyl, —$OR^a$, and —$NR^bR^c$, wherein $R^a$, $R^b$, and $R^c$ are each as defined herein; in another embodiment, $R^{2a}$ is hydrogen, methyl, hydroxylmethyl, methoxymethyl, aminomethyl, dimethylaminomethyl, or pyrrolidinylmethyl; in yet another embodiment, $R^{2a}$ is hydrogen, methyl, hydroxylmethyl, methoxymethyl, aminomethyl, dimethylaminomethyl, or pyrrolidin-1-ylmethyl; in still another embodiment, $R^{2a}$ is hydrogen.

In any one of Formulae (Ib) to (XVIIIb), in one embodiment, $R^{2b}$ is chloro, fluoro, bromo, iodo, methylsulfonyloxy, or methoxysulfonyloxy; in another embodiment, $R^{2b}$ is chloro or methylsulfonyloxy; in yet another embodiment, $R^{2b}$ is chloro.

In one embodiment, in any one of Formulae (I), (VIII) to (X), (XVII), (XVIII), (Ia), (VIIIa) to (Xa), (XVIIa), (Ib), (VIIIb) to (Xb), (XVIIb), and (XVIIIb), $R^3$ is $C_{1-6}$ alkyl, $C_{6-14}$ aryl, $C_{7-15}$ aralkyl, heteroaryl, or heterocyclyl;

$R^6$ is $C_{1-6}$ alkyl, $C_{3-10}$ cycloalkyl, or $C_{7-15}$ aralkyl; and $R^Y$ is hydrogen;

wherein each alkyl, cycloalkyl, aralkyl, heteroaryl, heterocyclyl is each optionally substituted with one or more substituents Q.

In another embodiment, in any one of Formulae (I), (VIII) to (X), (XVII), (XVIII), (Ia), (VIIIa) to (Xa), (XVIIa), (Ib), (VIIIb) to (Xb), (XVIIb), and (XVIIIb), $R^3$ is methyl, propyl, phenyl, 5,6-fused aryl, benzyl, 5,6-fused heteroaryl, 5,6-fused heterocyclyl, each optionally substituted with one or more substituents Q;

$R^6$ is $C_{1-6}$ alkyl, $C_{3-7}$ cycloalkyl, benzyl, or phenylethyl, each optionally substituted with one or more substituents Q; and $R^Y$ is hydrogen.

In yet another embodiment, in any one of Formulae (I), (VIII) to (X), (XVII), (XVIII), (Ia), (VIIIa) to (Xa), (XVIIa), (Ib), (VIIIb) to (Xb), (XVIIb), and (XVIIIb), $R^3$ is propyl, thienylmethyl, thiazolylmethyl, aminophenyl, cyanophenyl, chloro-phenyl, fluorophenyl, hydroxyphenyl, methoxyphenyl, methoxycarbonylphenyl, dichlorophenyl, chloro-fluorophenyl, chloro-iodophenyl, chloro-methoxyphenyl, methylsulfonylphenyl, oxo-2,3-dihydro-1H-indenyl, benzyl, methoxycarbonylbenzyl, benzo[c][1,2,5]oxadiazolyl, benzo[c][1,2,5]thiadiazolyl, benzo[d]thiazolyl, 1H-indazolyl, [1,2,4]triazolo[4,3-a]pyridinyl, or benzo[d][1,3]dioxolyl optionally substituted with one or two fluoro;

$R^6$ is butyl, benzyl, cyanobenzyl, fluorobenzyl, or phenylethyl; and $R^Y$ is hydrogen.

In yet another embodiment, in any one of Formulae (I), (VIII) to (X), (XVII), (XVIII), (Ia), (VIIIa) to (Xa), (XVIIa), (Ib), (VIIIb) to (Xb), (XVIIb), and (XVIIIb), $R^3$ is 2-propyl, thien-2-ylmethyl, thiazol-2-ylmethyl, thiazol-4-ylmethyl, thiazol-5-ylmethyl, 3-aminophenyl, 4-aminophenyl, 3-cyanophenyl, 4-cyanophenyl, 3-chlorophenyl, 4-chlorophenyl, 3-fluorophenyl, 3-hydroxyphenyl, 4-hydroxyphenyl, 3-methoxyphenyl, 4-methoxyphenyl, 3-hydroxymethylphenyl, 4-hydroxymethylphenyl, 3-methoxycarbonylphenyl, 4-methoxycarbonylphenyl, 2,3-dichlorophenyl, 3,4-dichlorophenyl, 3-chloro-2-fluorophenyl, 5-chloro-2-fluorophenyl, 5-chloro-2-iodophenyl, 3-chloro-4-methoxyphenyl, 3-methylsulfonylphenyl, 4-methylsulfonylphenyl, 3-acetamidophenyl, 4-acetamidophenyl, 3-methylsulfonamidophenyl, 4-methylsulfonamidophenyl, 3-carbamoylphenyl, 4-carbamoylphenyl, 3-sulfamoylphenyl, 4-sulfamoylphenyl, 1-oxo-2,3-dihydro-1H-inden-4-yl, benzyl, 4-methoxycarbonylbenzyl, benzo[c][1,2,5]oxadiazol-4-yl, benzo[c][1,2,5]thiadiazol-4-yl, benzo[c][1,2,5]thiadiazol-5-yl, benzo[d]thiazol-5-yl, benzo[d]thiazol-6-yl, 1-methyl-1H-indazol-5-yl, 1-methyl-1H-indazol-6-yl, [1,2,4]triazolo[4,3-a]pyridin-6-yl, benzo[d][1,3]dioxol-4-yl, benzo[d][1,3]dioxol-5-yl, or 2,2-difluorobenzo[d][1,3]dioxol-5-yl;

$R^6$ is tert-butyl, benzyl, 4-cyanobenzyl, 2-fluorobenzyl, 4-fluorobenzyl, or 2-phenylethyl; and $R^Y$ is hydrogen.

In yet another embodiment, in any one of Formulae (I), (VIII) to (X), (XVII), (XVIII), (Ia), (VIIIa) to (Xa), (XVIIa), (Ib), (VIIIb) to (Xb), (XVIIb), and (XVIIIb), $R^3$ is propyl, phenylethyl, thienylmethyl, thiazolylmethyl, cyclobutyl, phenylcyclopropyl, aminophenyl, cyanophenyl, chlorophenyl, fluorophenyl, hydroxyphenyl, methoxyphenyl, methoxycarbonylphenyl, dichlorophenyl, chloro-fluorophenyl, chloro-iodophenyl, chloro-methoxyphenyl, dimethoxyphenyl, acetamidophenyl, carbamoylphenyl, methylsulfonylphenyl, methylsulfonamidophenyl, (pyrazolyl)phenyl, (methylpyrazolyl) phenyl, morpholinophenyl, dimethylaminophenyl, oxo-2,3-dihydro-1H-indenyl, benzyl, hydroxylbenzyl, methoxycarbonylbenzyl, (pyrazolyl)methyl, chloropyridinyl, indolyl, methylindolyl, indazolyl, methylindazolyl, methylbenzo[d]imidazolyl, benzo[d]thiazolyl, benzo[c][1,2,5]oxadiazolyl, benzo[c][1,2,5]thiadiazolyl, benzo[d]thiazolyl, 1H-indazolyl, [1,2,4]triazolo [4,3-a]pyridinyl, oxo-dihydroisobenzofuranyl, iodobenzo[d][1,3]dioxolyl or benzo[d][1,3]dioxolyl optionally substituted with one or two fluoro;

$R^6$ is butyl, cyclopropylmethyl, oxetanylmethyl, (tetrahydropyranyl)methyl, hydroxycarbonylmethyl, ethoxycarbonylmethyl, hydroxyethylaminocarbonylmethyl, phenylaminocarbonylmethyl, benzylaminocarbonylmethyl, cyanobenzylaminocarbonylmethyl, chlorobenzylaminocarbonylmethyl, hydroxybenzylaminocarbonylmethyl, hydroxypiperidyl-carbonylmethyl, (hydroxymethyl)piperidylcarbonylmethyl, methoxycarbonylpiperidylcarbonyl-methyl, methylphenylsulfonylmethyl, benzyl, cyanobenzyl, chlorobenzyl, fluorobenzyl, or phenylethyl; and $R^Y$ is hydrogen.

In yet another embodiment, in any one of Formulae (I), (VIII) to (X), (XVII), (XVIII), (Ia), (VIIIa) to (Xa), (XVIIa), (Ib), (VIIIb) to (Xb), (XVIIb), and (XVIIIb), $R^3$ is 2-propyl, 2-phenylethyl, thien-2-ylmethyl, thiazol-2-ylmethyl, thiazol-4-ylmethyl, thiazol-5-ylmethyl, cyclobutyl, 1-phenylcyclopropyl, 3-aminophenyl, 4-aminophenyl, 3-cyanophenyl, 4-cyanophenyl, 3-chlorophenyl, 4-chlorophenyl, 3-fluorophenyl, 3-hydroxyphenyl, 4-hydroxyphenyl, 3-methoxyphenyl, 4-methoxyphenyl, 3-hydroxymethylphenyl, 4-hydroxymethylphenyl, 3-methoxycarbonylphenyl, 4-methoxycarbonylphenyl, 2,3-dichlorophenyl, 2,5-dichlorophenyl, 3,4-dichlorophenyl, 3-chloro-2-fluorophenyl, 5-chloro-2-fluoro-phenyl, 5-chloro-2-iodophenyl, 3-chloro-4-methoxyphenyl, 2,4-dimethoxyphenyl, 3-methylsulfonylphenyl, 4-methylsulfonylphenyl, 3-acetamidophenyl, 4-acetamidophenyl, 3-methylsulfonamidophenyl, 4-methylsulfonamidophenyl, 3-carbamoylphenyl, 4-carbamoyl-phenyl, 3-sulfamoylphenyl, 4-sulfamoylphenyl, 3-(pyrazol-3-yl)phenyl, 3-(1-methylpyrazol-3-yl)phenyl, 2-morpholinophenyl, 4-dimethylaminophenyl, 1-oxo-2,3-dihydro-1H-inden-4-yl, benzyl, 4-methoxycarbonylbenzyl, 3-hydroxylbenzyl, (1H-pyrazol-3-yl)methyl, 5-chloropyridin-3-yl, indol-5-yl, 1-mtehylindol-5-yl, indazol-5-yl, 1-methylindazol-7-yl, 1-methyl-benzo[d]imidazol-5-yl, 1-methylbenzo[d]imidazol-6-yl, benzo[d]thiazol-5-yl, benzo[c][1,2,5]oxadiazol-4-yl, benzo[c][1,2,5] thiadiazol-4-yl, benzo[c][1,2,5]thiadiazol-5-yl, benzo [d]thiazol-5-yl, benzo[d]thiazol-6-yl, 1-methyl-1H-indazol-5-yl, 1-methyl-1H-indazol-6-yl, [1,2,4]triazolo [4,3-a]pyridin-6-yl, [1,2,4]triazolo[4,3-a]pyridin-7-yl, [1,2,4]triazolo[4,3-a]pyridin-8-yl, 3-oxo-1,3-dihydroisobenzofuran-5-yl, benzo[d][1,3]dioxol-4-yl, benzo[d][1,3]dioxol-5-yl, 6-iodobenzo[d][1,3]dioxol-5-yl, or 2,2-difluorobenzo[d][1,3]dioxol-5-yl;

$R^6$ is tert-butyl, cyclopropylmethyl, oxetan-3-ylmethyl, (tetrahydropyran-4-yl)methyl, hydroxycarbonylmethyl, ethoxycarbonylmethyl, 2-hydroxyethylaminocarbonyl-methyl, phenylaminocarbonylmethyl, benzylaminocarbonylmethyl, 2-cyanobenzylaminocarbonylmethyl, 2-chlorobenzylaminocarbonylmethyl, 2-hydroxybenzylaminocarbonylmethyl, 3-hydroxypiperid-1-ylcarbonylmethyl, 3-(hydroxymethyl)piperid-1-ylcarbonylmethyl, 3-methoxycarbonylpiperid-1-ylcarbonylmethyl, 4-methylphenylsulfonylmethyl, benzyl, 2-cyanobenzyl, 4-cyanobenzyl, 3-chlorobenzyl, 2-fluorobenzyl, 4-fluorobenzyl, or 2-phenylethyl; and $R^Y$ is hydrogen.

In yet another embodiment, in any one of Formulae (I), (VIII) to (X), (XVII), (XVIII), (Ia), (VIIIa) to (Xa), (XVIIa), (Ib), (VIIIb) to (Xb), (XVIIb), and (XVIIIb), $R^3$ is phenyl, 5,6-fused aryl, benzyl, 5,6-fused heteroaryl, 5,6-fused heterocyclyl, each optionally substituted with one or more substituents Q;

$R^6$ is $C_{1-6}$ alkyl, $C_{3-7}$ cycloalkyl, benzyl, or phenylethyl, each optionally substituted with one or more substituents Q; and $R^Y$ is hydrogen.

In yet another embodiment, in any one of Formulae (I), (VIII) to (X), (XVII), (XVIII), (Ia), (VIIIa) to (Xa), (XVIIa), (Ib), (VIIIb) to (Xb), (XVIIb), and (XVIIIb), $R^3$ is cyanophenyl, chlorophenyl, fluorophenyl, hydroxyphenyl, methoxyphenyl, methoxycarbonylphenyl, dichlorophenyl, chloro-fluorophenyl, chloro-iodophenyl, chloro-methoxyphenyl, methylsulfonylphenyl, oxo-2,3-dihydro-1H-indenyl, methoxycarbonylbenzyl, benzo[c][1,2,5]oxadiazolyl, benzo[c][1,2,5]thiadiazolyl, benzo[d]thiazolyl, 1H-indazolyl, [1,2,4]triazolo [4,3-a]pyridinyl, or benzo[d][1,3]dioxolyl optionally substituted with one or two fluoro;

$R^6$ is butyl, benzyl, cyanobenzyl, fluorobenzyl, or phenylethyl; and $R^Y$ is hydrogen.

In yet another embodiment, in any one of Formulae (I), (VIII) to (X), (XVII), (XVIII), (Ia), (VIIIa) to (Xa), (XVIIa), (Ib), (VIIIb) to (Xb), (XVIIb), and (XVIIIb), $R^3$ is 3-cyanophenyl, 4-cyanophenyl, 3-chlorophenyl, 4-chlorophenyl, 3-fluorophenyl, 3-hydroxyphenyl, 3-methoxyphenyl, 4-methoxyphenyl, 3-methoxycarbonylphenyl, 4-methoxycarbonylphenyl, 2,3-dichlorophenyl, 3,4-dichlorophenyl, 3-chloro-2-fluorophenyl, 5-chloro-2-fluorophenyl, 5-chloro-2-iodophenyl, 3-chloro-4-methoxyphenyl, 3-methylsulfonylphenyl, 1-oxo-2,3-dihydro-1H-inden-4-yl, 4-methoxycarbonylbenzyl, benzo[c][1,2,5]oxadiazol-4-yl, benzo[c][1,2,5]thiadiazol-4-yl, benzo[c][1,2,5]thiadiazol-5-yl, benzo[d]thiazol-5-yl, benzo[d]thiazol-6-yl, 1-methyl-1H-indazol-5-yl, 1-methyl-1H-indazol-6-yl, [1,2,4]triazolo[4,3-a]pyridin-6-yl, benzo[d][1,3]dioxol-4-yl, benzo[d][1,3]dioxol-5-yl, or 2,2-difluorobenzo[d][1,3] dioxol-5-yl;

$R^6$ is tert-butyl, benzyl, 4-cyanobenzyl, 2-fluorobenzyl, 4-fluorobenzyl, or 2-phenylethyl; and $R^Y$ is hydrogen.

In yet another embodiment, in any one of Formulae (I), (VIII) to (X), (XVII), (XVIII), (Ia), (VIIIa) to (Xa), (XVIIa), (Ib), (VIIIb) to (Xb), (XVIIb), and (XVIIIb), $R^3$ is phenylethyl, cyclobutyl, phenylcyclopropyl, cyanophenyl, chlorophenyl, fluorophenyl, hydroxyphenyl, methoxyphenyl, methoxycarbonylphenyl, dichlorophenyl, chloro-fluorophenyl, chloro-iodophenyl, chloro-methoxyphenyl, dimethoxyphenyl, methylsulfonylphenyl, (pyrazolyl)phenyl, (methylpyrazolyl)phenyl, morpholinophenyl, dimethylaminophenyl, oxo-2,3-dihydro-1H-indenyl, methoxycarbonylbenzyl, hydroxylbenzyl, (pyrazolyl)methyl, chloropyridinyl, indolyl, methylindolyl, indazolyl, methylindazolyl, methylbenzo[d]imidazolyl, benzo[d]thiazolyl, benzo[c][1,2,5]oxadiazolyl, benzo[c][1,2,5]thiadiazolyl, benzo[d]thiazolyl, 1H-indazolyl, [1,2,4]triazolo[4,3-a]pyridinyl, oxo-dihydroisobenzofuranyl, iodobenzo[d][1,3]dioxolyl, or benzo[d][1,3]dioxolyl optionally substituted with one or two fluoro;

$R^6$ is butyl, cyclopropylmethyl, oxetanylmethyl, (tetrahydropyranyl)methyl, hydroxycarbonylmethyl, ethoxycarbonylmethyl, hydroxyethylaminocarbonylmethyl, phenylaminocarbonylmethyl, benzylaminocarbonylmethyl, cyanobenzylaminocarbonylmethyl, chlorobenzylaminocarbonylmethyl, hydroxybenzylaminocarbonylmethyl, hydroxypiperidyl-carbonylmethyl, (hydroxymethyl)piperidylcarbonylmethyl, methoxycarbonylpiperidylcarbonyl-methyl, methylphenylsulfonylmethyl, benzyl, cyanobenzyl, chlorobenzyl, fluorobenzyl, or phenylethyl; and $R^Y$ is hydrogen.

In still another embodiment, in any one of Formulae (I), (VIII) to (X), (XVII), (XVIII), (Ia), (VIIIa) to (Xa), (XVIIa), (Ib), (VIIIb) to (Xb), (XVIIb), and (XVIIIb), $R^3$ is 2-phenylethyl, cyclobutyl, 1-phenylcyclopropyl, 3-cyanophenyl, 4-cyanophenyl, 3-chlorophenyl, 4-chlorophenyl, 3-fluorophenyl, 3-hydroxyphenyl, 3-methoxyphenyl, 4-methoxyphenyl, 3-methoxycarbonylphenyl, 4-methoxycarbonylphenyl, 2,3-dichlorophenyl, 2,5-dichlorophenyl, 3,4-dichlorophenyl, 3-chloro-2-fluorophenyl, 5-chloro-2-fluorophenyl, 5-chloro-2-iodophenyl, 3-chloro-4-methoxyphenyl, 2,4-dimethoxyphenyl, 3-methylsulfonylphenyl, 3-(pyrazol-3-yl)phenyl, 3-(1-methylpyrazol-3-yl)phenyl, 2-morpholinophenyl, 4-dimethylaminophenyl, 1-oxo-2,3-dihydro-1H-inden-4-yl, 4-methoxycarbonylbenzyl, 3-hydroxylbenzyl, (1H-pyrazol-3-yl)methyl, 5-chloropyridin-3-yl, indol-5-yl, 1-mtehylindol-5-yl, indazol-5-yl, 1-methylindazol-7-yl, 1-methylbenzo[d]imidazol-5-yl, 1-methylbenzo[d]imidazol-6-yl, benzo[d]thiazol-5-yl, benzo[c][1,2,5]oxadiazol-4-yl, benzo[c][1,2,5]thiadiazol-4-yl, benzo[c][1,2,5]thiadiazol-5-yl, benzo[d]thiazol-5-yl, benzo[d]thiazol-6-yl, 1-methyl-1H-indazol-5-yl, 1-methyl-1H-indazol-6-yl, [1,2,4]triazolo[4,3-a]pyridin-6-yl, [1,2,4]triazolo[4,3-a]pyridin-7-yl, [1,2,4]triazolo[4,3-a]pyridin-8-yl, 3-oxo-1,3-dihydroisobenzofuran-5-yl, benzo[d][1,3]dioxol-4-yl, benzo[d][1,3]dioxol-5-yl, 6-iodobenzo[d][1,3]dioxol-5-yl, or 2,2-difluorobenzo[d][1,3]dioxol-5-yl;

$R^6$ is tert-butyl, cyclopropylmethyl, oxetan-3-ylmethyl, (tetrahydropyran-4-yl)methyl, hydroxycarbonylmethyl, ethoxycarbonylmethyl, 2-hydroxyethylaminocarbonyl-methyl, phenylaminocarbonylmethyl, benzylaminocarbonylmethyl, 2-cyanobenzylaminocarbonylmethyl, 2-chlorobenzylaminocarbonylmethyl, 2-hydroxybenzylaminocarbonylmethyl, 3-hydroxypiperid-1-ylcarbonylmethyl, 3-(hydroxymethyl)piperid-1-ylcarbonylmethyl, 3-methoxycarbonylpiperid-1-ylcarbonylmethyl, 4-methylphenylsulfonylmethyl, benzyl, 2-cyanobenzyl, 4-cyanobenzyl, 3-chlorobenzyl, 2-fluorobenzyl, 4-fluorobenzyl, or 2-phenylethyl; and $R^Y$ is hydrogen.

The groups, ring A, $R^1$, $R^3$, $R^4$, $R^5$, $R^6$, $R^{2a}$, $R^{2b}$, $R^{3a}$, $R^{3b}$, $R^{3c}$, $R^{3d}$, $R^{4a}$, $R^X$, $R^Y$, E, L, $U^1$, $U^2$, $U^3$, $U^4$, $V^1$, $V^2$, $V^3$, $V^4$, X, Y, Z, $Z^1$, $Z^2$, m, n, and p, in formulae described herein, including Formulae (I) to (XVIII), (Ia) to (XVIIIa), and (Ib) to (XVIIIb), are further defined in the embodiments described herein. All combinations of the embodiments provided herein for such groups are within the scope of this disclosure.

In certain embodiments, $R^1$ is

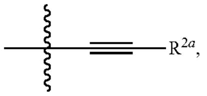

wherein $R^{2a}$ is as defined herein. In certain embodiments, $R^1$ is

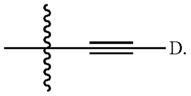

In certain embodiments, $R^1$ is

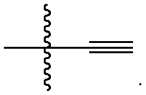 [SMILES: *C#C]

In certain embodiments, $R^1$ is

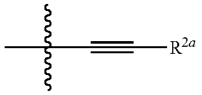

and $R^{2a}$ is $C_{1-6}$ alkyl optionally substituted with one or more substituents Q. In certain embodiments, $R^1$ is

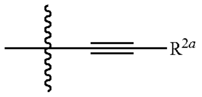

and $R^{2a}$ is methyl optionally substituted with one or more substituents Q. In certain embodiments, $R^1$ is

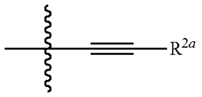

and $R^{2a}$ is methyl optionally substituted with one substituent Q selected from —$OR^a$ and —$NR^bR^c$, wherein $R^a$, $R^b$, and $R^c$ are each as defined herein. In certain embodiments, $R^1$ is

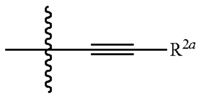

and $R^{2a}$ is methyl, hydroxylmethyl, methoxymethyl, aminomethyl, dimethylaminomethyl, or pyrrolidine-1-ylmethyl. In certain embodiments, $R^1$ is —$CH_2$—$R^{2b}$ and $R^{2b}$ is as defined herein. In certain embodiments, $R^1$ is —$CH_2$—$R^{2b}$ and $R^{2a}$ is chloro, fluoro, bromo, iodo, methylsulfonyloxy, or methoxysulfonyloxy. In certain embodiments, $R^1$ is —$CH_2$—Cl or —$CH_2$—$OSO_2CH_3$. In certain embodiments, $R^1$ is —$CH_2$—Cl.

In certain embodiments, $R^{2a}$ is hydrogen. In certain embodiments, $R^{2a}$ is deuterium. In certain embodiments, $R^{2a}$ is $C_{1-6}$ alkyl optionally substituted with one or more substituents Q. In certain embodiments, $R^{2a}$ is methyl optionally substituted with one or more substituents Q. In certain embodiments, $R^{2a}$ is methyl optionally substituted with —$OR^a$ or —$NR^bR^c$, wherein $R^a$, $R^b$, and $R^c$ are each as defined herein. In certain embodiments, $R^{2a}$ is methyl, hydroxylmethyl, methoxymethyl, aminomethyl, dimethylaminomethyl, pyrrolidin-1-ylmethyl, or 1-methyl-6-oxopiperidin-3-yl.

In certain embodiments, $R^{2b}$ is halo. In certain embodiments, $R^{2b}$ is fluoro. In certain embodiments, $R^{2b}$ is chloro. In certain embodiments, $R^{2b}$ is bromo. In certain embodiments, $R^{2b}$ is iodo. In certain embodiments, $R^{2b}$ is —$OS(O)_2R^{1a}$, wherein $R^{1a}$ is as defined herein. In certain embodiments, $R^{2b}$ is methylsulfonyloxy. In certain embodiments, $R^{2b}$ is —$OS(O)_2OR^{1a}$, wherein $R^{1a}$ is as defined herein. In certain embodiments, $R^{2b}$ is methoxysulfonyloxy.

In certain embodiments, $R^3$ is $C_{1-6}$ alkyl optionally substituted with one or more substituents Q. In certain embodiments, $R^3$ is propyl optionally substituted with one or more substituents Q. In certain embodiments, $R^3$ is 2-propyl. In certain embodiments, $R^3$ is heteroaryl-$C_{1-6}$ alkyl, i.e., $C_{1-6}$ alkyl substituted with heteroaryl, wherein the alkyl and heteroaryl are each optionally substituted with one or more substituents Q. In certain embodiments, $R^3$ is 6-membered heteroaryl-$C_{1-6}$ alkyl, wherein the alkyl and heteroaryl are each optionally substituted with one or more substituents Q. In certain embodiments, $R^3$ is 5-membered heteroaryl-$C_{1-6}$ alkyl, wherein the alkyl and heteroaryl are each optionally substituted with one or more substituents Q. In certain embodiments, $R^3$ is heteroaryl-methyl, optionally substituted with one or more substituents Q. In certain embodiments, $R^3$ is 6-membered heteroaryl-methyl, optionally substituted with one or more substituents Q. In certain embodiments, $R^3$ is 5-membered heteroaryl-methyl, optionally substituted with one or more substituents Q. In certain embodiments, $R^3$ is thienylmethyl or thiazolylmethyl, each optionally substituted with one or more substituents Q. In certain embodiments, $R^3$ is thien-2-ylmethyl, thiazol-2-ylmethyl, thiazol-4-ylmethyl, or thiazol-5-ylmethyl.

In certain embodiments, $R^3$ is $C_{2-6}$ alkenyl optionally substituted with one or more substituents Q. In certain embodiments, $R^3$ is $C_{2-6}$ alkynyl optionally substituted with one or more substituents Q. In certain embodiments, $R^3$ is $C_{3-10}$ cycloalkyl optionally substituted with one or more substituents Q. In certain embodiments, $R^3$ is $C_{6-14}$ aryl optionally substituted with one or more substituents Q. In certain embodiments, $R^3$ is phenyl optionally substituted with one or more substituents Q.

In certain embodiments, $R^3$ is $C_{6-14}$ aryl substituted with one or two substituents Q, each independently selected from cyano, halo, $C_{1-6}$ alkyl, —$C(O)R^a$, —$C(O)NR^bR^c$, —$NR^aC(O)R^d$, —$NR^aS(O)_2R^d$, —$OR^a$, —$S(O)_2R^a$, and —$S(O)NR^bR^c$, wherein the alkyl is optionally substituted with a substituent Q and each $R^a$, $R^b$, $R^c$, and $R^d$ is as defined herein. In certain embodiments, $R^3$ is phenyl substituted with one or two substituents Q, each independently selected from cyano, halo, $C_{1-6}$ alkyl, —$C(O)R^a$, —$C(O)NR^bR^c$, —$NR^aC(O)R^d$, —$NR^aS(O)_2R^d$, —$OR^a$, —$S(O)_2R^a$, and —$S(O)NR^bR^c$, wherein the alkyl is optionally substituted with a substituent Q and each $R^a$, $R^b$, $R^c$, and $R^d$ is as defined herein. In certain embodiments, $R^3$ is phenyl substituted with one or two substituents Q, each independently selected from cyano, chloro, fluoro, iodo, hydroxymethyl, methoxycarbonyl, acetamido, methylsulfonamido, hydroxy, methoxy, carbamoyl, sulfamoyl, and methylsulfonyl. In certain embodiments, $R^3$ is aminophenyl, cyanophenyl, chlorophenyl, fluorophenyl, hydroxymethylphenyl, hydroxyphenyl, methoxyphenyl, methoxycarbonylphenyl, chloro-fluorophenyl, chloro-iodophenyl, chloro-methoxyphenyl, methylsulfonylphenyl, acetamidophenyl, methylsulfonamidophenyl, carbamoylphenyl, or sulfamoylphenyl. In certain embodiments, $R^3$ is 3-aminophenyl, 4-aminophenyl, 3-cyanophenyl, 4-cyanophenyl, 3-chlorophenyl, 4-chlorophenyl, 3-fluorophenyl, 3-hydroxyphenyl, 4-hydroxyphenyl, 3-methoxyphenyl, 4-methoxyphenyl, 3-hydroxymethylphenyl, 4-hydroxymethylphenyl, 3-methoxycarbonylphenyl, 4-methoxycarbonylphenyl, 2,3-dichlorophenyl, 3,4-dichlorophenyl, 3-chloro-2-fluorophenyl, 5-chloro-2-fluorophenyl, 5-chloro-2-iodophenyl, 3-chloro-4-methoxyphenyl, 3-methylsulfonylphenyl, 4-methylsulfonylphenyl, 3-acetamidophenyl, 4-acetamidophenyl, 3-methylsulfonamidophenyl, 4-methylsulfonamidophenyl, 3-carbamoylphenyl, 4-carbamoylphenyl, 3-sulfamoylphenyl, or 4-sulfamoylphenyl.

In certain embodiments, $R^3$ is $C_{6-14}$ aryl substituted with one or two substituents Q, each independently selected from cyano, halo, $C_{1-6}$ alkyl, —$C(O)R^a$, —$NR^aC(O)R^d$, —$NR^aS(O)_2R^d$, —$OR^a$, and —$S(O)_2R^a$, wherein the alkyl is optionally substituted with a substituent Q and each $R^a$ and $R^d$ is as defined herein. In certain embodiments, $R^3$ is phenyl substituted with one or two substituents Q, each independently selected from cyano, halo, $C_{1-6}$ alkyl, —$C(O)R^a$, —$NR^aC(O)R^d$, —$NR^aS(O)_2R^d$, —$OR^a$, and —$S(O)_2R^a$, wherein the alkyl is optionally substituted with a substituent Q and each $R^a$ and $R^d$ is as defined herein. In certain embodiments, $R^3$ is phenyl substituted with one or two substituents Q, each independently selected from cyano, chloro, fluoro, iodo, hydroxymethyl, hydroxy, methoxy, methoxycarbonyl, methylsulfonyl, acetamido, and methylsulfonamido. In certain embodiments, $R^3$ is aminophenyl, cyanophenyl, chlorophenyl, fluorophenyl, hydroxyphenyl, methoxyphenyl, hydroxymethylphenyl, methoxycarbonylphenyl, dichlorophenyl, chloro-fluorophenyl, chloro-iodophenyl, chloro-methoxyphenyl, methylsulfonylphenyl, acetamidophenyl, or methylsulfonamidophenyl. In certain embodiments, $R^3$ is 3-aminophenyl, 4-aminophenyl, 3-cyanophenyl, 4-cyanophenyl, 3-chlorophenyl, 4-chlorophenyl, 3-fluorophenyl, 3-hydroxyphenyl, 4-hydroxyphenyl, 3-methoxyphenyl, 4-methoxyphenyl, 3-hydroxymethylphenyl, 4-hydroxymethylphenyl, 3-methoxycarbonylphenyl, 4-methoxycarbonylphenyl, 2,3-dichlorophenyl, 3,4-dichlorophenyl, 3-chloro-2-fluorophenyl, 5-chloro-2-fluorophenyl, 5-chloro-2-iodophenyl, 3-chloro-4-methoxyphenyl, 3-methylsulfonylphenyl, 4-methylsulfonylphenyl, 3-acetamidophenyl, 4-acetamidophenyl, 3-methylsulfonamidophenyl, or 4-methylsulfonamidophenyl.

In certain embodiments, $R^3$ is $C_{6-14}$ aryl substituted with one or two substituents Q, each independently selected from cyano, halo, $C_{1-6}$ alkyl, —C(O)$R^a$, —O$R^a$, and —$S(O)_2R^a$, wherein the alkyl is optionally substituted with a substituent Q and each $R^a$ is as defined herein. In certain embodiments, $R^3$ is phenyl substituted with one or two substituents Q, each independently selected from cyano, halo, $C_{1-6}$ alkyl, —C(O)$R^a$, —O$R^a$, and —$S(O)_2R^a$, wherein the alkyl is optionally substituted with a substituent Q and each $R^a$ is as defined herein. In certain embodiments, $R^3$ is phenyl substituted with one or two substituents Q, each independently selected from cyano, chloro, fluoro, iodo, hydroxymethyl, hydroxy, methoxy, methoxycarbonyl, and methylsulfonyl. In certain embodiments, $R^3$ is aminophenyl, cyanophenyl, chlorophenyl, fluorophenyl, hydroxyphenyl, methoxyphenyl, hydroxymethylphenyl, methoxycarbonylphenyl, dichlorophenyl, chloro-fluorophenyl, chloro-iodophenyl, chloro-methoxyphenyl, or methylsulfonylphenyl. In certain embodiments, $R^3$ is 3-aminophenyl, 3-cyanophenyl, 4-cyanophenyl, 3-chlorophenyl, 4-chlorophenyl, 3-fluorophenyl, 3-hydroxyphenyl, 3-methoxyphenyl, 4-methoxyphenyl, 4-hydroxymethylphenyl, 3-methoxycarbonylphenyl, 4-methoxycarbonylphenyl, 2,3-dichlorophenyl, 3,4-dichlorophenyl, 3-chloro-2-fluorophenyl, 5-chloro-2-fluorophenyl, 5-chloro-2-iodophenyl, 3-chloro-4-methoxyphenyl, or 4-methylsulfonylphenyl.

In certain embodiments, $R^3$ is $C_{6-14}$ aryl substituted with one or two substituents Q, each independently selected from cyano, halo, —C(O)$R^a$, —O$R^a$, and —$S(O)_2R^a$, wherein each $R^a$ is as defined herein. In certain embodiments, $R^3$ is phenyl substituted with one or two substituents Q, each independently selected from cyano, halo, —C(O)$R^a$, —O$R^a$, and —$S(O)_2R^a$, wherein each $R^a$ is as defined herein. In certain embodiments, $R^3$ is phenyl substituted with one or two substituents Q, each independently selected from cyano, chloro, fluoro, iodo, hydroxy, methoxy, methoxycarbonyl, and methylsulfonyl. In certain embodiments, $R^3$ is cyanophenyl, chlorophenyl, fluorophenyl, hydroxyphenyl, methoxyphenyl, methoxycarbonylphenyl, dichlorophenyl, chloro-fluorophenyl, chloro-iodophenyl, chloro-methoxyphenyl, or methylsulfonylphenyl. In certain embodiments, $R^3$ is 3-cyanophenyl, 4-cyanophenyl, 3-chlorophenyl, 4-chlorophenyl, 3-fluorophenyl, 3-hydroxyphenyl, 3-methoxyphenyl, 4-methoxyphenyl, 3-methoxycarbonylphenyl, 4-methoxycarbonylphenyl, 2,3-dichlorophenyl, 2,5-dichlorophenyl, 3,4-dichlorophenyl, 3-chloro-2-fluorophenyl, 5-chloro-2-fluorophenyl, 5-chloro-2-iodophenyl, 3-chloro-4-methoxyphenyl, or 3-methylsulfonylphenyl.

In certain embodiments, $R^3$ is bicyclic $C_{9-12}$ aryl optionally substituted with one or more substituents Q. In certain embodiments, $R^3$ is bicyclic $C_{9-10}$ aryl optionally substituted with one or more substituents Q. In certain embodiments, $R^3$ is 2,3-dihydro-1H-indenyl optionally substituted with one or more substituents Q. In certain embodiments, $R^3$ is 1-oxo-2,3-dihydro-1H-indenyl. In certain embodiments, $R^3$ is 1-oxo-2,3-dihydro-1H-inden-4-yl.

In certain embodiments, $R^3$ is $C_{7-15}$ aralkyl optionally substituted with one or more substituents Q. In certain embodiments, $R^3$ is benzyl optionally substituted with one or more substituents Q. In certain embodiments, $R^3$ is benzyl or methoxycarbonylbenzyl. In certain embodiments, $R^3$ is benzyl or 4-methoxycarbonylbenzyl.

In certain embodiments, $R^3$ is heteroaryl optionally substituted with one or more substituents Q. In certain embodiments, $R^3$ is bicyclic heteroaryl optionally substituted with one or more substituents Q. In certain embodiments, $R^3$ is 6,6-fused heteroaryl optionally substituted with one or more substituents Q. In certain embodiments, $R^3$ is 5,6-fused heteroaryl optionally substituted with one or more substituents Q. In certain embodiments, $R^3$ is benzo[c][1,2,5]oxadiazolyl, benzo[c][1,2,5]thiadiazolyl, benzo[d]thiazolyl, 1H-indazolyl, or [1,2,4]triazolo[4,3-a]pyridinyl, each optionally substituted with one or more substituents Q. In certain embodiments, $R^3$ is benzo[c][1,2,5]oxadiazolyl, benzo[c][1,2,5]thiadiazolyl, benzo[d]thiazolyl, 1H-indazolyl, or [1,2,4]triazolo[4,3-a]pyridinyl, each optionally substituted with methyl. In certain embodiments, $R^3$ is benzo[c][1,2,5]oxadiazol-4-yl, benzo[c][1,2,5]thiadiazol-4-yl, benzo[c][1,2,5]thiadiazol-5-yl, benzo[d]thiazol-5-yl, benzo[d]thiazol-6-yl, 1-methyl-1H-indazol-5-yl, 1-methyl-1H-indazol-6-yl, or [1,2,4]triazolo[4,3-a]pyridin-6-yl. In certain embodiments, $R^3$ is 5,5-fused heteroaryl optionally substituted with one or more substituents Q.

In certain embodiments, $R^3$ is heterocyclyl optionally substituted with one or more substituents Q. In certain embodiments, $R^3$ is bicyclic heterocyclyl optionally substituted with one or more substituents Q. In certain embodiments, $R^3$ is 6,6-fused heterocyclyl optionally substituted with one or more substituents Q. In certain embodiments, $R^3$ is 5,6-fused heterocyclyl optionally substituted with one or more substituents Q. In certain embodiments, $R^3$ is benzo[d][1,3]dioxolyl optionally substituted with one or more substituents Q. In certain embodiments, $R^3$ is benzo[d][1,3]dioxolyl optionally substituted with one or two fluoro. In certain embodiments, $R^3$ is benzo[d][1,3]dioxolyl or difluorobenzo[d][1,3]dioxolyl. In certain embodiments, $R^3$ is benzo[d][1,3]dioxol-4-yl, benzo[d][1,3]dioxol-5-yl, or 2,2-difluorobenzo[d][1,3]dioxol-5-yl. In certain embodiments, $R^3$ is 5,5-fused heterocyclyl optionally substituted with one or more substituents Q.

In certain embodiments, $R^4$ is hydrogen. In certain embodiments, $R^4$ is deuterium. In certain embodiments, $R^4$ is $C_{1-6}$ alkyl optionally substituted with one or more substituents Q. In certain embodiments, $R^4$ is $C_{2-6}$ alkenyl optionally substituted with one or more substituents Q. In certain embodiments, $R^4$ is $C_{2-6}$ alkynyl optionally substituted with one or more substituents Q. In certain embodiments, $R^4$ is $C_{3-10}$ cycloalkyl optionally substituted with one or more substituents Q. In certain embodiments, $R^4$ is $C_{6-14}$ aryl optionally substituted with one or more substituents Q. In certain embodiments, $R^4$ is $C_{7-15}$ aralkyl optionally substituted with one or more substituents Q. In certain embodiments, $R^4$ is heteroaryl optionally substituted with one or more substituents Q. In certain embodiments, $R^4$ is heterocyclyl optionally substituted with one or more substituents Q.

In certain embodiments, $R^5$ is hydrogen. In certain embodiments, $R^5$ is deuterium. In certain embodiments, $R^5$ is $C_{1-6}$ alkyl optionally substituted with one or more substituents Q. In certain embodiments, $R^5$ is $C_{3-10}$ cycloalkyl-$C_{1-6}$ alkyl, wherein the alkyl and cycloalkyl are each optionally substituted with one or more substituents Q. In certain embodiments, $R^5$ is methyl or cyclopropylmethyl. In certain embodiments, $R^5$ is $C_{2-6}$ alkenyl optionally substituted with one or more substituents Q. In certain embodiments, $R^5$ is $C_{2-6}$ alkynyl optionally substituted with one or more substituents Q.

In certain embodiments, $R^5$ is $C_{3-10}$ cycloalkyl optionally substituted with one or more substituents Q. In certain embodiments, $R^5$ is $C_{3-6}$ cycloalkyl optionally substituted with one or more substituents Q. In certain embodiments, $R^5$ is cyclopropyl, cyclobutyl, cyclopentyl, or cyclohexyl, each optionally substituted with one or more substituents Q. In certain embodiments, $R^5$ is cyclopropyl, cyclobutyl, cyclopentyl, cyclohexyl, or 4-methoxycarbonylcyclohexyl. In certain embodiments, $R^5$ is cyclopropyl or 4-methoxycarbonylcyclohexyl.

In certain embodiments, $R^5$ is $C_{6-14}$ aryl optionally substituted with one or more substituents Q. In certain embodiments, $R^5$ is $C_{6-14}$ aryl optionally substituted with one or two substituents Q, each independently selected from halo, nitro, $C_{1-6}$ alkyl, —$OR^a$, —$NR^bR^c$, and —$NR^aC(O)R^d$; wherein the alkyl is optionally substituted with a substituent Q and each $R^a$, $R^b$, $R^e$, and $R^d$ is as defined herein. In certain embodiments, $R^5$ is phenyl optionally substituted with one or more substituents Q. In certain embodiments, $R^5$ is phenyl optionally substituted with one or two substituents Q, each independently selected from halo, nitro, $C_{1-6}$ alkyl, —$OR^a$, —$NR^bR^c$, and —$NR^aC(O)R^d$, wherein the alkyl is optionally substituted with a substituent Q and each $R^a$, $R^b$, $R^e$, and $R^d$ is as defined herein. In certain embodiments, $R^5$ is phenyl optionally substituted with one or two substituents Q, each independently selected from amino, fluoro, nitro, methoxycarbonylmethoxy, hydroxyethyl, and hydroxyacetamido. In certain embodiments, $R^5$ is phenyl, aminophenyl, fluorophenyl, nitrophenyl, methoxycarbonylmethoxyphenyl, (hydroxyethyl)phenyl, or (hydroxyacetamido)phenyl. In certain embodiments, $R^5$ is phenyl, 3-aminophenyl, 4-aminophenyl, 2-fluorophenyl, 4-fluorophenyl, 3-nitrophenyl, 4-nitrophenyl, 1-methoxycarbonylmethoxyphenyl, 3-(2-hydroxyethyl)phenyl, or 4-(2-hydroxyacetamido)phenyl.

In certain embodiments, $R^5$ is $C_{7-15}$ aralkyl optionally substituted with one or more substituents Q. In certain embodiments, $R^5$ is heteroaryl optionally substituted with one or more substituents Q. In certain embodiments, $R^5$ is 5-membered heteroaryl optionally substituted with one or more substituents Q. In certain embodiments, $R^5$ is 6-membered heteroaryl optionally substituted with one or more substituents Q. In certain embodiments, $R^5$ is thienyl, thiazolyl, or pyridyl, each optionally substituted with one or more substituents Q. In certain embodiments, $R^5$ is 2-thienyl, 5-thiazolyl, or 4-pyridyl. In certain embodiments, $R^5$ is heterocyclyl optionally substituted with one or more substituents Q. In certain embodiments, $R^5$ is 5-membered heterocyclyl optionally substituted with one or more substituents Q. In certain embodiments, $R^5$ is 6-membered heterocyclyl optionally substituted with one or more substituents Q. In certain embodiments, $R^5$ is tetrahydro-2H-pyranyl optionally substituted with one or more substituents Q. In certain embodiments, $R^5$ is tetrahydro-2H-pyran-4-yl.

In certain embodiments, $R^4$ is hydrogen; and $R^5$ is methyl, cyclopropylmethyl, cyclopropyl, cyclobutyl, cyclopentyl, cyclohexyl, 4-methoxycarbonylcyclohexyl, phenyl, 3-aminophenyl, 4-aminophenyl, 2-fluorophenyl, 4-fluorophenyl, 3-nitrophenyl, 4-nitrophenyl, 1-methoxycarbonylmethoxyphenyl, 3-(2-hydroxyethyl)phenyl, 4-(2-hydroxyacetamido)phenyl, 2-thienyl, 5-thiazolyl, 4-pyridyl, or tetrahydro-2H-pyran-4-yl. In certain embodiments, $R^4$ is hydrogen; and $R^5$ is methyl, cyclopropyl, 4-methoxycarbonylcyclohexyl, phenyl, 3-aminophenyl, 4-aminophenyl, 2-fluorophenyl, 4-fluorophenyl, 3-nitrophenyl, 4-nitrophenyl, 1-methoxycarbonylmethoxyphenyl, 3-(2-hydroxyethyl)phenyl, 4-(2-hydroxyacetamido)phenyl, 2-thienyl, 4-pyridyl, or tetrahydro-2H-pyran-4-yl. In certain embodiments, $R^4$ is hydrogen; and $R^5$ is methyl, cyclopropyl, 4-methoxycarbonylcyclohexyl, phenyl, 3-aminophenyl, 4-aminophenyl, 2-fluorophenyl, 4-fluorophenyl, 3-nitrophenyl, 4-nitrophenyl, 1-methoxycarbonylmethoxyphenyl, 3-(2-hydroxyethyl)phenyl, 4-(2-hydroxyacetamido)phenyl, 2-thienyl, or tetrahydro-2H-pyran-4-yl.

In certain embodiments, $R^4$ and $R^5$ together with the carbon atom to which they are attached form $C_{3-10}$ cycloalkyl optionally substituted with one or more substituents Q. In certain embodiments, $R^4$ and $R^5$ together with the carbon atom to which they are attached form $C_{3-10}$ cycloalkyl optionally substituted with one or two substituents Q, each independently selected from halo, —$OR^a$, and —$C(O)OR^a$, wherein each $R^a$ is as defined herein. In certain embodiments, $R^4$ and $R^5$ together with the carbon atom to which they are attached form cyclohexyl optionally substituted with one or two substituents Q, each independently selected from halo, —$OR^a$, and —$C(O)OR^a$, wherein each $R^a$ is as defined herein. In certain embodiments, $R^4$ and $R^5$ together with the carbon atom to which they are attached form cyclohexyl optionally substituted with one or two substituents Q, each independently selected from hydroxy, fluoro, and methoxycarbonyl. In certain embodiments, $R^4$ and $R^5$ together with the carbon atom to which they are attached form cyclohexyl, hydroxycyclohexyl, difluorocyclohexyl, or methoxycarbonylcyclohexyl. In certain embodiments, $R^4$ and $R^5$ together with the carbon atom to which they are attached form cyclohexyl, 4-hydroxycyclohexyl, 4,4-difluorocyclohexyl, or 4-methoxycarbonylcyclohexyl.

In certain embodiments, $R^4$ and $R^5$ together with the carbon atom to which they are attached form heterocyclyl optionally substituted with one or more substituents Q. In certain embodiments, $R^4$ and $R^5$ together with the carbon atom to which they are attached form 3-, 4-, 5-, 6-, or 7-membered heterocyclyl, each optionally substituted with one or more substituents Q. In certain embodiments, $R^4$ and $R^5$ together with the carbon atom to which they are attached form oxetanyl or tetrahydro-2H-pyranyl, each optionally substituted with one or more substituents Q. In certain embodiments, $R^4$ and $R^5$ together with the carbon atom to which they are attached form oxetan-3-yl or tetrahydro-2H-pyran-4-yl.

In certain embodiments, $R^6$ is hydrogen. In certain embodiments, $R^6$ is deuterium. In certain embodiments, $R^6$ is $C_{1-6}$ alkyl optionally substituted with one or more substituents Q. In certain embodiments, $R^6$ is butyl optionally substituted with one or more substituents Q. In certain embodiments, $R^6$ is tert-butyl optionally substituted with one or more substituents Q. In certain embodiments, $R^6$ is $C_{1-6}$ alkyl substituted with heterocyclyl, i.e., $C_{1-6}$ alkyl-heterocyclyl, wherein the alkyl and heterocyclyl are each optionally substituted with one or more substituents Q. In certain embodiments, $R^6$ is oxetanylmethyl or tetrahydropyranylmethyl, each optionally substituted with one or more substituents Q. In certain embodiments, $R^6$ is oxetan-3-ylmethyl or tetrahydropyran-4-ylmethyl. In certain embodiments, $R^6$ is $C_{2-6}$ alkenyl optionally substituted with one or more substituents Q. In certain embodiments, $R^6$ is $C_{2-6}$ alkynyl optionally substituted with one or more substituents Q.

In certain embodiments, $R^6$ is $C_{3-10}$ cycloalkyl optionally substituted with one or more substituents Q. In certain embodiments, $R^6$ is $C_{3-7}$ cycloalkyl optionally substituted with one or more substituents Q. In certain embodiments, $R^6$ is cyclopropyl or cyclobutyl, each optionally substituted with one or more substituents Q. In certain embodiments, $R^6$ is $C_{6-14}$ aryl optionally substituted with one or more substituents Q. In certain embodiments, $R^6$ is $C_{7-15}$ aralkyl optionally substituted with one or more substituents Q. In certain embodiments, $R^6$ is benzyl or phenylethyl, each optionally substituted with one or more substituents Q. In certain embodiments, $R^6$ is benzyl or phenylethyl, each optionally substituted with cyano or halo. In certain embodiments, $R^6$ is benzyl, cyanobenzyl, fluorobenzyl, difluorobenzyl, or phenylethyl. In certain embodiments, $R^6$ is benzyl, 2-cyanobenzyl, 4-cyanobenzyl, 2-fluorobenzyl, 4-fluorobenzyl, 2,4-difluorobenzyl, or 2-phenylethyl. In certain embodiments, $R^6$ is heteroaryl optionally substituted with one or more substituents Q. In certain embodiments, $R^6$ is heterocyclyl optionally substituted with one or more substituents Q.

In certain embodiments, E is O. In certain embodiments, E is S. In certain embodiments, E is $NR^{1a}$, wherein $R^{1a}$ is as defined herein. In certain embodiments, E is NH. In certain embodiments, E is $NOR^{1a}$, wherein $R^{1a}$ is as defined herein.

In certain embodiments, L is a bond. In certain embodiments, L is $C_{1-6}$ alkylene optionally substituted with one or more substituents Q. In certain embodiments, L is $—(CH_2)_r—$, wherein r is an integer of 1, 2, 3, 4, 5, or 6. In certain embodiments, L is $C_{2-6}$ alkenylene optionally substituted with one or more substituents Q. In certain embodiments, L is $C_{2-6}$ alkynylene optionally substituted with one or more substituents Q. In certain embodiments, L is $C_{3-10}$ cycloalkylene optionally substituted with one or more substituents Q. In certain embodiments, L is $C_{6-14}$ arylene optionally substituted with one or more substituents Q. In certain embodiments, L is $C_{7-15}$ aralkylene optionally substituted with one or more substituents Q. In certain embodiments, L is heteroarylene optionally substituted with one or more substituents Q. In certain embodiments, L is heterocyclylene optionally substituted with one or more substituents Q.

In certain embodiments, X is a bond. In certain embodiments, X is —O—. In certain embodiments, X is $—NR^X—$, wherein $R^X$ is as defined herein. In certain embodiments, X is —NH—.

In certain embodiments, Y is a bond. In certain embodiments, Y is —O—. In certain embodiments, Y is $—NR^YO—$, wherein $R^Y$ is as defined herein. In certain embodiments, Y is —NHO—. In certain embodiments, Y is $—NR^Y—$, wherein $R^Y$ is as defined herein. In certain embodiments, Y is —NH—.

In certain embodiments, L and X are each a bond, and Y is —O—. In certain embodiments, L and X are each a bond, and Y is $—NR^YO—$, wherein $R^Y$ is as defined herein. In certain embodiments, L and X are each a bond, and Y is $—NR^Y—$, wherein $R^Y$ is as defined herein.

In certain embodiments, L is $C_{1-6}$ alkylene optionally substituted with one or more substituents Q, X is a bond, and Y is —O—. In certain embodiments, L is $C_{1-6}$ alkylene optionally substituted with one or more substituents Q, X is a bond, and Y is $—NR^YO—$, wherein R is as defined herein. In certain embodiments, L is $C_{1-6}$ alkylene optionally substituted with one or more substituents Q, X is a bond, and Y is $—NR^Y—$, wherein $R^Y$ is as defined herein.

In certain embodiments, L is $C_{1-6}$ alkylene optionally substituted with one or more substituents Q, X is —O—, and Y is —O—. In certain embodiments, L is $C_{1-6}$ alkylene optionally substituted with one or more substituents Q, X is —O—, and Y is $—NR^YO—$, wherein $R^Y$ is as defined herein. In certain embodiments, L is $C_{1-6}$ alkylene optionally substituted with one or more substituents Q, X is —O—, and Y is $—NR^Y—$, wherein $R^Y$ is as defined herein.

In certain embodiments, L is $C_{1-6}$ alkylene optionally substituted with one or more substituents Q, X is $—NR^X—$, and Y is —O—, wherein $R^X$ is as defined herein. In certain embodiments, L is $C_{1-6}$ alkylene optionally substituted with one or more substituents Q, X is $—NR^X—$, and Y is $—NR^YO—$, wherein $R^X$ and $R^Y$ are each as defined herein. In certain embodiments, L is $C_{1-6}$ alkylene optionally substituted with one or more substituents Q, X is $—NR^X—$, and Y is $—NR^Y—$, wherein $R^X$ and $R^Y$ are each as defined herein.

In certain embodiments, L is $C_{1-6}$ alkylene optionally substituted with one or more substituents Q, X is —O—, and Y is a bond. In certain embodiments, L is $C_{1-6}$ alkylene optionally substituted with one or more substituents Q, X is $—NR^X—$, and Y is a bond, wherein $R^X$ is as defined herein.

In certain embodiments, $R^X$ is hydrogen. In certain embodiments, $R^X$ is $C_{1-6}$ alkyl optionally substituted with one or more substituents Q. In certain embodiments, $R^X$ is $C_{2-6}$ alkenyl optionally substituted with one or more substituents Q. In certain embodiments, $R^X$ is $C_{2-6}$ alkynyl optionally substituted with one or more substituents Q. In certain embodiments, $R^X$ is $C_{3-10}$ cycloalkyl optionally substituted with one or more substituents Q. In certain embodiments, $R^X$ is $C_{6-14}$ aryl optionally substituted with one or more substituents Q. In certain embodiments, $R^X$ is $C_{7-15}$ aralkyl optionally substituted with one or more substituents Q. In certain embodiments, $R^X$ is heteroaryl optionally substituted with one or more substituents Q. In certain embodiments, $R^X$ is heterocyclyl optionally substituted with one or more substituents Q.

In certain embodiments, $R^Y$ is hydrogen. In certain embodiments, $R^Y$ is $C_{1-6}$ alkyl optionally substituted with one or more substituents Q. In certain embodiments, $R^Y$ is $C_{2-6}$ alkenyl optionally substituted with one or more substituents Q. In certain embodiments, $R^Y$ is $C_{2-6}$ alkynyl optionally substituted with one or more substituents Q. In certain embodiments, $R^Y$ is $C_{3-10}$ cycloalkyl optionally substituted with one or more substituents Q. In certain embodiments, $R^Y$ is $C_{6-14}$ aryl optionally substituted with one or more substituents Q. In certain embodiments, $R^Y$ is $C_{7-15}$ aralkyl optionally substituted with one or more substituents Q. In certain embodiments, $R^Y$ is heteroaryl optionally substituted with one or more substituents Q. In certain embodiments, $R^Y$ is heterocyclyl optionally substituted with one or more substituents Q.

In certain embodiments, $U^1$ is $—CR^{3a}═$, wherein $R^{3a}$ is as defined herein. In certain embodiments, $U^1$ is —CH═. In certain embodiments, $U^1$ is $—CR^{3a}R^{3b}—$, wherein $R^{3a}$ and $R^{3b}$ are each as defined herein. In certain embodiments, $U^1$ is $—CH_2—$ or —C(═O)—. In certain embodiments, $U^1$ is —N═. In certain embodiments, $U^1$ is $—NR^{3c}—$, wherein $R^{3a}$ is as defined herein. In certain embodiments, $U^1$ is —NH—. In certain embodiments, $U^1$ is $—N(CH_3)—$. In certain embodiments, $U^1$ is —O—. In certain embodiments, $U^1$ is —S—.

In certain embodiments, $U^2$ is $—CR^{3a}═$, wherein $R^{3a}$ is as defined herein. In certain embodiments, $U^2$ is —CH═. In certain embodiments, $U^2$ is $—CR^{3a}R^{3b}—$, wherein $R^{3a}$ and $R^{3b}$ are each as defined herein. In certain embodiments, $U^2$ is $—CH_2—$ or —C(═O)—. In certain embodiments, $U^2$ is —N═. In certain embodiments, $U^2$ is $—NR^{3c}—$, wherein $R^3$, is as defined herein. In certain embodiments, $U^2$ is —NH—. In certain embodiments, $U^2$ is $—N(CH_3)—$. In certain embodiments, $U^2$ is —O—. In certain embodiments, $U^2$ is —S—.

In certain embodiments, $U^3$ is $—CR^{3a}═$, wherein $R^{3a}$ is as defined herein. In certain embodiments, $U^3$ is —CH═. In certain embodiments, $U^3$ is $—CR^{3a}R^{3b}—$, wherein $R^{3a}$ and $R^{3b}$ are each as defined herein. In certain embodiments, $U^3$ is $—CH_2—$ or —C(═O)—. In certain embodiments, $U^3$ is —N═. In certain embodiments, $U^3$ is $—NR^{3c}—$, wherein $R^3$, is as defined herein. In certain embodiments, $U^3$ is —NH—. In certain embodiments, $U^3$ is —N($CH_3$)—. In certain embodiments, $U^3$ is —O—. In certain embodiments, $U^3$ is —S—.

In certain embodiments, $U^4$ is a bond. In certain embodiments, $U^4$ is —$CR^{3a}$ wherein $R^{3a}$ is as defined herein. In certain embodiments, $U^4$ is —CH═. In certain embodiments, $U^4$ is —$CR^{3a}R^{3b}$—, wherein $R^{3a}$ and $R^{3b}$ are each as defined herein. In certain embodiments, $U^4$ is —$CH_2$— or —C(═O)—. In certain embodiments, $U^4$ is —N═. In certain embodiments, $U^4$ is —$NR^{3c}$—, wherein $R^3$, is as defined herein. In certain embodiments, $U^4$ is —NH—. In certain embodiments, $U^4$ is —N($CH_3$)—. In certain embodiments, $U^4$ is —O—. In certain embodiments, $U^4$ is —S—.

In certain embodiments, $V^1$ is —$CR^{3a}$═, wherein $R^{3a}$ is as defined herein. In certain embodiments, $V^1$ is —CH═. In certain embodiments, $V^1$ is —$CR^{3a}R^{3b}$—, wherein $R^{3a}$ and $R^{3b}$ are each as defined herein. In certain embodiments, $V^1$ is —$CH_2$— or —C(═O)—. In certain embodiments, $V^1$ is —N═. In certain embodiments, $V^1$ is —$NR^{3c}$—, wherein $R^{3c}$ is as defined herein. In certain embodiments, $V^1$ is —NH—. In certain embodiments, $V^1$ is —N($CH_3$)—. In certain embodiments, $V^1$ is —O—. In certain embodiments, $V^1$ is —S—.

In certain embodiments, $V^2$ is —$CR^{3a}$═, wherein $R^{3a}$ is as defined herein. In certain embodiments, $V^2$ is —CH═. In certain embodiments, $V^2$ is —$CR^{3a}R^{3b}$—, wherein $R^{3a}$ and $R^{3b}$ are each as defined herein. In certain embodiments, $V^2$ is —$CH_2$— or —C(═O)—. In certain embodiments, $V^2$ is —N═. In certain embodiments, $V^2$ is —$NR^{3c}$—, wherein $R^3$, is as defined herein. In certain embodiments, $V^2$ is —NH—. In certain embodiments, $V^2$ is —N($CH_3$)—. In certain embodiments, $V^2$ is —O—. In certain embodiments, $V^2$ is —S—.

In certain embodiments, $V^3$ is —$CR^{3a}$═, wherein $R^{3a}$ is as defined herein. In certain embodiments, $V^3$ is —CH═. In certain embodiments, $V^3$ is —$CR^{3a}R^{3b}$—, wherein $R^{3a}$ and $R^{3b}$ are each as defined herein. In certain embodiments, $V^3$ is —$CH_2$— or —C(═O)—. In certain embodiments, $V^3$ is —N═. In certain embodiments, $V^3$ is —$NR^{3c}$—, wherein $R^3$, is as defined herein. In certain embodiments, $V^3$ is —NH—. In certain embodiments, $V^3$ is —N($CH_3$)—. In certain embodiments, $V^3$ is —O—. In certain embodiments, $V^3$ is —S—.

In certain embodiments, $V^4$ is a bond. In certain embodiments, $V^4$ is —$CR^{3a}$═, wherein $R^{3a}$ is as defined herein. In certain embodiments, $V^4$ is —CH═. In certain embodiments, $V^4$ is —$CR^{3a}R^{3b}$—, wherein $R^{3a}$ and $R^{3b}$ are each as defined herein. In certain embodiments, $V^4$ is —$CH_2$— or —C(═O)—. In certain embodiments, $V^4$ is —N═. In certain embodiments, $V^4$ is —$NR^{3c}$—, wherein $R^3$, is as defined herein. In certain embodiments, $V^4$ is —NH—. In certain embodiments, $V^4$ is —N($CH_3$)—. In certain embodiments, $V^4$ is —O—. In certain embodiments, $V^4$ is —S—.

In certain embodiments, $Z^1$ is C. In certain embodiments, $Z^1$ is $CR^{3a}$, wherein $R^{3a}$ is as defined herein. In certain embodiments, $Z^1$ is N.

In certain embodiments, $Z^2$ is C. In certain embodiments, $Z^2$ is $CR^{3a}$, wherein $R^{3a}$ is as defined herein. In certain embodiments, $Z^2$ is N.

In certain embodiments, $R^{3a}$ is hydrogen. In certain embodiments, $R^{3a}$ is deuterium. In certain embodiments, $R^{3a}$ is cyano. In certain embodiments, $R^{3a}$ is halo. In certain embodiments, $R^{3a}$ is nitro. In certain embodiments, $R^{3a}$ is $C_{1-6}$ alkyl optionally substituted with one or more substituents Q. In certain embodiments, $R^{3a}$ is $C_{2-6}$ alkenyl optionally substituted with one or more substituents Q. In certain embodiments, $R^{3a}$ is $C_{2-6}$ alkynyl optionally substituted with one or more substituents Q. In certain embodiments, $R^{3a}$ is $C_{3-7}$ cycloalkyl, $C_{6-14}$ aryl optionally substituted with one or more substituents Q. In certain embodiments, $R^{3a}$ is $C_{7-15}$ aralkyl optionally substituted with one or more substituents Q. In certain embodiments, $R^{3a}$ is heteroaryl optionally substituted with one or more substituents Q. In certain embodiments, $R^{3a}$ is heterocyclyl optionally substituted with one or more substituents Q.

In certain embodiments, $R^{3a}$ is —C(O)$R^{1a}$, wherein $R^{1a}$ is as defined herein. In certain embodiments, $R^{3a}$ is —C(O)O$R^{1a}$, wherein $R^{1a}$ is as defined herein. In certain embodiments, $R^{3a}$ is —C(O)O$R^{1a}$, wherein $R^{1a}$ is as defined herein. In certain embodiments, $R^{3a}$ is —C(O)$NR^{1b}R^{1c}$, wherein $R^{1b}$ and $R^{1c}$ are each as defined herein. In certain embodiments, $R^{3a}$ is —C($NR^{1a}$)$NR^{1b}R^{1c}$, wherein $R^{1a}$, $R^{1b}$, and $R^{1c}$ are each as defined herein. In certain embodiments, $R^{3a}$ is —O$R^{1a}$, wherein $R^{1a}$ is as defined herein. In certain embodiments, $R^{3a}$ is —OC(O)$R^{1a}$, wherein $R^{1a}$ is as defined herein. In certain embodiments, $R^{3a}$ is —OC(O)O$R^{1a}$, wherein $R^{1a}$ is as defined herein. In certain embodiments, $R^{3a}$ is —OC(O)$NR^{1b}R^{1c}$, wherein $R^{1b}$ and $R^{1c}$ are each as defined herein. In certain embodiments, $R^{3a}$ is —OC($NR^{1a}$)$NR^{1b}R^{1c}$, wherein $R^{1a}$, $R^{1b}$, and $R^{1c}$ are each as defined herein. In certain embodiments, $R^{3a}$ is —OS(O)$R^{1a}$, wherein $R^{1a}$ is as defined herein. In certain embodiments, $R^{3a}$ is —OS$(O)_2R^{1a}$, wherein $R^{1a}$ is as defined herein. In certain embodiments, $R^{3a}$ is —OS(O)$NR^{1b}R^{1c}$, wherein $R^{1b}$ and $R^{1c}$ are each as defined herein. In certain embodiments, $R^{3a}$ is —OS$(O)_2NR^{1b}R^{1c}$, wherein $R^{1b}$ and $R^{1c}$ are each as defined herein. In certain embodiments, $R^{3a}$ is —$NR^{1b}R^{1c}$, wherein $R^{1b}$ and $R^{1c}$ are each as defined herein. In certain embodiments, $R^{3a}$ is —$NR^{1a}$C(O)$R^{1d}$, wherein $R^{1a}$ and $R^{1d}$ are each as defined herein. In certain embodiments, $R^{3a}$ is —$NR^{1a}$C(O)O$R^{1d}$, wherein $R^{1a}$ and $R^{1d}$ are each as defined herein. In certain embodiments, $R^{3a}$ is —$NR^{1a}$C(O)$NR^{1b}R^{1c}$, wherein $R^{1a}$, $R^{1b}$, and $R^{1c}$ are each as defined herein. In certain embodiments, $R^{3a}$ is —$NR^{1a}$C($NR^{1d}$)$NR^{1b}R^{1c}$, wherein $R^{1a}$, $R^{1b}$, $R^{1c}$, and $R^{1d}$ are each as defined herein. In certain embodiments, $R^{3a}$ is —$NR^{1a}$S(O)$R^{1d}$, wherein $R^{1a}$ and $R^{1d}$ are each as defined herein. In certain embodiments, $R^{3a}$ is —$NR^{1a}$S$(O)_2R^{1d}$, wherein $R^{1a}$ and $R^{1d}$ are each as defined herein. In certain embodiments, $R^{3a}$ is —$NR^{1a}$S(O)$NR^{1b}R^{1c}$, wherein $R^{1a}$, $R^{1b}$, and $R^{1c}$ are each as defined herein. In certain embodiments, $R^{3a}$ is —$NR^{1a}$S$(O)_2NR^{1b}R^{1c}$, wherein $R^{1a}$, $R^{1b}$, and $R^{1c}$ are each as defined herein. In certain embodiments, $R^{3a}$ is —S$R^{1a}$, wherein $R^{1a}$ is as defined herein. In certain embodiments, $R^{3a}$ is —S(O)$R^{1a}$, wherein $R^{1a}$ is as defined herein. In certain embodiments, $R^{3a}$ is —S$(O)_2R^{1a}$, wherein $R^{1a}$ is as defined herein. In certain embodiments, $R^{3a}$ is —S(O)$NR^{1b}R^{1c}$, wherein $R^{1b}$ and $R^{1c}$ are each as defined herein. In certain embodiments, $R^{3a}$ is —S$(O)_2NR^{1b}R^{1c}$, wherein $R^{1b}$ and $R^{1c}$ are each as defined herein.

In certain embodiments, $R^{3b}$ is hydrogen. In certain embodiments, $R^{3b}$ is deuterium. In certain embodiments, $R^{3b}$ is cyano. In certain embodiments, $R^{3b}$ is halo. In certain embodiments, $R^{3b}$ is nitro. In certain embodiments, $R^{3b}$ is $C_{1-6}$ alkyl optionally substituted with one or more substituents Q. In certain embodiments, $R^{3b}$ is $C_{2-6}$ alkenyl optionally substituted with one or more substituents Q. In certain embodiments, $R^{3b}$ is $C_{2-6}$ alkynyl optionally substituted with one or more substituents Q. In certain embodiments, $R^{3b}$ is $C_{3-7}$ cycloalkyl, $C_{6-14}$ aryl optionally substituted with one or more substituents Q. In certain embodiments, $R^{3b}$ is $C_{7-15}$ aralkyl optionally substituted with one or more substituents Q. In certain embodiments, $R^{3b}$ is heteroaryl optionally substituted with one or more substituents Q. In certain embodiments, $R^{3b}$ is heterocyclyl optionally substituted with one or more substituents Q.

In certain embodiments, $R^{3b}$ is —C(O)$R^{1a}$, wherein $R^{1a}$ is as defined herein. In certain embodiments, $R^{3b}$ is —C(O)O$R^{1a}$, wherein $R^{1a}$ is as defined herein. In certain embodiments, $R^{3b}$ is —C(O)O$R^{1a}$, wherein $R^{1a}$ is as defined herein. In certain embodiments, $R^{3b}$ is —C(O)N$R^{1b}R^{1c}$, wherein $R^{1b}$ and $R^{1c}$ are each as defined herein. In certain embodiments, $R^{3b}$ is —C(N$R^{1a}$)N$R^{1b}R^{1c}$, wherein $R^{1a}$, $R^{1b}$, and $R^{1c}$ are each as defined herein. In certain embodiments, $R^{3b}$ is —O$R^{1a}$, wherein $R^{1a}$ is as defined herein. In certain embodiments, $R^{3b}$ is —OC(O)$R^{1a}$, wherein $R^{1a}$ is as defined herein. In certain embodiments, $R^{3b}$ is —OC(O)O$R^{1a}$, wherein $R^{1a}$ is as defined herein. In certain embodiments, $R^{3b}$ is —OC(O)N$R^{1b}R^{1c}$, wherein $R^{1b}$ and $R^{1c}$ are each as defined herein. In certain embodiments, $R^{3b}$ is —OC(N$R^{1a}$)N$R^{1b}R^{1c}$, wherein $R^{1a}$, $R^{1b}$, and $R^{1c}$ are each as defined herein. In certain embodiments, $R^{3b}$ is —OS(O)$R^{1a}$, wherein $R^{1a}$ is as defined herein. In certain embodiments, $R^{3b}$ is —OS$(O)_2R^{1a}$, wherein $R^{1a}$ is as defined herein. In certain embodiments, $R^{3b}$ is —OS(O)N$R^{1b}R^{1c}$, wherein $R^{1b}$ and $R^{1c}$ are each as defined herein. In certain embodiments, $R^{3b}$ is —OS$(O)_2$N$R^{1b}R^{1c}$, wherein $R^{1b}$ and $R^{1c}$ are each as defined herein. In certain embodiments, $R^{3b}$ is —N$R^{1b}R^{1c}$, wherein $R^{1b}$ and $R^{1c}$ are each as defined herein. In certain embodiments, $R^{3b}$ is —N$R^{1a}$C(O)$R^{1d}$, wherein $R^{1a}$ and $R^{1d}$ are each as defined herein. In certain embodiments, $R^{3b}$ is —N$R^{1a}$C(O)O$R^{1d}$, wherein $R^{1a}$ and $R^{1d}$ are each as defined herein. In certain embodiments, $R^{3b}$ is —N$R^{1a}$C(O)N$R^{1b}R^{1c}$, wherein $R^{1a}$, $R^{1b}$, and $R^{1c}$ are each as defined herein. In certain embodiments, $R^{3b}$ is —N$R^{1a}$C(N$R^{1d}$)N$R^{1b}R^{1c}$, wherein $R^{1a}$, $R^{1b}$, $R^{1c}$, and $R^{1d}$ are each as defined herein. In certain embodiments, $R^{3b}$ is —N$R^{1a}$S(O)$R^{1d}$, wherein $R^{1a}$ and $R^{1d}$ are each as defined herein. In certain embodiments, $R^{3b}$ is —N$R^{1a}$S$(O)_2R^{1d}$, wherein $R^{1a}$ and $R^{1d}$ are each as defined herein. In certain embodiments, $R^{3b}$ is —N$R^{1a}$S(O)N$R^{1b}R^{1c}$, wherein $R^{1a}$, $R^{1b}$, and $R^{1c}$ are each as defined herein. In certain embodiments, $R^{3b}$ is —N$R^{1a}$S$(O)_2$N$R^{1b}R^{1c}$, wherein $R^{1a}$, $R^{1b}$, and $R^{1c}$ are each as defined herein. In certain embodiments, $R^{3b}$ is —S$R^{1a}$, wherein $R^{1a}$ is as defined herein. In certain embodiments, $R^{3b}$ is —S(O)$R^{1a}$, wherein $R^{1a}$ is as defined herein. In certain embodiments, $R^{3b}$ is —S$(O)_2R^{1a}$, wherein $R^{1a}$ is as defined herein. In certain embodiments, $R^{3b}$ is —S(O)N$R^{1b}R^{1c}$, wherein $R^{1b}$ and $R^{1c}$ are each as defined herein. In certain embodiments, $R^{3b}$ is —S$(O)_2$N$R^{1b}R^{1c}$, wherein $R^{1b}$ and $R^{1c}$ are each as defined herein.

In certain embodiments, $R^{3C}$ is hydrogen. In certain embodiments, $R^3$, is cyano. In certain embodiments, $R^{3C}$ is halo. In certain embodiments, $R^3$, is nitro. In certain embodiments, $R^{3C}$ is $C_{1-6}$ alkyl optionally substituted with one or more substituents Q. In certain embodiments, $R^{3C}$ is $C_{2-6}$ alkenyl optionally substituted with one or more substituents Q. In certain embodiments, $R^{3C}$ is $C_{2-6}$ alkynyl optionally substituted with one or more substituents Q. In certain embodiments, $R^{3C}$ is $C_{3-7}$ cycloalkyl, $C_{6-14}$ aryl optionally substituted with one or more substituents Q. In certain embodiments, $R^{3C}$ is $C_{7-15}$ aralkyl optionally substituted with one or more substituents Q. In certain embodiments, $R^{3C}$ is heteroaryl optionally substituted with one or more substituents Q. In certain embodiments, $R^{3C}$ is heterocyclyl optionally substituted with one or more substituents Q.

In certain embodiments, $R^{3d}$ is deuterium. In certain embodiments, $R^{3d}$ is cyano. In certain embodiments, $R^{3d}$ is halo. In certain embodiments, $R^{3d}$ is nitro. In certain embodiments, $R^{3d}$ is $C_{1-6}$ alkyl optionally substituted with one or more substituents Q. In certain embodiments, $R^{3d}$ is $C_{2-6}$ alkenyl optionally substituted with one or more substituents Q. In certain embodiments, $R^{3d}$ is $C_{2-6}$ alkynyl optionally substituted with one or more substituents Q. In certain embodiments, $R^{3d}$ is $C_{3-7}$ cycloalkyl, $C_{6-14}$ aryl optionally substituted with one or more substituents Q. In certain embodiments, $R^{3d}$ is $C_{7-15}$ aralkyl optionally substituted with one or more substituents Q. In certain embodiments, $R^{3d}$ is heteroaryl optionally substituted with one or more substituents Q. In certain embodiments, $R^{3d}$ is heterocyclyl optionally substituted with one or more substituents Q.

In certain embodiments, $R^{3d}$ is —C(O)$R^{1a}$, wherein $R^{1a}$ is as defined herein. In certain embodiments, $R^{3d}$ is —C(O)O$R^{1a}$, wherein $R^{1a}$ is as defined herein. In certain embodiments, $R^{3d}$ is —C(O)O$R^{1a}$, wherein $R^{1a}$ is as defined herein. In certain embodiments, $R^{3d}$ is —C(O)N$R^{1b}R^{1c}$, wherein $R^{1b}$ and $R^{1c}$ are each as defined herein. In certain embodiments, $R^{3d}$ is —C(N$R^{1a}$)N$R^{1b}R^{1c}$, wherein $R^{1a}$, $R^{1b}$, and $R^{1c}$ are each as defined herein. In certain embodiments, $R^{3d}$ is —O$R^{1a}$, wherein $R^{1a}$ is as defined herein. In certain embodiments, $R^{3d}$ is —OC(O)$R^{1a}$, wherein $R^{1a}$ is as defined herein. In certain embodiments, $R^{3d}$ is —OC(O)O$R^{1a}$, wherein $R^{1a}$ is as defined herein. In certain embodiments, $R^{3d}$ is —OC(O)N$R^{1b}R^{1c}$, wherein $R^{1b}$ and $R^{1c}$ are each as defined herein. In certain embodiments, $R^{3d}$ is —OC(N$R^{1a}$)N$R^{1b}R^{1c}$, wherein $R^{1a}$, $R^{1b}$, and $R^{1c}$ are each as defined herein. In certain embodiments, $R^{3d}$ is —OS(O)$R^{1a}$, wherein $R^{1a}$ is as defined herein. In certain embodiments, $R^{3d}$ is —OS$(O)_2R^{1a}$, wherein $R^{1a}$ is as defined herein. In certain embodiments, $R^{3d}$ is —OS(O)N$R^{1b}R^{1c}$, wherein $R^{1b}$ and $R^{1c}$ are each as defined herein. In certain embodiments, $R^{3d}$ is —OS$(O)_2$N$R^{1b}R^{1c}$, wherein $R^{1b}$ and $R^{1c}$ are each as defined herein. In certain embodiments, $R^{3d}$ is —N$R^{1b}R^{1c}$, wherein $R^{1b}$ and $R^{1c}$ are each as defined herein. In certain embodiments, $R^{3d}$ is —N$R^{1a}$C(O)$R^{1d}$, wherein $R^{1a}$ and $R^{1d}$ are each as defined herein. In certain embodiments, $R^{3d}$ is —N$R^{1a}$C(O)O$R^{1d}$, wherein $R^{1a}$ and $R^{1d}$ are each as defined herein. In certain embodiments, $R^{3d}$ is —N$R^{1a}$C(O)N$R^{1b}R^{1c}$, wherein $R^{1a}$, $R^{1b}$, and $R^{1c}$ are each as defined herein. In certain embodiments, $R^{3d}$ is —N$R^{1a}$C(N$R^{1d}$)N$R^{1b}R^{1c}$, wherein $R^{1a}$, $R^{1b}$, $R^{1c}$, and $R^{1d}$ are each as defined herein. In certain embodiments, $R^{3d}$ is —N$R^{1a}$S(O)$R^{1d}$, wherein $R^{1a}$ and $R^{1d}$ are each as defined herein. In certain embodiments, $R^{3d}$ is —N$R^{1a}$S$(O)_2R^{1d}$, wherein $R^{1a}$ and $R^{1d}$ are each as defined herein. In certain embodiments, $R^{3d}$ is —N$R^{1a}$S(O)N$R^{1b}R^{1c}$, wherein $R^{1a}$, $R^{1b}$, and $R^{1c}$ are each as defined herein. In certain embodiments, $R^{3d}$ is —N$R^{1a}$S$(O)_2$N$R^{1b}R^{1c}$, wherein $R^{1a}$, $R^{1b}$, and $R^{1c}$ are each as defined herein. In certain embodiments, $R^{3d}$ is —S$R^{1a}$, wherein $R^{1a}$ is as defined herein. In certain embodiments, $R^{3d}$ is —S(O)$R^{1a}$, wherein $R^{1a}$ is as defined herein. In certain embodiments, $R^{3d}$ is —S$(O)_2R^{1a}$, wherein $R^{1a}$ is as defined herein. In certain embodiments, $R^{3d}$ is —S(O)N$R^{1b}R^{1c}$, wherein $R^{1b}$ and $R^{1c}$ are each as defined herein. In certain embodiments, $R^{3d}$ is —S$(O)_2$N$R^{1b}R^{1c}$, wherein $R^{1b}$ and $R^{1c}$ are each as defined herein.

In certain embodiments, ring A is $C_{3-10}$ cycloalkyl optionally substituted with one or more substituents Q. In certain embodiments, ring A is $C_{3-10}$ cycloalkyl optionally substituted with one or two substituents Q, each independently selected from halo, —O$R^a$, and —C(O)O$R^a$, wherein each $R^a$ is as defined herein. In certain embodiments, ring A is cyclohexyl optionally substituted with one or two substituents Q, each independently selected from halo, —O$R^a$, and —C(O)O$R^a$, wherein each $R^a$ is as defined herein. In certain embodiments, ring A is cyclohexyl optionally substituted with one or two substituents Q, each independently selected from hydroxy, fluoro, and methoxycarbonyl. In certain embodiments, ring A is cyclohexyl, hydroxycyclohexyl, difluorocyclohexyl, or methoxycarbonylcyclohexyl. In certain embodiments, ring A is cyclohexyl, 4-hydroxycyclohexyl, 4,4-difluorocyclohexyl, or 4-methoxycarbonylcyclohexyl.

In certain embodiments, ring A is heterocyclyl optionally substituted with one or more substituents Q. ring A is 3-, 4-, 5-, 6-, or 7-membered heterocyclyl, each optionally substituted with one or more substituents Q. In certain embodiments, ring A is oxetanyl or tetrahydro-2H-pyranyl, each optionally substituted with one or more substituents Q. In certain embodiments, ring A is oxetan-3-yl or tetrahydro-2H-pyran-4-yl.

In certain embodiments, Z is a bond. In certain embodiments, Z is —NH—. In certain embodiments, Z is —$NR^{4a}$—, wherein $R^{4a}$ is as defined herein. In certain embodiments, Z is —O—. In certain embodiments, Z is —S—. In certain embodiments, Z is —S(O)—. In certain embodiments, Z is —$S(O)_2$—;

In certain embodiments, $R^{4a}$ is deuterium. In certain embodiments, $R^{4a}$ is cyano. In certain embodiments, $R^{4a}$ is halo. In certain embodiments, $R^{4a}$ is nitro. In certain embodiments, $R^{4a}$ is $C_{1-6}$ alkyl optionally substituted with one or more substituents Q. In certain embodiments, $R^{4a}$ is $C_{2-6}$ alkenyl optionally substituted with one or more substituents Q. In certain embodiments, $R^{4a}$ is $C_{2-6}$ alkynyl optionally substituted with one or more substituents Q. In certain embodiments, $R^{4a}$ is $C_{3-7}$ cycloalkyl, $C_{6-14}$ aryl optionally substituted with one or more substituents Q. In certain embodiments, $R^{4a}$ is $C_{7-15}$ aralkyl optionally substituted with one or more substituents Q. In certain embodiments, $R^{4a}$ is heteroaryl optionally substituted with one or more substituents Q. In certain embodiments, $R^{4a}$ is heterocyclyl optionally substituted with one or more substituents Q.

In certain embodiments, $R^{4a}$ is —$C(O)R^{1a}$, wherein $R^{1a}$ is as defined herein. In certain embodiments, $R^{4a}$ is —$C(O)OR^{1a}$, wherein $R^{1a}$ is as defined herein. In certain embodiments, $R^{4a}$ is —$C(O)OR^{1a}$, wherein $R^{1a}$ is as defined herein. In certain embodiments, $R^{4a}$ is —$C(O)NR^{1b}R^{1c}$, wherein $R^{1b}$ and $R^{1c}$ are each as defined herein. In certain embodiments, $R^{4a}$ is —$C(NR^{1a})NR^{1b}R^{1c}$, wherein $R^{1a}$, $R^{1b}$, and $R^{1c}$ are each as defined herein. In certain embodiments, $R^{4a}$ is —$OR^{1a}$, wherein $R^{1a}$ is as defined herein. In certain embodiments, $R^{4a}$ is —$OC(O)R^{1a}$, wherein $R^{1a}$ is as defined herein. In certain embodiments, $R^{4a}$ is —$OC(O)OR^{1a}$, wherein $R^{1a}$ is as defined herein. In certain embodiments, $R^{4a}$ is —$OC(O)NR^{1b}R^{1c}$, wherein $R^{1b}$ and $R^{1c}$ are each as defined herein. In certain embodiments, $R^{4a}$ is —$OC(NR^{1a})NR^{1b}R^{1c}$, wherein $R^{1a}$, $R^{1b}$, and $R^{1c}$ are each as defined herein. In certain embodiments, $R^{4a}$ is —$OS(O)R^{1a}$, wherein $R^{1a}$ is as defined herein. In certain embodiments, $R^{4a}$ is —$OS(O)_2R^{1a}$, wherein $R^{1a}$ is as defined herein. In certain embodiments, $R^{4a}$ is —$OS(O)NR^{1b}R^{1c}$, wherein $R^{1b}$ and $R^{1c}$ are each as defined herein. In certain embodiments, $R^{4a}$ is —$OS(O)_2NR^{1b}R^{1c}$, wherein $R^{1b}$ and $R^{1c}$ are each as defined herein. In certain embodiments, $R^{4a}$ is —$NR^{1b}R^{1c}$, wherein $R^{1b}$ and $R^{1c}$ are each as defined herein. In certain embodiments, $R^{4a}$ is —$NR^{1a}C(O)R^{1d}$, wherein $R^{1a}$ and $R^{1d}$ are each as defined herein. In certain embodiments, $R^{4a}$ is —$NR^{1a}C(O)OR^{1d}$, wherein $R^{1a}$ and $R^{1d}$ are each as defined herein. In certain embodiments, $R^{4a}$ is —$NR^{1a}C(O)NR^{1b}R^{1c}$, wherein $R^{1a}$, $R^{1b}$, and $R^{1c}$ are each as defined herein. In certain embodiments, $R^{4a}$ is —$NR^{1a}C(NR^{1d})NR^{1b}R^{1c}$, wherein $R^{1a}$, $R^{1b}$, $R^{1c}$, and $R^{1d}$ are each as defined herein. In certain embodiments, $R^{4a}$ is —$NR^{1a}S(O)R^{1d}$, wherein $R^{1a}$ and $R^{1d}$ are each as defined herein. In certain embodiments, $R^{4a}$ is —$NR^{1a}S(O)_2R^{1d}$, wherein $R^{1a}$ and $R^{1d}$ are each as defined herein. In certain embodiments, $R^{4a}$ is —$NR^{1a}S(O)NR^{1b}R^{1c}$, wherein $R^{1a}$, $R^{1b}$, and $R^{1c}$ are each as defined herein. In certain embodiments, $R^{4a}$ is —$NR^{1a}S(O)_2NR^{1b}R^{1c}$, wherein $R^{1a}$, $R^{1b}$, and $R^{1c}$ are each as defined herein. In certain embodiments, $R^{4a}$ is —$SR^{1a}$, wherein $R^{1a}$ is as defined herein. In certain embodiments, $R^{4a}$ is —$S(O)R^{1a}$, wherein $R^{1a}$ is as defined herein. In certain embodiments, $R^{4a}$ is —$S(O)_2R^{1a}$, wherein $R^{1a}$ is as defined herein. In certain embodiments, $R^{4a}$ is —$S(O)NR^{1b}R^{1c}$, wherein $R^{1b}$ and $R^{1c}$ are each as defined herein. In certain embodiments, $R^{4a}$ is —$S(O)_2NR^{1b}R^{1c}$, wherein $R^{1b}$ and $R^{1c}$ are each as defined herein.

In certain embodiments, two $R^{4a}$ are linked together to form a bond. In certain embodiments, two $R^{4a}$ are linked together to form —$NR^{1a}$—, wherein $R^{1a}$ is as defined herein. In certain embodiments, two $R^{4a}$ are linked together to form —O—. In certain embodiments, two $R^{4a}$ are linked together to form —S—. In certain embodiments, two $R^{4a}$ are linked together to form $C_{1-6}$ alkylene optionally substituted with one or more substituents Q. In certain embodiments, two $R^{4a}$ are linked together to form $C_{1-6}$ heteroalkylene. optionally substituted with one or more substituents Q. In certain embodiments, two $R^{4a}$ are linked together to form $C_{2-6}$ alkenylene. optionally substituted with one or more substituents Q. In certain embodiments, two $R^{4a}$ are linked together to form $C_{2-6}$ heteroalkenylene optionally substituted with one or more substituents Q.

In certain embodiments, m is an integer of 0. In certain embodiments, m is an integer of 1. In certain embodiments, m is an integer of 2. In certain embodiments, m is an integer of 3.

In certain embodiments, n is an integer of 0. In certain embodiments, n is an integer of 1. In certain embodiments, n is an integer of 2. In certain embodiments, n is an integer of 3.

In certain embodiments, p is an integer of 0. In certain embodiments, p is an integer of 1. In certain embodiments, p is an integer of 2. In certain embodiments, p is an integer of 3.

In certain embodiments, q is an integer of 0. In certain embodiments, q is an integer of 1. In certain embodiments, q is an integer of 2. In certain embodiments, q is an integer of 3. In certain embodiments, q is an integer of 4. In certain embodiments, q is an integer of 5. In certain embodiments, q is an integer of 6.

In one embodiment, provided herein is a compound of:

A1

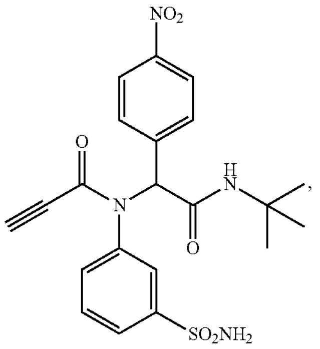

-continued
A2
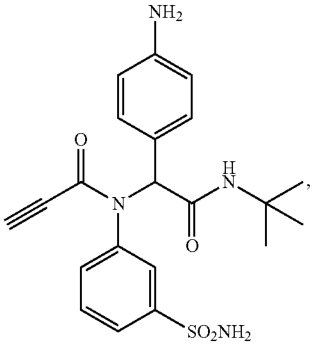
A3
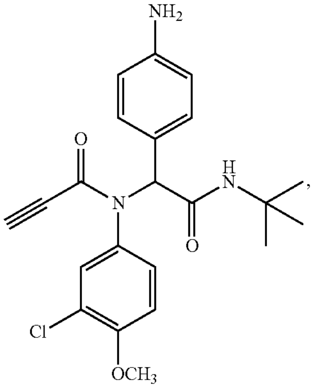
A4
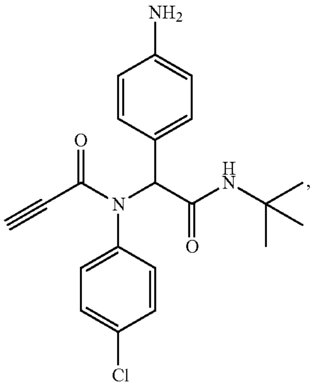
A5
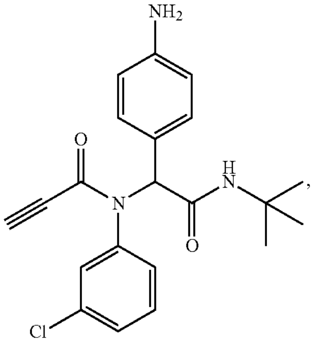
-continued
A6
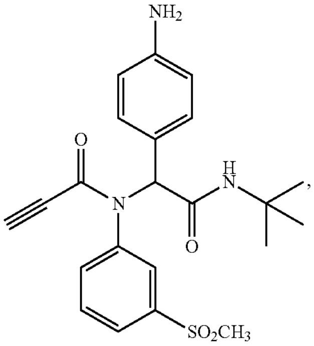
A7
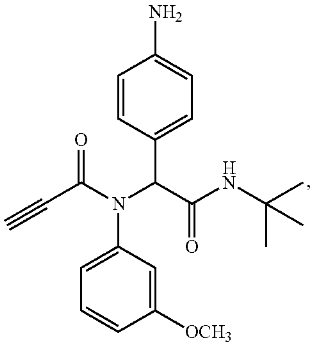
A8
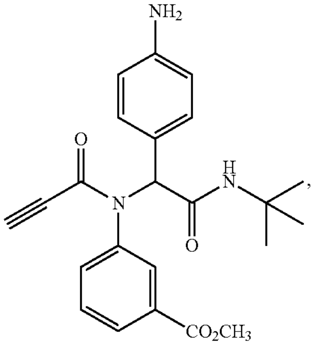
A9
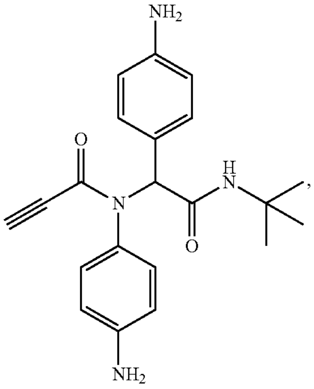

-continued
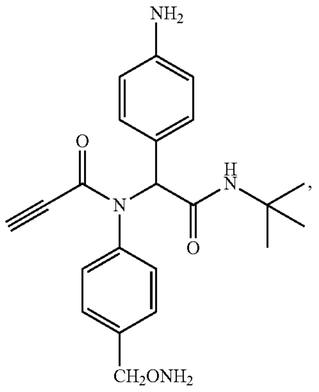
A10
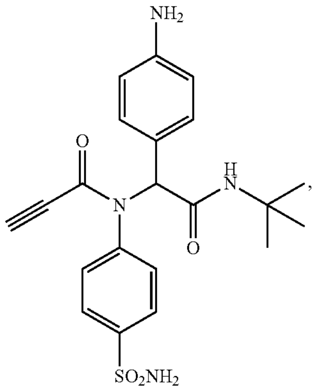
A11
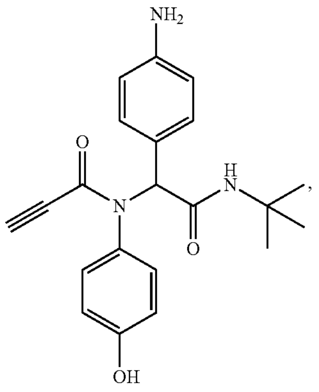
A12
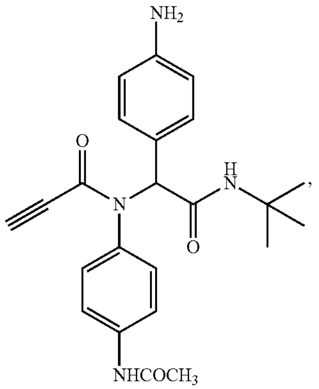
A13
-continued
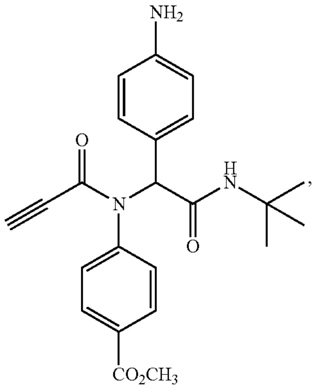
A14
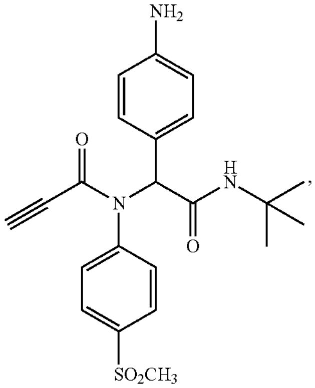
A15
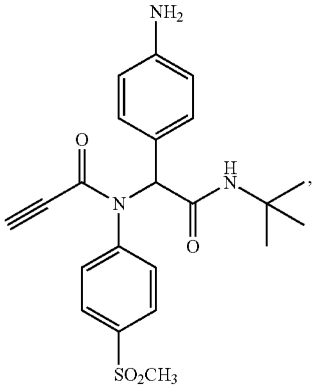
A16
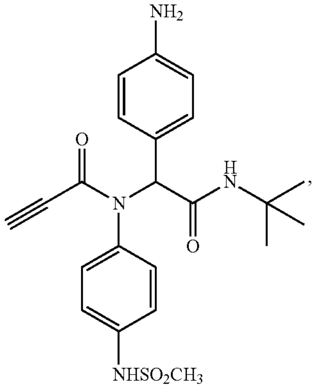
A17

-continued
A18
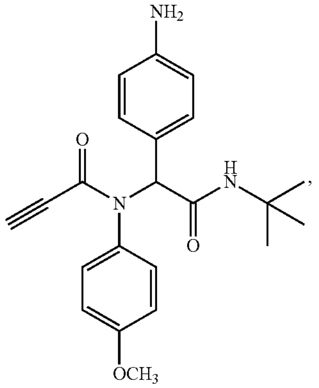
A19
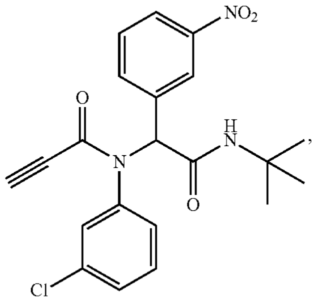
A20
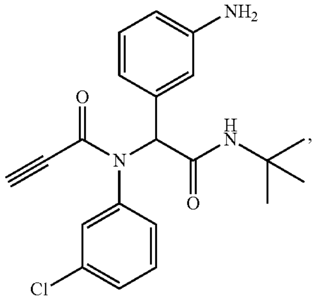
A21
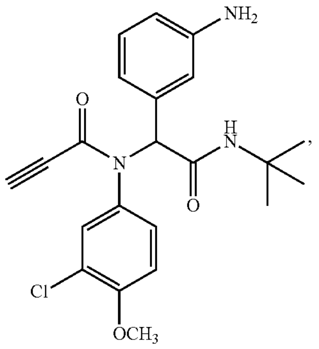
-continued
A22
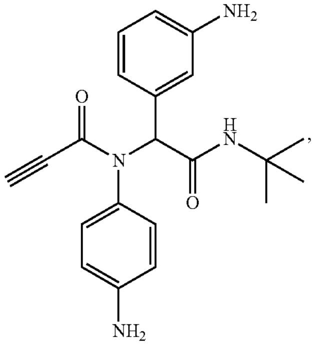
A23
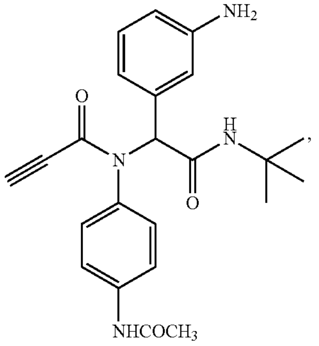
A24
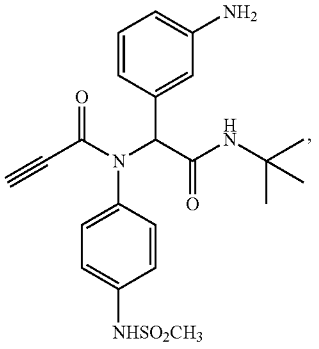
A25
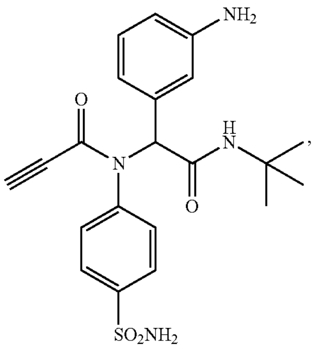

-continued
A26
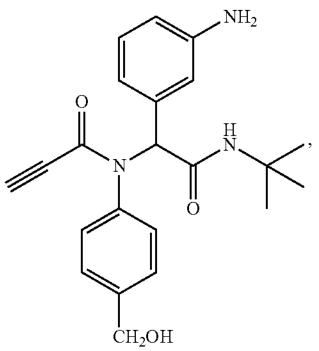
A27
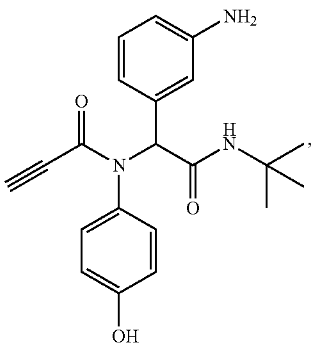
A28
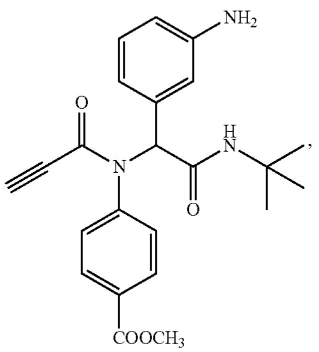
A29
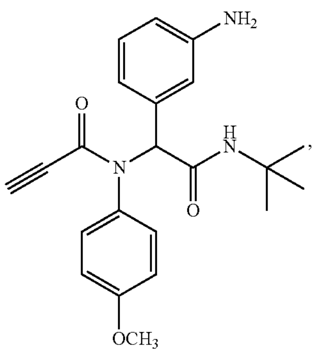
-continued
A30
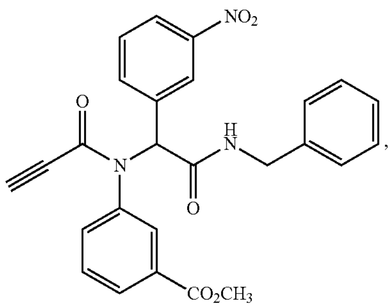
A31
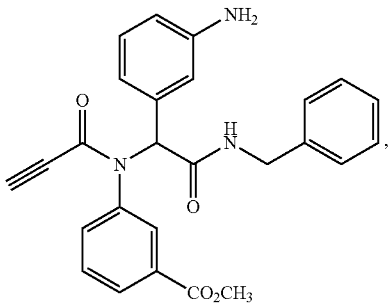
A32
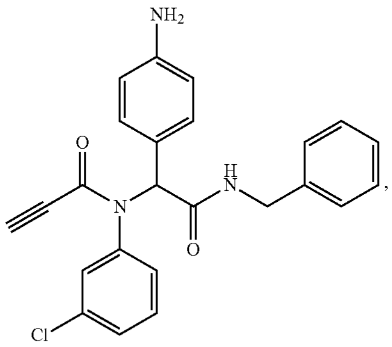
A33
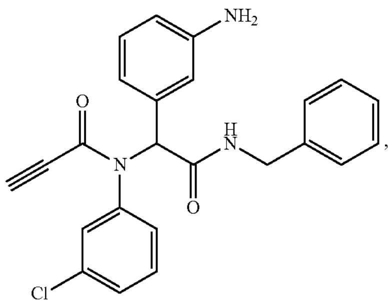
A34
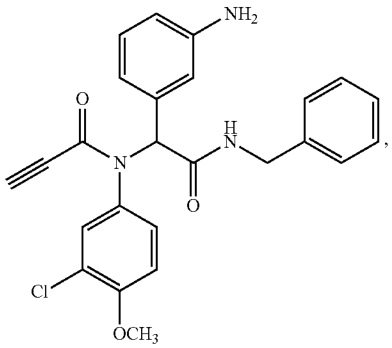

-continued
A35
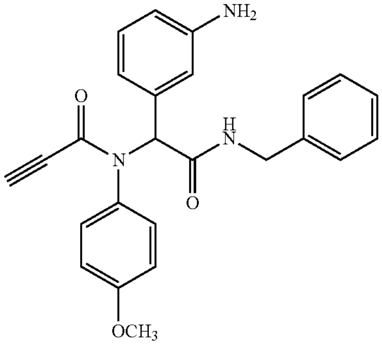,
A36
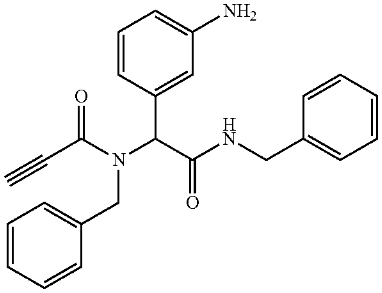,
A37
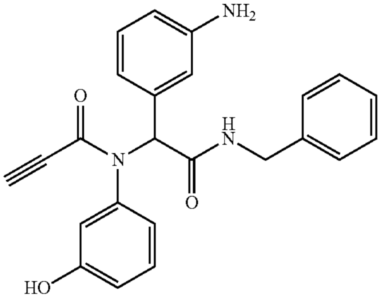,
A38
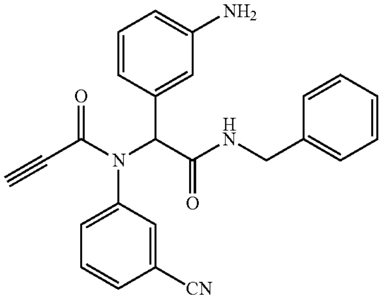,
A39
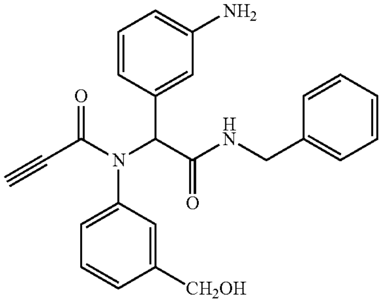,
-continued
A40
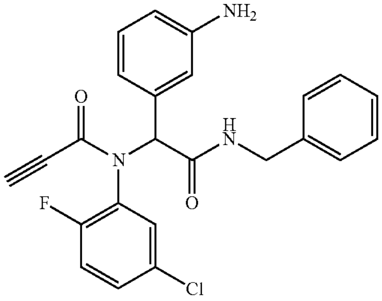,
A41
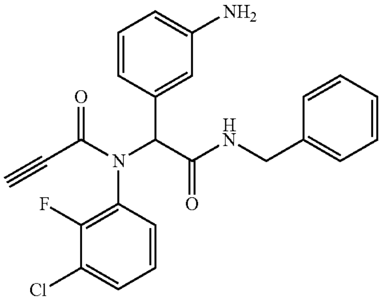,
A42
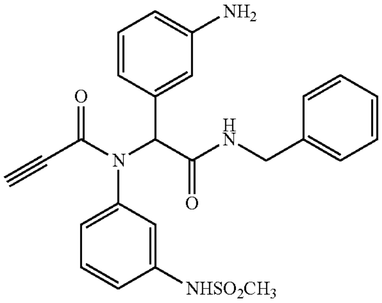,
A43
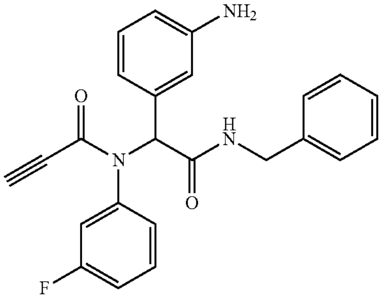,
A44
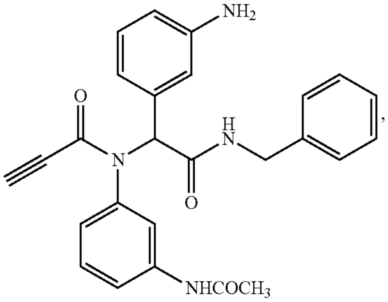, -continued
A45
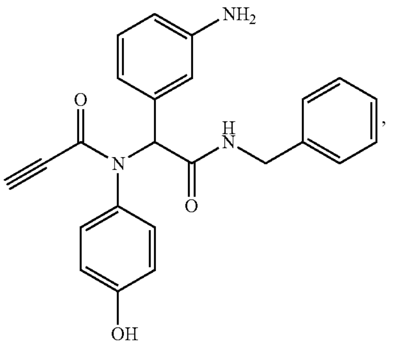
A46
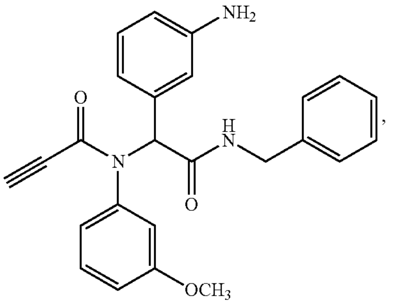
A47
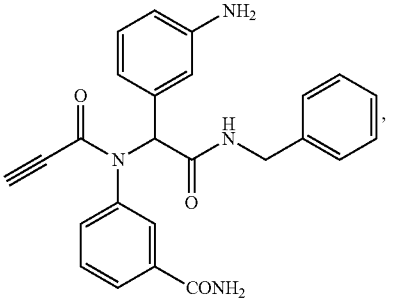
A48
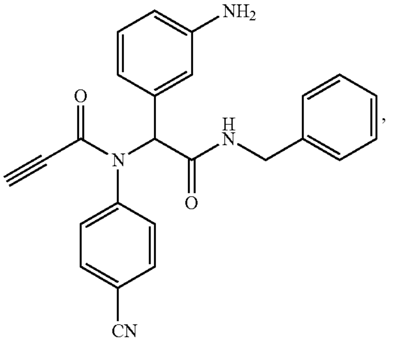
-continued
A49
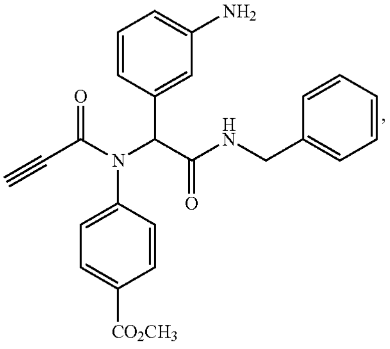
A50
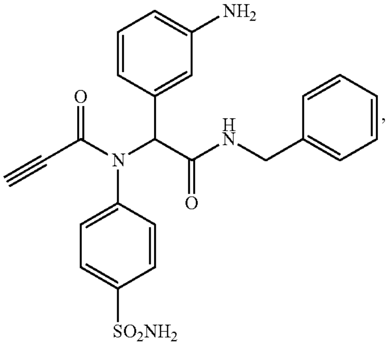
A51
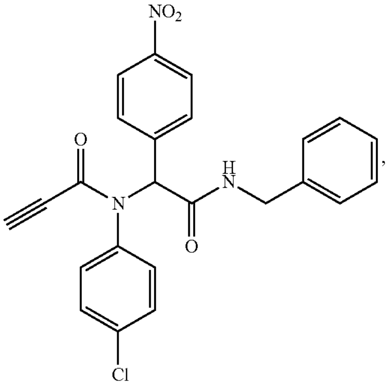
A52
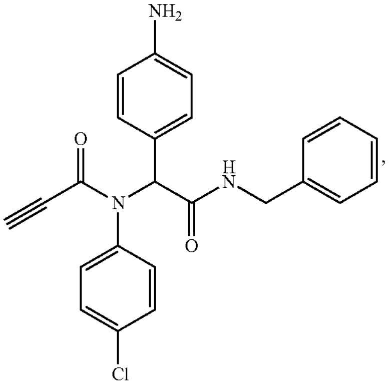

-continued
A53
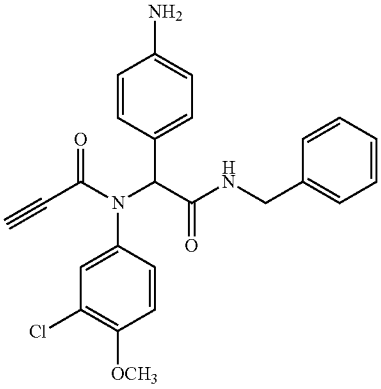
,
A54
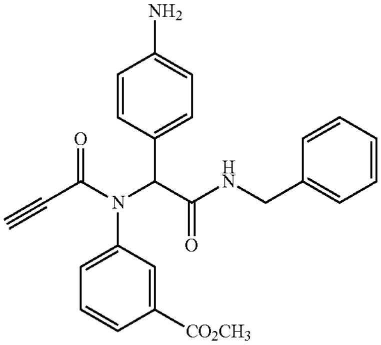
,
A55
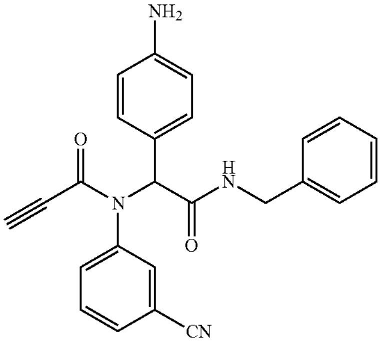
,
A56
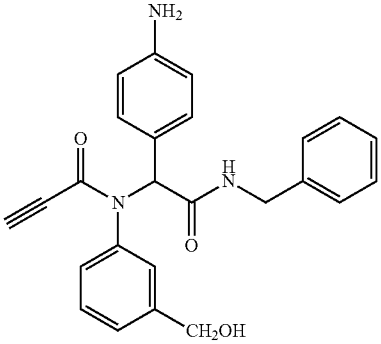
,
-continued
A57
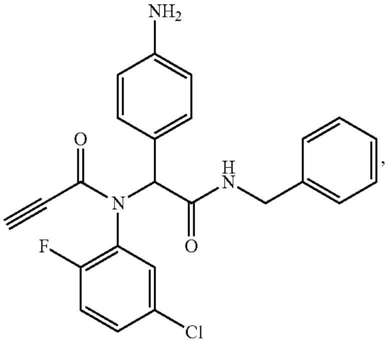
,
A58
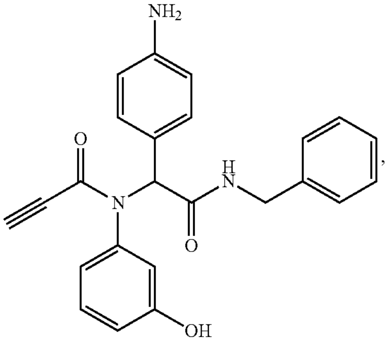
,
A59
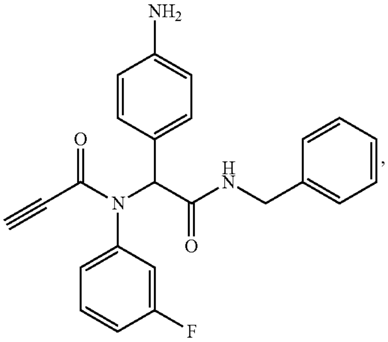
,
A60
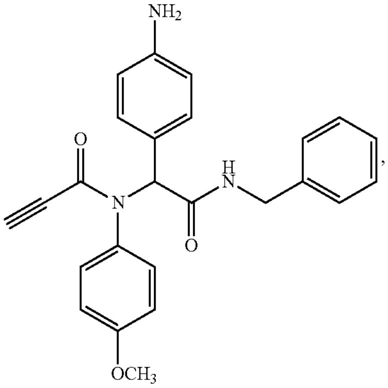
, -continued
A61
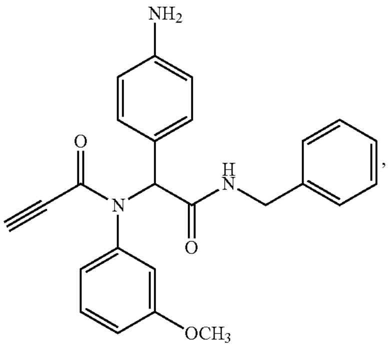
A62
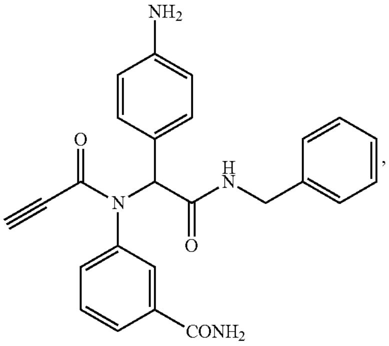
A63
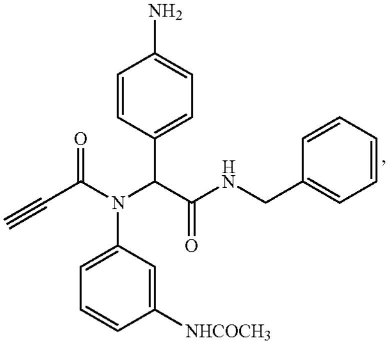
A64
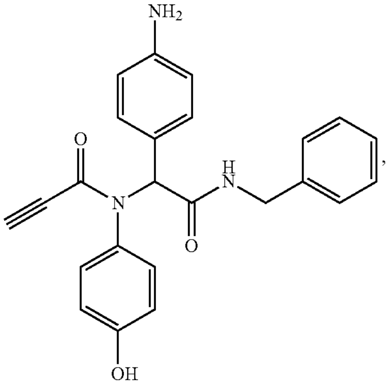
-continued
A65
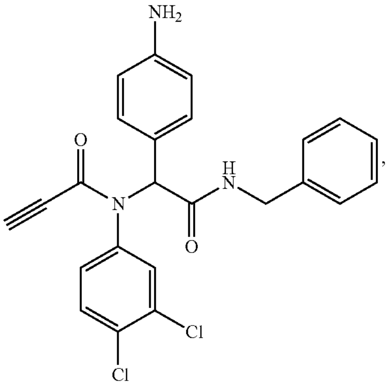
A66
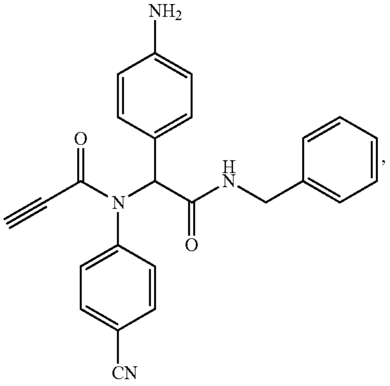
A67
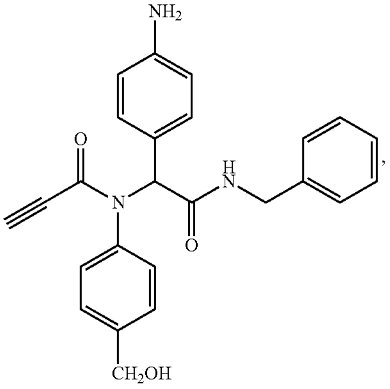
A68
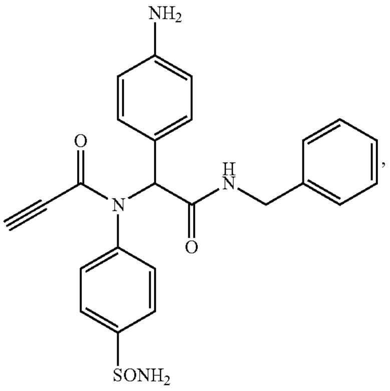

-continued
A69
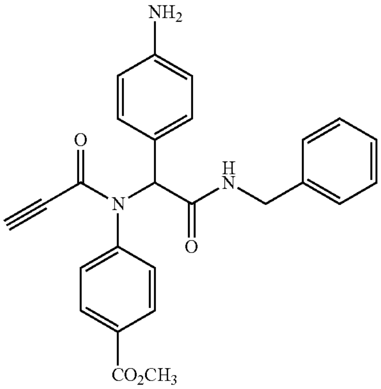
,
A70
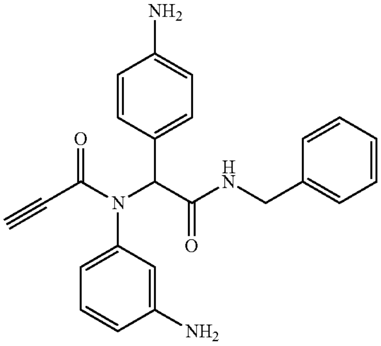
,
A71
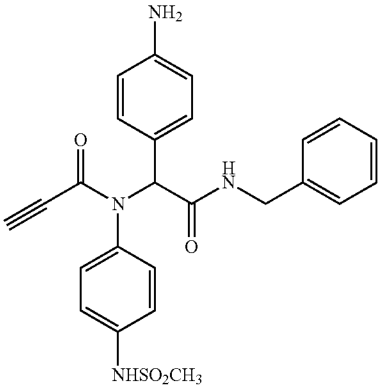
,
A72
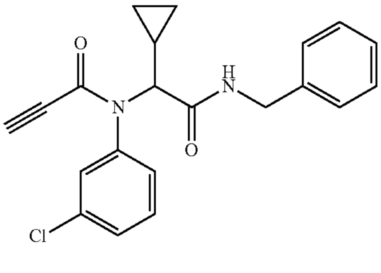
,
-continued
A73
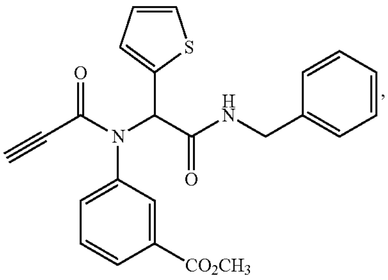
,
A74
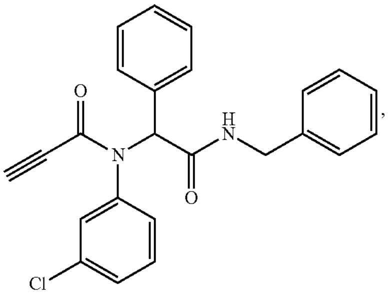
,
A75
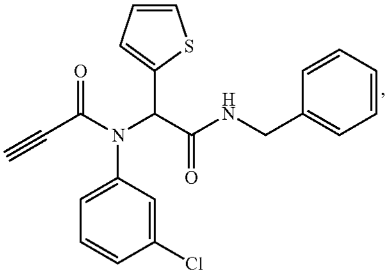
,
A76
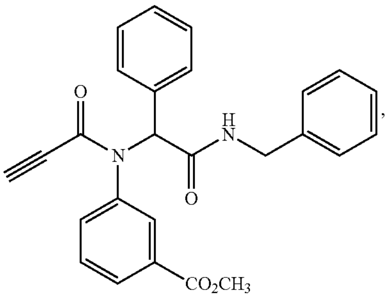
,
A77
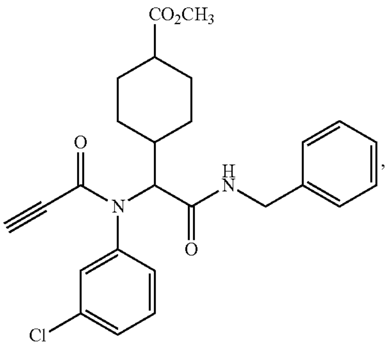
, -continued
A78
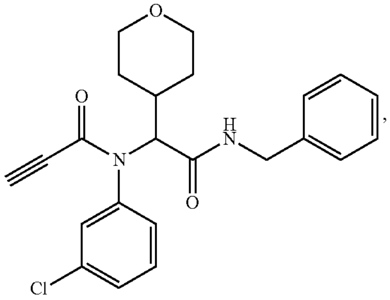
A79
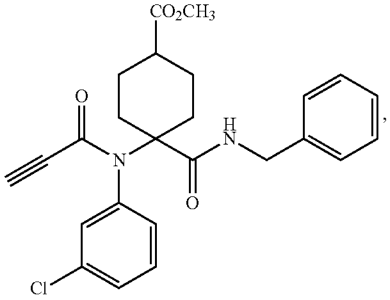
A80
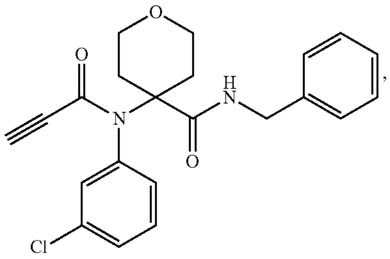
A81
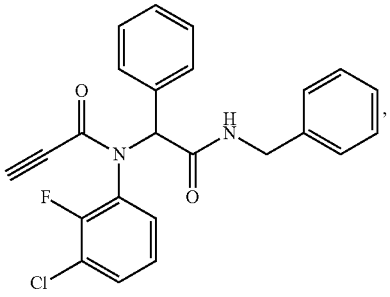
A82
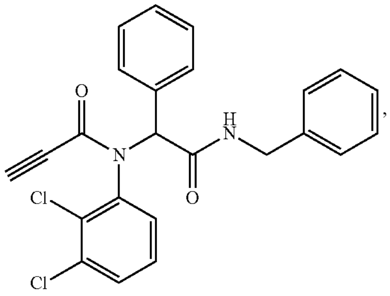
-continued
A83
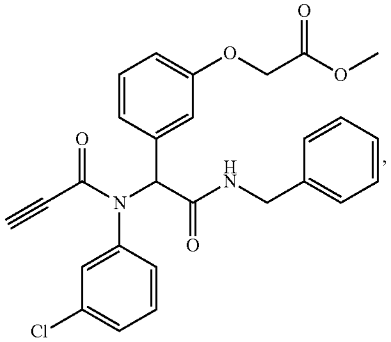
A84
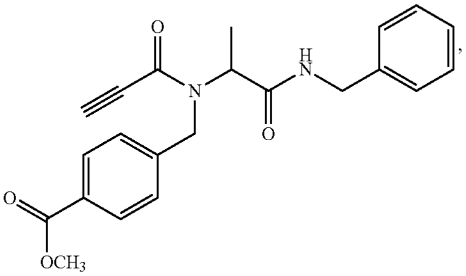
A85
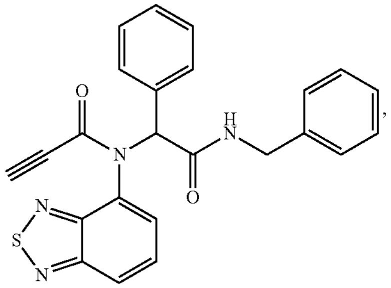
A86
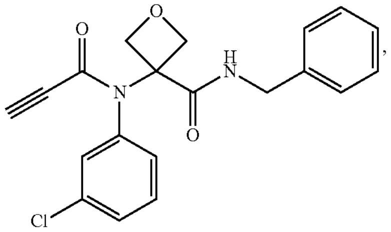
A87
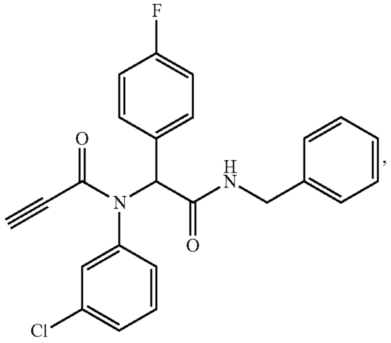

-continued
A88
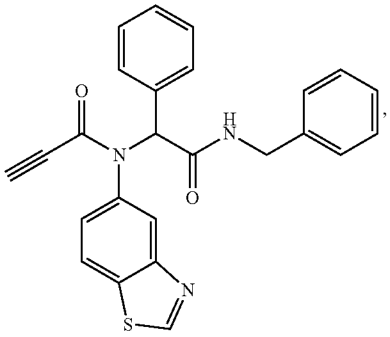
A89
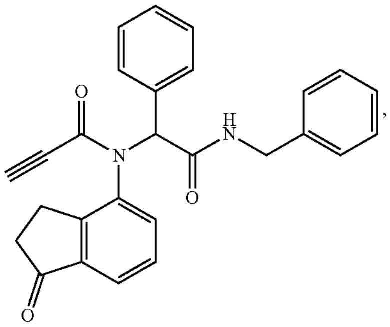
A90
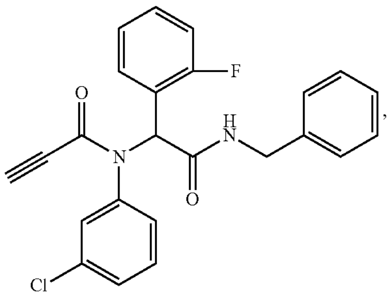
A91
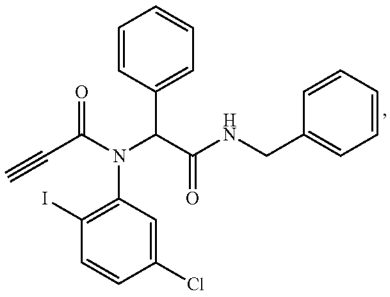
A92
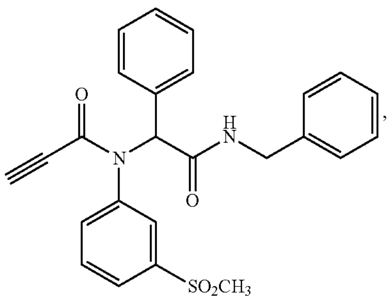
-continued
A93
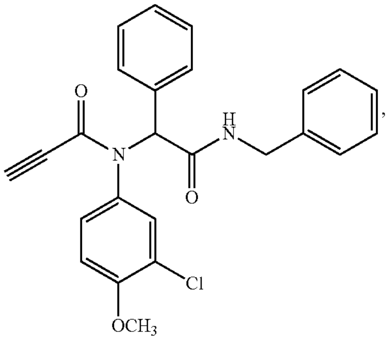
A94
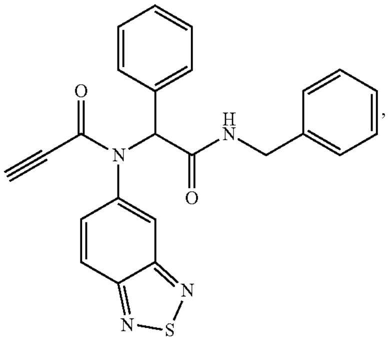
A95
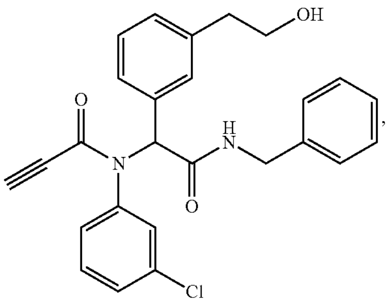
A96
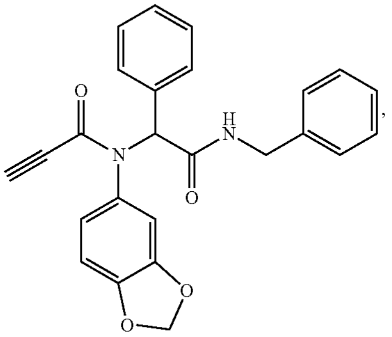
A97
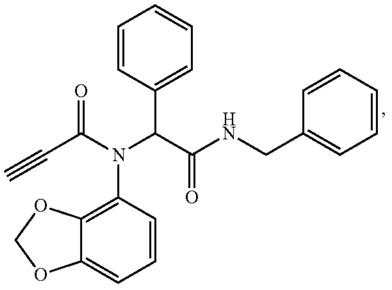

-continued
A98
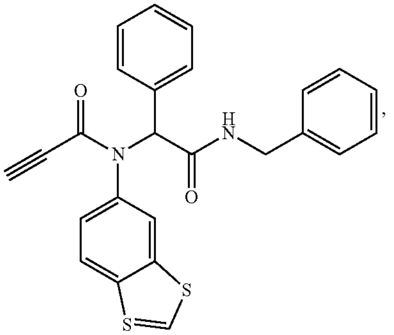
A99
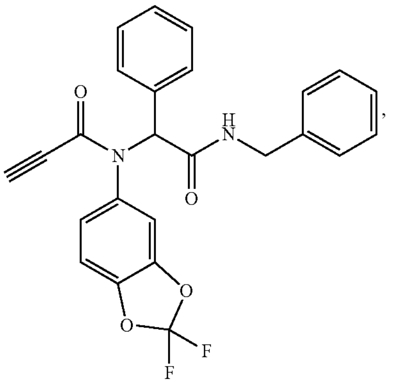
A100
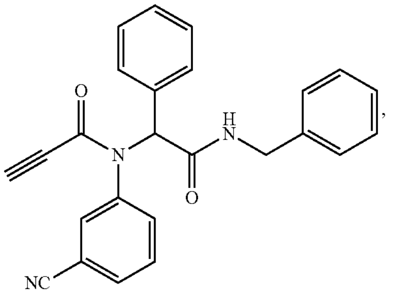
A101
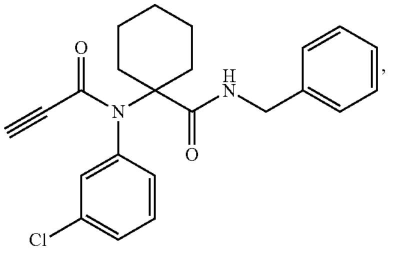
A102
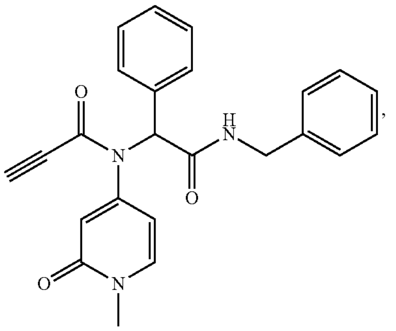
-continued
A103
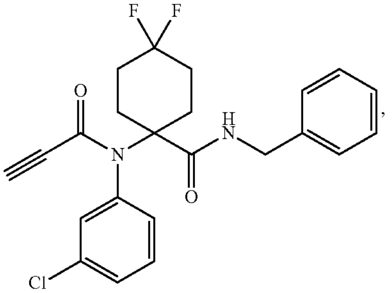
A104
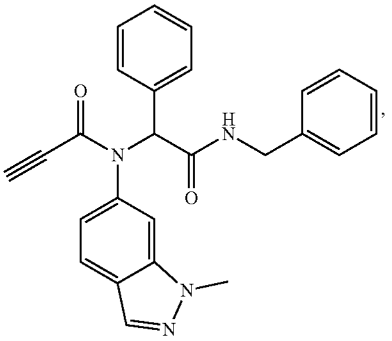
A105
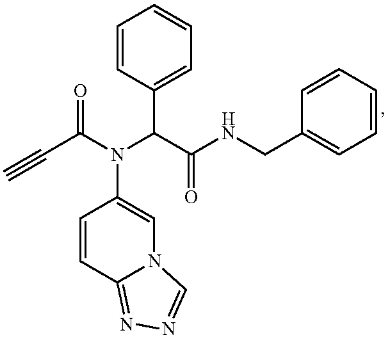
A106
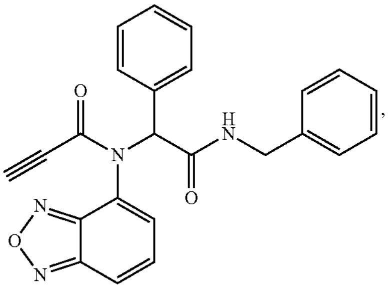
A107
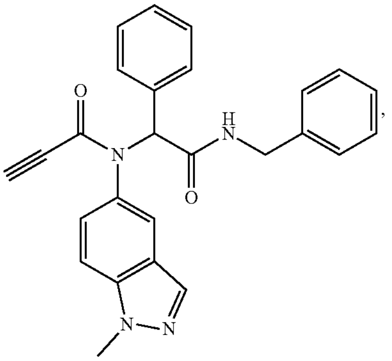

-continued
A108
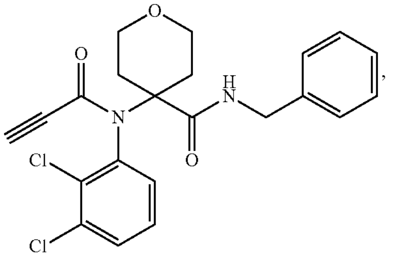
A109
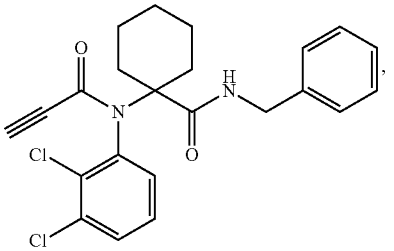
A110
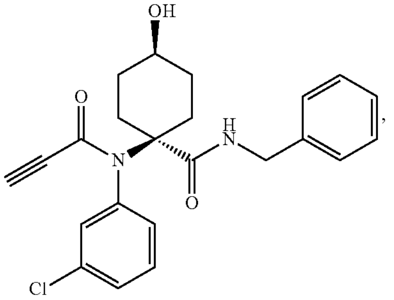
A111
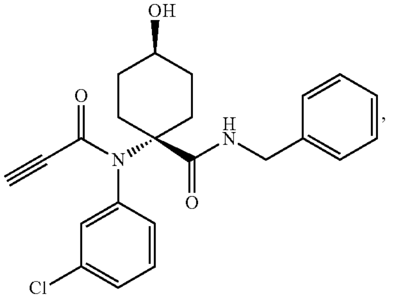
A112
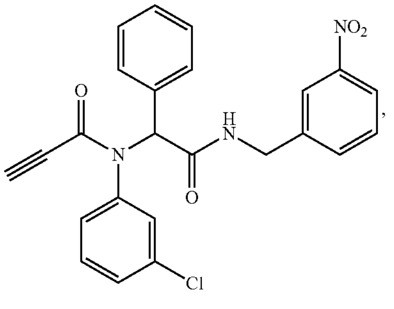
-continued
A113
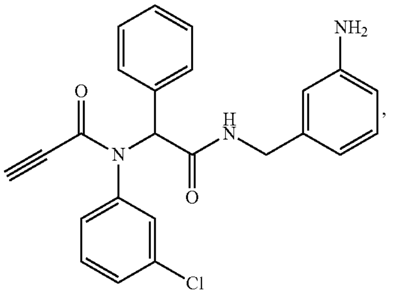
A114
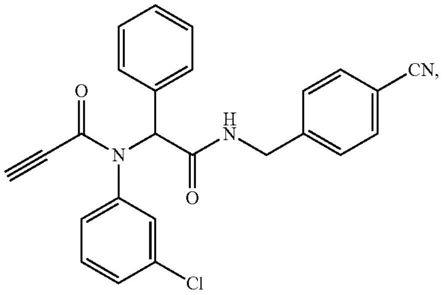
A115
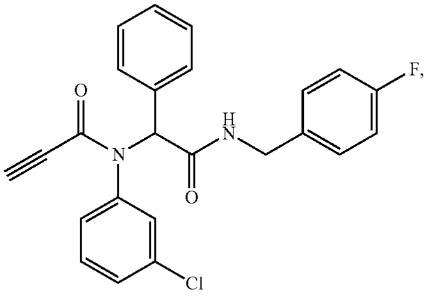
A116
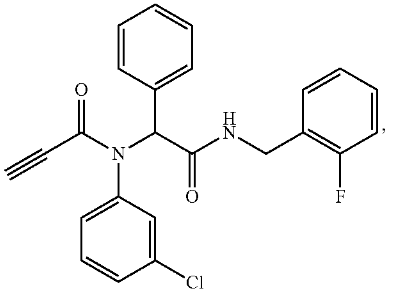
A117
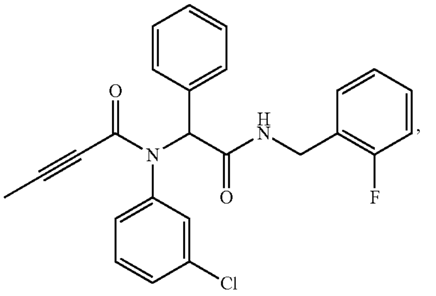

-continued
A118
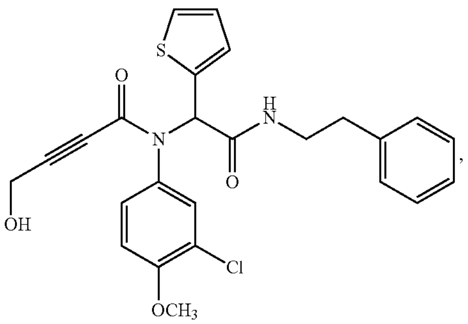
A119
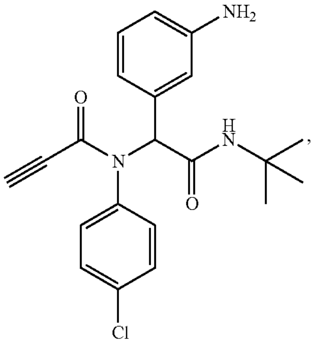
A120
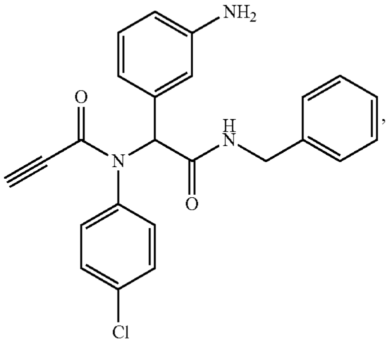
A121
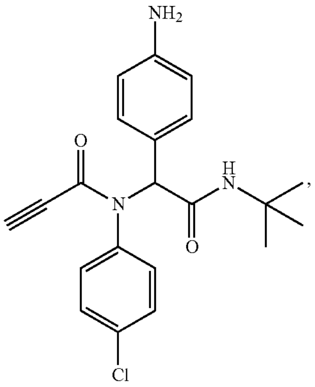
-continued
A122
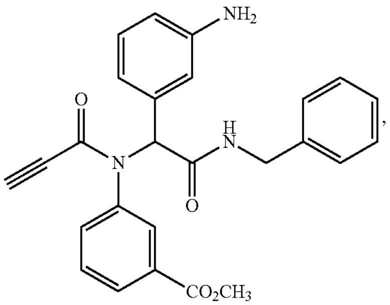
A123
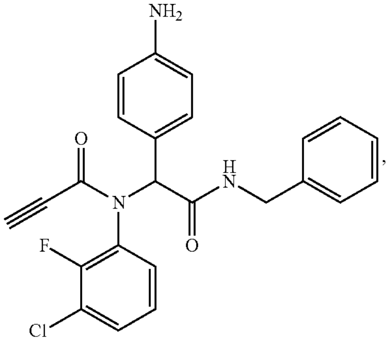
or
A124
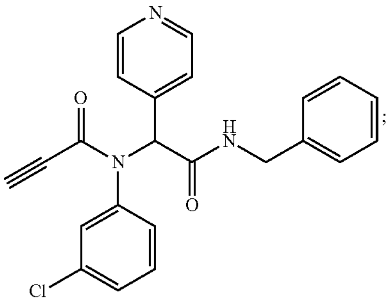
or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.
In another embodiment, provided herein is a compound of:
A125
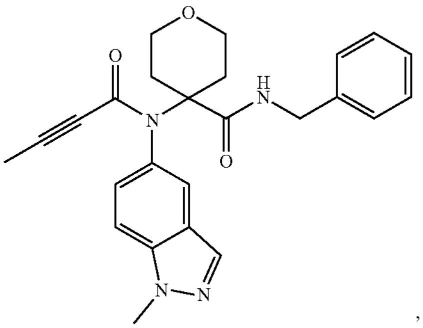
, A126
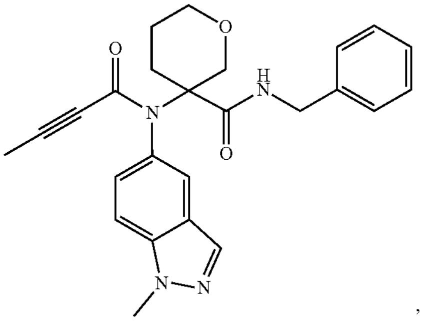
,
A127
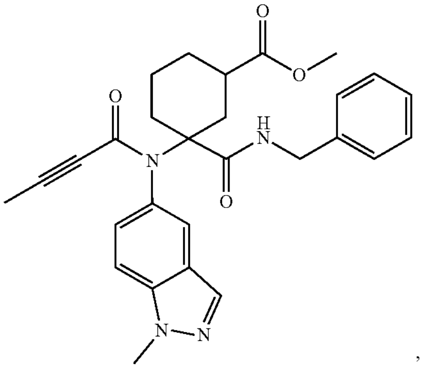
,
A128
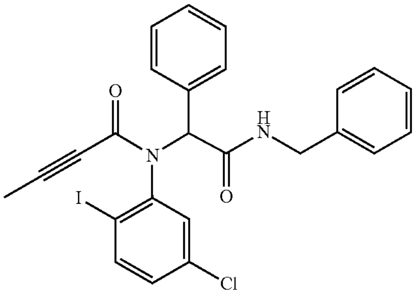
,
A129
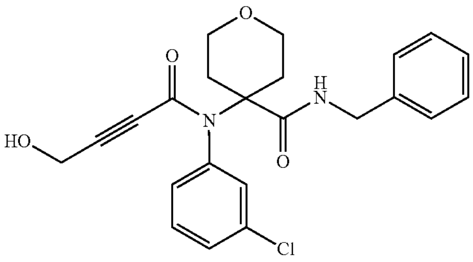
,
A130
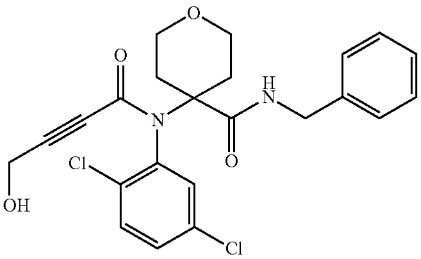
,
A131
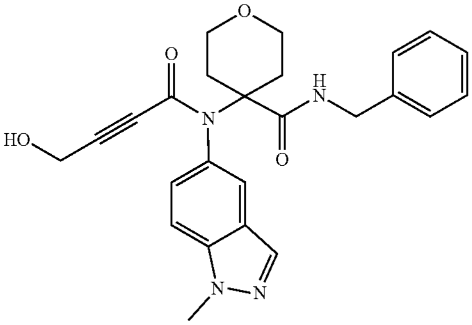
,
A132
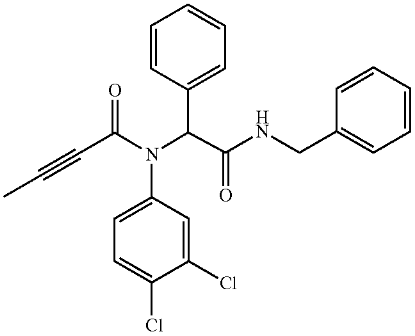
,
A133
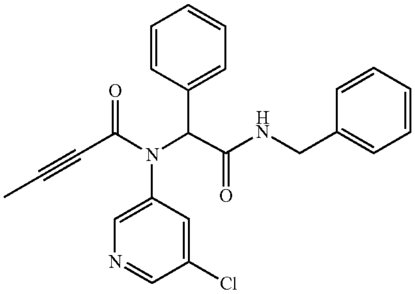
,
A134
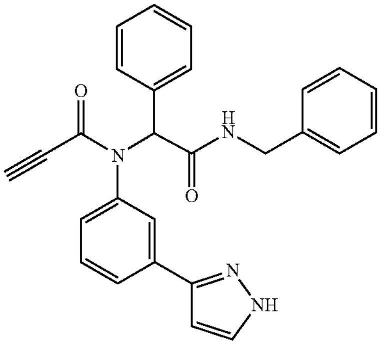
, A135
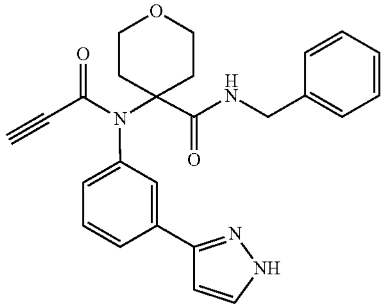
,
A136
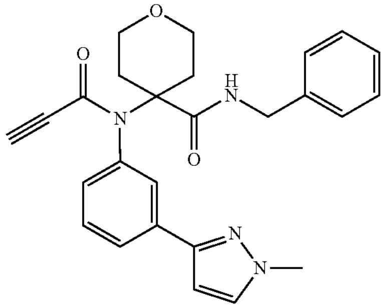
,
A137
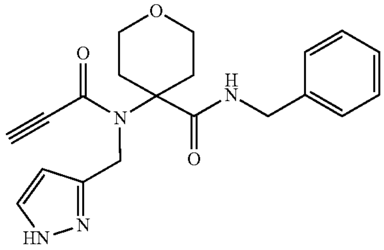
,
A138
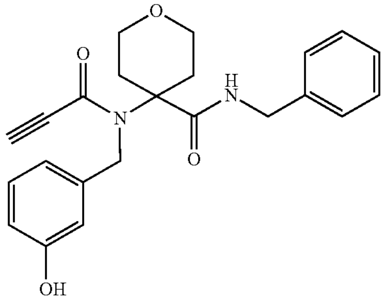
,
A139
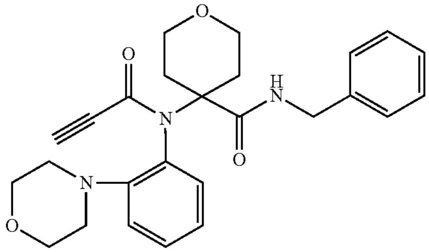
,
A140
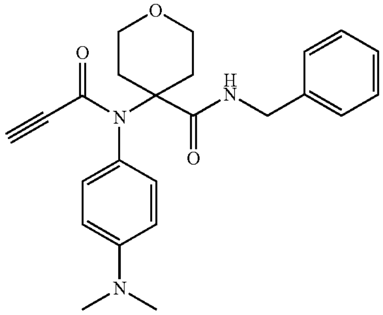
,
A141
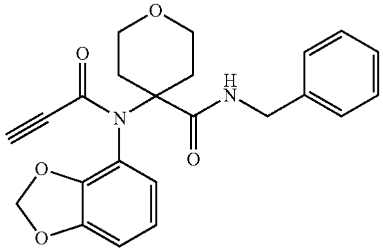
,
A142
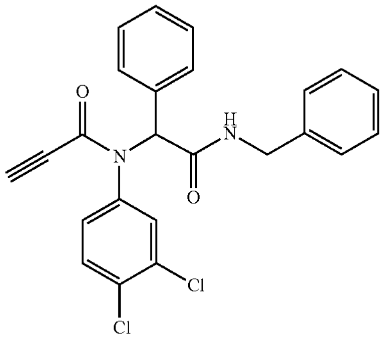
,
A143
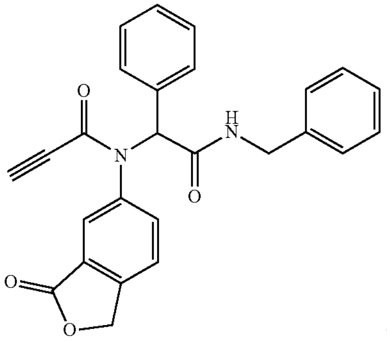
,
A144
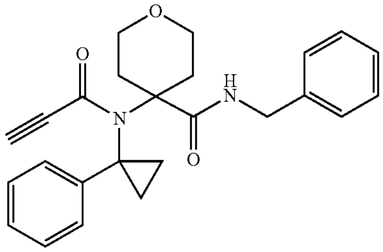
, -continued
A145
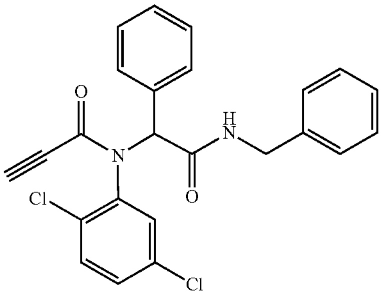
,
A146
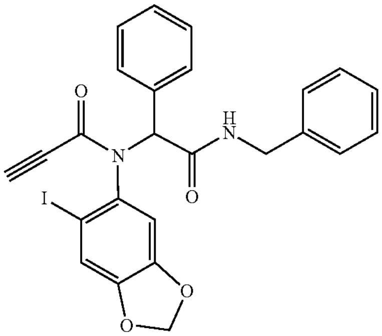
,
A147
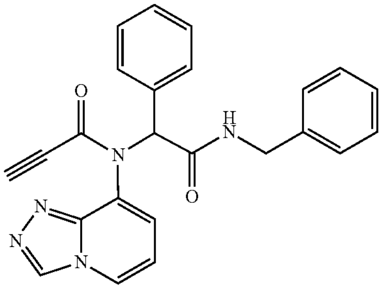
,
A148
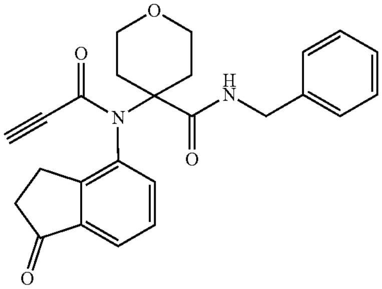
,
A149
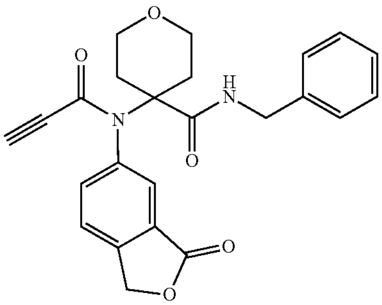
,
-continued
A150
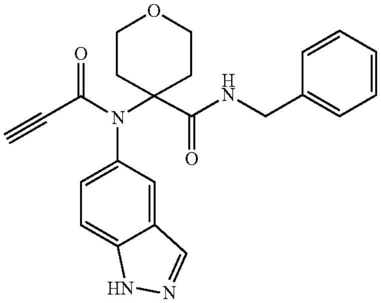
,
A151
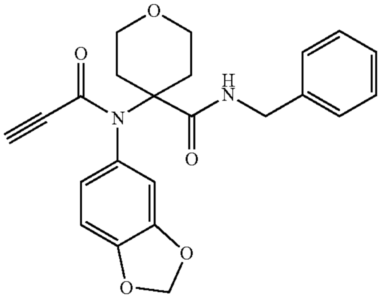
,
A152
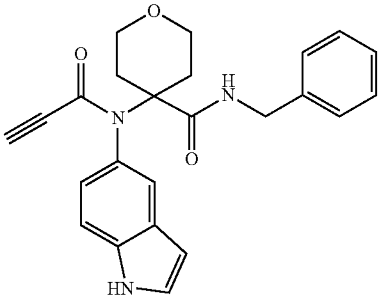
,
A153
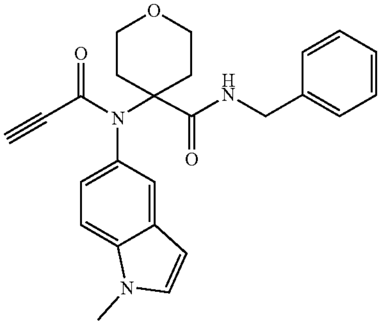
,
A154
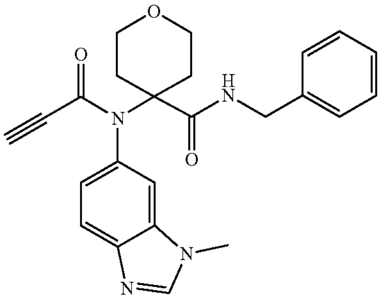
, -continued
A155
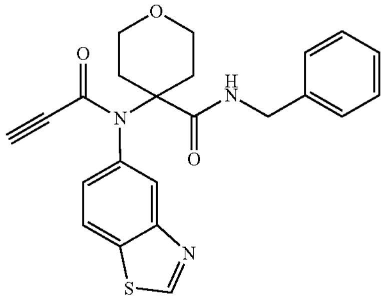
,
A156
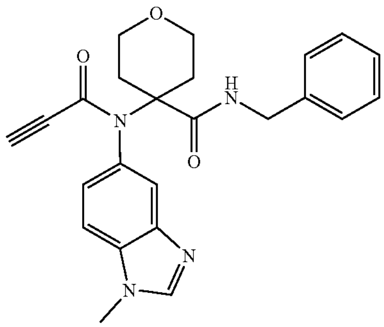
,
A157
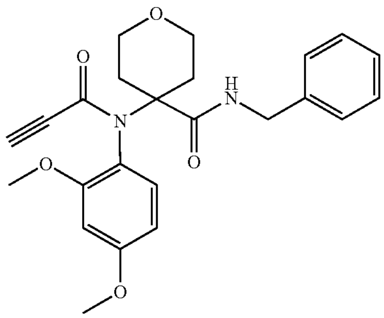
,
A158
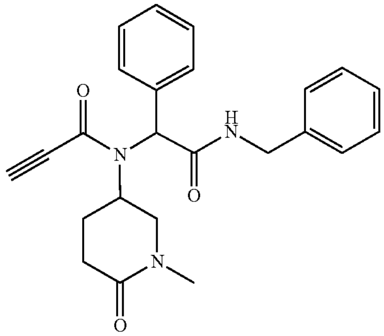
,
A159
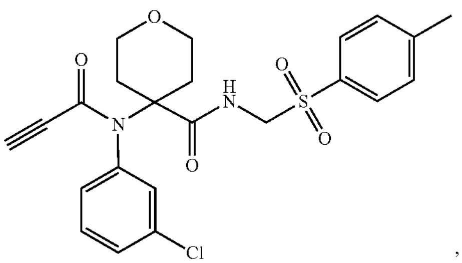
,
-continued
A160
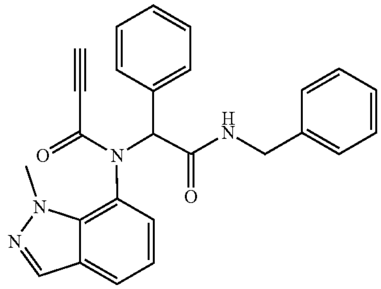
,
A161
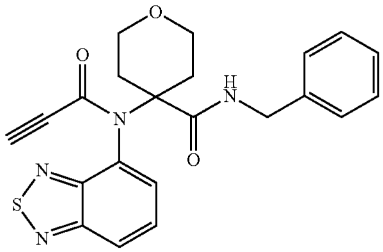
,
A162
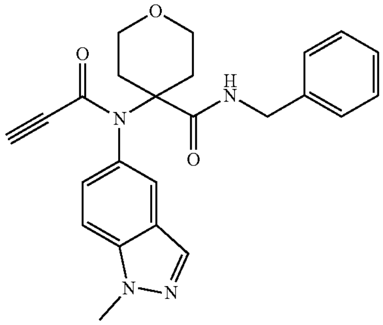
,
A163
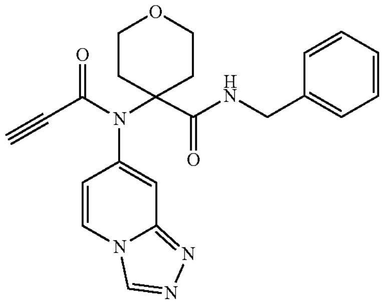
,
A164
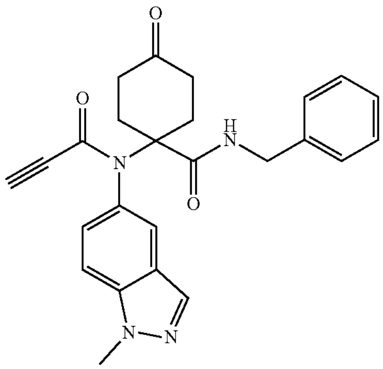
, -continued
A165
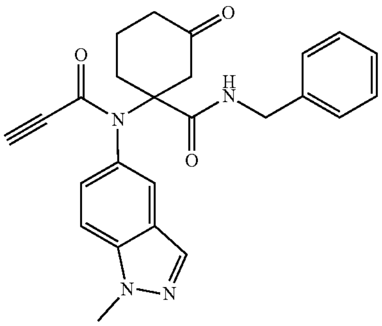
,
A166
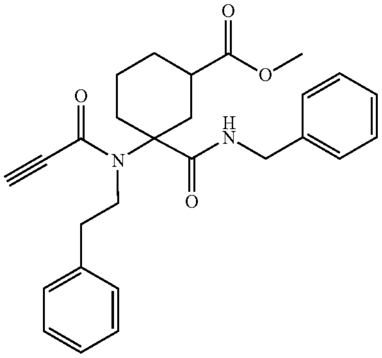
,
A167
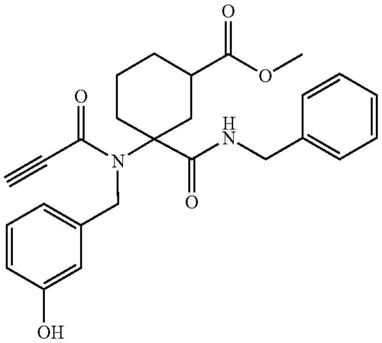
,
A168
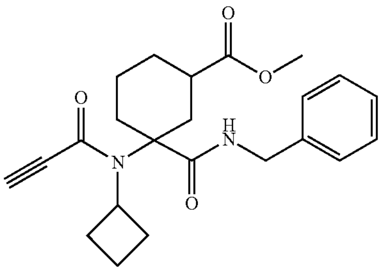
,
-continued
A169
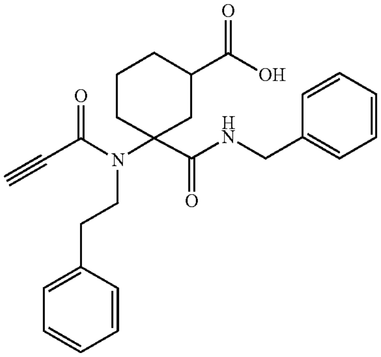
,
A170
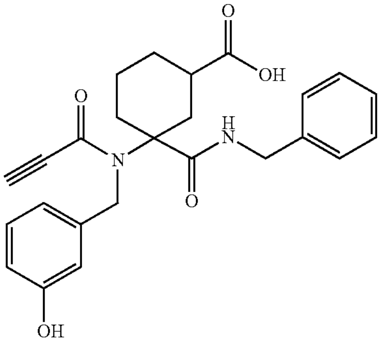
,
A171
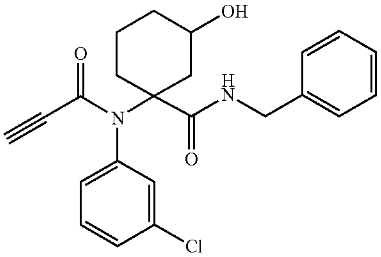
,
A172
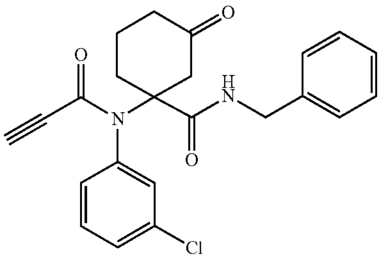
,
A173
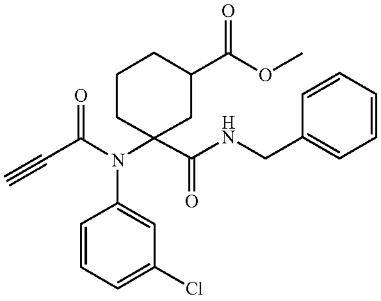
, -continued
A174
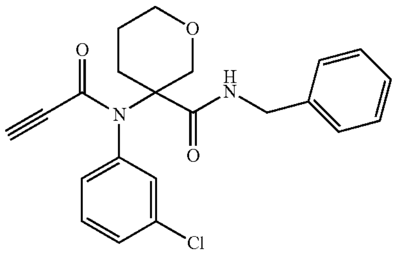
,
A175
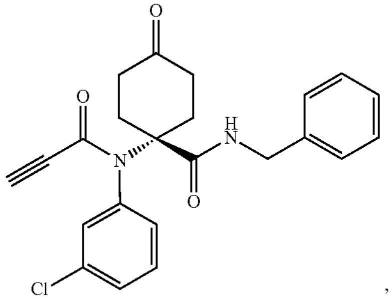
,
A176
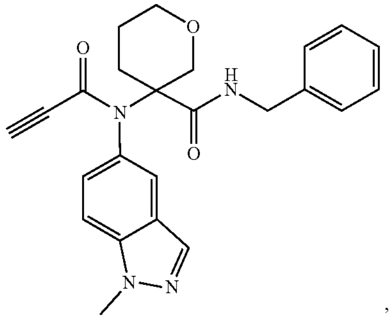
,
A177
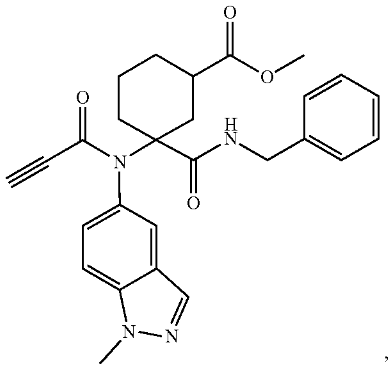
,
A178
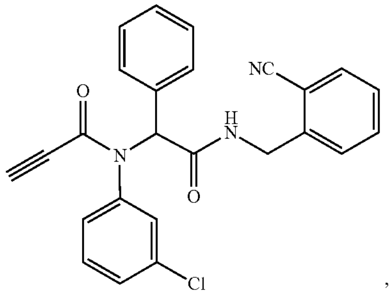
,
-continued
A179
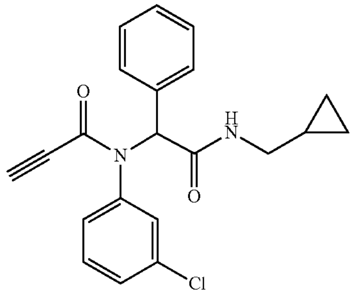
,
A180
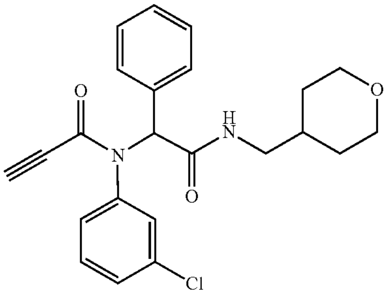
,
A181
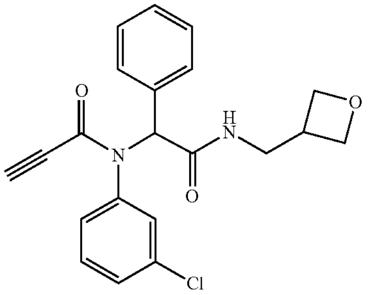
,
A182
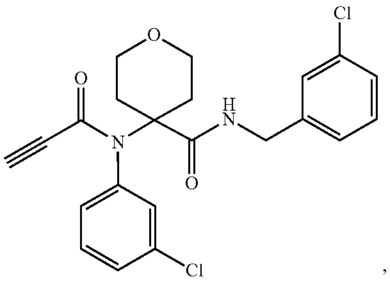
,
A183
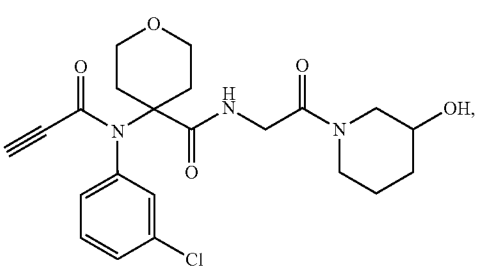
, -continued
A184
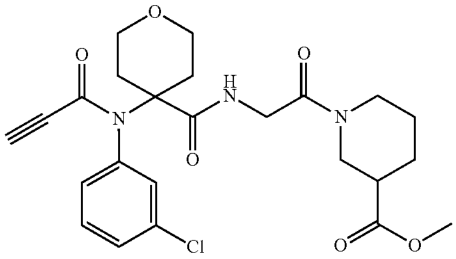,
A185
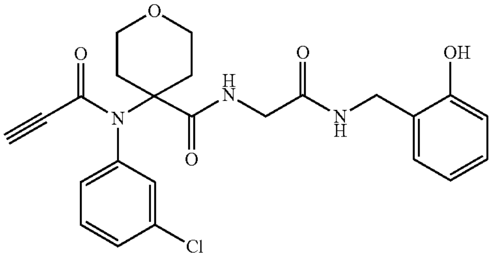,
A186
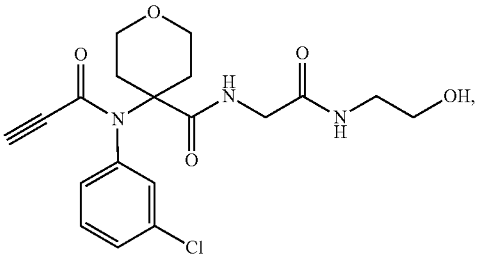
A187
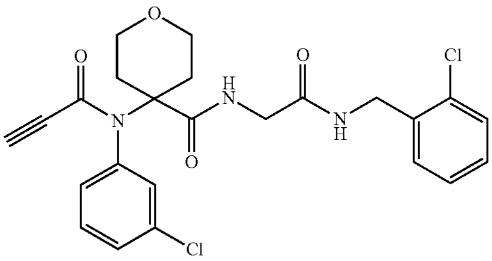,
A188
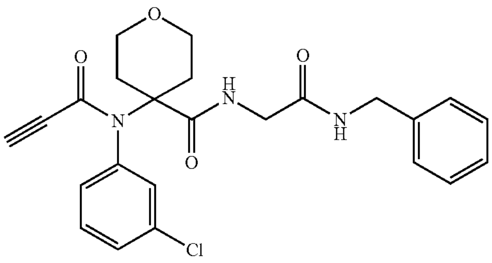,
A189
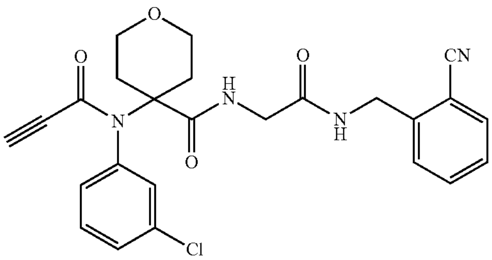,
-continued
A190
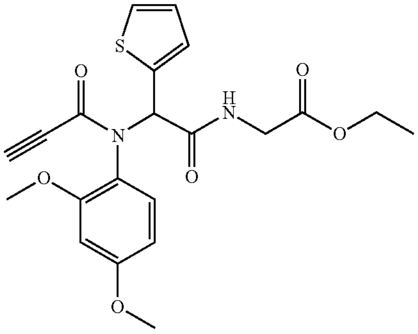,
A191
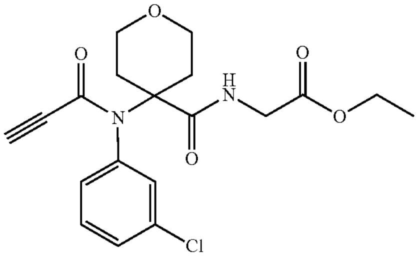,
A192
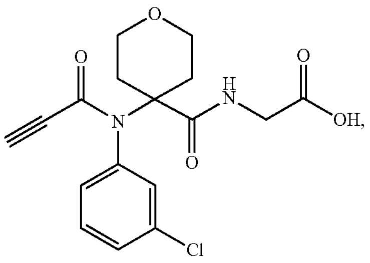
A193
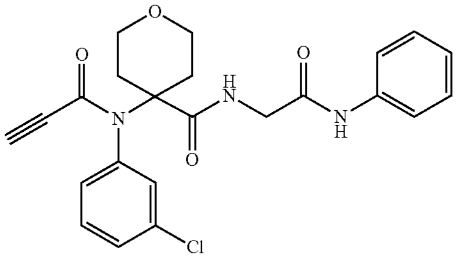,
A194
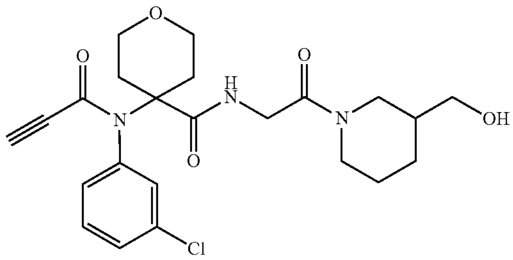, or -continued

A195

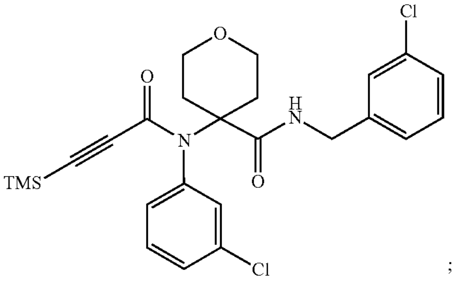

;

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In yet another embodiment, provided herein is a compound of:

B1

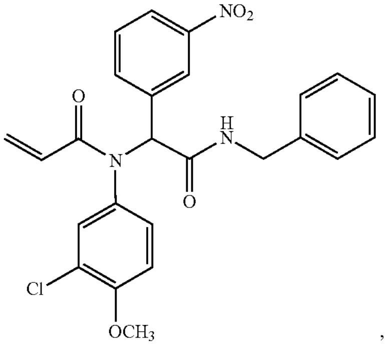

,

B2

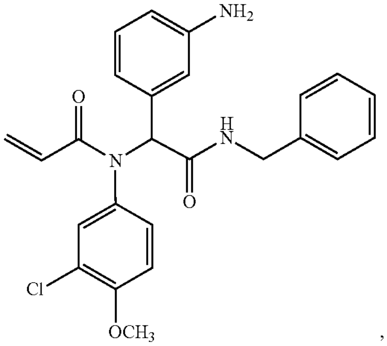

,

B3

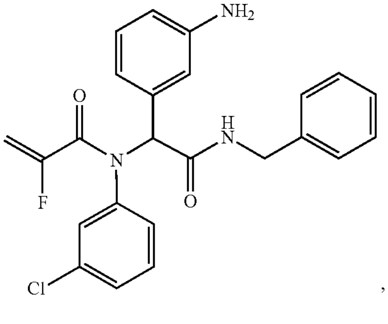

, or

-continued

B4

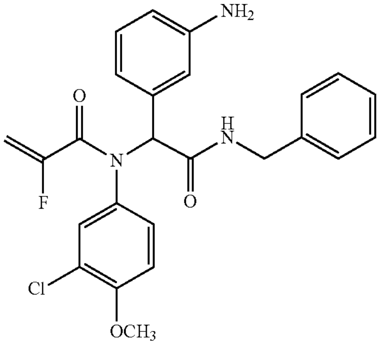

;

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In yet another embodiment, provided herein is a compound of:

B5

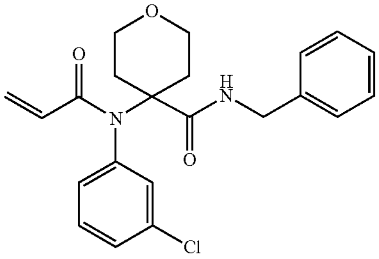

,

B6

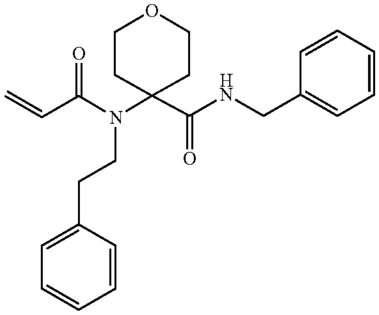

,

B7

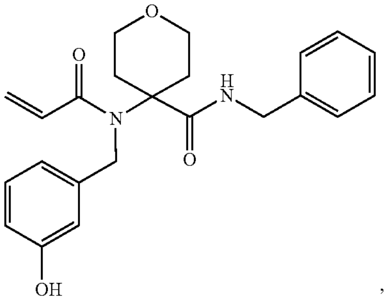

,

-continued
B8
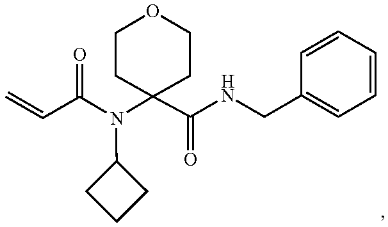
,
B9
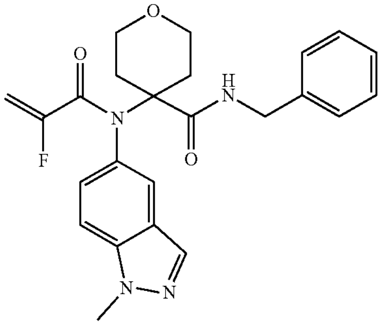
,
B10
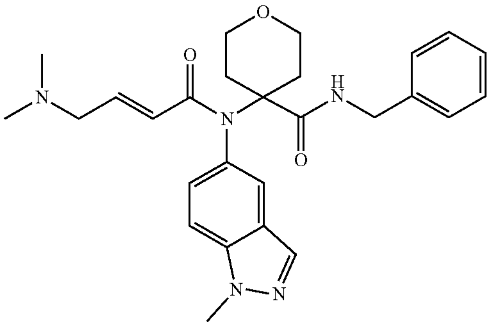
, or
B11
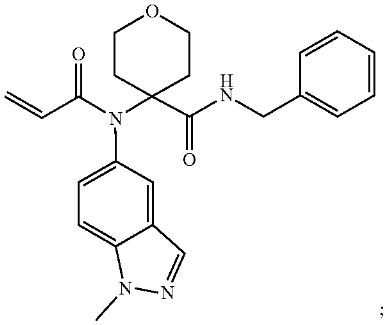
;
or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.
In yet another embodiment, provided herein is a compound of:
C1
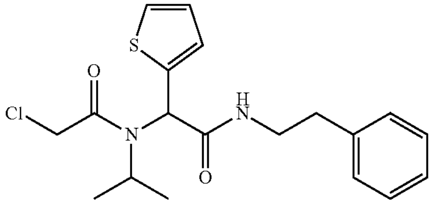
,
C2
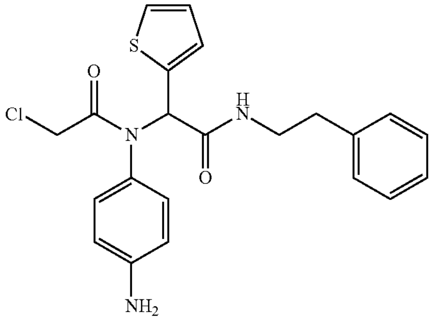
,
C3
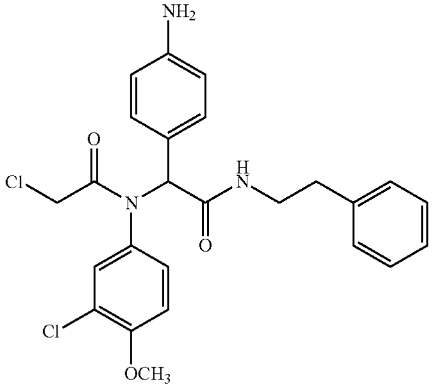
,
C4
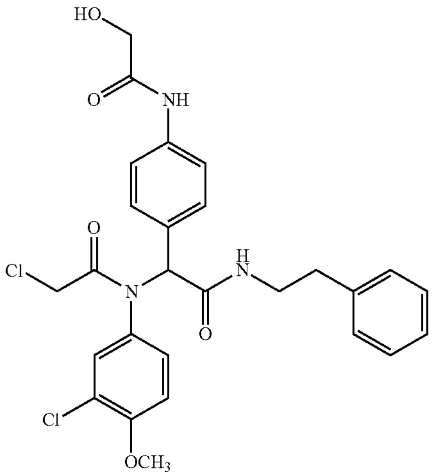
, -continued
C5
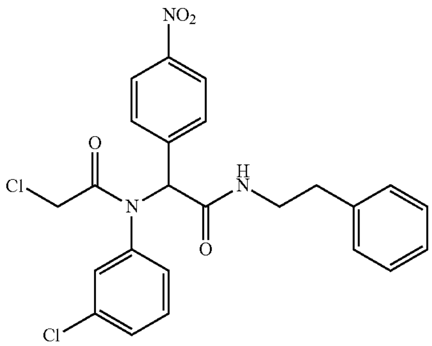
,
C6
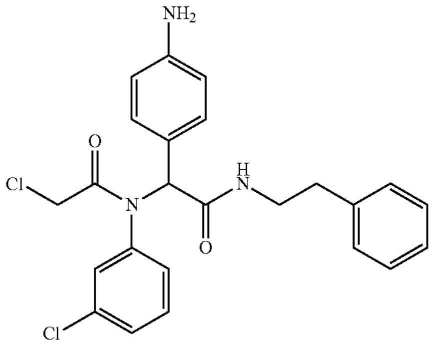
,
C7
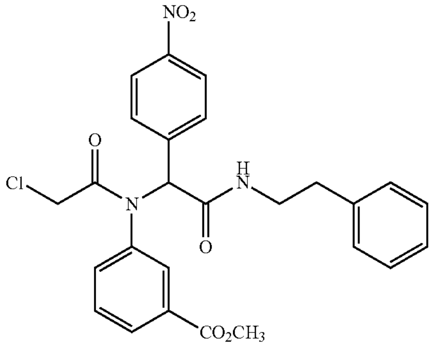
,
C8
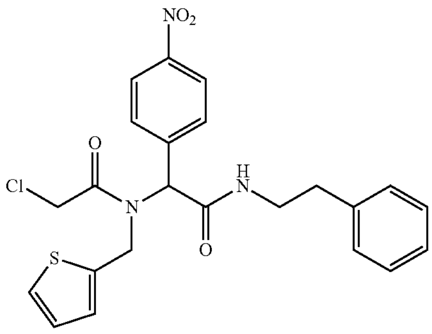
,
-continued
C9
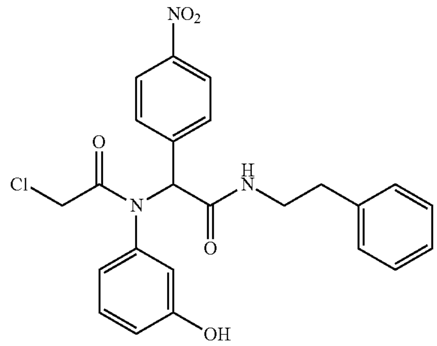
,
C10
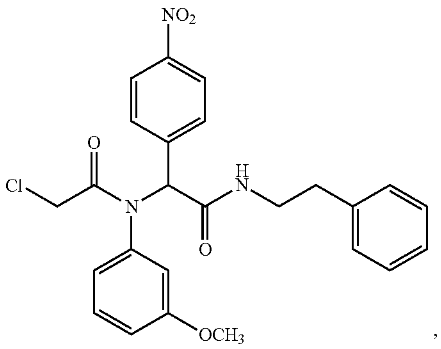
,
C11
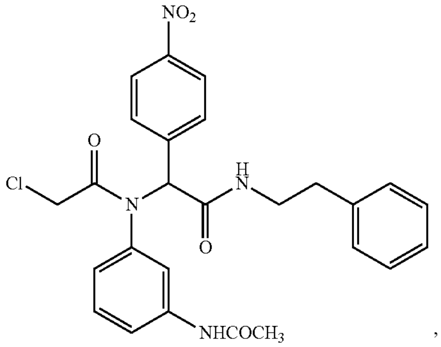
,
C12
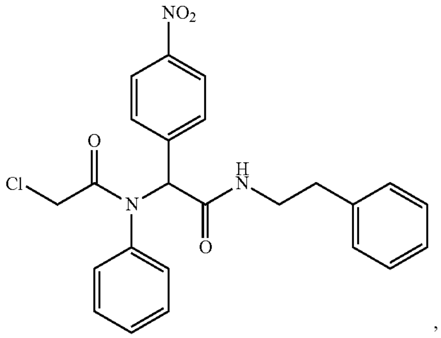
, -continued
C13
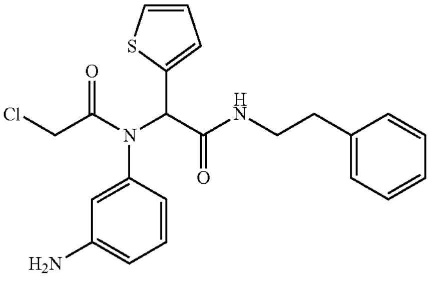
,
C14
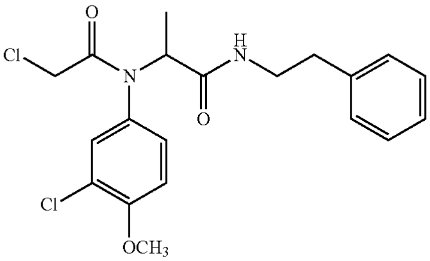
,
C15
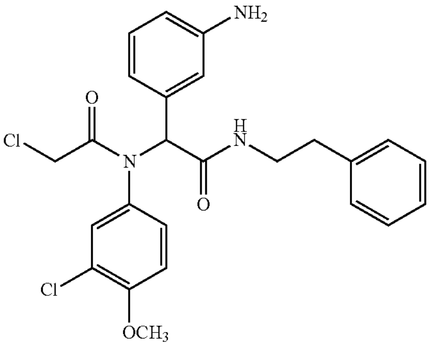
,
C16
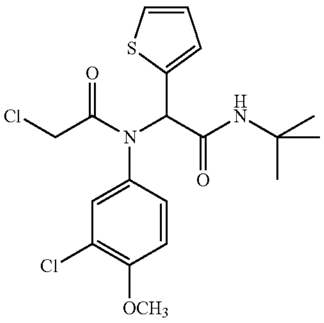
,
C17
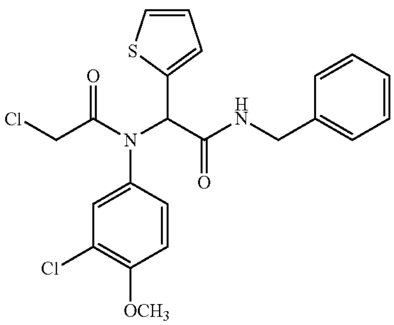
, or
-continued
C18
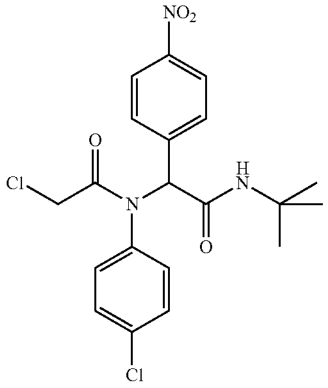
;
or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.
In yet another embodiment, provided herein is a compound of:
C19
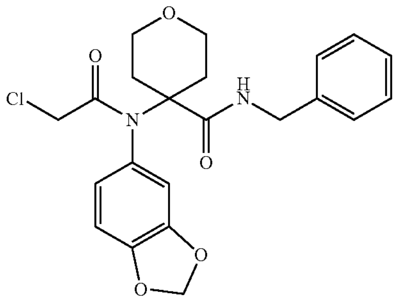
,
C20
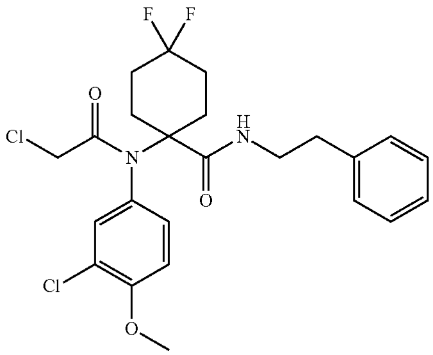
,
C21
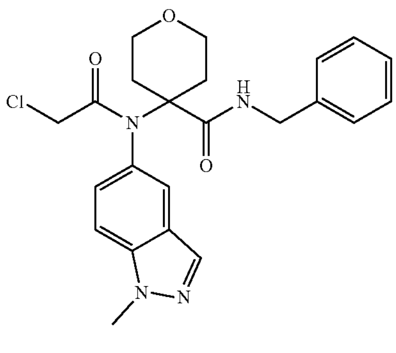
, -continued
C22
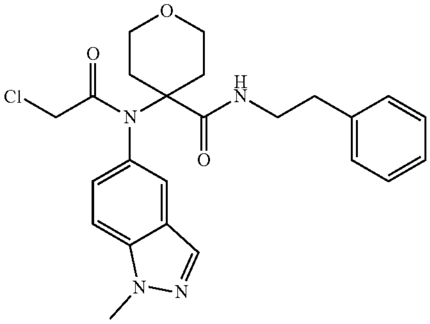
,
C23
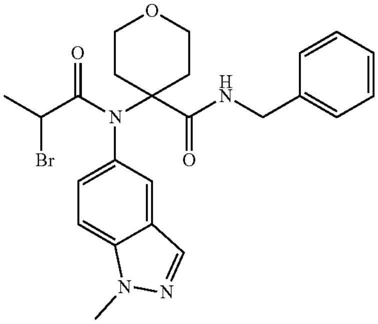
,
C24
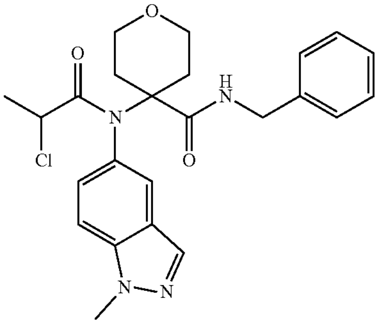
,
C25
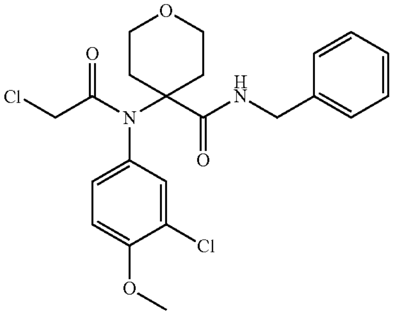
,
C26
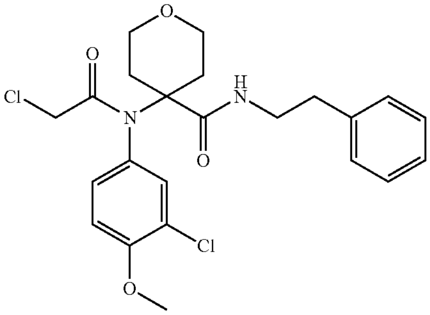
,
-continued
C27
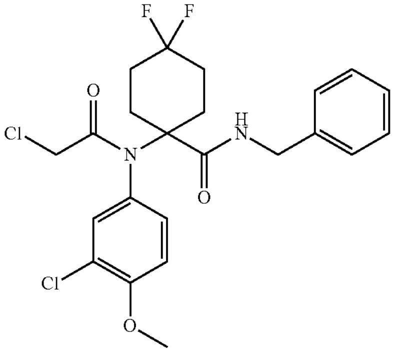
,
C28
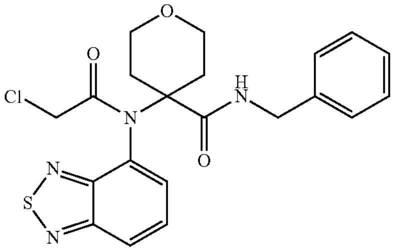
,
C29
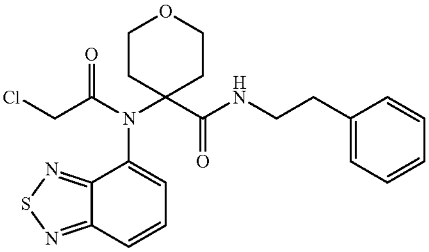
, or
C30
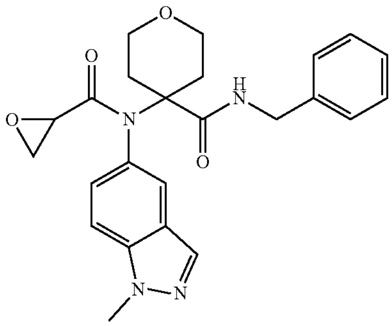
;
or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In still another embodiment, provided herein is a compound of:

D1

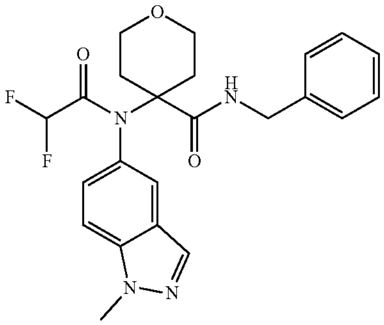

,

D2

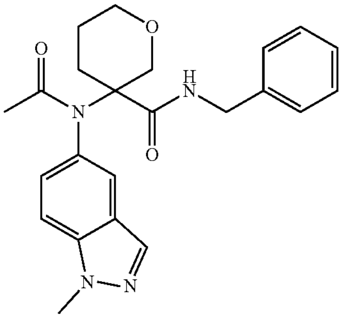

,

D3

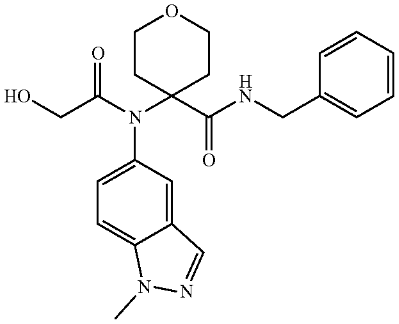

,

D4

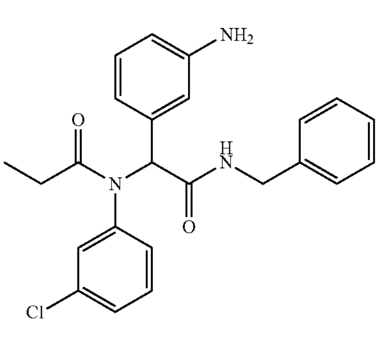

,

-continued

D5

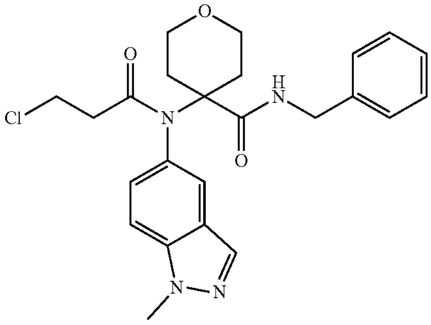

,

D6

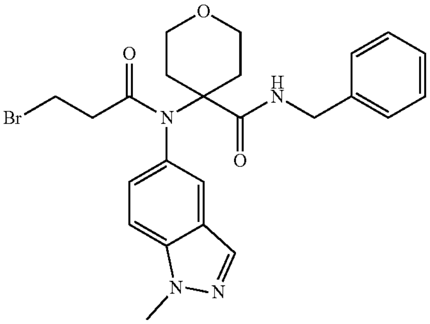

, or

D7

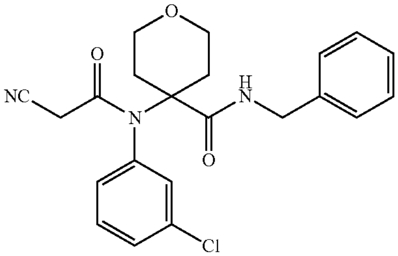

;

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In certain embodiments, a compound provided herein is deuterium-enriched. In certain embodiments, a compound provided herein is carbon-13 enriched. In certain embodiments, a compound provided herein is carbon-14 enriched. In certain embodiments, a compound provided herein contains one or more less prevalent isotopes for other elements, including, but not limited to, $^{15}N$ for nitrogen; $^{17}O$ or $^{18}O$ for oxygen, and $^{34}S$, $^{35}S$, or $^{36}S$ for sulfur.

In certain embodiments, a compound provided herein has an isotopic enrichment factor of no less than about 5, no less than about 10, no less than about 20, no less than about 50, no less than about 100, no less than about 200, no less than about 500, no less than about 1,000, no less than about 2,000, no less than about 5,000, or no less than about 10,000. In any events, however, an isotopic enrichment factor for a specified isotope is no greater than the maximum isotopic enrichment factor for the specified isotope, which is the isotopic enrichment factor when a compound at a given position is 100% enriched with the specified isotope. Thus, the maximum isotopic enrichment factor is different for different isotopes. The maximum isotopic enrichment factor is 6,410 for deuterium and 90 for carbon-13.

In certain embodiments, a compound provided herein has a deuterium enrichment factor of no less than about 64 (about 1% deuterium enrichment), no less than about 130 (about 2% deuterium enrichment), no less than about 320 (about 5% deuterium enrichment), no less than about 640 (about 10% deuterium enrichment), no less than about 1,300 (about 20% deuterium enrichment), no less than about 3,200 (about 50% deuterium enrichment), no less than about 4,800 (about 75% deuterium enrichment), no less than about 5,130 (about 80% deuterium enrichment), no less than about 5,450 (about 85% deuterium enrichment), no less than about 5,770 (about 90% deuterium enrichment), no less than about 6,090 (about 95% deuterium enrichment), no less than about 6,220 (about 97% deuterium enrichment), no less than about 6,280 (about 98% deuterium enrichment), no less than about 6,350 (about 99% deuterium enrichment), or no less than about 6,380 (about 99.5% deuterium enrichment). The deuterium enrichment can be determined using conventional analytical methods known to one of ordinary skill in the art, including mass spectrometry and nuclear magnetic resonance spectroscopy. In certain embodiments, at least one of the atoms of a compound provided herein, as specified as deuterium-enriched, has deuterium enrichment of no less than about 1%, no less than about 2%, no less than about 5%, no less than about 10%, no less than about 20%, no less than about 50%, no less than about 70%, no less than about 80%, no less than about 90%, or no less than about 98%.

In certain embodiments, a compound provided herein is isolated or purified. In certain embodiments, a compound provided herein has a purity of at least about 90%, at least about 95%, at least about 98%, at least about 99%, or at least about 99.5% by weight.

The compounds provided herein are intended to encompass all possible stereoisomers, unless a particular stereochemistry is specified. Where a compound provided herein contains an alkenyl group, the compound may exist as one or mixture of geometric cis/trans (or Z/E) isomers. Where structural isomers are interconvertible, the compound may exist as a single tautomer or a mixture of tautomers. This can take the form of proton tautomerism in the compound that contains, for example, an imino, keto, or oxime group; or so-called valence tautomerism in the compound that contains an aromatic moiety. It follows that a single compound may exhibit more than one type of isomerism.

The compound provided herein can be enantiomerically pure, such as a single enantiomer or a single diastereomer, or be stereoisomeric mixtures, such as a mixture of enantiomers, e.g., a racemic mixture of two enantiomers; or a mixture of two or more diastereomers. As such, one of ordinary skill in the art will recognize that administration of a compound in its (R) form is equivalent, for the compound that undergoes epimerization in vivo, to administration of the compound in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

When a compound provided herein contains an acidic or basic moiety, it can also be provided as a pharmaceutically acceptable salt. See, Berge et al., *J. Pharm. Sci.* 1977, 66, 1-19; *Handbook of Pharmaceutical Salts: Properties, Selection, and Use,* 2nd ed.; Stahl and Wermuth Eds.; John Wiley & Sons, 2011. In certain embodiments, a pharmaceutically acceptable salt of a compound provided herein is a solvate. In certain embodiments, a pharmaceutically acceptable salt of a compound provided herein is a hydrate.

Suitable acids for use in the preparation of pharmaceutically acceptable salts of a compound provided herein include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-aminosalicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts of a compound provided herein include, but are not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including, but not limited to, L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, triethanolamine, trimethylamine, triethylamine, N-methyl-D-glucamine, 2-amino-2-(hydroxymethyl)-1,3-propanediol, and tromethamine.

A compound provided herein may also be provided as a prodrug, which is a functional derivative of the compound and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis.

Methods of Synthesis

The compounds provided herein can be prepared, isolated, or obtained by any method known to one of ordinary skill in the art, for example, by following the procedures described by Boltjes et al. (*Org. Synth.* 2017, 94, 54-65). In certain embodiments, a compound provided herein, e.g., a compound of Formula (X), is synthesized by the Ugi reaction as shown in Scheme A, where $R^1$, $R^3$, $R^4$, $R^5$, and $R^6$ are each as defined herein and $R^Y$ is hydrogen.

Scheme A

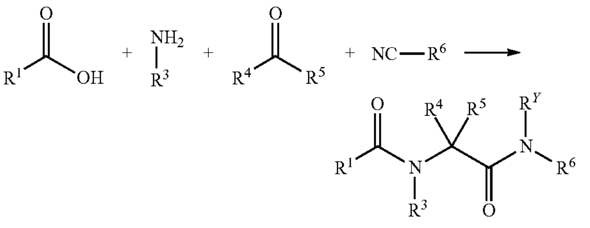

(X)

Pharmaceutical Compositions

In one embodiment, provided herein is a pharmaceutical composition, comprising a compound of Formula (I), or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and a pharmaceutically acceptable excipient.

The pharmaceutical composition provided herein can be formulated in various dosage forms, including, but not limited to, dosage forms for oral, parenteral, and topical administration. The pharmaceutical composition can also be formulated as modified release dosage forms, including delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art. See, e.g., *Remington: The Science and Practice of Pharmacy, supra; Modified-Release Drug Delivery Technology,* 2nd ed.; Rathbone et al., Eds.; Drugs and the Pharmaceutical Sciences 184; CRC Press: Boca Raton, F L, 2008.

In one embodiment, the pharmaceutical composition provided herein is formulated in a dosage form for oral administration. In another embodiment, the pharmaceutical composition provided herein is formulated in a dosage form for parenteral administration. In yet another embodiment, the pharmaceutical composition provided herein is formulated in a dosage form for intravenous administration. In yet another embodiment, the pharmaceutical composition provided herein is formulated in a dosage form for intramuscular administration. In yet another embodiment, the pharmaceutical composition provided herein is formulated in a dosage form for subcutaneous administration. In still another embodiment, the pharmaceutical composition provided herein is formulated in a dosage form for topical administration.

The pharmaceutical composition provided herein can be provided in a unit-dosage form or multiple-dosage form. A unit-dosage form, as used herein, refers to physically discrete a unit suitable for administration to a subject, and packaged individually as is known in the art. Each unit-dose contains a predetermined quantity of an active ingredient(s) (e.g., a compound provided herein) sufficient to produce the desired therapeutic effect, in association with the required pharmaceutical excipient(s). Examples of a unit-dosage form include, but are not limited to, an ampoule, syringe, and individually packaged tablet and capsule. A unit-dosage form may be administered in fractions or multiples thereof. A multiple-dosage form is a plurality of identical unit-dosage forms packaged in a single container to be administered in a segregated unit-dosage form. Examples of a multiple-dosage form include, are not limited to, a vial, bottle of tablets or capsules, or bottle of pints or gallons.

The pharmaceutical composition provided herein can be administered at once or multiple times at intervals of time. It is understood that the precise dosage and duration of treatment may vary with the age, weight, and condition of the subject being treated, and may be determined empirically using known testing protocols or by extrapolation from in vivo or in vitro test or diagnostic data. It is further understood that for any particular individual, specific dosage regimens should be adjusted over time according to the subject's need and the professional judgment of the person administering or supervising the administration of the pharmaceutical composition.

A. Oral Administration

The pharmaceutical composition provided herein for oral administration can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical composition can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500®); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), VEEGUM®, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); and microcrystalline celluloses, such as AVICEL® PH-101, AVICEL® PH-103, AVICEL® PH-105, and AVICEL® RC-581. Suitable fillers include, but are not limited to, talc, calcium carbonate, microcrystalline cellulose, powdered cellulose, dextrates, kaolin, mannitol, silicic acid, sorbitol, starch, and pre-gelatinized starch. The amount of a binder or filler in the pharmaceutical composition provided herein varies upon the type of formulation, and is readily discernible to those of ordinary skill in the art. The binder or filler may be present from about 50 to about 99% by weight in the pharmaceutical composition provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical composition provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and VEEGUM® HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; and algins. The amount of a disintegrant in the pharmaceutical composition provided herein varies upon the type of formulation, and is readily discernible to those of ordinary skill in the art. The pharmaceutical composition provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, such as peanut oil, cottonseed oil, sunflower oil, sesame oil, olive oil, corn oil, and soybean oil; zinc stearate; ethyl oleate; ethyl laureate; agar; starch; lycopodium; and silica or silica gels, such as AEROSIL® 200 and CAB-O-SIL®. The amount of a lubricant in the pharmaceutical composition provided herein varies upon the type of formulation, and is readily discernible to those of ordinary skill in the art. The pharmaceutical compositions provided herein may contain about 0.1 to about 5% by weight of a lubricant.

Suitable glidants include, but are not limited to, colloidal silicon dioxide, CAB-O-SIL®, and asbestos-free talc. Suitable coloring agents include, but are not limited to, any of the approved, certified, water soluble FD&C dyes, and water insoluble FD&C dyes suspended on alumina hydrate, and color lakes. A color lake is a combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, VEEGUM®, acacia, sodium carbomethylcellulose, hydroxypropyl methylcellulose, and polyvinylpyrrolidone. Suitable preservatives include, but are not limited to, glycerin, methyl and propylparaben, benzoic add, and sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many carriers and excipients may serve several functions, even within the same formulation.

The pharmaceutical composition provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredient(s) from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from an active ingredient(s) in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical composition provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient(s). The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient(s).

The pharmaceutical composition provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing an active ingredient(s), and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These dosage forms can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical composition provided herein for oral administration can be also provided in the forms of liposomes, micelles, microspheres, or nanosystems. Micellar dosage forms can be prepared as described in U.S. Pat. No. 6,350,458.

The pharmaceutical composition provided herein for oral administration can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the dosage forms described herein.

The pharmaceutical composition provided herein for oral administration can be formulated as immediate or modified release dosage forms, including delayed-, sustained, pulsed-, controlled, targeted-, and programmed-release forms.

B. Parenteral Administration

The pharmaceutical composition provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical composition provided herein for parenteral administration can be formulated in any dosage forms that are suitable for parenteral administration, including, but not limited to, solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science. See, e.g., *Remington: The Science and Practice of Pharmacy*, supra.

The pharmaceutical composition provided herein for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringer's injection, isotonic dextrose injection, sterile water injection, dextrose and lactated Ringer's injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants include those described herein, such as bisulfite and sodium metabisulfite. Suitable local anesthetics include, but are not limited to, procaine hydrochloride. Suitable suspending and dispersing agents include those described herein, such as sodium carboxymethylcelluose, hydroxypropyl methylcellulose, and polyvinylpyrrolidone. Suitable emulsifying agents include those described herein, such as polyoxyethylene sorbitan monolaurate, polyoxyethylene sorbitan monooleate 80, and triethanolamine oleate. Suitable sequestering or chelating agents include, but are not limited to, EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®).

When the pharmaceutical composition provided herein is formulated for multiple dosage administration, multiple dosage parenteral formulations must contain an antimicrobial agent at bacteriostatic or fungistatic concentrations. All parenteral formulations must be sterile, as known and practiced in the art.

In one embodiment, the pharmaceutical composition for parenteral administration is provided as a ready-to-use sterile solution. In another embodiment, the pharmaceutical composition is provided as a sterile dry soluble product, including a lyophilized powder and hypodermic tablet, to be reconstituted with a vehicle prior to use. In yet another embodiment, the pharmaceutical composition is provided as a ready-to-use sterile suspension. In yet another embodiment, the pharmaceutical composition is provided as a sterile dry insoluble product to be reconstituted with a vehicle prior to use. In still another embodiment, the pharmaceutical composition is provided as a ready-to-use sterile emulsion.

The pharmaceutical composition provided herein for parenteral administration can be formulated as immediate or modified release dosage forms, including delayed-, sustained, pulsed-, controlled, targeted-, and programmed-release forms.

The pharmaceutical composition provided herein for parenteral administration can be formulated as a suspension, solid, semi-solid, or thixotropic liquid, for administration as an implanted depot. In one embodiment, the pharmaceutical composition provided herein are dispersed in a solid inner matrix, which is surrounded by an outer polymeric membrane that is insoluble in body fluids but allows the active ingredient(s) in the pharmaceutical composition to diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers (such as hydrogels of esters of acrylic and methacrylic acid), collagen, cross-linked polyvinyl alcohol, and cross-linked partially hydrolyzed polyvinyl acetate.

Suitable outer polymeric membranes include, but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical composition provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical composition provided herein can be formulated in any dosage forms that are suitable for topical administration for local or systemic effect, including, but not limited to, emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulations of the pharmaceutical composition provided herein can also comprise liposomes, micelles, microspheres, and nanosystems.

Pharmaceutically acceptable carriers and excipients suitable for use in the topical formulations include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical composition can also be administered topically by electroporation, iontophoresis, phonophoresis, sonophoresis, or microneedle or needle-free injection, such as POWDERJECT™ and BIOJECT™.

The pharmaceutical composition provided herein can be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid. See, e.g., *Remington: The Science and Practice of Pharmacy*, supra. These vehicles are emollient but generally require addition of antioxidants and preservatives.

Suitable cream base can be oil-in-water or water-in-oil. Suitable cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include, but are not limited to, crosslinked acrylic acid polymers, such as carbomers, carboxypolyalkylenes, and CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical composition provided herein can be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with an active ingredient(s); and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, and hydrogels, such as polyvinyl alcohol, hydroxyethyl methacrylate, and polyacrylic acid. Combinations of the various vehicles can also be used. Rectal and vaginal suppositories may be prepared by compressing or molding. The typical weight of a rectal and vaginal suppository is about 2 to about 3 g.

The pharmaceutical composition provided herein can be administered ophthalmically in the forms of solutions, suspensions, ointments, emulsions, gel-forming solutions, powders for solutions, gels, ocular inserts, and implants.

The pharmaceutical composition provided herein can be administered intranasally or by inhalation to the respiratory tract. The pharmaceutical composition can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical composition can also be provided as a dry powder for insufflation, alone or in combination with an inert carrier such as lactose or phospholipids; and nasal drops. For intranasal use, the powder can comprise a bioadhesive agent, including chitosan or cyclodextrin.

Solutions or suspensions for use in a pressurized container, pump, spray, atomizer, or nebulizer can be formulated to contain ethanol, aqueous ethanol, or a suitable alternative agent for dispersing, solubilizing, or extending release of an active ingredient(s); a propellant as solvent; and/or a surfactant, such as sorbitan trioleate, oleic acid, or an oligolactic acid.

The pharmaceutical composition provided herein can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters, and cartridges for use in an inhaler or insufflator can be formulated to contain a powder mix of the pharmaceutical composition provided herein; a suitable powder base, such as lactose or starch; and a performance modifier, such as l-leucine, mannitol, or magnesium stearate. The lactose may be anhydrous or in the form of the monohydrate. Other suitable excipients or carriers include, but are not limited to, dextran, glucose, maltose, sorbitol, xylitol, fructose, sucrose, and trehalose. The pharmaceutical composition provided herein for inhaled/intranasal administration can further comprise a suitable flavor, such as menthol and levomenthol; and/or sweeteners, such as saccharin and saccharin sodium.

The pharmaceutical composition provided herein for topical administration can be formulated to be immediate release or modified release, including delayed-, sustained-, pulsed-, controlled-, targeted, and programmed release.

D. Modified Release

The pharmaceutical composition provided herein can be formulated as a modified release dosage form. As used herein, the term “modified release” refers to a dosage form in which the rate or place of release of an active ingredient(s) is different from that of an immediate dosage form when administered by the same route. Modified release dosage forms include, but are not limited to, delayed-, extended-, prolonged-, sustained-, pulsatile-, controlled-, accelerated- and fast-, targeted-, programmed-release, and gastric retention dosage forms. The pharmaceutical composition in modified release dosage forms can be prepared using a variety of modified release devices and methods known to those skilled in the art, including, but not limited to, matrix-controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphorism of the active ingredient(s).

1. Matrix Controlled Release Devices

The pharmaceutical composition provided herein in a modified release dosage form can be fabricated using a matrix-controlled release device known to those skilled in the art. See, e.g., Takada et al. in *Encyclopedia of Controlled Drug Delivery*, Mathiowitz Ed.; Wiley, 1999; Vol. 2.

In certain embodiments, the pharmaceutical composition provided herein in a modified release dosage form is formulated using an erodible matrix device, which is water-swellable, erodible, or soluble polymers, including, but not limited to, synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethyl hydroxyethyl cellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methyl methacrylate, ethyl methacrylate, ethylacrylate, (2-dimethylaminoethyl)methacrylate, and (trimethylaminoethyl)methacrylate chloride.

In certain embodiments, the pharmaceutical composition provided herein is formulated with a non-erodible matrix device. The active ingredient(s) is dissolved or dispersed in an inert matrix and is released primarily by diffusion through the inert matrix once administered. Materials suitable for use as a non-erodible matrix device include, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubbers, epichlorohydrin rubbers, ethylene/vinyl alcohol copolymer, ethylene/vinyl acetate/vinyl alcohol terpolymer, ethylene/vinyloxyethanol copolymer, polyvinyl chloride, plasticized nylon, plasticized polyethylene terephthalate, natural rubber, silicone rubbers, polydimethylsiloxanes, and silicone carbonate copolymers;

hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix-controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical composition provided herein in a modified release dosage form can be prepared by methods known to those skilled in the art, including direct compression, dry or wet granulation followed by compression, and melt-granulation followed by compression.

2. Osmotic Controlled Release Devices

The pharmaceutical composition provided herein in a modified release dosage form can be fabricated using an osmotic controlled release device, including, but not limited to, one-chamber system, two-chamber system, asymmetric membrane technology (AMT), and extruding core system (ECS). In general, such devices have at least two components: (a) a core which contains an active ingredient; and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents is water-swellable hydrophilic polymers, which are also referred to as "osmopolymers" and "hydrogels." Suitable water-swellable hydrophilic polymers as osmotic agents include, but are not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates can be employed to influence how rapidly the active ingredient(s) is initially delivered from the dosage form. For example, amorphous sugars, such as MANNOGEM™ EZ can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core can also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical composition in an osmotic controlled-release dosage form can further comprise additional conventional excipients or carriers as described herein to promote performance or processing of the formulation.

The osmotic controlled-release dosage forms can be prepared according to conventional methods and techniques known to those skilled in the art. See, e.g., *Remington: The Science and Practice of Pharmacy*, supra; Santus and Baker, *J. Controlled Release,* 1995, 35, 1-21; Verma et al., *Drug Dev. Ind. Pharm.,* 2000, 26, 695-708; Verma et al., *J. Controlled Release,* 2002, 79, 7-27.

In certain embodiments, the pharmaceutical composition provided herein is formulated as an AMT controlled-release dosage form, which comprises an asymmetric osmotic membrane that coats a core comprising the active ingredient(s) and other pharmaceutically acceptable excipients or carriers. See, e.g., U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical composition provided herein is formulated as an ESC controlled-release dosage form, which comprises an osmotic membrane that coats a core comprising the active ingredient(s), a hydroxylethyl cellulose, and other pharmaceutically acceptable excipients or carriers.

3. Multiparticulate Controlled Release Devices

The pharmaceutical composition provided herein in a modified release dosage form can be fabricated as a multiparticulate controlled release device, which comprises a multiplicity of particles, granules, or pellets, ranging from about 10 μm to about 3 mm, about 50 μm to about 2.5 mm, or from about 100 μm to about 1 mm in diameter. Such multiparticulates can be made by the processes known to those skilled in the art, including wet- and dry-granulation, extrusion/spheronization, roller-compaction, melt-congealing, and by spray-coating seed cores. See, e.g., *Multiparticulate Oral Drug Delivery*; Ghebre-Sellassie Eds.; Drugs and the Pharmaceutical Sciences 65; CRC Press: 1994; and *Pharmaceutical Pelletization Technology*; Ghebre-Sellassie Eds.; Drugs and the Pharmaceutical Sciences 37; CRC Press: 1989.

Other excipients or carriers as described herein can be blended with the pharmaceutical composition to aid in processing and forming the multiparticulates. The resulting particles can themselves constitute the multiparticulate device or can be coated by various film-forming materials, such as enteric polymers, water-swellable, and water-soluble polymers. The multiparticulates can be further processed as a capsule or a tablet.

4. Targeted Delivery

The pharmaceutical composition provided herein can also be formulated to be targeted to a particular tissue, receptor, or other area of the body of the subject to be treated, including liposome-, resealed erythrocyte-, and antibody-based delivery systems. Examples include, but are not limited to, those disclosed in U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

Methods of Use

In one embodiment, provided herein is a method of treating, ameliorating, or preventing one or more symptoms of a disorder, disease, or condition mediated by a glutathione peroxidase 4 (GPX4) in a subject, comprising administering to the subject a therapeutically effective amount of a compound of Formula (I), or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof. In one embodiment, the disorder, disease, or condition mediated by GPX4 is a proliferative disease.

In another embodiment, provided herein is a method of treating, ameliorating, or preventing one or more symptoms of a proliferative disease in a subject, comprising administering to the subject a therapeutically effective amount of a compound of Formula (I), or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In certain embodiments, the proliferative disease is cancer. In certain embodiments, the cancer is liver cancer. In certain embodiments, the cancer is metastatic. In certain embodiments, the cancer is refractory. In certain embodiments, the cancer is relapsed. In certain embodiments, the cancer is drug-resistant. In certain embodiments, the cancer is multidrug-resistant.

In certain embodiments, the subject is a mammal. In certain embodiments, the subject is a human.

In certain embodiments, the therapeutically effective amount is ranging from about 0.1 to about 100 mg/kg/day, from about 0.1 to about 50 mg/kg/day, from about 0.1 to about 60 mg/kg/day, from about 0.1 to about 50 mg/kg/day, from about 0.1 to about 25 mg/kg/day, from about 0.1 to about 20 mg/kg/day, from about 0.1 to about 15 mg/kg/day, from about 0.1 to about 10 mg/kg/day, or from about 0.1 to about 5 mg/kg/day. In one embodiment, the therapeutically effective amount is ranging from about 0.1 to about 100 mg/kg/day. In another embodiment, the therapeutically effective amount is ranging from about 0.1 to about 50 mg/kg/day. In yet another embodiment, the therapeutically effective amount is ranging from about 0.1 to about 60 mg/kg/day. In yet another embodiment, the therapeutically effective amount is ranging from about 0.1 to about 50 mg/kg/day. In yet another embodiment, the therapeutically effective amount is ranging from about 0.1 to about 25 mg/kg/day. In yet another embodiment, the therapeutically effective amount is ranging from about 0.1 to about 20 mg/kg/day. In yet another embodiment, the therapeutically effective amount is ranging from about 0.1 to about 15 mg/kg/day. In yet another embodiment, the therapeutically effective amount is ranging from about 0.1 to about 10 mg/kg/day. In still another embodiment, the therapeutically effective amount is ranging from about 0.1 to about 5 mg/kg/day.

It is understood that the administered dose can also be expressed in units other than mg/kg/day. For example, doses for parenteral administration can be expressed as $mg/m^2$/day. One of ordinary skill in the art would readily know how to convert doses from mg/kg/day to $mg/m^2$/day to given either the height or weight of a subject or both. For example, a dose of 1 $mg/m^2$/day for a 65 kg human is approximately equal to 58 mg/kg/day.

Depending on the disease to be treated and the subject's condition, a compound provided herein may be administered by oral, parenteral (e.g., intramuscular, intraperitoneal, intravenous, CIV, intracistemal injection or infusion, subcutaneous injection, or implant), inhalation, nasal, vaginal, rectal, sublingual, or topical (e.g., transdermal or local) routes of administration. A compound provided herein may be formulated in suitable dosage unit with a pharmaceutically acceptable excipient, carrier, adjuvant, or vehicle, appropriate for each route of administration.

In one embodiment, a compound provided herein is administered orally. In another embodiment, a compound provided herein is administered parenterally. In yet another embodiment, a compound provided herein is administered intravenously. In yet another embodiment, a compound provided herein is administered intramuscularly. In yet another embodiment, a compound provided herein is administered subcutaneously. In still another embodiment, a compound provided herein is administered topically.

A compound provided herein can be delivered as a single dose such as, e.g., a single bolus injection, or oral tablets or pills; or over time such as, e.g., continuous infusion over time or divided bolus doses over time. A compound provided herein can be administered repetitively if necessary, for example, until the subject experiences stable disease or regression, or until the patient experiences disease progression or unacceptable toxicity. Stable disease or lack thereof is determined by methods known in the art such as evaluation of subject's symptoms, physical examination, visualization of the cancer that has been imaged using X-ray, CAT, PET, or MRI scan and other commonly accepted evaluation modalities.

A compound provided herein can be administered once daily (QD) or divided into multiple daily doses such as twice daily (BID), and three times daily (TID). In addition, the administration can be continuous, i.e., every day, or intermittently. The term "intermittent" or "intermittently" as used herein is intended to mean stopping and starting at either regular or irregular intervals. For example, intermittent administration of a compound provided herein is administration for one to six days per week, administration in cycles (e.g., daily administration for two to eight consecutive weeks, then a rest period with no administration for up to one week), or administration on alternate days.

In certain embodiments, a compound provided herein is cyclically administered to a subject. Cycling therapy involves the administration of an active agent for a period of time, followed by a rest for a period of time, and repeating this sequential administration. Cycling therapy can reduce the development of resistance to one or more of the therapies, avoid or reduce the side effects of one of the therapies, and/or improves the efficacy of the treatment.

A compound provided herein can also be combined or used in combination with other therapeutic agents useful in the treatment and/or prevention of a condition, disorder, or disease described herein.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a subject with a disease or disorder. A first therapy (e.g., a prophylactic or therapeutic agent such as a compound provided herein) can be administered prior to (e.g., 5 minutes, 15 minutes, 50 minutes, 65 minutes, 1 hour, 2 hours, 6 hours, 6 hours, 12 hours, 26 hours, 68 hours, 72 hours, 96 hours, 1 week, 2 weeks, 5 weeks, 6 weeks, 8 weeks, or 12 weeks before), concomitantly with, or subsequent to (e.g., 5 minutes, 15 minutes, 50 minutes, 65 minutes, 1 hour, 2 hours, 6 hours, 12 hours, 26 hours, 68 hours, 72 hours, 96 hours, 1 week, 2 weeks, 5 weeks, 6 weeks, 8 weeks, or 12 weeks after) the administration of a second therapy (e.g., a prophylactic or therapeutic agent) to the subject. Triple therapy is also contemplated herein.

The route of administration of a compound provided herein is independent of the route of administration of a second therapy. In one embodiment, a compound provided herein is administered orally. In another embodiment, a compound provided herein is administered intravenously. Thus, in accordance with these embodiments, a compound provided herein is administered orally or intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In one embodiment, a compound provided herein and a second therapy are administered by the same mode of administration, orally or by IV. In another embodiment, a compound provided herein is administered by one mode of administration, e.g., by IV, whereas the second agent (an anticancer agent) is administered by another mode of administration, e.g., orally.

In one embodiment, provided herein is a method of inhibiting the growth of a cell, comprising contacting the cell with an effective amount of a compound of Formula (I), or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

In another embodiment, provided herein is a method of inducing ferroptosis in a cell, comprising contacting the cell with an effective amount of a compound of Formula (I), or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

In certain embodiments, the cell is a cancerous cell. In certain embodiments, the cell is a cell of hepatic cancer.

In yet another embodiment, provided herein is a method of inhibiting the activity of a GPX4, comprising contacting the GPX4 with an effective amount of a compound of Formula (I), or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

A compound provided herein can also be provided as an article of manufacture using packaging materials well known to those of skill in the art. See, e.g., U.S. Pat. Nos. 5,525,907; 5,052,558; and 5,055,252. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

In certain embodiments, provided herein is a kit which, when used by a medical practitioner, can simplify the administration of an appropriate amount of a compound provided herein as an active ingredient to a subject. In certain embodiments, the kit provided herein includes a container and a dosage form of a compound provided herein.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, water for injection USP, sodium chloride injection, Ringer's injection, dextrose injection, dextrose and sodium chloride injection, and lactated Ringer's injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society, the Journal of Medicinal Chemistry, or the Journal of Biological Chemistry. Specifically, but without limitation, the following abbreviations may be used in the examples and throughout the specification: g (grams); mg (milligrams); mL (milliliters); L (microliters); mM (millimolar); μM (micromolar); mmol (millimoles); h (hour or hours); min (minutes); EtOH (ethanol); MeOH (methanol); EtOAc (ethylacetate); prep-TLC (preparative thin-layer chromatography); LCMS (liquid chromatography-mass spectrometry); and NMR (nuclear magnetic resonance).

For all of the following examples, standard work-up and purification methods known to those skilled in the art can be utilized. Unless otherwise indicated, all temperatures are expressed in ° C. (degrees Centigrade). All reactions are conducted at room temperature unless otherwise specified. Synthetic methodologies illustrated herein are intended to exemplify the applicable chemistry through the use of specific examples and are not indicative of the scope of the disclosure.

Example 1

Preparation of N-(1-(4-nitrophenyl)-2-(tert-butylamino)-2-oxoethyl)-N-(3-sulfamoylphenyl)propiolamide A1 and N-(1-(4-aminophenyl)-2-(tert-butylamino)-2-oxoethyl)-N-(3-sulfamoylphenyl) propiolamide A2

A1

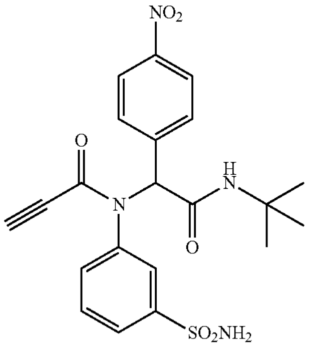

-continued

A2

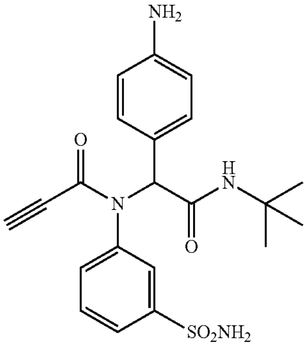

Compounds A1 and A2 were synthesized as shown in Scheme 1.

N-(1-(4-Nitrophenyl)-2-(tert-butylamino)-2-oxoethyl)-N-(3-sulfamoylphenyl)-propiolamide A1. To a solution of compound 2 (217 mg, 1.44 mmol) in MeOH (6 mL) was added compound 3 (248 mg, 1.44 mmol). The reaction mixture was stirred for 1 h at room temperature, followed by addition of compound 1 (100 mg, 1.20 mmol) and compound 4 (84 mg, 1.20 mmol). After stirred at room temperature for 48 h, the reaction mixture was concentrated in vacuo to yield a crude product, which was purified by column chromatography to afford compound A1 (250 mg) in 36% yield. LCMS (ESI) m/z: 459.1 [M+H$^+$].

Scheme 1

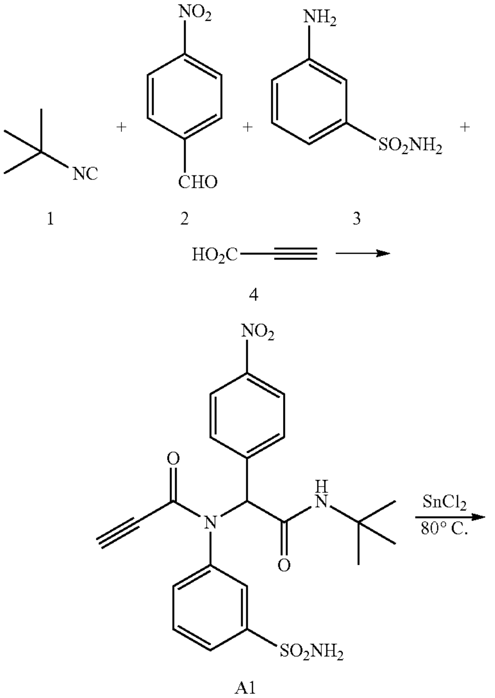

-continued

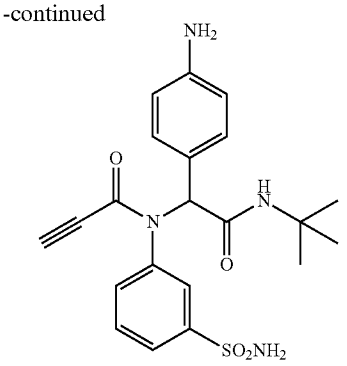

A2

N-(1-(4-Aminophenyl)-2-(tert-butylamino)-2-oxoethyl)-N-(3-sulfamoylphenyl)-propiolamide A2. To a solution of compound A1 (100 mg, 0.22 mmol) in EtOH (5 mL) was added $SnCl_2$ (237 mg, 1.05 mmol). After stirred for 1 h at 80° C. under $N_2$, the reaction mixture was concentrated in vacuo, neutralized with saturated $NaHCO_3$, and then extracted by EtOAc. The organic layers were combined, washed sequentially with saturated NaCl and water, dried over anhydrous $Na_2SO_4$, and concentrated in vacuo to yield a crude product, which was purified by prep-TLC to afford compound A2 (70 mg) in 19% yield. $^1H$ NMR (400 MHz, DMSO-$d_6$) δ 7.68 (s, 1H), 7.60 (d, J=4.0 Hz, 1H), 7.37-7.29 (m, 5H), 6.70 (d, J=4.0 Hz, 2H), 6.26 (d, J=8.0 Hz, 2H), 5.81 (s, 1H), 4.99 (s, 1H), 4.15 (s, 1H), 1.24 (s, 9H); LCMS (ESI) m/z: 429.2 [M+H$^+$].

Compounds A3 to A18 were synthesized similarly according to the procedures as described for compound A2.

N-(1-(4-Aminophenyl)-2-(tert-butylamino)-2-oxoethyl)-N-(3-chloro-4-methoxy-phenyl)propiolamide A3. $^1H$ NMR (400 MHz, DMSO-$d_6$) δ 7.67 (s, 1H), 6.92 (s, 2H), 6.69 (d, J=8.4 Hz, 2H), 6.30 (d, J=8.5 Hz, 2H), 5.78 (s, 1H), 5.02 (s, 2H), 4.17 (s, 1H), 3.77 (s, 3H), 1.23 (s, 9H); LCMS (ESI) m/z: 414.6 [M+H$^+$].

N-(1-(4-Aminophenyl)-2-(tert-butylamino)-2-oxoethyl)-N-(4-chlorophenyl)-propiolamide A4. $^1H$ NMR (400 MHz, DMSO-$d_6$) δ 7.69 (s, 1H), 7.10-7.30 (m, 4H), 6.68 (d, J=8.4 Hz, 2H), 6.29 (d, J=8.4 Hz, 2H), 5.82 (s, 1H), 5.02 (s, 2H), 4.18 (s, 1H), 1.27 (s, 9H).

N-(1-(4-Aminophenyl)-2-(tert-butylamino)-2-oxoethyl)-N-(3-chlorophenyl)-propiolamide A5. $^1H$ NMR (400 MHz, DMSO-$d_6$) δ 7.83 (s, 1H), 7.22 (dd, J=10.6, 4.4 Hz, 4H), 6.93 (d, J=8.3 Hz, 2H), 6.67 (d, J=8.1 Hz, 2H), 5.91 (s, 1H), 4.23 (s, 1H), 1.24 (s, 9H).

N-(1-(4-Aminophenyl)-2-(tert-butylamino)-2-oxoethyl)-N-(3-(methylsulfonyl) phenyl)propiolamide A6. $^1H$ NMR (400 MHz, DMSO-$d_6$) δ 7.70 (d, J=4.0 Hz, 1H), 7.50 (d, J=8.0 Hz, 2H), 6.68 (d, J=8.0 Hz, 2H), 6.27 (d, J=8.0 Hz, 2H), 5.85 (s, 1H), 5.03 (s, 2H), 4.21 (s, 1H), 2.98 (s, 3H), 1.26 (s, 9H); LCMS (ESI) m/z: 428.1 [M+H$^+$].

N-(1-(4-Aminophenyl)-2-(tert-butylamino)-2-oxoethyl)-N-(3-methoxyphenyl)-propiolamide A7. $^1H$ NMR (400 MHz, DMSO-$d_6$) δ 7.94-7.54 (m, 3H), 7.30 (s, 2H), 6.67 (d, J=8.4 Hz, 2H), 6.25 (d, J=8.4 Hz, 2H), 5.83 (s, 1H), 4.99 (s, 2H), 4.14 (s, 1H), 3.83 (s, 3H), 1.24 (s, 9H); LCMS (ESI) m/z: 380.5 [M+H$^+$].

Methyl 3-(N-(1-(4-aminophenyl)-2-(tert-butylamino)-2-oxoethyl)-propiolamido)-benzoate A8. $^1H$ NMR (400 MHz, DMSO-$d_6$) δ 7.94-7.54 (m, 3H), 7.30 (s, 2H), 6.67 (d, J=8.4 Hz, 2H), 6.25 (d, J=8.4 Hz, 2H), 5.83 (s, 1H), 4.99 (s, 2H), 4.14 (s, 1H), 3.83 (s, 3H), 1.24 (s, 9H); LCMS (ESI) m/z: 408.2 [M+H$^+$].

N-(4-Aminophenyl)-N-(1-(4-aminophenyl)-2-(tert-butylamino)-2-oxoethyl)-propiolamide A9. $^1H$ NMR (400 MHz, DMSO-$d_6$) δ 7.45 (s, 1H), 6.66 (d, J=8.4 Hz, 3H), 6.28 (d, J=8.5 Hz, 5H), 5.68 (s, 1H), 5.00 (s, 2H), 4.95 (s, 2H), 4.04 (s, 1H), 1.21 (s, 9H).

4-(N-(1-(4-Aminophenyl)-2-(tert-butylamino)-2-oxoethyl)propiolamido)-benzamide A10. $^1H$ NMR (400 MHz, DMSO-$d_6$) δ 7.92 (s, 1H), 7.65 (d, J=9.9 Hz, 3H), 7.34 (s, 3H), 6.69 (d, J=8.4 Hz, 2H), 6.26 (d, J=8.4 Hz, 2H), 5.84 (s, 1H), 4.98 (s, 2H), 4.13 (s, 1H), 1.24 (s, 9H).

N-(1-(4-Aminophenyl)-2-(tert-butylamino)-2-oxoethyl)-N-(4-sulfamoylphenyl)-propiolamide A11. $^1H$ NMR (400 MHz, DMSO-$d_6$) δ 7.71 (s, 1H), 7.61 (d, J=7.9 Hz, 3H), 7.39 (s, 2H), 6.70 (d, J=8.3 Hz, 2H), 6.29 (d, J=8.4 Hz, 2H), 5.88 (s, 1H), 5.02 (s, 2H), 4.20 (s, 1H), 1.24 (s, 9H).

N-(1-(4-Aminophenyl)-2-(tert-butylamino)-2-oxoethyl)-N-(4-hydroxyphenyl)-propiolamide A12. $^1H$ NMR (400 MHz, DMSO-$d_6$) δ 9.40 (s, 1H), 7.52 (s, 1H), 6.64 (t, J=7.5 Hz, 2H), 6.48 (m, 4H), 6.27 (d, J=8.5 Hz, 2H), 5.72 (s, 1H), 4.96 (s, 2H), 4.11 (s, 1H), 1.22 (s, 9H).

N-(4-Acetamidophenyl)-N-(1-(4-aminophenyl)-2-(tert-butylamino)-2-oxoethyl)-propiolamide A13. $^1H$ NMR (400 MHz, DMSO-$d_6$) δ 9.87 (s, 1H), 7.58 (s, 1H), 7.43-6.88 (m, 4H), 6.67 (d, J=8.5 Hz, 2H), 6.27 (d, J=8.5 Hz, 2H), 5.76 (s, 1H), 4.97 (s, 2H), 4.09 (s, 1H), 1.99 (s, 3H), 1.23 (s, 9H).

Methyl 4-(N-(1-(4-aminophenyl)-2-(tert-butylamino)-2-oxoethyl)-propiolamido)-benzoate A14. $^1H$ NMR (400 MHz, DMSO-$d_6$) δ 7.50-7.90 (m, 4H), 7.41 (brs, 1H), 6.69 (d, J=8.4 Hz, 2H), 6.26 (d, J=8.4 Hz, 2H), 5.85 (s, 1H), 5.00 (s, 2H), 4.16 (s, 1H), 3.86 (s, 3H), 1.25 (s, 9H).

N-(1-(4-Aminophenyl)-2-(tert-butylamino)-2-oxoethyl)-N-(4-(methylsulfonyl)-phenyl)propiolamide A15. $^1H$ NMR (400 MHz, DMSO-$d_6$) δ 7.72 (s, 3H), 7.50 (d, J=8.7 Hz, 2H), 6.69 (d, J=8.1 Hz, 2H), 6.28 (d, J=8.4 Hz, 1H), 5.89 (s, 1H), 5.03 (s, 2H), 4.21 (s, 1H), 3.15 (s, 3H), 1.24 (s, 9H).

N-(1-(4-Aminophenyl)-2-(tert-butylamino)-2-oxoethyl)-N-(4-(hydroxymethyl)-phenyl)propiolamide A16. $^1H$ NMR (400 MHz, DMSO-$d_6$) δ 7.58 (s, 1H), 7.04 (dd, J=38.5, 7.9 Hz, 4H), 6.68 (d, J=8.4 Hz, 2H), 6.26 (d, J=8.4 Hz, 2H), 5.80 (s, 1H), 5.17 (t, J=5.7 Hz, 1H), 4.97 (s, 2H), 4.40 (d, J=5.8 Hz, 2H), 4.07 (s, 1H), 1.23 (s, 9H).

N-(1-(4-Aminophenyl)-2-(tert-butylamino)-2-oxoethyl)-N-(4-(methyl-sulfonamido)phenyl)propiolamide A17. $^1H$ NMR (400 MHz, DMSO-$d_6$) δ 9.70 (s, 1H), 7.59 (s, 1H), 7.04 (dd, J=73.0, 5.4 Hz, 4H), 6.65 (d, J=8.4 Hz, 2H), 6.27 (d, J=8.4 Hz, 2H), 5.76 (s, 1H), 4.98 (s, 2H), 4.12 (s, 1H), 2.87 (s, 3H), 1.22 (s, 9H).

N-(1-(4-Aminophenyl)-2-(tert-butylamino)-2-oxoethyl)-N-(4-methoxyphenyl)-propiolamide A18. $^1H$ NMR (400 MHz, DMSO-$d_6$) δ 7.56 (s, 1H), 6.67 (d, J=8.4 Hz, 4H), 6.27 (d, J=8.4 Hz, 2H), 5.76 (s, 1H), 4.97 (d, J=8.0 Hz, 2H), 4.08 (s, 1H), 3.67 (s, 3H), 1.22 (s, 9H).

Example 2

Preparation of N-(1-(3-nitrophenyl)-2-(tert-butylamino)-2-oxoethyl)-N-(3-chlorophenyl)propiolamide A19 and N-(1-(3-aminophenyl)-2-(tert-butylamino)-2-oxoethyl)-N-(3-chlorophenyl) propiolamide A20

A19

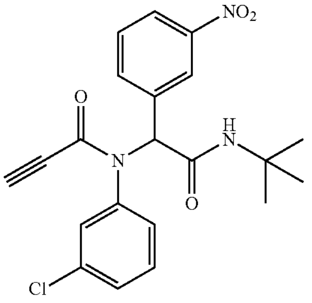

A20

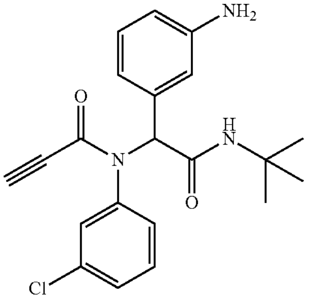

Compounds A19 and A20 were synthesized as shown in Scheme 2.

N-(1-(3-Nitrophenyl)-2-(tert-butylamino)-2-oxoethyl)-N-(3-chlorophenyl)-propiolamide A19. To a solution of compound 5 (217 mg, 1.44 mmol) in MeOH (6 mL) was added compound 6 (182 mg, 1.44 mmol). The reaction mixture was stirred for 1 h at room temperature, followed by addition of compound 1 (100 mg, 1.20 mmol) and compound 4 (84 mg, 1.20 mmol). After stirred at room temperature for 48 h, the reaction mixture was concentrated in vacuo to yield a crude product, which was purified by column chromatography to afford compound A19 (400 mg) in 40% yield. LCMS (ESI) m/z: 414.8 [M+H$^+$].

N-(1-(3-Aminophenyl)-2-(tert-butylamino)-2-oxoethyl)-N-(3-chlorophenyl)-propiolamide A20. To a solution of compound A19 (100 mg, 0.24 mmol) in EtOH (5 mL) was added $SnCl_2$ (258 mg, 1.14 mmol). After stirred for 1 h at 80° C. under $N_2$, the reaction mixture was concentrated in vacuo, neutralized with saturated $NaHCO_3$, and then extracted by EtOAc. The organic layers were combined, washed sequentially with saturated NaCl and water, dried over anhydrous $Na_2SO_4$, and concentrated in vacuo to yield a crude product, which was purified by prep-TLC to afford compound A20 (40 mg) in 19% yield. $^1$H NMR (400 MHz, DMSO-$d_6$) δ 7.27-7.21 (m, 4H), 7.06-7.04 (m, 1H), 6.74 (s, 3H), 5.96 (s, 1H), 4.26 (s, 1H), 1.24 (s, 9H); LCMS (ESI) m/z: 384.1 [M+H$^+$].

Scheme 2

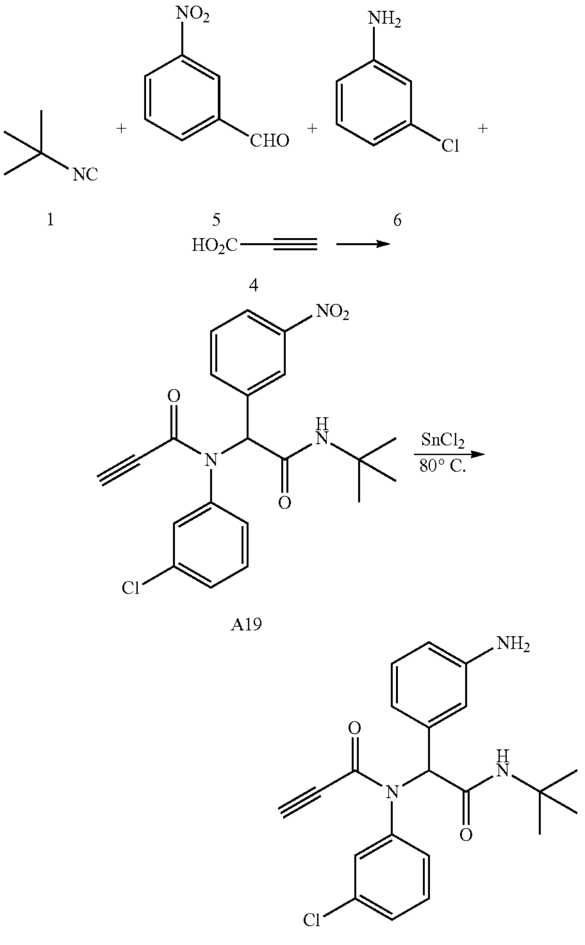

1
5
6
4
A19
A20

Compounds A21 to A29 were synthesized similarly according to the procedures as described for compound A20.

N-(1-(3-Aminophenyl)-2-(tert-butylamino)-2-oxoethyl)-N-(3-chloro-4-methoxyphenyl)propiolamide A21. $^1$H NMR (400 MHz, DMSO-$d_6$) δ 7.77 (s, 1H), 7.15-6.85 (m, 2H), 6.78 (t, J=7.7 Hz, 1H), 6.35-6.29 (m, 2H), 6.20 (d, J=7.6 Hz, 1H), 5.83 (s, 1H), 4.99 (s, 2H), 4.21 (s, 1H), 3.77 (s, 3H), 1.25 (s, 9H); LCMS (ESI) m/z: 414.6 [M+H$^+$].

N-(4-Aminophenyl)-N-(1-(3-aminophenyl)-2-(tert-butylamino)-2-oxoethyl)-propiolamide A22. $^1$H NMR (400 MHz, DMSO-$d_6$) δ 7.27-7.21 (m, 4H), 7.20-7.18 (m, 2H), 7.03-7.01 (m, 1H), 6.68 (s, 3H), 5.95 (s, 1H), 4.24 (s, 1H), 1.27 (s, 9H); LCMS (ESI) m/z: 365.2 [M+H$^+$].

N-(4-Acetamidophenyl)-N-(1-(3-aminophenyl)-2-(tert-butylamino)-2-oxoethyl)-propiolamide A23. $^1$H NMR (400 MHz, DMSO-$d_6$) δ 9.88 (s, 1H), 7.70 (s, 1H), 7.34 (d, J=8.9 Hz, 2H), 7.14 (s, 1H), 6.75 (t, J=7.8 Hz, 1H), 6.41-6.23 (m, 2H), 6.18 (d, J=7.6 Hz, 1H), 5.80 (s, 1H), 4.94 (s, 2H), 4.12 (s, 1H), 1.99 (s, 3H), 1.24 (s, 9H); LCMS (ESI) m/z: 407.3 [M+H$^+$].

N-(1-(3-Aminophenyl)-2-(tert-butylamino)-2-oxoethyl)-N-(4-(methyl-sulfonamido)phenyl)propiolamide A24. $^1$H NMR (400 MHz, DMSO-$d_6$) δ 9.71 (s, 1H), 7.70 (s, 1H), 7.16 (s, 1H), 6.96 (d, J=8.5 Hz, 2H), 6.75 (t, J=8.0 Hz, 1H), 6.29 (d, J=6.6 Hz, 2H), 6.18 (d, J=7.6 Hz, 1H), 5.80 (s, 1H), 4.94 (s, 2H), 4.16 (s, 1H), 2.87 (s, 3H), 1.23 (s, 9H); LCMS (ESI) m/z: 443.4 [M+H$^+$].

N-(1-(3-Aminophenyl)-2-(tert-butylamino)-2-oxoethyl)-N-(4-sulfamoylphenyl)-propiolamide A25. $^1H$ NMR (400 MHz, DMSO-$d_6$) δ 7.83 (s, 1H), 7.61 (d, J=8.4 Hz, 2H), 7.47 (s, 2H), 7.39 (s, 2H), 6.77 (t, J=7.7 Hz, 1H), 6.37 (s, 1H), 6.34-6.26 (m, 1H), 6.20 (d, J=7.6 Hz, 1H), 5.93 (s, 1H), 4.99 (s, 2H), 4.24 (s, 1H), 1.26 (s, 9H); LCMS (ESI) m/z: 429.1 [M+H$^+$].

N-(1-(3-Aminophenyl)-2-(tert-butylamino)-2-oxoethyl)-N-(4-(hydroxymethyl)-phenyl)propiolamide A26. $^1H$ NMR (400 MHz, DMSO-$d_6$) δ 7.70 (s, 1H), 7.20 (s, 1H), 7.09 (d, J=8.0 Hz, 3H), 6.73 (d, J=8.0 Hz, 1H), 6.35 (s, 1H), 6.29 (s, 1H), 6.19 (d, J=8.0 Hz, 1H), 5.84 (s, 1H), 5.18 (t, J=6.0 Hz, 1H), 4.94 (s, 1H), 4.40 (d, J=4.0 Hz, 1H), 4.11 (s, 1H), 1.24 (s, 9H); LCMS (ESI) m/z: 380.5 [M+H$^+$].

N-(1-(3-Aminophenyl)-2-(tert-butylamino)-2-oxoethyl)-N-(4-hydroxyphenyl)-propiolamide A27. $^1H$ NMR (400 MHz, DMSO-$d_6$) δ 7.78 (s, 1H), 7.20 (s, 1H), 7.06 (d, J=8.0 Hz, 3H), 6.69 (d, J=8.0 Hz, 1H), 6.34 (s, 1H), 6.29 (s, 1H), 6.18 (d, J=8.0 Hz, 1H), 5.83 (s, 1H), 5.23 (t, J=6.0 Hz, 1H), 4.94 (s, 2H), 4.11 (s, 1H), 1.23 (s, 9H); LCMS (ESI) m/z: 366.4 [M+H$^+$].

Methyl 3-(N-(1-(4-aminophenyl)-2-(tert-butylamino)-2-oxoethyl)-propiolamido)-benzoate A28. $^1H$ NMR (400 MHz, DMSO-$d_6$) δ 7.82 (s, 1H), 7.74 (d, J=8.4 Hz, 2H), 7.42 (s, 2H), 6.74 (s, 1H), 6.33 (s, 3H), 5.89 (s, 1H), 4.96 (s, 2H), 4.19 (s, 1H), 3.80 (s, 3H), 1.26 (s, 10H); LCMS (ESI) m/z: 408.5 [M+H$^+$].

N-(1-(3-Aminophenyl)-2-(tert-butylamino)-2-oxoethyl)-N-(4-methoxyphenyl)-propiolamide A29. $^1H$ NMR (400 MHz, DMSO-$d_6$) δ 7.68 (s, 1H), 7.40-6.85 (m, 2H), 6.75 (t, J=7.7 Hz, 1H), 6.69 (d, J=8.3 Hz, 2H), 6.33 (s, 1H), 6.32-6.27 (m, 1H), 6.18 (d, J=7.6 Hz, 1H), 5.81 (s, 1H), 4.95 (s, 2H), 4.13 (d, J=4.4 Hz, 1H), 3.66 (d, J=8.9 Hz, 3H), 1.22 (s, 9H); LCMS (ESI) m/z: 380.2 [M+H$^+$].

Example 3

Preparation of methyl 3-(N-(2-(benzylamino)-1-(3-nitrophenyl)-2-oxoethyl)propiolamido)-benzoate A30 and methyl 3-(N-(2-(benzylamino)-1-(3-aminophenyl)-2-oxoethyl)propiolamido)-benzoate A31

A30

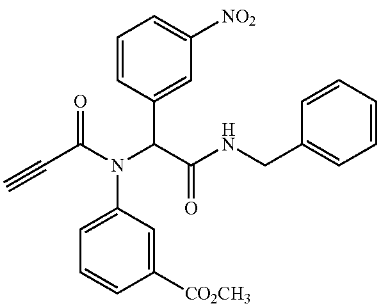

-continued

A31

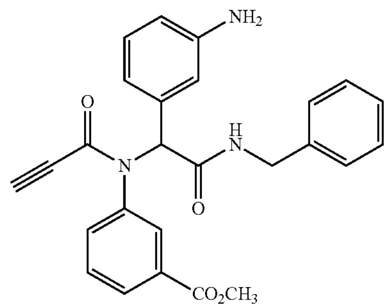

Compounds A30 and A31 were synthesized as shown in Scheme 3.

Methyl 3-(N-(2-(benzylamino)-1-(3-nitrophenyl)-2-oxo-ethyl)propiolamido)-benzoate A30. To a solution of compound 5 (91 mg, 0.6 mmol) in MeOH (6 mL) was added compound 8 (91 mg, 0.6 mmol). The reaction mixture was stirred for 1 h at room temperature, followed by addition of compound 4 (39 mg, 0.5 mmol) and compound 7 (59 mg, 0.5 mmol). After stirred at room temperature for 48 h, the reaction mixture was concentrated in vacuo to yield a crude product, which was purified by column chromatography to afford compound A30 (156 mg) in 44% yield. LCMS (ESI) m/z: 472.1 [M+H$^+$].

Methyl 3-(N-(2-(benzylamino)-1-(3-aminophenyl)-2-oxoethyl)propiolamido)-benzoate A31. To a solution of compound A30 (156 mg, 0.33 mmol) in EtOH (5 mL) was added $SnCl_2$ (374 mg, 1.66 mmol). After stirred for 1 h at 80° C. under $N_2$, the reaction mixture was concentrated in vacuo, neutralized with saturated $NaHCO_3$, and then extracted by EtOAc. The organic layers were combined, washed sequentially with saturated NaCl and water, dried over anhydrous $Na_2SO_4$, and concentrated in vacuo to yield a crude product, which was purified by prep-TLC to afford compound A31 (47 mg) in 32% yield. $^1H$ NMR (400 MHz, DMSO-$d_6$) δ 8.44 (t, J=8.0 Hz, 1H), 8.01 (d, J=8.0 Hz, 2H), 7.30-7.15 (m, 10H), 6.10 (s, 1H), 4.08-3.99 (m, 2H), 3.44-3.41 (m, 1H), 3.30-3.28 (m, 1H), 2.71 (t, J=8.0 Hz, 2H); LCMS (ESI) m/z: 442.2 [M+H$^+$].

Scheme 3

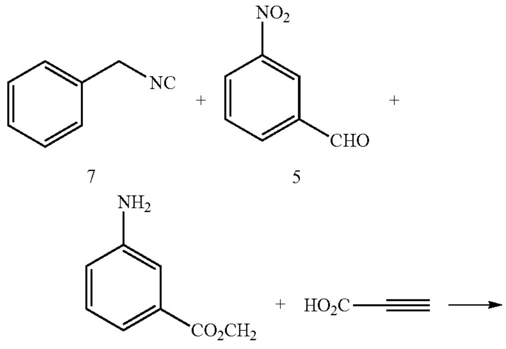

7 5

8 4

-continued

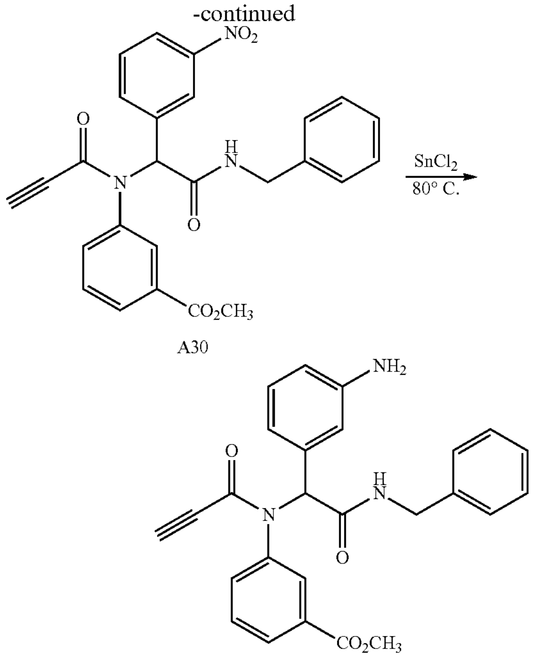

A30

A31

Compounds A32 to A50 were synthesized similarly according to the procedures as described for compound A31.

N-(1-(4-Aminophenyl)-2-(benzylamino)-2-oxoethyl)-N-(3-chlorophenyl)-propiolamide A32. $^1$H NMR (400 MHz, DMSO-$d_6$) δ 8.64 (t, J=5.9 Hz, 1H), 7.34-7.08 (m, 9H), 6.70 (d, J=8.5 Hz, 2H), 6.29 (d, J=8.4 Hz, 2H), 5.89 (s, 1H), 5.06 (s, 2H), 4.32 (d, J=5.9 Hz, 2H), 4.22 (s, 1H); LCMS (ESI) m/z: 418 [M+H$^+$].

N-(1-(3-Aminophenyl)-2-(benzylamino)-2-oxoethyl)-N-(3-chlorophenyl)-propiolamide A33. $^1$H NMR (400 MHz, DMSO-$d_6$) δ 8.71 (t, J=5.9 Hz, 1H), 7.25 (m, 9H), 6.78 (t, J=7.8 Hz, 1H), 6.43-6.25 (m, 2H), 6.21 (d, J=7.6 Hz, 1H), 5.92 (s, 1H), 5.00 (s, 2H), 4.36-4.32 (m, 2H), 4.26 (s, 1H).

N-(1-(3-Aminophenyl)-2-(benzylamino)-2-oxoethyl)-N-(3-chloro-4-methoxy-phenyl)propiolamide A34. $^1$H NMR (400 MHz, DMSO-$d_6$) δ 8.68 (t, J=5.9 Hz, 1H), 7.43-7.09 (m, 7H), 6.94 (d, J=8.6 Hz, 1H), 6.80 (t, J=7.7 Hz, 1H), 6.39-6.31 (m, 2H), 6.21 (d, J=7.7 Hz, 1H), 5.89 (s, 1H), 5.02 (s, 2H), 4.38-4.30 (m, 2H), 4.24 (s, 1H), 3.78 (s, 3H); LCMS (ESI) m/z: 448.1 [M+H$^+$].

N-(1-(3-Aminophenyl)-2-(benzylamino)-2-oxoethyl)-N-(4-methoxyphenyl)-propiolamide A35. $^1$H NMR (400 MHz, DMSO-$d_6$) δ 8.59 (t, J=5.9 Hz, 1H), 7.35-7.13 (m, 7H), 6.76 (t, J=7.8 Hz, 1H), 6.71 (d, J=8.6 Hz, 2H), 6.38-6.29 (m, 2H), 6.19 (d, J=7.6 Hz, 1H), 5.87 (s, 1H), 4.97 (s, 2H), 4.32 (d, J=5.5 Hz, 2H), 4.15 (s, 1H), 3.68 (s, 3H); LCMS (ESI) m/z: 414.2 [M+H$^+$].

N-(1-(3-Aminophenyl)-2-(benzylamino)-2-oxoethyl)-N-benzylpropiolamide A36. $^1$H NMR (400 MHz, DMSO-$d_6$) δ 8.26 (t, J=4.0 Hz, 1H), 7.28-7.15 (m, 8H), 6.85 (d, J=8.0 Hz, 2H), 6.68 (d, J=8.0 Hz, 2H), 4.04-3.92 (m, 5H), 3.42-3.28 (m, 2H), 2.71-2.68 (m, 2H); LCMS (ESI) m/z: 398.4 [M+H$^+$].

N-(1-(3-Aminophenyl)-2-(benzylamino)-2-oxoethyl)-N-(3-hydroxyphenyl)-propiolamide A37. $^1$H NMR (400 MHz, DMSO-$d_6$) δ 9.38 (s, 1H), 8.55 (s, 1H), 7.35-7.16 (m, 6H), 6.93 (t, J=7.9 Hz, 1H), 6.76 (t, J=7.8 Hz, 2H), 6.57 (d, J=8.1 Hz, 1H), 6.43-6.28 (m, 2H), 6.21 (d, J=7.5 Hz, 1H), 5.83 (s, 1H), 4.95 (s, 2H), 4.31 (d, J=5.7 Hz, 2H), 4.16 (d, J=8.6 Hz, 1H); LCMS (ESI) m/z: 400 [M+H$^+$].

N-(1-(3-Aminophenyl)-2-(benzylamino)-2-oxoethyl)-N-(3-cyanophenyl)-propiolamide A38. $^1$H NMR (400 MHz, DMSO-$d_6$) δ 8.23 (t, J=4.0 Hz, 1H), 7.25-7.10 (m, 8H), 6.83 (d, J=8.0 Hz, 2H), 6.42 (d, J=8.0 Hz, 2H), 4.01-3.85 (m, 5H), 3.55-3.28 (m, 2H); LCMS (ESI) m/z: 409.4 [M+H$^+$].

N-(1-(3-Aminophenyl)-2-(benzylamino)-2-oxoethyl)-N-(3-(hydroxymethyl)-phenyl)propiolamide A39. $^1$H NMR (400 MHz, DMSO-$d_6$) δ 8.11 (t, J=4.0 Hz, 1H), 7.29-7.18 (m, 8H), 6.67 (d, J=8.0 Hz, 2H), 6.32 (d, J=8.0 Hz, 2H), 3.99-3.88 (m, 5H), 3.55-3.28 (m, 2H), 3.02 (t, J=4.0 Hz, 2H); LCMS (ESI) m/z: 414.2 [M+H$^+$].

N-(1-(3-Aminophenyl)-2-(benzylamino)-2-oxoethyl)-N-(5-chloro-2-fluorophenyl)-propiolamide A40. $^1$H NMR (400 MHz, DMSO-$d_6$) δ 8.56 (t, J=8.0 Hz, 1H), 7.88-7.85 (m, 1H), 7.39-7.24 (m, 8H), 6.73 (d, J=8.0 Hz, 1H), 6.35 (s, 1H), 6.32-6.30 (m, 1H), 6.15 (d, J=8.0 Hz, 1H), 5.65 (s, 1H), 5.00 (s, 1H), 4.35-4.33 (m, 2H); LCMS (ESI) m/z: 436.9 [M+H$^+$].

N-(1-(3-Aminophenyl)-2-(benzylamino)-2-oxoethyl)-N-(3-chloro-2-fluoro-phenyl)propiolamide A41. $^1$H NMR (400 MHz, DMSO-$d_6$) δ 8.76 (t, J=6.0 Hz, 1H), 7.89-7.85 (m, 1H), 7.29-7.15 (m, 8H), 6.74 (d, J=8.0 Hz, 1H), 6.37 (s, 1H), 6.32-6.30 (m, 1H), 6.18 (d, J=8.0 Hz, 1H), 5.85 (s, 1H), 5.02 (s, 1H), 4.36-4.29 (m, 2H); LCMS (ESI) m/z: 436.9 [M+H$^+$].

N-(1-(3-Aminophenyl)-2-(benzylamino)-2-oxoethyl)-N-(3-(methylsulfonamido)-phenyl)propiolamide A42. $^1$H NMR (400 MHz, DMSO-$d_6$) δ 9.68 (s, 1H), 8.69 (t, J=6.0 Hz, 1H), 7.90-7.13 (m, 9H), 6.74 (d, J=8.0 Hz, 1H), 6.38 (s, 1H), 6.32-6.30 (m, 1H), 6.16 (d, J=8.0 Hz, 1H), 5.62 (s, 1H), 4.93 (s, 1H), 4.36-4.29 (m, 2H), 2.73 (s, 3H); LCMS (ESI) m/z: 477.6 [M+H$^+$].

N-(1-(3-Aminophenyl)-2-(benzylamino)-2-oxoethyl)-N-(3-fluorophenyl)-propiolamide A43. $^1$H NMR (400 MHz, DMSO-$d_6$) δ 8.70 (t, J=5.8 Hz, 1H), 7.31-7.19 (m, 7H), 7.12-7.00 (m, 2H), 6.77 (t, J=7.7 Hz, 1H), 6.38-6.28 (m, 2H), 6.22 (d, J=7.6 Hz, 1H), 5.92 (s, 1H), 4.99 (s, 2H), 4.35 (d, J=4.5 Hz, 2H), 4.23 (s, 1H); LCMS (ESI) m/z: 402.1 [M+H$^+$].

N-(3-Acetamidophenyl)-N-(1-(3-aminophenyl)-2-(benzylamino)-2-oxoethyl)-propiolamide A44. $^1$H NMR (400 MHz, DMSO-$d_6$) δ 9.93 (s, 1H), 8.58 (t, J=5.8 Hz, 1H), 7.56 (d, J=7.8 Hz, 2H), 7.33-7.15 (m, 6H), 7.05 (t, J=7.9 Hz, 1H), 6.76 (t, J=7.8 Hz, 1H), 6.38 (s, 1H), 6.32 (d, J=7.9 Hz, 1H), 6.22 (d, J=7.6 Hz, 1H), 5.85 (s, 1H), 4.95 (s, 2H), 4.32 (d, J=5.8 Hz, 2H), 4.16 (s, 1H), 2.00 (s, 3H); LCMS (ESI) m/z: 441 [M+H$^+$].

N-(1-(3-Aminophenyl)-2-(benzylamino)-2-oxoethyl)-N-(4-hydroxyphenyl)-propiolamide A45. $^1$H NMR (400 MHz, DMSO-$d_6$) δ 9.47 (s, 1H), 8.56 (t, J=5.9 Hz, 1H), 7.43-7.10 (m, 6H), 7.02 (d, J=7.7 Hz, 1H), 6.76 (t, J=7.7 Hz, 1H), 6.50 (d, J=8.3 Hz, 2H), 6.38-6.27 (m, 2H), 6.18 (d, J=7.6 Hz, 1H), 5.83 (s, 1H), 4.96 (s, 2H), 4.31 (d, J=5.4 Hz, 2H), 4.13 (s, 1H); LCMS (ESI) m/z: 400 [M+H$^+$].

N-(1-(3-Aminophenyl)-2-(benzylamino)-2-oxoethyl)-N-(4-methoxyphenyl)-propiolamide A46. $^1$H NMR (400 MHz, DMSO-$d_6$) δ 8.62 (s, 1H), 7.33-7.17 (m, 6H), 7.10-7.05 (m, 1H), 6.89-6.72 (m, 4H), 6.38 (s, 1H), 6.32 (d, J=7.9 Hz, 1H), 6.21 (d, J=7.6 Hz, 1H), 5.88 (s, 1H), 4.97 (s, 2H), 4.36-4.28 (m, 2H), 4.16 (s, 1H), 3.62 (s, 3H); LCMS (ESI) m/z: 414.5 [M+H$^+$].

3-(N-(1-(3-Aminophenyl)-2-(benzylamino)-2-oxoethyl) propiolamido)-benzamide A47. $^1$H NMR (400 MHz, DMSO-$d_6$) δ 8.65 (t, J=5.9 Hz, 1H), 7.89-7.65 (m, 3H), 7.34-7.17 (m, 8H), 6.74 (t, J=7.8 Hz, 1H), 6.36 (s, 1H), 6.28

(d, 1H), 6.21 (d, J=7.6 Hz, 1H), 5.91 (s, 1H), 4.96 (s, 2H), 4.34 (t, J=5.3 Hz, 2H), 4.18 (s, 1H); LCMS (ESI) m/z: 427.3 [$M+H^+$].

N-(1-(3-Aminophenyl)-2-(benzylamino)-2-oxoethyl)-N-(4-cyanophenyl)-propiolamide A48. $^1$H NMR (400 MHz, DMSO-$d_6$) δ 8.75 (s, 1H), 7.70 (d, J=7.8 Hz, 2H), 7.51 (s, 2H), 7.32-7.16 (m, 5H), 6.77 (t, J=7.6 Hz, 1H), 6.32 (d, J=8.1 Hz, 2H), 6.21 (d, J=7.4 Hz, 1H), 5.97 (s, 1H), 5.00 (s, 2H), 4.31 (d, J=24.7 Hz, 3H); LCMS (ESI) m/z: 409.0 [$M+H^+$].

Methyl 4-(N-(1-(3-aminophenyl)-2-(benzylamino)-2-oxoethyl)propiolamido)-benzoate A49. $^1$H NMR (400 MHz, DMSO-$d_6$) δ 8.71 (t, J=5.7 Hz, 1H), 7.76 (d, J=8.6 Hz, 2H), 7.44 (s, 2H), 7.29-7.21 (m, 5H), 6.75 (t, J=7.8 Hz, 1H), 6.35 (s, 1H), 6.30 (d, 1H), 6.22 (d, J=7.6 Hz, 1H), 5.95 (s, 1H), 4.98 (s, 2H), 4.33 (t, J=12.4, 7.1 Hz, 2H), 4.20 (s, 1H), 3.81 (s, 3H); LCMS (ESI) m/z: 442.2 [$M+H^+$].

N-(1-(3-Aminophenyl)-2-(benzylamino)-2-oxoethyl)-N-(4-sulfamoylphenyl)-propiolamide A50. $^1$H NMR (400 MHz, DMSO-$d_6$) δ 8.72 (t, J=6.0 Hz, 1H), 7.63 (d, J=8.0 Hz, 2H), 7.40 (s, 1H), 7.29-7.22 (m, 9H), 6.77 (t, J=8.0 Hz, 1H), 6.40 (s, 1H), 6.33 (d, J=8.0 Hz, 1H), 6.21 (d, J=8.0 Hz, 1H), 5.98 (s, 1H), 5.01 (s, 2H), 4.36-4.27 (m, 3H); LCMS (ESI) m/z: 463.5 [$M+H^+$].

Example 4

Preparation of N-(2-(benzylamino)-1-(4-nitrophenyl)-2-oxoethyl)-N-(4-chlorophenyl)propiolamide A51 and N-(2-(benzylamino)-1-(4-aminophenyl)-2-oxoethyl)-N-(4-chlorophenyl)propiolamide A52

A51

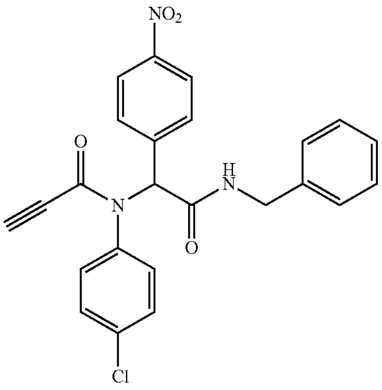

A52

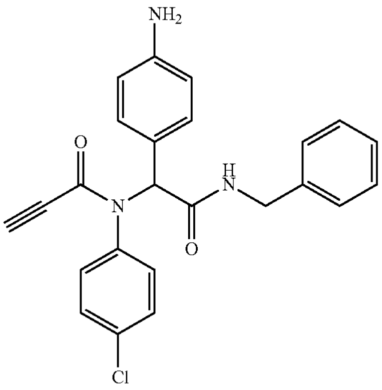

Compounds A51 and A52 were synthesized as shown in Scheme 4.

Scheme 4

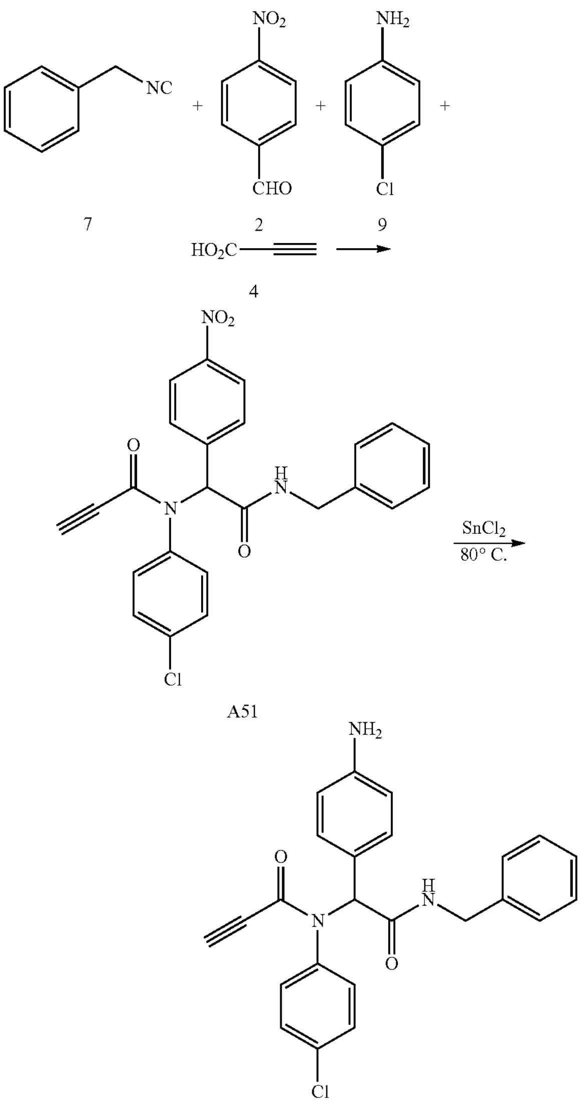

7 2 9 4 A51 A52

N-(2-(Benzylamino)-1-(4-nitrophenyl)-2-oxoethyl)-N-(4-chlorophenyl)-propiolamide A51. To a solution of compound 2 (91 mg, 0.6 mmol) in MeOH (6 mL) was added compound 9 (76 mg, 0.6 mmol). The reaction mixture was stirred for 1 h at room temperature, followed by addition of compound 4 (39 mg, 0.5 mmol) and compound 7 (59 mg, 0.5 mmol). After stirred at room temperature for 48 h, the reaction mixture was concentrated in vacuo to yield a crude product, which was purified by column chromatography to afford compound A51 (178 mg) in 44% yield. LCMS (ESI) m/z: 448.9 [$M+H^+$].

N-(2-(Benzylamino)-1-(4-aminophenyl)-2-oxoethyl)-N-(4-chlorophenyl)-propiolamide A52. To a solution of compound A51 (163 mg, 0.36 mmol) in EtOH (5 mL) was added $SnCl_2$ (249 mg, 1.8 mmol). After stirred for 1 h at 80° C. under $N_2$, the reaction mixture was concentrated in vacuo, neutralized with saturated $NaHCO_3$, and then extracted by EtOAc. The organic layers were combined, washed sequentially with saturated NaCl and water, dried over anhydrous $Na_2SO_4$, and concentrated in vacuo to yield a crude product, which was purified by prep-TLC to afford compound A52 (20 mg) in 13% yield. $^1H$ NMR (400 MHz, DMSO-$d_6$) δ 8.60 (t, J=6.0 Hz, 1H), 7.29-7.20 (m, 9H), 6.69 (d, J=8.0 Hz, 2H), 6.29 (d, J=8.0 Hz, 2H), 5.88 (s, 1H), 5.06 (s, 2H), 4.31 (d, J=4.0 Hz, 2H), 4.20 (s, 1H); LCMS (ESI) m/z: 418.2 [M+H$^+$].

Compounds A53 to A71 were synthesized similarly according to the procedures as described for compound A52.

N-(1-(4-Aminophenyl)-2-(benzylamino)-2-oxoethyl)-N-(3-chloro-4-methoxy-phenyl)propiolamide A53. $^1H$ NMR (400 MHz, DMSO-$d_6$) δ 8.60 (t, J=5.9 Hz, 1H), 7.33-7.14 (m, 6H), 6.94 (d, J=8.1 Hz, 1H), 6.70 (d, J=8.5 Hz, 2H), 6.31 (d, J=8.5 Hz, 2H), 5.86 (s, 1H), 5.07 (s, 2H), 4.31 (d, J=6.0 Hz, 2H), 4.20 (s, 1H), 3.78 (s, 3H); LCMS (ESI) m/z: 448.5 [M+H$^+$].

Methyl 3-(N-(1-(4-aminophenyl)-2-(benzylamino)-2-oxoethyl)propiolamido)-benzoate A54. $^1H$ NMR (400 MHz, DMSO-$d_6$) δ 8.63 (t, J=5.9 Hz, 1H), 7.77 (d, J=7.4 Hz, 1H), 7.26 (dt, J=20.4, 7.9 Hz, 7H), 6.69 (d, J=8.4 Hz, 2H), 6.26 (d, J=8.4 Hz, 2H), 5.91 (s, 1H), 5.06 (s, 2H), 4.32 (d, J=5.9 Hz, 2H), 4.17 (s, 1H), 3.84 (d, J=8.6 Hz, 3H); LCMS (ESI) m/z: 442.5 [M+H$^+$].

N-(1-(4-Aminophenyl)-2-(benzylamino)-2-oxoethyl)-N-(3-cyanophenyl)-propiolamide A55. $^1H$ NMR (400 MHz, DMSO-$d_6$) δ 8.70 (t, J=5.9 Hz, 1H), 7.67 (d, J=7.6 Hz, 2H), 7.42 (t, J=7.8 Hz, 1H), 7.25 (dd, J=20.4, 6.8 Hz, 6H), 6.69 (d, J=8.4 Hz, 2H), 6.29 (d, J=8.4 Hz, 2H), 5.92 (s, 1H), 5.08 (s, 2H), 4.33 (d, J=5.9 Hz, 2H), 4.25 (s, 1H).

N-(1-(4-Aminophenyl)-2-(benzylamino)-2-oxoethyl)-N-(3-(hydroxymethyl)-phenyl)propiolamide A56. $^1H$ NMR (400 MHz, DMSO-$d_6$) δ 8.50 (t, J=6.0 Hz, 1H), 7.31-7.17 (m, 7H), 7.11 (s, 2H), 6.69 (d, J=8.4 Hz, 2H), 6.26 (d, J=8.4 Hz, 2H), 5.85 (s, 1H), 5.19 (t, J=7.4 Hz, 1H), 5.02 (s, 2H), 4.37 (d, J=5.1 Hz, 2H), 4.31 (d, J=5.9 Hz, 2H), 4.10 (s, 1H).

N-(1-(4-Aminophenyl)-2-(benzylamino)-2-oxoethyl)-N-(5-chloro-2-fluoro-phenyl)propiolamide A57. $^1H$ NMR (400 MHz, DMSO-$d_6$) δ 8.73 (t, J=5.9 Hz, 1H), 7.94 (dd, J=6.4, 2.8 Hz, 1H), 7.34 (t, J=7.7 Hz, 1H), 7.33 (dd, J=11.9, 5.3 Hz, 2H) 7.32-7.25 (m, 3H), 7.10 (t, J=9.0 Hz, 1H), 6.70 (d, J=8.4 Hz, 2H), 6.29 (d, J=8.5 Hz, 2H), 5.90 (s, 1H), 5.10 (s, 2H), 4.33 (s, 2H), 4.28 (s, 1H).

N-(1-(4-Aminophenyl)-2-(benzylamino)-2-oxoethyl)-N-(3-hydroxyphenyl)-propiolamide A58. $^1H$ NMR (400 MHz, DMSO-$d_6$) δ 9.38 (s, 1H), 8.48 (t, J=6.0 Hz, 1H), 7.17-7.32 (m, 5H), 6.93 (t, J=7.6 Hz, 1H), 6.64-6.84 (m, 3H), 6.44-6.63 (m, 2H), 6.28 (d, J=8.4 Hz, 1H), 5.81 (s, 1H), 5.02 (s, 2H), 4.27-4.41 (m, 2H), 4.12 (s, 1H).

N-(1-(4-Aminophenyl)-2-(benzylamino)-2-oxoethyl)-N-(3-fluorophenyl)-propiolamide A59. $^1H$ NMR (400 MHz, DMSO-$d_6$) δ 8.62 (t, J=5.9 Hz, 1H), 7.35-6.98 (m, 9H), 6.70 (d, J=8.4 Hz, 2H), 6.28 (d, J=8.4 Hz, 2H), 5.89 (s, 1H), 5.05 (s, 2H), 4.32 (d, J=5.9 Hz, 2H), 4.20 (s, 1H).

N-(1-(4-Aminophenyl)-2-(benzylamino)-2-oxoethyl)-N-(4-methoxyphenyl)-propiolamide A60. $^1H$ NMR (400 MHz, DMSO-$d_6$) δ 8.51 (t, J=6.0 Hz, 1H), 7.24 (ddd, J=9.8, 7.6, 2.6 Hz, 6H), 6.69 (dd, J=13.2, 8.5 Hz, 4H), 6.28 (d, J=8.5 Hz, 2H), 5.84 (s, 1H), 5.03 (s, 2H), 4.30 (d, J=5.9 Hz, 2H), 4.12 (s, 1H), 3.67 (s, 3H).

N-(1-(4-Aminophenyl)-2-(benzylamino)-2-oxoethyl)-N-(3-methoxyphenyl)-propiolamide A61. $^1H$ NMR (400 MHz, DMSO-$d_6$) δ 8.54 (t, J=5.9 Hz, 1H), 7.34-7.25 (m, 2H), 7.21 (d, J=7.0 Hz, 3H), 7.07 (t, J=8.0 Hz, 1H), 6.74 (dd, J=30.4, 18.2 Hz, 5H), 6.27 (d, J=8.4 Hz, 2H), 5.86 (s, 1H), 5.03 (s, 2H), 4.31 (d, J=5.8 Hz, 2H), 4.15 (d, J=16.1 Hz, 1H), 3.61 (s, 3H).

3-(N-(1-(4-Aminophenyl)-2-(benzylamino)-2-oxoethyl)propiolamido)-benzamide A62. $^1H$ NMR (400 MHz, DMSO-$d_6$) δ 8.57 (t, J=5.9 Hz, 1H), 7.85 (s, 1H), 7.68 (d, J=7.4 Hz, 1H), 7.24 (dd, J=19.6, 7.1 Hz, 7H), 6.69 (d, J=8.4 Hz, 2H), 6.25 (d, J=8.4 Hz, 2H), 5.88 (s, 1H), 5.02 (s, 2H), 4.32 (d, J=5.9 Hz, 2H), 4.15 (s, 1H).

N-(3-Acetamidophenyl)-N-(1-(4-aminophenyl)-2-(benzylamino)-2-oxoethyl)-propiolamide A63. $^1H$ NMR (400 MHz, DMSO-$d_6$) δ 9.92 (s, 1H), 8.50 (t, J=5.9 Hz, 1H), 7.55 (d, J=7.2 Hz, 2H), 7.33-7.13 (m, 6H), 7.12-6.93 (m, 1H), 6.71 (d, J=8.4 Hz, 2H), 6.27 (d, J=8.4 Hz, 2H), 5.82 (s, 1H), 5.02 (s, 2H), 4.32 (s, 2H), 4.13 (s, 1H), 2.00 (s, 3H).

N-(1-(4-Aminophenyl)-2-(benzylamino)-2-oxoethyl)-N-(4-hydroxyphenyl)-propiolamide A64. $^1H$ NMR (400 MHz, DMSO-$d_6$) δ 9.42 (s, 1H), 8.47 (t, J=5.9 Hz, 1H), 7.23 (dt, J=11.4, 7.4 Hz, 7H), 6.66 (d, J=8.5 Hz, 2H), 6.50 (d, J=7.5 Hz, 2H), 6.28 (d, J=8.5 Hz, 2H), 5.80 (s, 1H), 5.01 (s, 2H), 4.29 (d, J=6.0 Hz, 2H), 4.10 (s, 1H).

N-(1-(4-Aminophenyl)-2-(benzylamino)-2-oxoethyl)-N-(3,4-dichlorophenyl)-propiolamide A65. $^1H$ NMR (400 MHz, DMSO-$d_6$) δ 8.69 (t, J=5.9 Hz, 1H), 7.51 (t, J=23.9 Hz, 2H), 7.36-7.24 (m, 3H), 7.22 (d, J=3.2 Hz, 3H), 6.71 (d, J=8.5 Hz, 2H), 6.31 (d, J=8.5 Hz, 2H), 5.90 (s, 1H), 5.10 (s, 2H), 4.33 (d, J=5.8 Hz, 2H), 4.29 (s, 1H).

N-(1-(4-Aminophenyl)-2-(benzylamino)-2-oxoethyl)-N-(4-cyanophenyl)-propiolamide A66. $^1H$ NMR (400 MHz, DMSO-$d_6$) δ 8.68 (s, 1H), 7.70 (d, J=8.5 Hz, 2H), 7.48 (s, 2H), 7.31-7.25 (m, 2H), 7.22 (d, J=6.2 Hz, 3H), 6.69 (d, J=8.5 Hz, 2H), 6.28 (d, J=8.4 Hz, 2H), 5.94 (s, 1H), 5.08 (s, 2H), 4.33 (d, J=3.0 Hz, 2H), 4.24 (s, 1H).

N-(1-(4-Aminophenyl)-2-(benzylamino)-2-oxoethyl)-N-(4-(hydroxymethyl)-phenyl)propiolamide A67. $^1H$ NMR (400 MHz, DMSO-$d_6$) δ 8.52 (t, J=5.9 Hz, 1H), 7.29-7.09 (m, 9H), 6.69 (d, J=8.4 Hz, 2H), 6.27 (d, J=8.4 Hz, 2H), 5.87 (s, 1H), 5.19 (t, J=5.7 Hz, 1H), 5.02 (s, 2H), 4.41 (d, J=5.3 Hz, 2H), 4.30 (d, J=5.9 Hz, 2H), 4.11 (s, 1H).

N-(1-(4-Aminophenyl)-2-(benzylamino)-2-oxoethyl)-N-(4-sulfamoylphenyl)-propiolamide A68. $^1H$ NMR (400 MHz, DMSO-$d_6$) δ 8.63 (t, J=5.8 Hz, 1H), 7.63 (d, J=8.5 Hz, 2H), 7.40 (s, 2H), 7.33-7.17 (m, 7H), 6.71 (d, J=8.4 Hz, 2H), 6.29 (d, J=8.4 Hz, 2H), 5.95 (s, 1H), 5.07 (s, 2H), 4.32 (d, J=5.8 Hz, 2H), 4.23 (s, 1H).

Methyl 4-(N-(1-(4-aminophenyl)-2-(benzylamino)-2-oxoethyl)propiolamido)-benzoate A69. $^1H$ NMR (400 MHz, DMSO-$d_6$) δ 8.63 (t, J=4.8 Hz, 1H), 7.76 (d, J=8.4 Hz, 2H), 7.40 (s, 2H), 7.31-7.25 (m, 2H), 7.22 (d, J=7.0 Hz, 3H), 6.69 (d, J=8.4 Hz, 2H), 6.26 (d, J=8.4 Hz, 2H), 5.92 (s, 1H), 5.04 (s, 2H), 4.32 (d, J=5.7 Hz, 2H), 4.18 (s, 1H), 3.81 (s, 3H).

N-(3-Aminophenyl)-N-(1-(4-aminophenyl)-2-(benzylamino)-2-oxoethyl)-propiolamide A70. $^1H$ NMR (400 MHz, DMSO-$d_6$) δ 8.38 (t, J=5.9 Hz, 1H), 7.31-7.14 (m, 6H), 6.75 (dd, J=16.7, 8.1 Hz, 3H), 6.37-6.23 (m, 4H), 5.74 (s, 1H), 5.00 (s, 4H), 4.33-4.25 (m, 2H), 4.08 (s, 1H).

N-(1-(4-Aminophenyl)-2-(benzylamino)-2-oxoethyl)-N-(4-(methylsulfonamido)-phenyl)propiolamide A71. $^1H$ NMR (400 MHz, DMSO-$d_6$) δ 9.64 (s, 1H), 8.55 (t, J=5.9 Hz, 1H), 7.31-7.10 (m, 7H), 7.00 (d, J=7.1 Hz, 1H), 6.70 (d, J=8.4 Hz, 2H), 6.27 (d, J=8.5 Hz, 2H), 5.84 (s, 1H), 5.03 (s, 2H), 4.31 (d, J=5.8 Hz, 2H), 4.18 (s, 1H), 2.73 (s, 3H).

Example 5

Preparation of N-(2-(benzylamino)-1-cyclopropyl-2-oxoethyl)-N-(3-chlorophenyl)propiolamide A72

A72

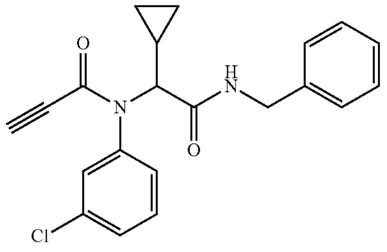

Compound A72 was synthesized as shown in Scheme 5.

Scheme 5

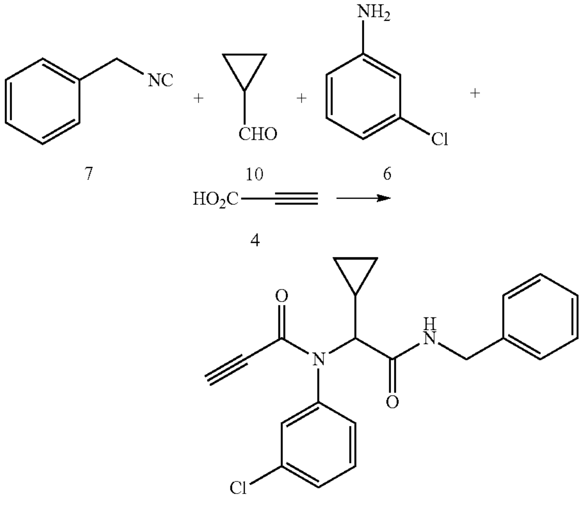

7 10 6

4

A72

N-(2-(Benzylamino)-1-cyclopropyl-2-oxoethyl)-N-(3-chlorophenyl)-propiolamide A72. To a solution of compound 10 (42 mg, 0.6 mmol) in MeOH (6 mL) was added compound 6 (76 mg, 0.6 mmol). The reaction mixture was stirred for 1 h at room temperature, followed by addition of compound 4 (39 mg, 0.5 mmol) and compound 7 (59 mg, 0.5 mmol). After stirred at room temperature for 48 h, the reaction mixture was concentrated in vacuo to yield a crude product, which was purified by column chromatography to afford compound A72 (90 mg) in 49% yield. $^1$H NMR (400 MHz, DMSO-$d_6$) δ 8.59 (t, J=5.9 Hz, 1H), 7.78 (s, 1H), 7.67-7.56 (m, 1H), 7.52-7.45 (m, 2H), 7.35-7.23 (m, 5H), 4.36 (dd, J=5.8, 2.1 Hz, 2H), 4.27 (s, 1H), 4.00 (d, J=10.3 Hz, 1H), 0.81-0.72 (m, 1H), 0.62-0.48 (m, 2H), 0.38-0.31 (m, 1H), 0.30-0.20 (m, 1H); LCMS (ESI) m/z: 367.1 [M+H$^+$].

Compounds A73 to Alit were synthesized similarly according to the procedures as described for compound A72.

Methyl 3-(N-(2-(benzylamino)-2-oxo-1-(thiophen-2-yl)ethyl)propiolamido)-benzoate A73. $^1$H NMR (400 MHz, DMSO-$d_6$) δ 8.84 (t, J=5.9 Hz, 1H), 8.00 (s, 1H), 7.84 (d, J=7.8 Hz, 1H), 7.52 (d, J=7.3 Hz, 1H), 7.38 (dd, J=10.4, 5.1 Hz, 2H), 7.27 (dt, J=20.4, 7.7 Hz, 5H), 6.94 (d, J=3.1 Hz, 1H), 6.82 (dd, J=5.1, 3.6 Hz, 1H), 6.33 (s, 1H), 4.38-4.24 (m, 3H), 3.85 (d, J=6.8 Hz, 3H); LCMS (ESI) m/z: 433 [M+H$^+$].

N-(2-(Benzylamino)-2-oxo-1-phenylethyl)-N-(3-chlorophenyl)propiolamide A74. $^1$H NMR (400 MHz, DMSO-$d_6$) δ 8.80 (t, J=5.8 Hz, 1H), 7.31-7.27 (m, 3H), 7.24-7.20 (m, 5H), 7.18-7.14 (m, 4H), 7.12-7.09 (m, 2H), 6.08 (s, 1H), 4.35 (t, J=5.3 Hz, 2H), 4.27 (s, 1H); LCMS (ESI) m/z: 403.1 [M+H$^+$].

N-(2-(Benzylamino)-2-oxo-1-(thiophen-2-yl)ethyl)-N-(3-chlorophenyl)-propiolamide A75. $^1$H NMR (400 MHz, DMSO-$d_6$) δ 8.84 (t, J=6.0 Hz, 1H), 7.49 (s, 1H), 7.41 (dd, J=5.1, 0.9 Hz, 1H), 7.35-7.31 (m, 1H), 7.31-7.22 (m, 7H), 6.95 (d, J=3.0 Hz, 1H), 6.85 (dd, J=5.1, 3.6 Hz, 1H), 6.31 (s, 1H), 4.34 (d, J=5.8 Hz, 2H), 4.31 (s, 1H); LCMS (ESI) m/z: 409.1 [M+H$^+$].

Methyl 3-(N-(2-(benzylamino)-2-oxo-1-phenylethyl)propiolamido)benzoate A76. $^1$H NMR (400 MHz, DMSO-$d_6$) δ 8.80 (d, J=5.8 Hz, 1H), 7.75 (d, J=7.6 Hz, 1H), 7.32-7.19 (m, 7H), 7.14-7.07 (m, 6H), 6.11 (s, 1H), 4.36 (d, J=6.6 Hz, 2H), 4.22 (s, 1H), 3.82 (s, 3H); LCMS (ESI) m/z: 427.1 [M+H$^+$].

Methyl 4-(2-(benzylamino)-1-(N-(3-chlorophenyl)propiolamido)-2-oxoethyl)-cyclohexane-1-carboxylate A77. $^1$H NMR (400 MHz, DMSO-$d_6$) δ 8.81 (t, J=6.0 Hz, 1H), 7.52-7.30 (m, 6H), 7.26-7.23 (m, 3H), 4.77 (d, J=8.0 Hz, 2H), 4.32-4.16 (m, 3H), 3.56 (s, 3H), 2.23 (t, J=12.0 Hz, 1H), 3.11 (t, J=12.0 Hz, 3H), 1.60-1.47 (m, 2H), 1.19-1.00 (m, 4H); LCMS (ESI) m/z: 467.2 [M+H$^+$].

N-(2-(Benzylamino)-2-oxo-1-(tetrahydro-2H-pyran-4-yl)ethyl)-N-(3-chloro-phenyl)propiolamide A78. $^1$H NMR (400 MHz, DMSO-$d_6$) δ 8.85 (t, J=5.9 Hz, 1H), 7.62-7.55 (m, 1H), 7.53-7.47 (m, 1H), 7.45-7.38 (m, 2H), 7.35-7.30 (m, 2H), 7.28-7.21 (m, 3H), 4.84 (d, J=10.5 Hz, 1H), 4.35-4.16 (m, 3H), 3.84-3.71 (m, 2H), 3.21-3.05 (m, 2H), 1.96-1.80 (m, 1H), 1.64 (d, J=13.0 Hz, 1H), 1.35-1.19 (m, 3H); LCMS (ESI) m/z: 411.9 [M+H$^+$].

Methyl 4-(benzylcarbamoyl)-4-(N-(3-chlorophenyl)propiolamido)-cyclohexane-carboxylate A79. $^1$H NMR (400 MHz, DMSO-$d_6$) δ 8.24 (dd, J=12.7, 6.0 Hz, 1H), 7.83 (dd, J=9.3, 1.8 Hz, 1H), 7.53 (dddd, J=14.2, 11.9, 5.5, 2.8 Hz, 3H), 7.32-7.20 (m, 5H), 4.34 (d, J=5.7 Hz, 2H), 4.22 (s, 1H), 3.54 (d, J=1.3 Hz, 3H), 2.45-2.37 (m, 1H), 2.28-2.02 (m, 2H), 2.04-1.81 (m, 2H), 1.72-1.56 (m, 2H), 1.44-1.21 (m, 2H); LCMS (ESI) m/z: 453 [M+H$^+$].

N-Benzyl-4-(N-(3-chlorophenyl)propiolamido)tetrahydro-2H-pyran-4-carboxamide A80. $^1$H NMR (400 MHz, DMSO-$d_6$) δ 8.35 (t, J=5.9 Hz, 1H), 7.88 (t, J=1.9 Hz, 1H), 7.66-7.48 (m, 3H), 7.35-7.18 (m, 5H), 4.36 (d, J=5.9 Hz, 2H), 4.25 (s, 1H), 3.69-3.43 (m, 4H), 2.27 (d, J=13.7 Hz, 1H), 2.05 (d, J=14.9 Hz, 1H), 1.75 (td, J=9.1, 4.6 Hz, 1H), 1.65-1.53 (m, 1H); LCMS (ESI) m/z: 397 [M+H$^+$].

N-(2-(Benzylamino)-2-oxo-1-phenylethyl)-N-(3-chloro-2-fluorophenyl)-propiolamide A81. $^1$H NMR (400 MHz, DMSO-$d_6$) δ 8.63 (t, J=8.0 Hz, 1H), 7.80 (t, J=6.0 Hz, 1H), 7.44 (d, J=8.0 Hz, 1H), 7.35 (t, J=8.0 Hz, 1H), 7.25-7.06 (m, 10H), 6.02 (s, 1H), 4.33-4.28 (m, 2H), 4.19 (s, 1H); LCMS (ESI) m/z: 421.9 [M+H$^+$].

N-(2-(Benzylamino)-2-oxo-1-phenylethyl)-N-(2,3-dichlorophenyl)-propiolamide A82. $^1$H NMR (400 MHz, DMSO-$d_6$) δ 8.78 (t, J=8.0 Hz, 1H), 7.99 (d, J=6.0 Hz, 1H), 7.50 (d, J=8.0 Hz, 1H), 7.35 (t, J=8.0 Hz, 1H), 7.27-7.10 (m, 10H), 6.02 (s, 1H), 4.39-4.28 (m, 2H), 4.25 (s, 1H); LCMS (ESI) m/z: 437.1 [M+H$^+$].

Methyl 2-(3-(2-(benzylamino)-1-(N-(3-chlorophenyl)propiolamido)-2-oxoethyl)-phenoxy)acetate A83. $^1$H NMR (400 MHz, DMSO-$d_6$) δ 8.82 (t, J=5.9 Hz, 1H), 7.49 (s, 1H), 7.31-7.28 (m, 2H), 7.27-7.17 (m, 6H), 7.06 (t, J=7.8 Hz, 1H), 6.75-6.72 (m, 2H), 6.68 (d, J=7.6 Hz, 1H), 6.03 (s, 1H), 4.65 (d, J=5.3 Hz, 2H), 4.35 (qd, J=15.2, 5.9 Hz, 2H), 4.28 (s, 1H), 3.69 (s, 3H); LCMS (ESI) m/z: 491.2 [M+H$^+$].

Methyl 4-((N-(1-(benzylamino)-1-oxopropan-2-yl)propiolamido)methyl)-benzoate A84. $^1$H NMR (400 MHz, DMSO-d$_6$) δ 8.68-8.45 (m, 1H), 7.93-7.77 (m, 2H), 7.64-7.43 (m, 2H), 7.32-7.20 (m, 5H), 5.09-4.83 (m, 2H), 4.79-4.66 (m, 1H), 4.52-4.40 (m, 1H), 4.28-4.15 (m, 2H), 3.85 (d, J=4.8 Hz, 3H), 1.24 (dd, J=69.2, 7.2 Hz, 3H); LCMS (ESI) m/z: 379.3 [M+H$^+$].

N-(Benzo[c][1,2,5]thiadiazol-4-yl)-N-(2-(benzylamino)-2-oxo-1-phenylethyl)-propiolamide A85. $^1$H NMR (400 MHz, DMSO-d$_6$) δ 8.86 (t, J=5.5 Hz, 1H), 8.14 (d, J=7.0 Hz, 1H), 7.93 (d, J=8.8 Hz, 1H), 7.68 (t, 1H), 7.30-7.22 (m, 5H), 7.04 (d, J=5.9 Hz, 2H), 6.93-6.83 (m, 3H), 6.24 (s, 1H), 4.43-4.34 (m, 2H), 3.99 (s, 1H); LCMS (ESI) m/z: 427.4 [M+H$^+$].

N-Benzyl-3-(N-(3-chlorophenyl)propiolamido)oxetane-3-carboxamide A86. $^1$H NMR (400 MHz, DMSO-d$_6$) δ 8.92 (t, J=6.0 Hz, 1H), 7.78-7.70 (m, 1H), 7.60-7.49 (m, 3H), 7.35-7.23 (m, 5H), 4.72 (d, J=7.4 Hz, 2H), 4.50 (d, J=7.4 Hz, 2H), 4.44 (d, J=5.9 Hz, 2H), 4.38 (s, 1H); LCMS (ESI) m/z: 368.8 [M+H$^+$].

N-(2-(Benzylamino)-1-(4-fluorophenyl)-2-oxoethyl)-N-(3-chlorophenyl)-propiolamide A87. $^1$H NMR (400 MHz, DMSO-d$_6$) δ 8.81 (t, J=5.9 Hz, 1H), 7.44 (s, 1H), 7.31-7.12 (m, 10H), 7.04-6.97 (m, 2H), 6.07 (s, 1H), 4.46-4.25 (m, 3H); LCMS (ESI) m/z: 420.9 [M+H$^+$].

N-(Benzo[d]thiazol-5-yl)-N-(2-(benzylamino)-2-oxo-1-phenylethyl)-propiolamide A88. $^1$H NMR (400 MHz, DMSO-d$_6$) δ 9.34 (s, 1H), 8.80 (s, 1H), 7.94 (d, J=8.5 Hz, 1H), 7.35-7.17 (m, 6H), 7.19-6.99 (m, 6H), 6.16 (s, 1H), 4.37 (dd, J=5.9, 3.1 Hz, 2H), 4.16 (s, 1H); LCMS (ESI) m/z: 425.5 [M+H$^+$].

N-(2-(Benzylamino)-2-oxo-1-phenylethyl)-N-(1-oxo-2,3-dihydro-1H-inden-4-yl)propiolamide A89. $^1$H NMR (400 MHz, DMSO-d$_6$) δ 8.79 (t, J=8.0 Hz, 1H), 7.50 (brs, 1H), 7.37 (d, J=8.0 Hz, 1H), 7.28 (t, J=6.0 Hz, 2H), 7.23-7.08 (m, 8H), 6.12 (s, 1H), 4.36-4.22 (m, 2H), 3.30 (s, 1H), 2.99 (t, J=4.0 Hz, 2H), 2.59 (t, J=4.0 Hz, 2H); LCMS (ESI) m/z: 423.9 [M+H$^+$].

N-(2-(Benzylamino)-1-(2-fluorophenyl)-2-oxoethyl)-N-(3-chlorophenyl)-propiolamide A90. $^1$H NMR (400 MHz, DMSO-d$_6$) δ 8.92 (t, J=5.8 Hz, 1H), 7.76-7.36 (m, 1H), 7.35-7.18 (m, 9H), 7.15-7.08 (m, 1H), 6.99-6.88 (m, 2H), 6.34 (s, 1H), 4.34 (s, 3H); LCMS (ESI) m/z: 421.7 [M+H$^+$].

N-(2-(Benzylamino)-2-oxo-1-phenylethyl)-N-(5-chloro-2-iodophenyl)-propiolamide A91. $^1$H NMR (400 MHz, DMSO-d$_6$) δ 8.80 (t, J=5.9 Hz, 1H), 8.05 (d, J=2.5 Hz, 1H), 7.63 (d, J=8.5 Hz, 1H), 7.27-7.15 (m, 10H), 7.07 (dd, J=8.5, 2.6 Hz, 1H), 6.00 (s, 1H), 4.39-4.25 (m, 3H); LCMS (ESI) m/z: 529.8 [M+H$^+$].

N-(2-(Benzylamino)-2-oxo-1-phenylethyl)-N-(3-(methylsulfonyl)-phenyl)-propiolamide A92. $^1$H NMR (400 MHz, DMSO-d$_6$) δ 8.85 (t, J=5.8 Hz, 1H), 7.75-7.61 (m, 2H), 7.48 (t, 1H), 7.32-7.08 (m, 11H), 6.13 (s, 1H), 4.43-4.29 (m, 3H), 2.96 (s, 3H); LCMS (ESI) m/z: 447.3 [M+H$^+$].

N-(2-(Benzylamino)-2-oxo-1-phenylethyl)-N-(3-chloro-4-methoxyphenyl)-propiolamide A93. $^1$H NMR (400 MHz, DMSO-d$_6$) δ 8.76 (t, 1H), 7.74-7.25 (m, 3H), 7.25-7.08 (m, 9H), 6.92 (d, J=8.5 Hz, 1H), 6.05 (s, 1H), 4.39-4.30 (m, 2H), 4.25 (s, 1H), 3.75 (s, 3H); LCMS (ESI) m/z: 433.8 [M+H$^+$].

N-(Benzo[c][1,2,5]thiadiazol-5-yl)-N-(2-(benzylamino)-2-oxo-1-phenylethyl)-propiolamide A94. $^1$H NMR (400 MHz, DMSO-d$_6$) δ 8.89 (s, 1H), 8.11 (s, 1H), 7.87 (d, J=9.2 Hz, 1H), 7.66 (s, 1H), 7.33-7.22 (m, 5H), 7.20-7.15 (m, 2H), 7.10 (dd, J=9.1, 3.9 Hz, 3H), 6.21 (s, 1H), 4.39 (dd, J=5.9, 3.7 Hz, 2H), 4.24 (s, 1H); LCMS (ESI) m/z: 426.5 [M+H$^+$].

N-(2-(Benzylamino)-1-(3-(2-hydroxyethyl)phenyl)-2-oxoethyl)-N-(3-chloro-phenyl)propiolamide A95. $^1$H NMR (400 MHz, DMSO-d$_6$) δ 8.79 (t, J=5.9 Hz, 1H), 7.30-7.27 (m, 2H), 7.25-7.12 (m, 7H), 7.06 (t, J=7.5 Hz, 1H), 7.00 (d, J=7.7 Hz, 1H), 6.95-6.89 (m, 2H), 6.05 (s, 1H), 4.59 (t, J=5.2 Hz, 1H), 4.35 (ddd, J=32.2, 15.4, 6.0 Hz, 2H), 4.27 (s, 1H), 3.39-3.35 (m, 2H), 2.56-2.52 (m, 2H); LCMS (ESI) m/z: 447.1 [M+H$^+$].

N-(Benzo[d][1,3]dioxol-5-yl)-N-(2-(benzylamino)-2-oxo-1-phenylethyl)-propiolamide A96. $^1$H NMR (400 MHz, DMSO-d$_6$) δ 8.71 (t, J=8.0 Hz, 1H), 7.28-7.10 (m, 10H), 7.68-7.66 (m, 3H), 6.00 (s, 1H), 5.96 (d, J=4.0 Hz, 2H), 4.33 (dd, J=8.0, 4.0 Hz, 2H), 4.22 (s, 1H); LCMS (ESI) m/z: 413.0 [M+H$^+$].

N-(Benzo[d][1,3]dioxol-4-yl)-N-(2-(benzylamino)-2-oxo-1-phenylethyl)-propiolamide A97. $^1$H NMR (400 MHz, DMSO-d$_6$) δ 8.72 (s, 1H), 7.36-7.01 (m, 11H), 6.73 (d, J=3.5 Hz, 2H), 5.97 (d, J=25.7 Hz, 2H), 5.30 (s, 1H), 4.33 (t, J=7.0 Hz, 2H), 4.21 (s, 1H); LCMS (ESI) m/z: 412.4 [M+H$^+$].

N-(Benzo[d]thiazol-6-yl)-N-(2-(benzylamino)-2-oxo-1-phenylethyl)-propiolamide A98. $^1$H NMR (400 MHz, DMSO-d$_6$) δ 9.36 (s, 1H), 8.79 (t, J=8.0 Hz, 1H), 8.13-7.83 (m, 2H), 7.41-708 (m, 11H), 6.13 (s, 1H), 4.36 (dd, J=4.0, 4.0 Hz, 2H), 4.17 (s, 1H); LCMS (ESI) m/z: 426.0 [M+H$^+$].

N-(2-(Benzylamino)-2-oxo-1-phenylethyl)-N-(2,2-difluorobenzo[d][1,3]dioxol-5-yl)propiolamide A99. $^1$H NMR (400 MHz, DMSO-d$_6$) δ 8.81 (t, J=8.0 Hz, 1H), 7.30-7.09 (m, 13H), 6.07 (s, 1H), 4.35 (dd, J=4.0, 4.0 Hz, 2H), 4.29 (s, 1H); LCMS (ESI) m/z: 449.0 [M+H$^+$].

N-(2-(Benzylamino)-2-oxo-1-phenylethyl)-N-(3-cyanophenyl)propiolamide A100. $^1$H NMR (400 MHz, DMSO-d$_6$) δ 8.86 (t, J=8.0 Hz, 1H), 7.67-7.65 (m, 3H), 7.42-7.08 (m, 11H), 6.12 (s, 1H), 4.36 (dd, J=8.0, 4.0 Hz, 2H), 4.31 (s, 1H); LCMS (ESI) m/z: 394.0 [M+H$^+$].

N-Benzyl-1-(N-(3-chlorophenyl)propiolamido)cyclohexanecarboxamide A101. $^1$H NMR (400 MHz, DMSO-d$_6$) δ 8.18 (t, J=5.9 Hz, 1H), 7.85 (t, J=2.0 Hz, 1H), 7.62-7.45 (m, 3H), 7.30 (h, J=4.2, 3.6 Hz, 4H), 7.24-7.18 (m, 1H), 4.33 (dd, J=6.1, 2.4 Hz, 2H), 4.19 (d, J=1.1 Hz, 1H), 2.18 (s, 1H), 1.95 (d, J=8.2 Hz, 1H), 1.64 (d, J=9.4 Hz, 2H), 1.41 (d, J=31.7 Hz, 5H), 1.15 (s, 1H); LCMS (ESI) m/z: 394.9 [M+H$^+$].

N-(2-(Benzylamino)-2-oxo-1-phenylethyl)-N-(1-methyl-2-oxo-1,2-dihydropyridin-4-yl)propiolamide A102. $^1$H NMR (400 MHz, DMSO-d$_6$) δ 8.81 (t, J=8.0 Hz, 1H), 7.48 (d, J=8.0 Hz, 1H), 7.31-7.18 (m, 10H), 6.39 (s, 1H), 6.22 (d, J=4.0 Hz, 1H), 6.07 (s, 1H), 4.44 (s, 1H), 4.35 (dd, J=4.0, 4.0 Hz, 2H), 3.26 (s, 3H); LCMS (ESI) m/z: 400.0 [M+H$^+$].

N-Benzyl-1-(N-(3-chlorophenyl)propiolamido)-4,4-difluorocyclohexane-carboxamide A103. $^1$H NMR (400 MHz, DMSO-d$_6$) δ 8.41 (t, J=5.9 Hz, 1H), 7.97 (t, J=2.0 Hz, 1H), 7.65-7.48 (m, 3H), 7.31 (h, J=5.9 Hz, 4H), 7.25-7.18 (m, 1H), 4.34 (d, J=5.9 Hz, 2H), 4.28 (s, 1H), 2.39 (d, J=13.5 Hz, 1H), 2.11 (d, J=14.1 Hz, 2H), 1.81 (d, J=38.8 Hz, 4H), 1.60 (s, 1H); LCMS (ESI) m/z: 430.9 [M+H$^+$].

N-(2-(Benzylamino)-2-oxo-1-phenylethyl)-N-(1-methyl-1H-indazol-6-yl)-propiolamide A104. $^1$H NMR (400 MHz, DMSO-d$_6$) δ 8.75 (t, J=5.9 Hz, 1H), 7.93 (d, J=1.0 Hz, 1H), 7.49 (d, J=8.5 Hz, 1H), 7.33-7.18 (m, 6H), 7.17-7.02 (m, 6H), 6.11 (s, 1H), 4.36 (dd, J=12.1, 5.9 Hz, 2H), 4.12 (s, 1H), 3.91 (s, 3H); LCMS (ESI) m/z: 422.5 [M+H$^+$].

N-([1,2,4]Triazolo[4,3-a]pyridin-6-yl)-N-(2-(benzylamino)-2-oxo-1-phenylethyl)-propiolamide A105. $^1$H NMR (400 MHz, DMSO-d$_6$) δ 8.92 (t, J=5.9 Hz, 2H), 8.48

(s, 1H), 7.66 (d, J=8.6 Hz, 1H), 7.39-7.08 (m, 11H), 6.16 (s, 1H), 4.44-4.36 (m, 2H), 4.34 (s, 1H); LCMS (ESI) m/z: 409.4 [M+H$^+$].

N-(Benzo[c][1,2,5]oxadiazol-4-yl)-N-(2-(benzylamino)-2-oxo-1-phenylethyl)-propiolamide A106. $^1$H NMR (400 MHz, DMSO-$d_6$) δ 8.89 (t, J=8.0 Hz, 1H), 7.95 (d, J=12.0 Hz, 1H), 7.59 (t, J=8.0 Hz, 1H), 7.31-7.03 (m, 11H), 6.24 (s, 1H), 4.36 (s, 2H), 4.20 (s, 1H); LCMS (ESI) m/z: 411.0 [M+H$^+$].

N-(2-(Benzylamino)-2-oxo-1-phenylethyl)-N-(1-methyl-1H-indazol-5-yl)-propiolamide A107. $^1$H NMR (400 MHz, DMSO-$d_6$) δ 8.73 (t, J=8.0 Hz, 1H), 7.98 (s, 1H), 7.30-7.07 (m, 13H), 6.10 (s, 1H), 4.35 (dd, J=8.0, 4.0 Hz, 2H), 4.09 (s, 1H), 3.95 (s, 3H); LCMS (ESI) m/z: 423.0 [M+H$^+$].

N-Benzyl-4-(N-(3,4-dichlorophenyl)propiolamido)tetrahydro-2H-pyran-4-carboxamide A108. $^1$H NMR (400 MHz, DMSO-$d_6$) δ 8.38 (t, J=8.0 Hz, 1H), 8.11 (d, J=4.0 Hz, 1H), 7.78 (d, J=8.0 Hz, 1H), 7.69 (d, J=2.0 Hz, 1H), 7.33-7.28 (m, 4H), 7.24-7.20 (m, 1H), 4.36 (d, J=8.0 Hz, 2H), 4.31 (s, 1H), 3.65-3.47 (m, 4H), 2.24 (d, J=12.0 Hz, 1H), 2.09 (d, J=12.0 Hz, 1H), 1.77-1.63 (m, 2H).

N-Benzyl-1-(N-(3,4-dichlorophenyl)propiolamido)cyclohexanecarboxamide A109. $^1$H NMR (400 MHz, DMSO-$d_6$) δ 8.22 (t, J=8.0 Hz, 1H), 8.07 (d, J=2.0 Hz, 1H), 7.76 (d, J=12.0 Hz, 1H), 7.64 (dd, J=10.0, 4.0 Hz, 1H), 7.33-7.28 (m, 4H), 7.23-7.20 (m, 1H), 4.33 (dd, J=6.0, 4.0 Hz, 2H), 4.27 (s, 1H), 2.15 (b, 1H), 1.99-1.97 (m, 1H), 1.64-1.62 (m, 2H), 1.50-1.47 (m, 1H), 1.37 (b, 4H), 1.18 (b, 1H).

(1S,4S)—N-Benzyl-1-(N-(3-chlorophenyl)propiolamido)-4-hydroxycyclohexane-carboxamide A110. $^1$H NMR (400 MHz, DMSO-$d_6$) δ 8.21 (t, J=5.9 Hz, 1H), 7.85 (t, J=2.0 Hz, 1H), 7.57-7.44 (m, 3H), 7.30 (d, J=5.2 Hz, 4H), 7.21 (ddt, J=6.4, 4.6, 3.0 Hz, 1H), 4.50 (d, J=4.1 Hz, 1H), 4.33 (dd, J=6.1, 1.8 Hz, 2H), 4.20 (s, 1H), 2.39-2.31 (m, 1H), 2.10 (s, 1H), 1.56 (td, J=23.1, 22.5, 10.6 Hz, 4H), 1.35 (t, J=7.8 Hz, 2H); LCMS (ESI) m/z: 410.9 [M+H$^+$].

(1R,4R)—N-Benzyl-1-(N-(3-chlorophenyl)propiolamido)-4-hydroxycyclohexane-carboxamide A111. $^1$H NMR (400 MHz, DMSO-$d_6$) δ 8.18 (t, J=5.9 Hz, 1H), 7.83 (t, J=1.9 Hz, 1H), 7.60-7.45 (m, 3H), 7.28 (d, J=5.8 Hz, 4H), 7.22-7.17 (m, 1H), 4.38 (d, J=3.4 Hz, 1H), 4.31 (dd, J=5.9, 3.0 Hz, 2H), 4.19 (s, 1H), 3.53 (s, 1H), 1.98 (s, 2H), 1.87-1.68 (m, 3H), 1.57-1.43 (m, 1H), 1.31-1.09 (m, 2H); LCMS (ESI) m/z: 410.9 [M+H$^+$].

Example 6

Preparation of N-(3-chlorophenyl)-N-(2-((2-nitrophenyl)amino)-2-oxo-1-phenylethyl)propiolamide A112, N-(3-chlorophenyl)-N-(2-((2-aminophenyl)amino)-2-oxo-1-phenylethyl)propiolamide A113, and N-(3-chlorophenyl)-N-(2-((4-cyanobenzyl)amino)-2-oxo-1-phenylethyl)propiolamide A114

A112

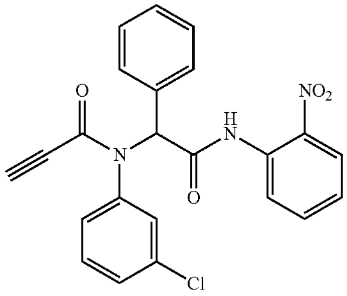

-continued

A113

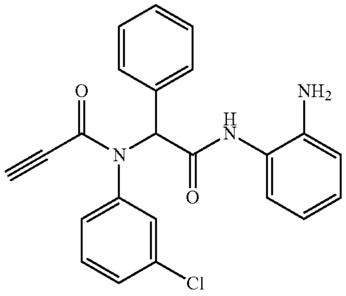

A114

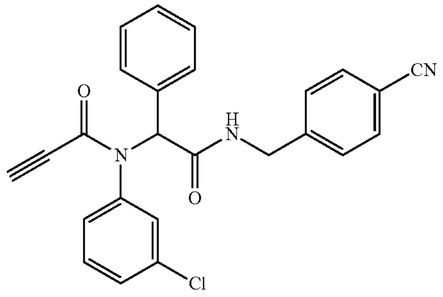

Compounds A112, A113, and A114 were synthesized as shown in Scheme 6.

Scheme 6

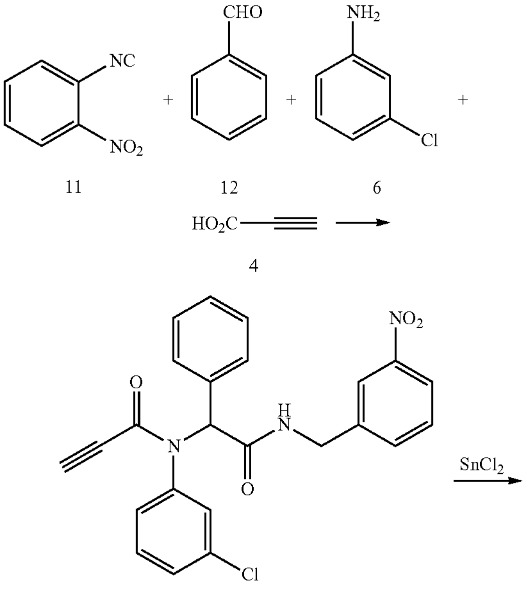

11 12 6 4

A112

-continued

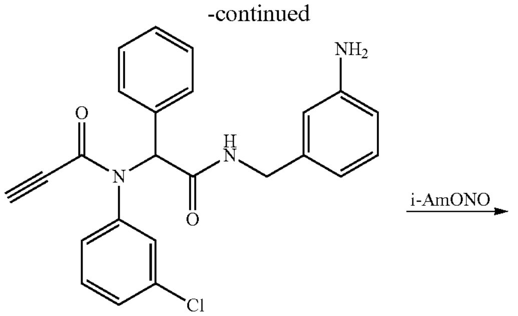

A113

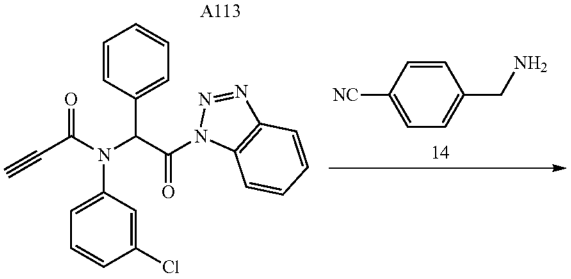

14

13

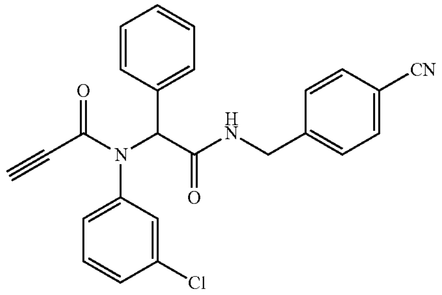

A114

N-(3-Chlorophenyl)-N-(2-((2-nitrophenyl)amino)-2-oxo-1-phenylethyl)-propiolamide A112. To a solution of m-chloroaniline 6 (700 mg, 5.51 mmol) in 2,2,2-trifluoroethyl alcohol (6 mL) was added benzaldehyde 12 (584 mg, 5.51 mmol). The reaction mixture was stirred for 1 h at room temperature, followed by addition of propiolic acid 4 (321 mg, 4.59 mmol) and compound 11 (680 mg, 4.59 mmol). After stirred at room temperature for 48 h, the reaction mixture was concentrated in vacuo to yield a crude product, which was purified by column chromatography to afford compound A112 (510 mg). LCMS (ESI) m/z: 434 [M+H$^+$].

N-(3-Chlorophenyl)-N-(2-((2-aminophenyl)amino)-2-oxo-1-phenylethyl)-propiolamide A113. To a solution of compound A112 (510 mg, 1.2 mmol) in EtOH (15 mL) was added $SnCl_2$ (1.36 g, 6.0 mmol). After stirred for 1 h at 80° C. under $N_2$, the reaction mixture was concentrated in vacuo, neutralized with saturated $NaHCO_3$, and then extracted by EtOAc. The organic layers were combined, washed sequentially with saturated NaCl and water, dried over anhydrous $Na_2SO_4$, and concentrated in vacuo to yield a crude product, which was purified by column chromatography to afford compound A113 (350 mg). LCMS (ESI) m/z: 404 [M+H$^+$].

Compound 13. To a solution of compound A113 (350 mg, 0.87 mmol) in $CH_2Cl_2$ was added i-AmONO (isopentyl nitrile) (305.4 mg, 2.6 mmol) at room temperature. After stirred overnight at room temperature, the reaction mixture was concentrated in vacuo to yield a crude product, which was purified by prep-TLC to afford compound 13 (208 mg). LCMS (ESI) m/z: 415 [M+H$^+$].

N-(3-Chlorophenyl)-N-(2-((4-cyanobenzyl)amino)-2-oxo-1-phenylethyl)-propiolamide A114. To a solution of compound 13 (21.0 mg, 0.05 mmol) in $CH_2Cl_2$ was added 4-(aminomethyl)benzonitrile 14 (6.6 mg, 0.05 mmol) at room temperature. After stirred overnight at room temperature, the reaction mixture was concentrated in vacuo to yield a crude product, which was purified by prep-TLC to afford compound A114 (6 mg). $^1$H NMR (400 MHz, DMSO-$d_6$) δ 8.93 (t, J=6.0 Hz, 1H), 7.78 (d, J=8.0 Hz, 2H), 7.42 (d, J=8.0 Hz, 3H), 7.23-7.09 (m, 9H), 6.07 (s, 1H), 4.50 (dd, J=16.0, 4.0 Hz, 1H), 4.37 (dd, J=20.0, 6.0 Hz, 1H), 4.28 (s, 1H); LCMS (ESI) m/z: 428.9 [M+H$^+$].

Compounds A115 and A116 were synthesized similarly according to the procedures as described for compound A114.

N-(3-Chlorophenyl)-N-(2-((4-fluorobenzyl)amino)-2-oxo-1-phenylethyl)-propiolamide A115. $^1$H NMR (400 MHz, DMSO-$d_6$) δ 8.76 (t, J=6.0 Hz, 1H), 7.38 (s, 2H), 7.30-7.10 (m, 13H), 6.06 (s, 1H), 4.33 (d, J=4.0 Hz, 2H), 4.24 (s, 1H); LCMS (ESI) m/z: 421.1 [M+H$^+$].

N-(3-Chlorophenyl)-N-(2-((2-fluorobenzyl)amino)-2-oxo-1-phenylethyl)-propiolamide A116. $^1$H NMR (400 MHz, DMSO-$d_6$) δ 8.81 (t, J=6.0 Hz, 1H), 7.41 (brs, 1H), 7.32-7.07 (m, 14H), 6.09 (s, 1H), 4.39 (d, J=4.0 Hz, 2H), 4.27 (s, 1H); LCMS (ESI) m/z: 421.9 [M+H$^+$].

Example 7

Preparation of N-(2-(benzylamino)-1-(3-nitrophenyl)-2-oxoethyl)-N-(3-chloro-4-methoxyphenyl) acrylamide B1 and N-(2-(benzylamino)-1-(3-aminophenyl)-2-oxoethyl)-N-(3-chloro-4-methoxyphenyl) acrylamide B2

B1

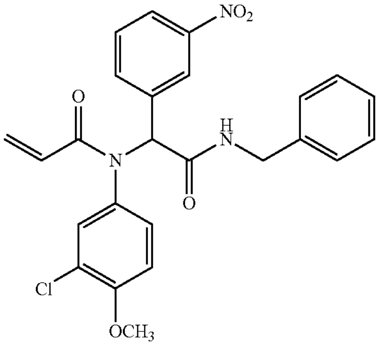

B2

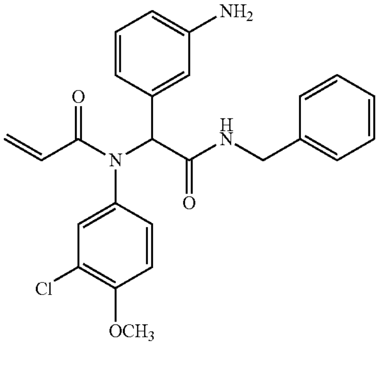

Compounds B1 and B2 were synthesized as shown in Scheme 7.

N-(2-(Benzylamino)-1-(3-nitrophenyl)-2-oxoethyl)-N-(3-chloro-4-methoxy-phenyl)acrylamide B1. To a solution of compound 5 (91 mg, 0.6 mmol) in MeOH (6 mL) was added compound 15 (76 mg, 0.6 mmol). The reaction mixture was stirred for 1 h at room temperature, followed by addition of compound 7 (59 mg, 0.5 mmol) and compound 16 (39 mg, 0.5 mmol). After stirred at room temperature for 48 h, the reaction mixture was concentrated in vacuo to yield a crude product, which was purified by column chromatography to afford compound B1.

N-(2-(Benzylamino)-1-(3-aminophenyl)-2-oxoethyl)-N-(3-chloro-4-methoxy-phenyl)acrylamide B2. To a solution of compound B1 (120 mg, 0.36 mmol) in EtOH (5 mL) was added $SnCl_2$ (1.8 mmol). After stirred for 1 h at 80° C. under $N_2$, the reaction mixture was concentrated in vacuo, neutralized with saturated $NaHCO_3$, and then extracted by EtOAc. The organic layers were combined, washed sequentially with saturated NaCl and water, dried over anhydrous $Na_2SO_4$, and concentrated in vacuo to yield a crude product, which was purified by prep-TLC to afford compound B1 (70 mg) in 50% yield. $^1$H NMR (400 MHz, DMSO-$d_6$) δ 8.62 (t, J=5.7 Hz, 1H), 7.66-7.17 (m, 6H), 7.07-6.54 (m, 3H), 6.39-6.31 (m, 2H), 6.21-6.13 (m, 2H), 6.02 (s, 1H), 5.90-5.79 (m, 1H), 5.64-5.50 (m, 1H), 4.99 (s, 2H), 4.38-4.27 (m, 2H), 3.78 (s, 3H); LCMS (ESI) m/z: 450.1 [M+H$^+$].

Scheme 7

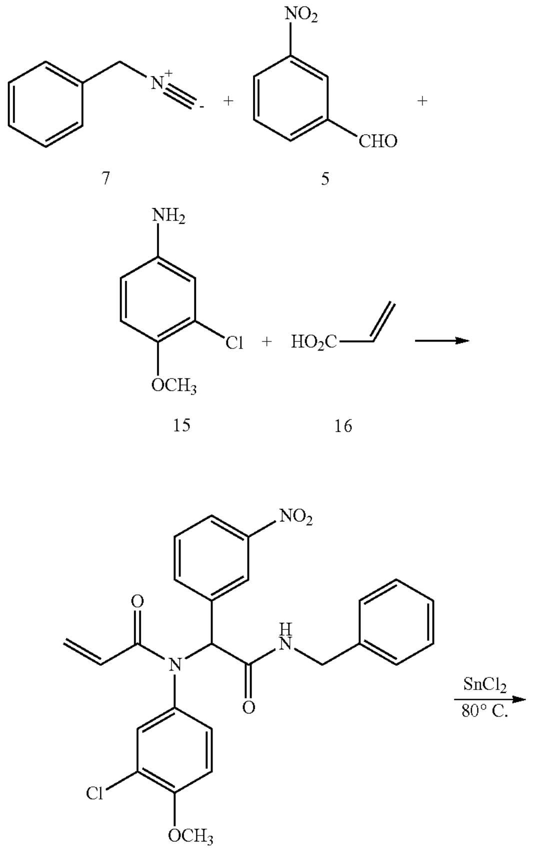

B1

-continued

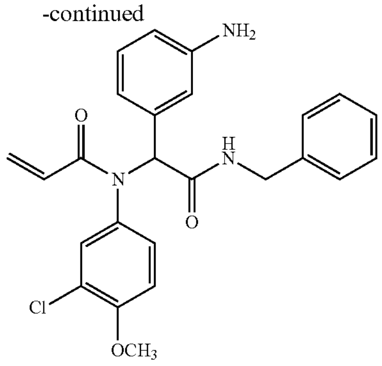

B2

Compounds A117, B3, B4, and D4 were synthesized similarly according to the procedures as described for compound B2.

N-(2-(Benzylamino)-2-oxo-1-phenylethyl)-N-(3-chlorophenyl)but-2-ynamide A117. $^1$H NMR (400 MHz, DMSO-$d_6$) δ 8.77 (t, J=5.8 Hz, 1H), 7.40 (s, 1H), 7.31-7.26 (m, 2H), 7.24-7.14 (m, 9H), 7.12-7.07 (m, 2H), 6.08 (s, 1H), 4.42-4.29 (m, 2H), 1.72 (s, 3H); LCMS (ESI) m/z: 417.1 [M+H$^+$].

N-(1-(4-Aminophenyl)-2-(benzylamino)-2-oxoethyl)-N-(3-chlorophenyl)-2-fluoroacrylamide B3. $^1$H NMR (400 MHz, DMSO-$d_6$) δ 8.60 (t, J=5.9 Hz, 1H), 7.30-7.25 (m, 2H), 7.23-7.13 (m, 6H), 6.68 (d, J=8.4 Hz, 2H), 6.31 (d, J=8.5 Hz, 2H), 5.92 (s, 1H), 5.13 (dd, J=13.6, 3.8 Hz, 1H), 5.10-5.02 (m, 3H), 4.32 (qd, J=15.3, 5.9 Hz, 2H).

N-(1-(3-Aminophenyl)-2-(benzylamino)-2-oxoethyl)-N-(3-chloro-4-methoxy-phenyl)-2-fluoroacrylamide B4. $^1$H NMR (400 MHz, DMSO-$d_6$) δ 8.65 (t, J=5.9 Hz, 1H), 7.31-7.18 (m, 6H), 6.90 (d, J=7.0 Hz, 1H), 6.85-6.76 (m, 1H), 6.37 (t, J=3.5 Hz, 2H), 6.20 (d, J=7.6 Hz, 1H), 5.91 (s, 1H), 5.10 (s, 1H), 5.07-4.97 (m, 3H), 4.38-4.28 (m, 2H), 3.77 (s, 3H); LCMS (ESI) m/z: 468.1 [M+H$^+$].

N-(1-(4-Aminophenyl)-2-(benzylamino)-2-oxoethyl)-N-(3-chlorophenyl)-propionamide D4. $^1$H NMR (400 MHz, DMSO-$d_6$) δ 8.51 (t, J=5.8 Hz, 1H), 7.37-7.23 (m, 3H), 7.20 (dd, J=10.3, 4.3 Hz, 5H), 6.65 (d, J=8.4 Hz, 2H), 6.28 (d, J=8.5 Hz, 2H), 5.93 (s, 1H), 5.02 (s, 1H), 4.31 (dt, J=15.3, 9.3 Hz, 2H), 3.32 (s, 2H), 2.03-1.86 (m, 2H), 0.90 (t, J=7.4 Hz, 3H); LCMS (ESI) m/z: 422.2 [M+H$^+$].

Example 8

Preparation of 2-chloro-N-isopropyl-N-(2-oxo-2-(phenethylamino)-1-(thiophen-2-yl)ethyl)acetamide C1

C1

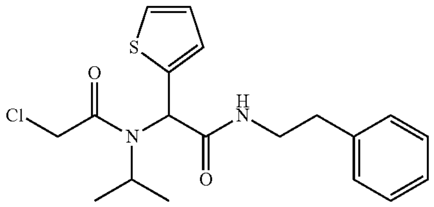

Compound $C_1$ was synthesized as shown in Scheme 8.

Scheme 8

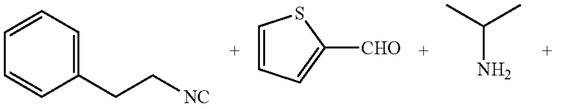

17 18 19

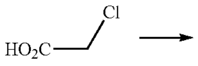

20

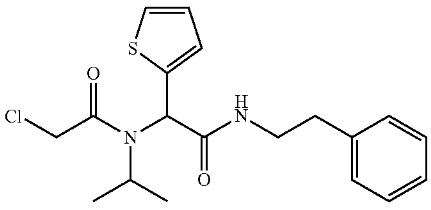

C1

2-Chloro-N-isopropyl-N-(2-oxo-2-(phenethylamino)-1-(thiophen-2-yl)ethyl)-acetamide C1. A solution of thiophene-2-carbaldehyde 18 (135 mg, 1.2 mmol) and propan-2-amine 19 (71 mg, 1.2 mmol) in MeOH (5 mL) was stirred for 1 h at room temperature, followed by addition of (2-isocyanoethyl)benzene 17 (131 mg, 1 mmol) and 2-chloroacetic acid 20 (94 mg, 1 mmol). After stirred at room temperature for 48 h, the reaction mixture was concentrated in vacuo to yield a crude product, which was purified by column chromatography to afford compound C1 (90 mg) in 24% yield. $^{1}H$ NMR (400 MHz, DMSO-$d_6$) δ 8.53 (s, 1H), 7.48 (d, J=54.3 Hz, 1H), 7.30-7.17 (m, 5H), 6.88 (d, J=41.2 Hz, 2H), 5.43 (d, J=79.2 Hz, 1H), 4.32 (dd, J=83.5, 71.2 Hz, 3H), 3.17 (s, 2H), 2.73 (d, J=49.4 Hz, 2H), 1.36-1.15 (m, 3H), 1.07 (s, 3H); LCMS (ESI) m/z: 379 [M+H$^+$].

Compound C2 was synthesized similarly according to the procedures as described for compound C1.

N-(4-Aminophenyl)-2-chloro-N-(2-oxo-2-(phenethylamino)-1-(thiophen-2-yl)-ethyl)acetamide C2. $^{1}H$ NMR (400 MHz, DMSO-$d_6$) δ 8.22 (t, J=5.6 Hz, 1H), 7.38 (dd, J=5.0, 1.2 Hz, 1H), 7.31-7.09 (m, 7H), 6.85-6.79 (m, 2H), 6.45 (s, 2H), 6.19 (d, J=11.5 Hz, 1H), 3.91 (dd, J=17.5, 9.9 Hz, 2H), 3.37 (ddd, J=20.4, 18.0, 11.7 Hz, 4H), 2.69 (dt, J=11.7, 5.8 Hz, 2H); LCMS (ESI) m/z: 428 [M+H$^+$].

Example 9

Preparation of 2-chloro-N-(3-chloro-4-methoxyphenyl)-N-(1-(4-(2-hydroxyacetamido)phenyl)-2-oxo-2-(phenethylamino)ethyl)acetamide C4

C4

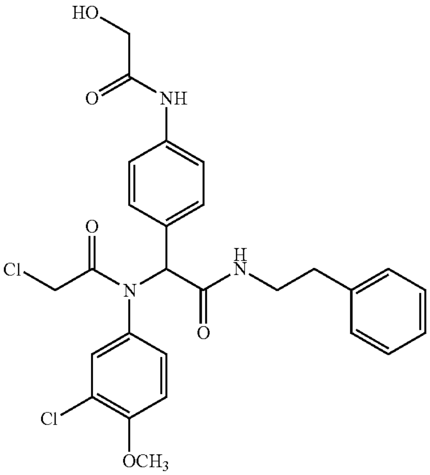

Compound $C_4$ was synthesized as shown in Scheme 9.

Scheme 9

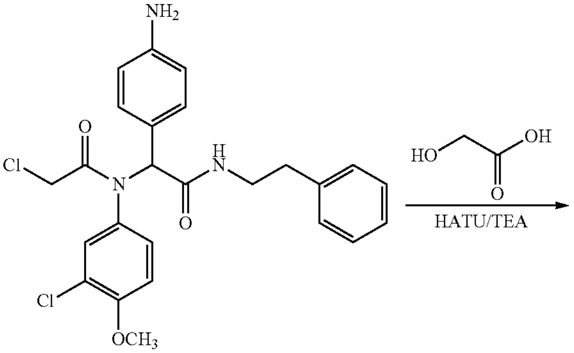

C3

-continued

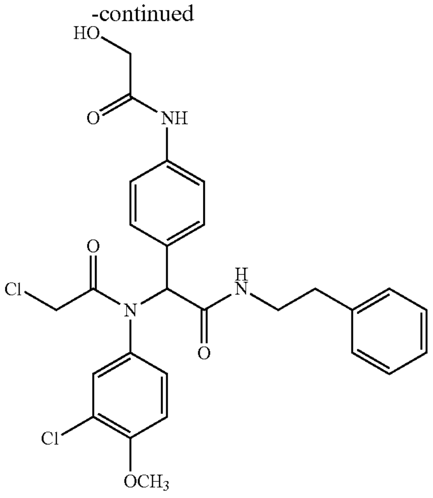

C4

2-Chloro-N-(3-chloro-4-methoxyphenyl)-N-(1-(4-(2-hydroxyacetamido)phenyl)-2-oxo-2-(phenethylamino)ethyl) acetamide C4. To a solution of 2-(4-aminophenyl)-2-(2-chloro-N-(3-chloro-4-methoxyphenyl)acetamido)-N-phenethylacetamide C3 (12 mg, 0.03 mmol) in DMF (2 mL) was added TEA (3.8 mg), HATU (14 mg), and glycolic acid (4.4 mg) at room temperature. The reaction mixture was stirred at room temperature for 3 h, and the starting material was consumed completely as detected by LC-MS. After addition of water (2 mL), the reaction mixture was extracted by ethyl acetate, washed with saturated NaCl and then water. The organic layers were combined, dried over anhydrous $Na_2SO_4$, and concentrated in vacuo to yield a crude production, which was purified by prep-TLC to afford compound C4 (5.0 mg) in 19% yield. $^1$H NMR (400 MHz, DMSO-$d_6$) δ 9.59 (s, 1H), 8.25 (s, 1H), 7.49 (d, J=12.0 Hz, 2H), 7.25-7.14 (m, 6H), 5.94 (s, 1H), 5.60 (t, J=4.0 Hz, 1H), 4.0-3.9 (m, 4H), 3.77 (s, 3H), 2.69 (t, J=4.0 Hz, 1H); LCMS (ESI) m/z: 545.4 [M+H$^+$].

Example 10

Preparation of 2-chloro-N-(3-chlorophenyl)-N-(1-(4-nitrophenyl)-2-oxo-2-(phenethylamino)ethyl) acetamide C5 and 2-chloro-N-(3-chlorophenyl)-N-(1-(4-aminophenyl)-2-oxo-2-(phenethylamino)ethyl) acetamide C6

C5

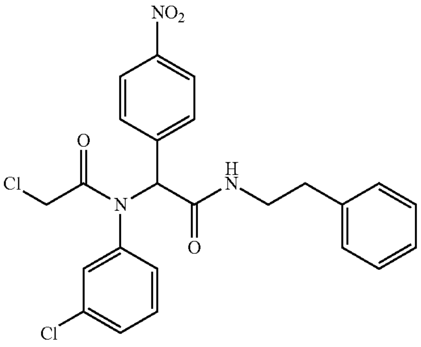

-continued

C6

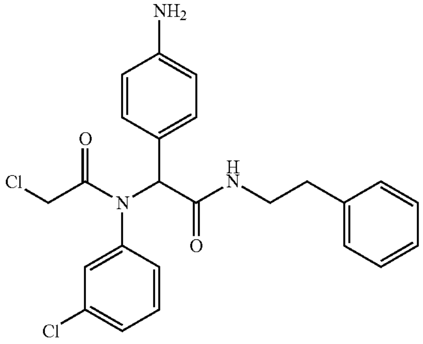

Compounds C5 and C6 were synthesized as shown in Scheme 10.

2-Chloro-N-(3-chlorophenyl)-N-(1-(4-nitrophenyl)-2-oxo-2-(phenethylamino)-ethyl)acetamide C5. To a solution of compound 2 (277 mg, 1.84 mmol) in MeOH (6 mL) was added compound 6 (235 mg, 1.84 mmol). The reaction mixture was stirred for 1 h at room temperature, followed by addition of compound 17 (200 mg, 1.84 mmol) and compound 20 (144 mg, 1.53 mmol). After stirred at room temperature for 48 h, the reaction mixture was concentrated in vacuo to yield a crude product, which was purified by column chromatography to afford compound C5 (580 mg) in 41% yield. $^1$H NMR (400 MHz, DMSO-$d_6$) δ 8.44 (t, J=8.0 Hz, 1H), 8.01 (d, J=8.0 Hz, 2H), 7.30-7.15 (m, 10H), 6.10 (s, 1H), 4.08-3.99 (m, 2H), 3.44-3.41 (m, 1H), 3.30-3.28 (m, 1H), 2.71 (t, J=8.0 Hz, 2H); LCMS (ESI) m/z: 486.1 [M+H$^+$].

Scheme 10

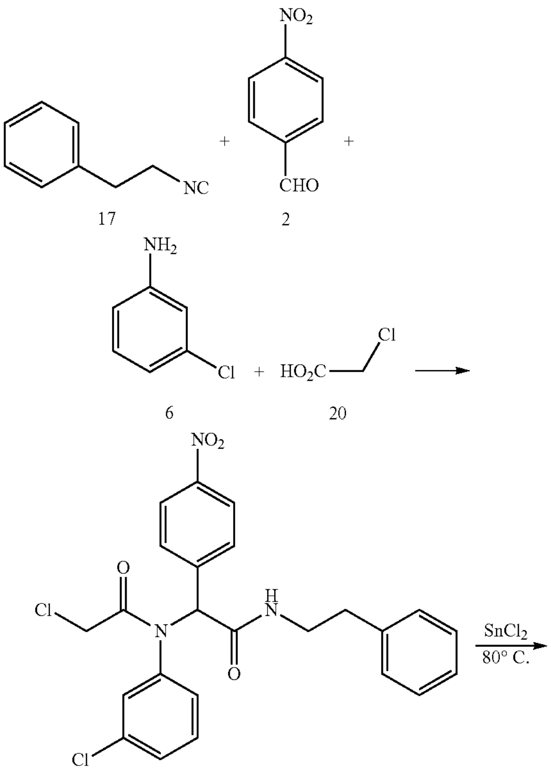

17 2

6 20

C5

-continued

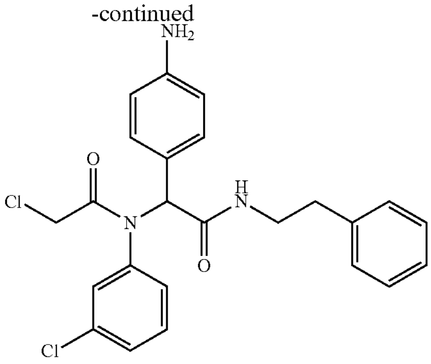

C6

2-Chloro-N-(3-chlorophenyl)-N-(1-(4-aminophenyl)-2-oxo-2-(phenethylamino)-ethyl)acetamide C6. To a solution of compound C5 (100 mg, 0.21 mmol) in EtOH (5 mL) was added $SnCl_2$ (237 mg, 1.05 mmol). After stirred for 1 h at 80° C. under $N_2$, the reaction mixture was concentrated in vacuo, neutralized with saturated $NaHCO_3$, and then extracted by EtOAc. The organic layers were combined, washed sequentially with saturated NaCl and water, dried over anhydrous $Na_2SO_4$, and concentrated in vacuo to yield a crude product, which was purified by prep-TLC to afford compound C6 (70 mg) in 25% yield. $^1$H NMR (400 MHz, DMSO-$d_6$) δ 8.26 (t, J=4.0 Hz, 1H), 7.28-7.15 (m, 8H), 6.85 (d, J=8.0 Hz, 2H), 6.68 (d, J=8.0 Hz, 2H), 4.04-3.92 (m, 5H), 3.42-3.28 (m, 2H), 2.71-2.68 (m, 2H); LCMS (ESI) m/z: 457.4 [M+H$^+$].

Compounds C7 to C12 were synthesized similarly according to the procedures as described for compound C5.

Methyl-3-(2-chloro-N-(1-(4-nitrophenyl)-2-oxo-2-(phenethylamino)ethyl)-acetamido)benzoate C7. LCMS (ESI) m/z: 510.1 [M+H$^+$].

2-Chloro-N-(1-(4-nitrophenyl)-2-oxo-2-(phenethylamino)ethyl)-N-(thiophen-2-ylmethyl)acetamide C8. LCMS (ESI) m/z: 472.1 [M+H$^+$].

2-Chloro-N-(3-hydroxyphenyl)-N-(1-(4-nitrophenyl)-2-oxo-2-(phenethylamino)-ethyl)acetamide C9. LCMS (ESI) m/z: 468 [M+H$^+$].

2-Chloro-N-(3-methoxyphenyl)-N-(1-(4-nitrophenyl)-2-oxo-2-(phenethylamino)-ethyl)acetamide C10. LCMS (ESI) m/z: 482 [M+H$^+$].

N-(3-Acetamidophenyl)-2-chloro-N-(1-(4-nitrophenyl)-2-oxo-2-(phenethyl-amino)ethyl)acetamide C11. LCMS (ESI) m/z: 509.2 [M+H$^+$].

N-Benzyl-2-chloro-N-(1-(4-nitrophenyl)-2-oxo-2-(phenethylamino)ethyl)-acetamide C12. LCMS (ESI) m/z: 466.5 [M+H$^+$].

Compounds A125 to A195, B5 to B11, C19 to C30, D1 to D3, and D5 to D7 were synthesized similarly according to the procedures described herein.

N-Benzyl-4-(N-(1-methyl-1H-indazol-5-yl)but-2-ynamido)tetrahydro-2H-pyran-4-carboxamide A125. $^1$H NMR (400 MHz, DMSO-$d_6$) δ 8.28 (t, J=6.0 Hz, 1H), 8.13 (s, 1H), 8.01 (s, 1H), 7.70 (d, J=8.0 Hz, 1H), 7.60 (d, J=8.0 Hz, 1H), 7.32-7.29 (m, 4H), 7.25-7.20 (m, 1H), 4.37 (d, J=8.0 Hz, 2H), 4.09 (s, 3H), 3.55-3.49 (m, 4H), 2.16 (t, J=14.0 Hz, 2H), 1.71-1.63 (m, 2H), 1.58 (s, 3H); LCMS (ESI) m/z: 431.5 [M+H$^+$].

N-Benzyl-3-(N-(1-methyl-1H-indazol-5-yl)but-2-ynamido)tetrahydro-2H-pyran-3-carboxamide A126. $^1$H NMR (400 MHz, DMSO-$d_6$) δ 8.29 (t, J=6.0 Hz, 1H), 8.14 (s, 1H), 8.07 (s, 1H), 7.66 (d, J=8.0 Hz, 1H), 7.34-7.29 (m, 4H), 7.25-7.20 (m, 1H), 4.39 (d, J=4.0 Hz, 2H), 4.11 (s, 3H), 3.89-3.76 (m, 2H), 3.60-3.54 (m, 4H), 2.16 (d, J=12.0 Hz, 2H), 1.71-1.63 (m, 2H); LCMS (ESI) m/z: 431.2 [M+H$^+$].

Methyl3-(benzylcarbamoyl)-3-(N-(1-methyl-1H-indazol-5-yl)but-2-ynamido)-cyclohexane-1-carboxylate A127. $^1$H NMR (400 MHz, DMSO-$d_6$) δ 8.44 (t, J=6.0 Hz, 1H), 8.21 (s, 1H), 7.66 (d, J=8.0 Hz, 1H), 7.34-7.29 (m, 4H), 7.25-7.20 (m, 1H), 4.29 (d, J=4.0 Hz, 2H), 4.06 (s, 3H), 3.89-3.76 (m, 2H), 3.60-3.54 (m, 4H), 3.55 (s, 3H), 2.13 (d, J=12.0 Hz, 4H), 1.70-1.66 (m, 2H); LCMS (ESI) m/z: 487.5 [M+H$^+$].

N-(2-(Benzylamino)-2-oxo-1-phenylethyl)-N-(5-chloro-2-iodophenyl)but-2-ynamide A128. $^1$H NMR (400 MHz, DMSO-$d_6$) δ 8.77 (t, J=5.9 Hz, 1H), 8.04 (d, J=2.5 Hz, 1H), 7.62 (d, J=8.5 Hz, 1H), 7.27-7.15 (m, 10H), 7.04 (dd, J=8.5, 2.6 Hz, 1H), 5.99 (s, 1H), 4.33 (qd, J=15.4, 5.9 Hz, 2H), 1.72 (s, 3H); LCMS (ESI) m/z: 543.1 [M+H$^+$].

N-Benzyl-4-(N-(3-chlorophenyl)-4-hydroxybut-2-ynamido)tetrahydro-2H-pyran-4-carboxamide A129. $^1$H NMR (400 MHz, DMSO-$d_6$) δ 8.34 (t, J=5.7 Hz, 1H), 7.85 (s, 1H), 7.53 (dt, J=23.5, 7.8 Hz, 3H), 7.31 (dd, J=7.8, 5.5 Hz, 4H), 7.25-7.20 (m, 1H), 5.26 (s, 1H), 4.36 (d, J=5.8 Hz, 2H), 3.91 (s, 2H), 3.68-3.45 (m, 4H), 2.30-2.26 (m, 1H), 2.06-2.02 (m, 1H), 1.76-1.73 (m, 1H), 1.66-1.54 (m, 1H).

N-Benzyl-4-(N-(2,5-dichlorophenyl)-4-hydroxybut-2-ynamido)tetrahydro-2H-pyran-4-carboxamide A130. $^1$H NMR (400 MHz, DMSO-$d_6$) δ 8.51 (t, J=5.9 Hz, 1H), 7.95 (d, J=2.5 Hz, 1H), 7.68 (d, J=8.7 Hz, 1H), 7.59 (dd, J=8.7, 2.6 Hz, 1H), 7.36-7.30 (m, 4H), 7.27-7.20 (m, 1H), 5.27 (t, J=5.9 Hz, 1H), 4.46-4.34 (m, 2H), 3.92 (d, J=5.4 Hz, 2H), 3.86-3.68 (m, 2H), 3.48 (dd, J=7.9, 4.0 Hz, 1H), 3.19 (t, J=10.2 Hz, 1H), 2.94 (d, J=12.2 Hz, 1H), 2.26-2.13 (m, 1H), 1.75 (d, J=13.0 Hz, 1H), 1.34-1.24 (m, 1H).

N-Benzyl-4-(4-hydroxy-N-(1-methyl-1H-indazol-5-yl)but-2-ynamido)tetrahydro-2H-pyran-4-carboxamide A131. $^1$H NMR (400 MHz, DMSO-$d_6$) δ 8.32 (t, 1H), 8.13 (s, 1H), 8.04-8.00 (m, 1H), 7.72-7.67 (m, 1H), 7.63-7.58 (m, 1H), 7.34-7.29 (m, 4H), 7.25-7.20 (m, 1H), 5.15 (t, 1H), 4.38 (d, J=5.9 Hz, 2H), 4.08 (s, 3H), 3.80 (d, J=6.0 Hz, 2H), 3.59-3.49 (m, 4H), 2.17 (t, J=12.5 Hz, 2H), 1.74-1.64 (m, 2H); LCMS (ESI) m/z: 447.5 [M+H$^+$].

N-(2-(Benzylamino)-2-oxo-1-phenylethyl)-N-(3,4-dichlorophenyl)but-2-ynamide A132. $^1$H NMR (400 MHz, DMSO-$d_6$) δ 8.81 (t, J=8.0 Hz, 1H), 7.44 (d, J=8.0 Hz, 1H), 7.31-7.19 (m, 10H), 7.11 (dd, J=8.0, 4.0 Hz, 2H), 6.10 (s, 1H), 4.37-4.34 (m, 2H), 1.75 (s, 3H); LCMS (ESI) m/z: 451.3 [M+H$^+$].

N-(2-(Benzylamino)-2-oxo-1-phenylethyl)-N-(5-chloropyridin-3-yl)but-2-ynamide A133. $^1$H NMR (400 MHz, DMSO-$d_6$) δ 8.89 (t, J=8.0 Hz, 1H), 8.41 (s, 1H), 8.34 (s, 1H), 7.89 (s, 1H), 7.31-7.09 (m, 10H), 6.15 (s, 1H), 4.39-4.35 (m, 2H), 1.75 (s, 3H); LCMS (ESI) m/z: 417.9 [M+H$^+$].

N-(3-(1H-Pyrazol-3-yl)phenyl)-N-(2-(benzylamino)-2-oxo-1-phenylethyl)-propiolamide A134. $^1$H NMR (400 MHz, DMSO-$d_6$) δ 12.80 (s, 1H), 8.72 (t, J=6.0 Hz, 1H), 7.74 (s, 1H), 7.57 (s, 2H), 7.30-7.18 (m, 6H), 7.13 (d, J=8.0 Hz, 6H), 6.52 (s, 1H), 6.08 (s, 1H), 4.40-4.30 (s, 1H), 4.19 (s, 1H); LCMS (ESI) m/z: 435.2 [M+H$^+$].

4-(N-(3-(1H-Pyrazol-3-yl)phenyl)propiolamido)-N-benzyltetrahydro-2H-pyran-4-carboxamide A135. $^1$H NMR (400 MHz, DMSO-$d_6$) δ 12.96 (s, 1H), 8.35 (s, 1H), 8.02 (s, 1H), 7.89 (d, J=8.0 Hz, 1H), 7.81 (s, 1H), 7.51 (d, J=8.0 Hz, 1H), 7.32-7.29 (m, 4H), 7.25-7.20 (m, 1H), 6.79 (d, J=4.0 Hz, 1H), 4.39 (d, J=4.0 Hz, 1H), 4.16 (s, 1H), 3.62-3.57 (m, 4H), 2.32-2.20 (m, 2H), 1.65-1.52 (m, 2H); LCMS (ESI) m/z: 429.2 [M+H$^+$].

N-Benzyl-4-(N-(3-(1-methyl-1H-pyrazol-3-yl)phenyl)propiolamido)tetrahydro-2H-pyran-4-carboxamide A136.

$^1H$ NMR (400 MHz, DMSO-$d_6$) δ 8.37 (t, J=6.0 Hz, 1H), 7.98 (s, 1H), 7.86-7.84 (m, 1H), 7.76 (d, J=4.0 Hz, 1H), 7.53-7.47 (m, 2H), 7.32-7.29 (m, 4H), 7.24-7.20 (m, 1H), 6.76 (s, 1H), 4.38 (d, J=8.0 Hz, 2H), 4.15 (s, 3H), 3.56 (d, J=4.0 Hz, 4H), 2.20 (d, J=12.0 Hz, 2H), 1.76-1.68 (m, 2H); LCMS (ESI) m/z: 443.2 [M+H$^+$].

4-(N-((1H-Pyrazol-3-yl)methyl)propiolamido)-N-benzyltetrahydro-2H-pyran-4-carboxamide A137. $^1H$ NMR (400 MHz, DMSO-$d_6$) δ 8.43 (s, 1H), 8.21 (t, J=6.0 Hz, 1H), 7.66-7.57 (m, 5H), 4.55 (d, J=8.0 Hz, 2H), 3.59-3.53 (m, 4H), 2.31-2.27 (m, 2H), 1.66-1.61 (m, 2H).

N-Benzyl-4-(N-(3-hydroxybenzyl)propiolamido)tetrahydro-2H-pyran-4-carboxamide A138. $^1H$ NMR (400 MHz, DMSO-$d_6$) δ 9.84 (s, 1H), 8.25 (t, J=6.0 Hz, 1H), 7.32-7.10 (m, 7H), 6.85 (d, J=8.0 Hz, 2H), 4.98 (s, 1H), 4.42 (s, 1H), 4.27 (d, J=8.0 Hz, 2H), 3.62-3.59 (m, 4H), 2.32 (d, J=12.0 Hz, 2H), 1.66-1.58 (m, 2H); LCMS (ESI) m/z: 393.5 [M+H$^+$].

N-Benzyl-4-(N-(2-morpholinophenyl)propiolamido)tetrahydro-2H-pyran-4-carboxamide A139. $^1H$ NMR (400 MHz, DMSO-$d_6$) δ 8.85 (t, J=6.0 Hz, 1H), 7.63-7.61 (m, 1H), 7.56-7.52 (m, 1H), 7.48-7.45 (m, 1H), 7.36-7.30 (m, 5H), 7.27-7.21 (m, 1H), 4.60-4.45 (m, 2H), 4.25 (s, 1H), 3.94-3.87 (m, 1H), 3.72-3.61 (m, 2H), 3.47-3.42 (m, 6H), 3.15-3.10 (m, 2H), 2.69-2.64 (m, 3H), 1.82 (d, J=16.0 Hz, 1H), 1.71-1.64 (m, 1H), 1.51-1.43 (m, 1H); LCMS (ESI) m/z: 448.2 [M+H$^+$].

N-Benzyl-4-(N-(4-(dimethylamino)phenyl)propiolamido)tetrahydro-2H-pyran-4-carboxamide A140. $^1H$ NMR (400 MHz, DMSO-$d_6$) δ 8.21 (t, J=6.0 Hz, 1H), 7.35 (d, J=4.0 Hz, 2H), 7.31-7.28 (m, 4H), 7.25-7.19 (m, 1H), 6.71 (d, J=8.0 Hz, 2H), 4.34 (d, J=4.0 Hz, 2H), 4.13 (s, 1H), 3.56-3.53 (m, 4H), 2.95 (s, 6H), 2.12 (d, J=12.0 Hz, 1H), 1.69-1.62 (m, 2H); LCMS (ESI) m/z: 406.2 [M+H$^+$].

4-(N-(Benzo[d][1,3]dioxol-4-yl)propiolamido)-N-benzyltetrahydro-2H-pyran-4-carboxamide A141. $^1H$ NMR (400 MHz, DMSO-$d_6$) δ 8.08 (t, J=6.0 Hz, 1H), 7.34-7.28 (m, 4H), 7.25-7.18 (m, 2H), 7.04 (d, J=8.0 Hz, 1H), 6.93 (t, J=8.0 Hz, 1H), 4.36 (t, J=4.0 Hz, 2H), 4.18 (s, 1H), 3.76-3.66 (m, 2H), 3.47-3.42 (m, 2H), 2.43 (d, J=12.0 Hz, 1H), 1.99-1.94 (m, 2H), 1.60-1.53 (m, 1H); LCMS (ESI) m/z: 407.4 [M+H$^+$].

N-(3-Chlorophenyl)-N-(2-((cyclopropylmethyl)amino)-2-oxo-1-phenylethyl)-propiolamide A142. $^1H$ NMR (400 MHz, DMSO-$d_6$) δ 8.85 (t, J=5.8 Hz, 1H), 7.63 (s, 1H), 7.46 (d, J=8.5 Hz, 1H), 7.31-7.27 (m, 2H), 7.24-7.17 (m, 7H), 7.12 (dd, J=6.6, 2.9 Hz, 2H), 6.10 (s, 1H), 4.37 (dd, J=12.8, 7.4 Hz, 2H), 4.34 (s, 1H); LCMS (ESI) m/z: 437.1 [M+H$^+$].

N-(2-(Benzylamino)-2-oxo-1-phenylethyl)-N-(3-oxo-1,3-dihydroisobenzofuran-5-yl)propiolamide A143. $^1H$ NMR (400 MHz, DMSO-$d_6$) δ 8.84 (t, J=5.9 Hz, 1H), 7.49-7.47 (m, 1H), 7.40-7.27 (m, 3H), 7.25-7.20 (m, 3H), 7.19-7.01 (m, 6H), 6.16 (s, 1H), 5.35 (s, 2H), 4.37 (dd, J=5.6, 2.9 Hz, 2H), 4.26 (s, 1H); LCMS (ESI) m/z: 425.1 [M+H$^+$].

N-Benzyl-4-(N-(1-phenylcyclopropyl)propiolamido)tetrahydro-2H-pyran-4-carboxamide A144. $^1H$ NMR (400 MHz, DMSO-$d_6$) δ 8.17 (t, J=5.8 Hz, 1H), 7.37-7.25 (m, 9H), 7.23-7.19 (m, 1H), 4.39 (s, 1H), 4.37-4.26 (m, 2H), 3.70-3.60 (m, 2H), 3.52 (t, J=11.4 Hz, 1H), 3.28 (d, J=14.1 Hz, 1H), 2.89 (d, J=13.8 Hz, 1H), 2.38 (d, J=11.8 Hz, 1H), 2.08-2.00 (m, 1H), 1.95-1.86 (m, 2H), 1.80-1.72 (m, 2H), 1.22-1.14 (m, 1H).

N-(2-(Benzylamino)-2-oxo-1-phenylethyl)-N-(2,5-dichlorophenyl)propiolamide A145. $^1H$ NMR (400 MHz, DMSO-$d_6$) δ 8.85 (t, J=5.9 Hz, 1H), 8.10 (d, J=2.3 Hz, 1H), 7.31-7.14 (m, 12H), 6.06 (s, 1H), 4.40-4.31 (m, 2H), 4.28 (s, 1H); LCMS (ESI) m/z: 438.4 [M+H$^+$].

N-(2-(Benzylamino)-2-oxo-1-phenylethyl)-N-(6-iodobenzo[d][1,3]dioxol-5-yl)-propiolamide A146. $^1H$ NMR (400 MHz, DMSO-$d_6$) δ 8.86-8.49 (m, 1H), 7.57-6.76 (m, 12H), 6.22-5.98 (m, 2H), 5.88 (d, J=35.6 Hz, 1H), 4.81-3.96 (m, 3H); LCMS (ESI) m/z: 539.2 [M+H$^+$].

N-([1,2,4]Triazolo[4,3-a]pyridin-8-yl)-N-(2-(benzylamino)-2-oxo-1-phenylethyl)-propiolamide A147. $^1H$ NMR (400 MHz, DMSO-$d_6$) δ 8.94 (s, 1H), 8.76 (d, J=6.8 Hz, 1H), 8.33 (s, 1H), 7.83 (s, 1H), 7.33-7.23 (m, 5H), 7.18-7.14 (m, 2H), 7.09-7.01 (m, 4H), 6.16 (s, 1H), 4.44-4.38 (m, 2H), 3.98-3.68 (m, 1H); LCMS (ESI) m/z: 410.5 [M+H$^+$].

N-Benzyl-4-(N-(1-oxo-2,3-dihydro-1H-inden-4-yl)propiolamido)tetrahydro-2H-pyran-4-carboxamide A148. $^1H$ NMR (400 MHz, DMSO-$d_6$) δ 8.49 (t, 1H), 7.94-7.89 (m, 1H), 7.74 (d, J=6.9 Hz, 1H), 7.55 (t, J=7.6 Hz, 1H), 7.34-7.29 (m, 4H), 7.25-7.20 (m, 1H), 4.40 (d, J=5.8 Hz, 2H), 4.09 (s, 1H), 3.74-3.67 (m, 1H), 3.61-3.53 (m, 2H), 3.32-3.25 (m, 2H), 3.11-3.02 (m, 1H), 2.75-2.61 (m, 3H), 2.13 (d, J=12.0 Hz, 1H), 1.88-1.79 (m, 1H), 1.62-1.53 (m, 1H); LCMS (ESI) m/z: 417.5 [M+H$^+$].

N-Benzyl-4-(N-(3-oxo-1,3-dihydroisobenzofuran-5-yl)propiolamido)tetrahydro-2H-pyran-4-carboxamide A149. $^1H$ NMR (400 MHz, DMSO-$d_6$) δ 8.44 (t, J=5.8 Hz, 1H), 8.29-8.26 (m, 1H), 8.01 (dd, J=8.1, 1.8 Hz, 1H), 7.80 (d, J=8.1 Hz, 1H), 7.33-7.29 (m, 4H), 7.25-7.21 (m, 1H), 5.51 (d, J=4.5 Hz, 2H), 4.37 (d, J=5.9 Hz, 2H), 4.23 (s, 1H), 3.70-3.64 (m, 1H), 3.60-3.43 (m, 3H), 2.31 (d, J=13.6 Hz, 1H), 2.04 (d, J=13.8 Hz, 1H), 1.81-1.74 (m, 1H), 1.63-1.55 (m, 1H); LCMS (ESI) m/z: 419.5 [M+H$^+$].

4-(N-(1H-Indazol-5-yl)propiolamido)-N-benzyltetrahydro-2H-pyran-4-carboxamide A150. $^1H$ NMR (400 MHz, DMSO-$d_6$) δ 13.28 (s, 1H), 8.33 (t, J=5.9 Hz, 1H), 8.16 (s, 1H), 8.06 (s, 1H), 7.63-7.53 (m, 2H), 7.35-7.28 (m, 4H), 7.26-7.20 (m, 1H), 4.38 (d, J=5.9 Hz, 2H), 4.07 (s, 1H), 3.60-3.49 (m, 4H), 2.18 (t, J=14.0 Hz, 2H), 1.77-1.66 (m, 2H); LCMS (ESI) m/z: 403.5 [M+H$^+$].

4-(N-(Benzo[d][1,3]dioxol-5-yl)propiolamido)-N-benzyltetrahydro-2H-pyran-4-carboxamide A151. $^1H$ NMR (400 MHz, DMSO-$d_6$) δ 8.23 (t, 1H), 7.31-7.28 (m, 5H), 7.24-7.19 (m, 1H), 7.07 (dd, J=8.2, 2.1 Hz, 1H), 6.99 (d, 1H), 6.12 (dd, J=15.1, 0.9 Hz, 2H), 4.34 (d, J=5.9 Hz, 2H), 4.20 (s, 1H), 3.63-3.55 (m, 3H), 3.52-3.45 (m, 1H), 2.21 (d, J=13.2 Hz, 1H), 2.07 (d, 1H), 1.75-1.61 (m, 2H); LCMS (ESI) m/z: 407.5 [M+H$^+$].

4-(N-(1H-Indol-5-yl)propiolamido)-N-benzyltetrahydro-2H-pyran-4-carboxamide A152. $^1H$ NMR (400 MHz, DMSO-$d_6$) δ 11.30 (s, 1H), 8.25 (t, J=5.9 Hz, 1H), 7.79 (d, J=1.9 Hz, 1H), 7.44-7.41 (m, 2H), 7.32-7.21 (m, 6H), 6.51-6.48 (m, 1H), 4.37 (d, J=5.9 Hz, 2H), 4.01 (s, 1H), 3.59-3.50 (m, 4H), 2.16 (dd, J=30.5, 13.0 Hz, 2H), 1.74-1.64 (m, 2H); LCMS (ESI) m/z: 402.5 [M+H$^+$].

N-Benzyl-4-(N-(1-methyl-1H-indol-5-yl)propiolamido)tetrahydro-2H-pyran-4-carboxamide A153. $^1H$ NMR (400 MHz, DMSO-$d_6$) δ 8.26 (t, J=5.9 Hz, 1H), 7.79 (d, J=1.9 Hz, 1H), 7.49 (d, J=8.7 Hz, 1H), 7.41 (d, J=3.1 Hz, 1H), 7.35 (dd, J=8.6, 2.0 Hz, 1H), 7.33-7.29 (m, 4H), 7.25-7.19 (m, 1H), 6.49 (d, J=3.1 Hz, 1H), 4.38 (d, J=5.9 Hz, 2H), 4.02 (s, 1H), 3.83 (s, 3H), 3.59-3.50 (m, 4H), 2.16 (t, J=14.7 Hz, 2H), 1.74-1.63 (m, 2H); LCMS (ESI) m/z: 416.5 [M+H$^+$].

N-Benzyl-4-(N-(1-methyl-1H-benzo[d]imidazol-6-yl)propiolamido)tetrahydro-2H-pyran-4-carboxamide A154. $^1H$ NMR (400 MHz, DMSO-$d_6$) δ 8.30 (d, J=5.3 Hz, 2H), 7.90 (s, 1H), 7.70 (d, J=8.5 Hz, 1H), 7.44 (d, J=8.5 Hz, 1H), 7.34-7.29 (m, 4H), 7.25-7.20 (m, 1H), 4.40 (d, J=5.9 Hz, 2H), 4.06 (s, 1H), 3.87 (s, 3H), 3.61-3.51 (m, 4H), 2.20 (t, J=11.8 Hz, 2H), 1.76-1.65 (m, 2H); LCMS (ESI) m/z: 417.6 $[M+H^+]$.

4-(N-(Benzo[d]thiazol-5-yl)propiolamido)-N-benzyltetrahydro-2H-pyran-4-carboxamide A155. $^1H$ NMR (400 MHz, DMSO-$d_6$) δ 9.50 (s, 1H), 8.48 (d, 1H), 8.39 (t, J=5.9 Hz, 1H), 8.28 (d, J=8.5 Hz, 1H), 7.74 (dd, J=8.5, 2.0 Hz, 1H), 7.32 (d, J=4.4 Hz, 4H), 7.25-7.21 (m, 1H), 4.39 (d, J=5.9 Hz, 2H), 4.13 (s, 1H), 3.64-3.47 (m, 4H), 2.28 (d, 1H), 2.09 (d, 1H), 1.81-1.73 (m, 1H), 1.70-1.63 (m, 1H); LCMS (ESI) m/z: 420.5 $[M+H^+]$.

N-Benzyl-4-(N-(1-methyl-1H-benzo[d]imidazol-5-yl)propiolamido)tetrahydro-2H-pyran-4-carboxamide A156. $^1H$ NMR (400 MHz, DMSO-$d_6$) δ 8.33-8.26 (m, 2H), 8.00 (d, J=1.8 Hz, 1H), 7.65 (d, J=8.5 Hz, 1H), 7.50 (dd, J=8.5, 1.9 Hz, 1H), 7.32 (d, J=4.5 Hz, 4H), 7.25-7.21 (m, 1H), 4.39 (d, J=5.9 Hz, 2H), 4.06 (s, 1H), 3.89 (s, 3H), 3.63-3.47 (m, 4H), 2.26 (d, J=13.2 Hz, 1H), 2.10 (d, J=13.4 Hz, 1H), 1.76-1.62 (m, 2H); LCMS (ESI) m/z: 417.5 $[M+H^+]$.

N-Benzyl-4-(N-(2,4-dimethoxyphenyl)propiolamido)tetrahydro-2H-pyran-4-carboxamide A157. $^1H$ NMR (400 MHz, DMSO-$d_6$) δ 7.92 (t, J=9.8, 4.3 Hz, 1H), 7.38-7.26 (m, 6H), 6.69 (d, J=2.6 Hz, 1H), 6.62 (dd, J=8.7, 2.7 Hz, 1H), 4.35 (t, J=12.3, 7.2 Hz, 2H), 4.06 (s, 1H), 3.82-3.78 (m, 4H), 3.62-3.55 (m, 5H), 3.47-3.41 (m, 1H), 2.42-2.36 (m, 1H), 1.79 (d, J=12.3 Hz, 1H), 1.66-1.56 (m, 2H); LCMS (ESI) m/z: 423.5 $[M+H^+]$.

N-(2-(Benzylamino)-2-oxo-1-phenylethyl)-N-(1-methyl-6-oxopiperidin-3-yl)-propiolamide A158. $^1H$ NMR (400 MHz, DMSO-$d_6$) δ 8.95 (t, J=4.0 Hz, 1H), 7.46-7.25 (m, 10H), 6.31 (s, 1H), 4.73 (s, 1H), 4.38 (t, J=4.0 Hz, 2H), 3.68-3.65 (m, 1H), 3.54 (t, J=8.0 Hz, 1H), 2.60 (s, 1H), 2.44 (s, 3H), 2.28-2.24 (m, 1H), 2.09 (t, J=8.0 Hz, 2H), 1.94 (dd, J=8.0, 4.0 Hz, 1H); LCMS (ESI) m/z: 403.5 $[M+H^+]$.

4-(N-(3-Chlorophenyl)propiolamido)-N-(tosylmethyl)tetrahydro-2H-pyran-4-carboxamide A159. $^1H$ NMR (400 MHz, DMSO-$d_6$) δ 8.68 (t, J=6.5 Hz, 1H), 7.74 (d, J=8.3 Hz, 2H), 7.68 (t, J=1.9 Hz, 1H), 7.59-7.55 (m, 1H), 7.51 (t, J=7.9 Hz, 1H), 7.48-7.42 (m, 3H), 4.77 (dd, J=14.0, 6.7 Hz, 1H), 4.65 (dd, J=14.0, 6.3 Hz, 1H), 4.25 (s, 1H), 3.60-3.42 (m, 3H), 3.31-3.17 (m, 1H), 2.42 (s, 3H), 2.13 (d, J=13.4 Hz, 1H), 1.86 (d, J=13.3 Hz, 1H), 1.66-1.53 (m, 1H), 1.52-1.37 (m, 1H).

N-(2-(Benzylamino)-2-oxo-1-phenylethyl)-N-(1-methyl-1H-indazol-7-yl)propiolamide A160. $^1H$ NMR (400 MHz, DMSO-$d_6$) δ 8.82 (t, J=4.0 Hz, 1H), 8.02 (s, 1H), 8.58 (d, J=8.0 Hz, 1H), 7.24-7.13 (m, 10H), 6.79 (t, J=8.0 Hz, 1H), 6.74 (dd, J=8.0, 4.0 Hz, 1H), 6.03 (s, 1H), 4.35 (s, 3H), 4.31 (d, J=4.0 Hz, 1H), 4.22 (d, J=4.0 Hz, 1H), 4.16 (s, 1H); LCMS (ESI) m/z: 422.5 $[M+H^+]$.

4-(N-(Benzo[c][1,2,5]thiadiazol-4-yl)propiolamido)-N-benzyltetrahydro-2H-pyran-4-carboxamide A161. $^1H$ NMR (400 MHz, DMSO-$d_6$) δ 8.73 (t, J=4.0 Hz, 1H), 8.26 (d, J=8.0 Hz, 1H), 8.09 (t, J=4.0 Hz, 1H), 7.88-7.90 (m, 1H), 7.36-7.31 (m, 4H), 7.27-7.24 (m, 1H), 4.46 (dd, J=8.0, 4.0 Hz, 2H), 3.95 (s, 1H), 3.67-3.62 (m, 2H), 3.55-3.48 (m, 2H), 2.36 (d, J=12.0 Hz, 1H), 2.08 (d, J=12.0 Hz, 1H), 1.95-1.88 (m, 1H), 1.67-1.60 (m, 1H); LCMS (ESI) m/z: 420.5 $[M+H^+]$.

N-Benzyl-4-(N-(1-methyl-1H-indazol-5-yl)propiolamido)tetrahydro-2H-pyran-4-carboxamide A162. $^1H$ NMR (400 MHz, DMSO-$d_6$) δ 8.34 (t, J=4.0 Hz, 1H), 8.14 (s, 1H), 8.05 (s, 1H), 7.72 (d, J=12.0 Hz, 1H), 7.64 (d, J=8.0 Hz, 1H), 7.32 (d, J=4.0 Hz, 4H), 7.24-7.21 (m, 1H), 4.39 (d, J=4.0 Hz, 2H), 4.09 (d, J=4.0 Hz, 4H), 3.55 (s, 4H), 2.18 (d, J=8.0 Hz, 2H), 1.73-1.70 (m, 2H); LCMS (ESI) m/z: 416.5 $[M+H^+]$.

4-(N-([1,2,4]Triazolo[4,3-a]pyridin-7-yl)propiolamido)-N-benzyltetrahydro-2H-pyran-4-carboxamide A163. $^1H$ NMR (400 MHz, DMSO-$d_6$) δ 9.59 (s, 1H), 8.63 (s, 1H), 8.43 (t, J=4.0 Hz, 1H), 8.01-7.95 (m, 2H), 7.34-7.26 (m, 4H), 7.25-7.21 (m, 1H), 4.39 (d, J=4.0 Hz, 2H), 4.30 (s, 1H), 3.65-3.52 (m, 4H), 2.26-2.16 (m, 2H), 1.83-1.75 (m, 2H); LCMS (ESI) m/z: 403.4 $[M+H^+]$.

N-Benzyl-1-(N-(1-methyl-1H-indazol-5-yl)propiolamido)-4-oxocyclohexane-1-carboxamide A164. $^1H$ NMR (400 MHz, DMSO-$d_6$) δ 8.39 (t, J=6.0 Hz, 1H), 8.13 (s, 2H), 7.71 (s, 2H), 7.34-7.28 (m, 4H), 7.24-7.20 (m, 1H), 4.38 (d, J=8.0 Hz, 2H), 4.11 (s, 1H), 4.07 (s, 3H), 2.46-2.39 (m, 2H), 2.37-2.27 (m, 2H), 2.14-2.07 (m, 2H), 2.04-1.96 (m, 2H); LCMS (ESI) m/z: 429.2 $[M+H^+]$.

N-Benzyl-1-(N-(1-methyl-1H-indazol-5-yl)propiolamido)-3-oxocyclohexane-1-carboxamide A165. $^1H$ NMR (400 MHz, DMSO-$d_6$) δ 8.39 (t, J=6.0 Hz, 1H), 8.13 (d, J=8.0 Hz, 1H), 7.71 (s, 2H), 7.32-7.28 (m, 4H), 7.24-7.20 (m, 1H), 4.39 (d, J=8.0 Hz, 2H), 4.10-4.07 (m, 4H), 2.46-2.39 (m, 2H), 2.36-2.27 (m, 2H), 2.14-2.10 (m, 2H), 2.04-1.97 (m, 2H); LCMS (ESI) m/z: 429.5 $[M+H^+]$.

Methyl 3-(benzylcarbamoyl)-3-(N-phenethylpropiolamido)cyclohexane-1-carboxylate A166. $^1H$ NMR (400 MHz, DMSO-$d_6$) δ 8.07 (t, J=6.0 Hz, 1H), 7.35-7.19 (m, 10H), 4.62 (d, J=4.0 Hz, 2H), 4.31-4.20 (m, 2H), 3.60-3.54 (m, 4H), 3.55 (s, 3H), 2.13 (d, J=12.0 Hz, 4H), 1.44-1.24 (m, 2H); LCMS (ESI) m/z: 447.2 $[M+H^+]$.

Methyl 3-(benzylcarbamoyl)-3-(N-(3-hydroxybenzyl)propiolamido)cyclohexane-1-carboxylate A167. $^1H$ NMR (400 MHz, DMSO-$d_6$) δ 8.11 (t, J=6.0 Hz, 1H), 7.35-7.16 (m, 8H), 4.57 (d, J=4.0 Hz, 2H), 4.33-4.28 (m, 3H), 3.69-3.44 (m, 5H), 3.57 (s, 3H), 2.38-2.32 (m, 3H), 1.67-1.63 (m, 2H); LCMS (ESI) m/z: 449.5 $[M+H^+]$.

Methyl 3-(benzylcarbamoyl)-3-(N-cyclobutylpropiolamido)cyclohexane-1-carboxylate A168. $^1H$ NMR (400 MHz, DMSO-$d_6$) δ 8.06 (t, J=6.0 Hz, 1H), 7.44-7.21 (m, 8H), 4.56 (d, J=4.0 Hz, 2H), 4.53-4.41 (m, 3H), 3.69-3.44 (m, 5H), 3.43 (s, 3H), 2.16-2.08 (m, 2H), 1.58-1.51 (m, 2H); LCMS (ESI) m/z: 397.4 $[M+H^+]$.

3-(Benzylcarbamoyl)-3-(N-phenethylpropiolamido)cyclohexane-1-carboxylic acid A169. $^1H$ NMR (400 MHz, DMSO-$d_6$) δ 12.23 (s, 1H), 8.06 (t, J=6.0 Hz, 1H), 7.35-7.18 (m, 10H), 4.64 (s, 1H), 4.31-4.20 (m, 2H), 3.76 (brs, 2H), 3.07-3.03 (m, 6H), 2.70 (d, J=12.0 Hz, 1H), 2.37 (t, J=12.0 Hz, 1H), 1.99-1.86 (m, 2H), 1.74-1.67 (m, 2H), 1.51-1.24 (m, 3H); LCMS (ESI) m/z: 433.2 $[M+H^+]$.

3-(Benzylcarbamoyl)-3-(N-(3-hydroxybenzyl)propiolamido)cyclohexane-1-carboxylic acid A170. $^1H$ NMR (400 MHz, DMSO-$d_6$) δ 12.02 (s, 1H), 9.80 (s, 1H), 8.19-8.03 (m, 1H), 7.31-7.07 (m, 8H), 6.85-6.79 (m, 2H), 4.93 (s, 1H), 4.99 (s, 1H), 2.33-2.07 (m, 2H), 1.71-1.14 (m, 6H); LCMS (ESI) m/z: 435.2 $[M+H^+]$.

N-Benzyl-1-(N-(3-chlorophenyl)propiolamido)-3-hydroxycyclohexane-carboxamide A171. $^1H$ NMR (400 MHz, DMSO-$d_6$) δ 8.69 (t, J=6.0 Hz, 1H), 7.31-7.27 (m, 2H), 7.24-7.20 (m, 3H), 7.03 (t, J=8.0 Hz, 1H), 6.56 (t, J=2.0 Hz, 1H), 6.48 (dd, J=8.0, 2.0 Hz, 2H), 5.78 (d, J=8.3 Hz, 1H), 4.58 (s, 1H), 4.33-4.25 (m, 2H), 3.73-3.63 (m, 1H), 2.75 (d, J=12.1 Hz, 1H), 2.27 (d, J=11.7 Hz, 1H), 1.85-1.67 (m, 3H), 1.45-1.35 (m, 2H), 1.30-1.20 (m, 2H); LCMS (ESI) m/z: 411.9 $[M+H^+]$.

N-Benzyl-1-(N-(3-chlorophenyl)propiolamido)-3-oxocyclohexanecarboxamide A172. $^1H$ NMR (400 MHz, DMSO-$d_6$) δ 7.55-7.51 (m, 2H), 7.46-7.26 (m, 6H), 7.25-7.20 (m, 1H), 6.48 (d, J=10.6 Hz, 1H), 4.38 (d, J=15.3 Hz, 1H), 4.26 (d, J=12.0 Hz, 1H), 4.15 (d, J=15.5 Hz, 1H), 3.17 (t, 1H), 2.00-1.91 (m, 1H), 1.70-1.63 (m, 1H), 1.58-1.50 (m, 1H), 1.49-1.40 (m, 1H), 1.14-1.01 (m, 2H), 0.96-0.85 (m, 1H); LCMS (ESI) m/z: 409.9 [M+H$^+$].

Methyl 3-(benzylcarbamoyl)-3-(N-(3-chlorophenyl)propiolamido)cyclohexane-carboxylate A173. $^1$H NMR (400 MHz, DMSO-d$_6$) δ 8.38-8.20 (m, 1H), 8.04-7.43 (m, 4H), 7.32-7.20 (m, 5H), 4.32 (d, J=5.7 Hz, 2H), 4.26-4.20 (m, 1H), 3.61-3.51 (m, 3H), 3.23-2.55 (m, 2H), 1.99-1.69 (m, 2H), 1.58-1.23 (m, 3H), 1.19-0.83 (m, 2H); LCMS (ESI) m/z: 453.9 [M+H$^+$].

N-Benzyl-3-(N-(3-chlorophenyl)propiolamido)tetrahydro-2H-pyran-3-carboxamide A174. $^1$H NMR (400 MHz, DMSO-d$_6$) δ 8.05 (t, J=4.0 Hz, 1H), 7.70 (d, J=4.0 Hz, 1H), 7.60-7.52 (m, 3H), 7.51 (t, J=4.0 Hz, 4H), 7.33-7.22 (m, 1H), 4.48-4.38 (m, 3H), 4.25 (d, J=8.0 Hz, 1H), 3.69-3.64 (m, 2H), 3.43 (t, J=8.0 Hz, 1H), 1.72-1.46 (m, 4H); LCMS (ESI) m/z: 396.1 [M+H$^+$].

N-Benzyl-1-(N-(3-chlorophenyl)propiolamido)-4-oxocyclohexane-1-carboxamide A175. $^1$H NMR (400 MHz, DMSO-d$_6$) δ 8.40 (t, J=4.0 Hz, 1H), 7.97 (s, 1H), 7.67 (d, J=4.0 Hz, 1H), 7.57 (d, J=8.0 Hz, 1H), 7.53-7.49 (m, 1H), 7.30-7.28 (m, 4H), 7.26-7.22 (m, 1H), 4.36 (d, J=8.0 Hz, 2H), 4.28 (s, 1H), 2.43-2.39 (m, 1H), 2.30-2.00 (m, 5H), 1.93-1.83 (m, 1H), 1.71-1.61 (m, 1H); LCMS (ESI) m/z: 408.9 [M+H$^+$].

N-Benzyl-3-(N-(1-methyl-1H-indazol-5-yl)propiolamido)tetrahydro-2H-pyran-3-carboxamide A176. $^1$H NMR (400 MHz, DMSO-d$_6$) δ 8.40 (t, J=4.0 Hz, 1H), 7.97 (s, 1H), 7.67 (d, J=4.0 Hz, 1H), 7.57 (d, J=8.0 Hz, 1H), 4.09-4.07 (m, 4H), 3.55 (s, 3H), 2.77-2.79 (m, 1H), 2.11-2.09 (m, 1H), 1.97-1.94 (m, 1H), 1.81-1.77 (m, 1H), 1.64-1.61 (m, 1H) 1.33-1.27 (m, 2H), 1.16-1.07 (m, 2H); LCMS (ESI) m/z: 416.5 [M+H$^+$].

Methyl 3-(benzylcarbamoyl)-3-(N-(1-methyl-1H-indazol-5-yl)propiolamido)-cyclohexane-1-carboxylate A177. $^1$H NMR (400 MHz, DMSO-d$_6$) δ 8.31 (t, J=4.0 Hz, 1H), 8.18-7.67 (m, 4H), 7.35-7.30 (m, 4H), 7.26-7.21 (m, 1H), 4.38-4.34 (m, 2H), 4.09-4.07 (m, 4H), 3.55 (s, 3H), 2.77-2.79 (m, 1H), 2.11-2.09 (m, 1H), 1.97-1.94 (m, 1H), 1.81-1.77 (m, 1H), 1.64-1.61 (m, 1H) 1.33-1.27 (m, 2H), 1.16-1.07 (m, 2H); LCMS (ESI) m/z: 472.5 [M+H$^+$].

N-(3-Chlorophenyl)-N-(2-((2-cyanobenzyl)amino)-2-oxo-1-phenylethyl)-propiolamide A178. $^1$H NMR (400 MHz, DMSO-d$_6$) δ 8.90 (t, J=6.0 Hz, 1H), 7.71 (d, J=8.0 Hz, 1H), 7.60-7.52 (m, 3H), 7.40 (brs, 1H), 7.25-7.17 (m, 6H), 7.11-7.09 (m, 2H), 6.07 (s, 1H), 4.48-4.33 (m, 2H), 4.29 (s, 1H); LCMS (ESI) m/z: 428.1 [M+H$^+$].

N-(2-(Benzylamino)-2-oxo-1-phenylethyl)-N-(3,4-dichlorophenyl)propiolamide A179. $^1$H NMR (400 MHz, DMSO-d$_6$) δ 8.34 (t, J=5.6 Hz, 1H), 7.43 (s, 1H), 7.23 (dd, J=9.1, 1.9 Hz, 1H), 7.20-7.14 (m, 5H), 7.10 (dd, J=7.2, 2.2 Hz, 2H), 6.05 (s, 1H), 4.25 (s, 1H), 3.01-2.95 (m, 2H), 0.91-0.82 (m, 1H), 0.39-0.34 (m, 2H), 0.15-0.12 (m, 2H); LCMS (ESI) m/z: 367.1 [M+H$^+$].

N-(3-Chlorophenyl)-N-(2-oxo-1-phenyl-2-(((tetrahydro-2H-pyran-4-yl)methyl)-amino)ethyl)propiolamide A180. $^1$H NMR (400 MHz, DMSO-d$_6$) δ 8.30 (t, J=5.7 Hz, 1H), 7.43 (s, 1H), 7.23-7.07 (m, 8H), 6.01 (s, 1H), 4.26 (s, 1H), 3.83-3.75 (m, 2H), 3.25-3.17 (m, 2H), 3.06-2.96 (m, 2H), 1.69-1.59 (m, 1H), 1.45 (t, J=13.3 Hz, 2H), 1.15-1.03 (m, 2H); LCMS (ESI) m/z: 411.9 [M+H$^+$].

N-(3-Chlorophenyl)-N-(2-((oxetan-3-ylmethyl)amino)-2-oxo-1-phenylethyl)-propiolamide A181. $^1$H NMR (400 MHz, DMSO-d$_6$) δ 8.41 (t, J=4.0 Hz, 1H), 7.41 (s, 1H), 7.24-7.07 (m, 8H), 5.99 (s, 1H), 4.55-4.51 (m, 2H), 4.26 (s, 1H), 4.24 (dd, J=8.0, 4.0 Hz, 2H), 3.39 (t, J=4.0 Hz, 2H), 3.07-3.00 (m, 1H); LCMS (ESI) m/z: 382.8 [M+H$^+$].

N-(3-Chlorobenzyl)-4-(N-(3-chlorophenyl)propiolamido)tetrahydro-2H-pyran-4-carboxamide A182. $^1$H NMR (400 MHz, DMSO-d$_6$) δ 8.39 (t, J=5.9 Hz, 1H), 7.87 (t, J=1.9 Hz, 1H), 7.62-7.51 (m, 3H), 7.38-7.32 (m, 2H), 7.30-7.24 (m, 2H), 4.36 (d, J=5.8 Hz, 2H), 4.26 (s, 1H), 3.68-3.53 (m, 3H), 3.46 (t, J=9.5 Hz, 1H), 2.26 (d, J=14.2 Hz, 1H), 2.04 (d, J=14.5 Hz, 1H), 1.77-1.69 (m, 1H), 1.64-1.56 (m, 1H); LCMS (ESI) m/z: 432.3 [M+H$^+$].

4-(N-(3-Chlorophenyl)propiolamido)-N-(2-(3-hydroxypiperidin-1-yl)-2-oxoethyl)tetrahydro-2H-pyran-4-carboxamide A183. $^1$H NMR (400 MHz, DMSO-d$_6$) δ 7.92-7.70 (m, 2H), 7.67-7.45 (m, 3H), 4.89 (s, 1H), 4.24 (s, 1H), 4.11-3.88 (m, 2H), 3.77-3.37 (m, 7H), 3.11 (ddd, J=57.0, 18.8, 9.2 Hz, 1H), 2.63 (dd, J=21.3, 8.9 Hz, 1H), 2.26 (d, J=13.1 Hz, 1H), 2.11 (t, J=11.9 Hz, 1H), 1.91-1.24 (m, 6H); LCMS (ESI) m/z: 448.1 [M+H$^+$].

Methyl 1-(2-(4-(N-(3-chlorophenyl)propiolamido)tetrahydro-2H-pyran-4-carboxamido)acetyl)piperidine-3-carboxylate A184. $^1$H NMR (400 MHz, DMSO-d$_6$) δ 7.82 (s, 2H), 7.60-7.50 (m, 3H), 4.35 (d, J=9.0 Hz, 1H), 4.23 (s, 1H), 4.15-3.87 (m, 2H), 3.81-3.52 (m, 10H), 3.45 (dd, J=13.9, 5.7 Hz, 1H), 3.19 (d, J=9.9 Hz, 1H), 3.05 (t, J=12.5 Hz, 1H), 2.89-2.77 (m, 1H), 2.66 (dd, J=6.9, 5.1 Hz, 1H), 2.33 (d, J=1.8 Hz, 1H), 2.26 (d, J=12.6 Hz, 1H), 2.11 (d, J=12.4 Hz, 1H), 2.02-1.83 (m, 2H), 1.58 (ddd, J=58.7, 41.3, 13.9 Hz, 6H); LCMS (ESI) m/z: 490.2 [M+H$^+$].

4-(N-(3-Chlorophenyl)propiolamido)-N-(2-((2-hydroxybenzyl)amino)-2-oxoethyl)tetrahydro-2H-pyran-4-carboxamide A185. $^1$H NMR (400 MHz, DMSO-d$_6$) δ 9.51 (s, 1H), 8.20 (t, J=5.7 Hz, 1H), 7.92 (t, J=6.0 Hz, 1H), 7.87 (d, J=1.9 Hz, 1H), 7.65-7.51 (m, 3H), 7.14 (d, J=7.5 Hz, 1H), 7.09-7.00 (m, 1H), 6.79 (d, J=8.0 Hz, 1H), 6.74 (d, J=0.9 Hz, 1H), 4.28 (s, 1H), 4.24 (d, J=6.1 Hz, 2H), 3.79 (d, J=5.8 Hz, 2H), 3.60 (ddd, J=24.9, 19.7, 7.6 Hz, 4H), 2.24 (s, 1H), 2.07 (d, J=8.3 Hz, 1H), 1.75-1.62 (m, 1H), 1.62-1.47 (m, 1H); LCMS (ESI) m/z: 470.1 [M+H$^+$].

4-(N-(3-Chlorophenyl)propiolamido)-N-(2-((2-hydroxyethyl)amino)-2-oxoethyl)-tetrahydro-2H-pyran-4-carboxamide A186. $^1$H NMR (400 MHz, DMSO-d$_6$) δ 8.12 (t, J=5.8 Hz, 1H), 7.85 (t, J=1.8 Hz, 1H), 7.65-7.44 (m, 4H), 4.64 (s, 1H), 4.30 (s, 1H), 3.69 (dd, J=16.7, 7.9 Hz, 3H), 3.58-3.50 (m, 2H), 3.46-3.35 (m, 3H), 3.21-3.09 (m, 2H), 2.24 (d, J=13.6 Hz, 1H), 2.06 (d, J=13.4 Hz, 1H), 1.77-1.62 (m, 1H), 1.62-1.47 (m, 1H); LCMS (ESI) m/z: 408.1 [M+H$^+$].

N-(2-((2-Chlorobenzyl)amino)-2-oxoethyl)-4-(N-(3-chlorophenyl)propiolamido)-tetrahydro-2H-pyran-4-carboxamide A187. $^1$H NMR (400 MHz, DMSO-d$_6$) δ 8.27 (d, J=5.1 Hz, 1H), 8.08 (d, J=5.0 Hz, 1H), 7.87 (s, 1H), 7.56 (dd, J=13.9, 6.9 Hz, 3H), 7.42 (s, 2H), 7.30 (d, J=5.1 Hz, 2H), 4.38 (s, 2H), 4.28 (d, J=5.1 Hz, 1H), 3.81 (s, 2H), 3.73-3.47 (m, 4H), 2.27 (d, J=13.0 Hz, 1H), 2.08 (d, J=12.0 Hz, 1H), 1.69 (s, 1H), 1.57 (s, 1H); LCMS (ESI) m/z: 488.1 [M+H$^+$].

N-(2-(Benzylamino)-2-oxoethyl)-4-(N-(3-chlorophenyl)propiolamido)tetrahydro-2H-pyran-4-carboxamide A188. $^1$H NMR (400 MHz, DMSO-d$_6$) δ 7.51 (s, 1H), 7.47 (d, J=7.4 Hz, 1H), 7.43-7.30 (m, 6H), 7.28-7.23 (m, 1H), 7.17 (s, 1H), 6.87 (s, 1H), 4.49 (d, J=5.6 Hz, 2H), 4.10 (s, 2H), 3.81-3.60 (m, 4H), 2.85 (s, 1H), 2.32 (t, J=13.7 Hz, 2H), 1.97-1.82 (m, 2H); LCMS (ESI) m/z: 489.2 [M+H$^+$].

4-(N-(3-Chlorophenyl)propiolamido)-N-(2-((2-cyanobenzyl)amino)-2-oxoethyl)-tetrahydro-2H-pyran-4-carboxamide A189. $^1$H NMR (400 MHz, DMSO-d$_6$) δ 8.24 (dd, J=13.7, 5.8 Hz, 1H), 7.86 (t, J=1.8 Hz, 1H), 7.81 (d, J=7.7 Hz, 1H), 7.70-7.63 (m, 1H), 7.61-7.50 (m, 2H), 7.45 (t, J=7.6 Hz, 1H), 4.49 (d, J=5.9 Hz, 1H), 4.27 (s, 1H), 3.80 (d, J=5.8 Hz, 1H), 3.68 (t, J=9.6 Hz, 1H), 3.56 (dt, J=30.7, 11.2

Hz, 2H), 2.25 (d, J=13.6 Hz, 1H), 2.13-1.97 (m, 1H), 1.74-1.62 (m, 1H), 1.60-1.49 (m, 1H); LCMS (ESI) m/z: 479.1 [M+$H^+$].

Ethyl 2-(2-(N-(2,4-dimethoxyphenyl)propiolamido)-2-(thiophen-2-yl)acetamido)-acetate A190. $^1$H NMR (400 MHz, DMSO-$d_6$) δ 8.60 (t, J=5.7 Hz, 1H), 8.40 (s, 1H), 7.47 (d, J=8.7 Hz, 1H), 7.45 (dd, J=5.2, 1.2 Hz, 1H), 7.35 (dd, J=5.1, 1.2 Hz, 1H), 7.09 (d, J=2.9 Hz, 1H), 6.91 (dd, J=5.1, 3.5 Hz, 1H), 6.85 (d, J=2.8 Hz, 1H), 6.79 (dd, J=5.1, 3.6 Hz, 1H), 6.73 (d, J=8.6 Hz, 1H), 6.57 (d, J=2.7 Hz, 1H), 6.43 (dd, J=8.7, 2.7 Hz, 1H), 6.35 (t, J=4.0 Hz, 1H), 6.18 (s, 1H), 6.05 (s, 1H), 4.13-4.00 (m, 3H), 3.97-3.89 (m, 1H), 3.83 (d, J=5.7 Hz, 1H), 3.77 (dd, J=15.3, 7.9 Hz, 1H), 3.70 (s, 3H), 3.55 (s, 3H), 1.17 (q, J=7.0 Hz, 4H); LCMS (ESI) m/z: 431.1 [M+$H^+$].

Ethyl 2-(4-(N-(3-chlorophenyl)propiolamido)tetrahydro-2H-pyran-4-carboxamido)acetate A191. $^1$H NMR (400 MHz, DMSO-$d_6$) δ 8.20 (t, J=5.7 Hz, 1H), 7.84 (t, J=1.8 Hz, 1H), 7.60-7.49 (m, 3H), 4.24 (s, 1H), 4.10 (dt, J=7.1, 5.8 Hz, 2H), 3.92-3.78 (m, 2H), 3.75-3.66 (m, 1H), 3.65-3.51 (m, 3H), 2.26 (d, J=12.5 Hz, 1H), 2.06 (d, J=12.3 Hz, 1H), 1.74-1.62 (m, 1H), 1.60-1.47 (m, 1H), 1.24-1.16 (m, 3H).

2-(4-(N-(3-Chlorophenyl)propiolamido)tetrahydro-2H-pyran-4-carboxamido)-acetic acid A192. $^1$H NMR (400 MHz, DMSO-$d_6$) δ 12.47 (s, 1H), 8.08 (d, J=5.6 Hz, 1H), 7.84 (t, J=1.8 Hz, 1H), 7.61-7.48 (m, 3H), 4.24 (s, 1H), 3.83-3.66 (m, 3H), 3.63-3.53 (m, 3H), 2.26 (d, J=12.3 Hz, 1H), 2.06 (d, J=11.8 Hz, 1H), 1.71-1.62 (m, 1H), 1.55 (dt, J=13.8, 7.1 Hz, 1H).

4-(N-(3-Chlorophenyl)propiolamido)-N-(2-oxo-2-(phenylamino)ethyl)tetrahydro-2H-pyran-4-carboxamide A193. $^1$H NMR (400 MHz, DMSO-$d_6$) δ 9.53 (s, 1H), 8.31 (t, J=5.6 Hz, 1H), 7.88 (d, J=1.9 Hz, 1H), 7.68-7.52 (m, 5H), 7.35-7.25 (m, 2H), 7.07 (t, J=7.4 Hz, 1H), 4.34 (s, 1H), 3.92 (d, J=5.7 Hz, 2H), 3.72 (t, J=9.8 Hz, 1H), 3.61 (dd, J=22.9, 6.0 Hz, 3H), 2.35-2.24 (m, 1H), 2.10 (d, J=15.4 Hz, 1H), 1.69 (dd, J=16.2, 7.2 Hz, 1H), 1.63-1.52 (m, 1H); LCMS (ESI) m/z: 440.2 [M+$H^+$].

4-(N-(3-Chlorophenyl)propiolamido)-N-(2-(3-(hydroxymethyl)piperidin-1-yl)-2-oxoethyl)tetrahydro-2H-pyran-4-carboxamide A194. $^1$H NMR (400 MHz, DMSO-$d_6$) δ 7.81 (dd, J=17.3, 8.2 Hz, 2H), 7.64-7.43 (m, 3H), 4.55 (dd, J=22.3, 17.0 Hz, 1H), 4.35 (d, J=11.8 Hz, 1H), 4.24 (s, 1H), 3.97 (ddd, J=30.2, 16.5, 5.0 Hz, 2H), 3.73 (dd, J=23.2, 11.3 Hz, 2H), 3.59 (d, J=10.8 Hz, 3H), 3.23 (dd, J=14.5, 8.9 Hz, 1H), 2.94 (d, J=12.3 Hz, 1H), 2.41-2.31 (m, 1H), 2.14 (dd, J=42.3, 32.3 Hz, 2H), 1.68 (t, J=29.0 Hz, 5H), 1.48-1.12 (m, 2H); LCMS (ESI) m/z: 462.1 [M+$H^+$].

N-(3-Chlorobenzyl)-4-(N-(3-chlorophenyl)-3-(trimethylsilyl)propiolamido)-tetrahydro-2H-pyran-4-carboxamide A195. $^1$H NMR (400 MHz, DMSO-$d_6$) δ 8.44 (t, 1H), 7.93 (t, J=1.9 Hz, 1H), 7.68-7.63 (m, 2H), 7.60-7.56 (m, 1H), 7.42 (dd, J=9.9, 4.8 Hz, 2H), 7.34 (dd, J=13.3, 4.8 Hz, 2H), 4.42 (d, J=5.9 Hz, 2H), 3.71-3.54 (m, 4H), 2.31 (d, J=13.7 Hz, 1H), 2.13 (d, J=12.3 Hz, 1H), 1.84-1.76 (m, 2H), 0.011--0.02 (m, 9H); LCMS (ESI) m/z: 504.5 [M+$H^+$].

N-Benzyl-4-(N-(3-chlorophenyl)acrylamido)tetrahydro-2H-pyran-4-carboxamide B5. $^1$H NMR (400 MHz, DMSO-$d_6$) δ 8.24 (t, J=6.0 Hz, 1H), 7.82 (t, J=1.6 Hz, 1H), 7.59-7.51 (m, 2H), 7.47 (dt, J=7.4, 1.6 Hz, 1H), 7.30-7.27 (m, 4H), 7.22-7.19 (m, 1H), 6.12 (dd, J=16.7, 2.3 Hz, 1H), 5.71 (dd, J=16.7, 10.3 Hz, 1H), 5.52 (dd, J=10.3, 2.3 Hz, 1H), 4.40-4.28 (m, 2H), 3.73-3.50 (m, 4H), 2.36-2.33 (m, 1H), 2.07-2.04 (m, 1H), 1.56 (d, J=56 Hz, 2H).

N-Benzyl-4-(N-phenethylacrylamido)tetrahydro-2H-pyran-4-carboxamide B6. $^1$H NMR (400 MHz, DMSO-$d_6$) δ 7.98 (t, J=5.7 Hz, 1H), 7.35-7.22 (m, 10H), 6.74 (dd, J=16.6, 10.4 Hz, 1H), 6.11 (dd, J=16.6, 2.4 Hz, 1H), 5.69 (dd, J=10.4, 2.4 Hz, 1H), 4.25 (d, J=5.9 Hz, 2H), 3.75 (d, J=6.4 Hz, 4H), 3.67-3.61 (m, 2H), 2.91-2.85 (m, 2H), 2.38 (d, J=12.8 Hz, 2H), 2.00-1.90 (m, 2H).

N-Benzyl-4-(N-(3-hydroxybenzyl)acrylamido)tetrahydro-2H-pyran-4-carboxamide B7. $^1$H NMR (400 MHz, DMSO-$d_6$) δ 9.80 (s, 1H), 8.13 (s, 1H), 7.29-7.23 (m, 4H), 7.22-7.18 (m, 1H), 7.13-7.05 (m, 2H), 6.87-6.81 (m, 2H), 6.51 (dd, J=16.6, 10.3 Hz, 1H), 6.19 (dd, J=16.6, 2.5 Hz, 1H), 5.65 (dd, J=10.3, 2.5 Hz, 1H), 4.73 (s, 2H), 4.28 (d, J=5.9 Hz, 2H), 3.67-3.56 (m, 4H), 2.41 (d, J=12.8 Hz, 2H), 1.71-1.64 (m, 2H).

N-Benzyl-4-(N-cyclobutylacrylamido)tetrahydro-2H-pyran-4-carboxamide B8. $^1$H NMR (400 MHz, DMSO-$d_6$) δ 8.25 (t, J=6.0 Hz, 1H), 7.33-7.22 (m, 5H), 6.50 (dd, J=16.8, 10.2 Hz, 1H), 6.08 (dd, J=16.8, 2.0 Hz, 1H), 5.66 (dd, J=10.2, 2.0 Hz, 1H), 4.32 (d, J=6.0 Hz, 2H), 4.17-4.09 (m, 1H), 3.68-3.62 (m, 2H), 3.45-3.39 (m, 2H), 2.24-2.04 (m, 8H), 1.61-1.53 (m, 2H).

N-Benzyl-4-(2-fluoro-N-(1-methyl-1H-indazol-5-yl)acrylamido)tetrahydro-2H-pyran-4-carboxamide B9. $^1$H NMR (400 MHz, DMSO-$d_6$) δ 8.44-8.35 (m, 1H), 8.14-8.08 (m, 1H), 7.85 (d, J=1.5 Hz, 1H), 7.73-7.67 (m, 1H), 7.65-7.60 (m, 1H), 7.34-7.27 (m, 4H), 7.25-7.20 (m, 1H), 5.05-4.87 (m, 2H), 4.46-4.33 (m, 2H), 4.08 (s, 3H), 3.70 (t, J=10.4 Hz, 1H), 3.65-3.57 (m, 2H), 3.51 (t, J=10.8 Hz, 1H), 2.33 (d, J=12.5 Hz, 1H), 2.17 (d, J=12.6 Hz, 1H), 1.69-1.59 (m, 1H), 1.58-1.48 (m, 1H)); LCMS (ESI) m/z: 437.5 [M+$H^+$].

(E)-N-Benzyl-4-(4-(dimethylamino)-N-(1-methyl-1H-indazol-5-yl)but-2-enamido)tetrahydro-2H-pyran-4-carboxamide B10. $^1$H NMR (400 MHz, DMSO-$d_6$) δ 8.25 (t, J=5.9 Hz, 1H), 8.14-8.11 (m, 1H), 7.95-7.91 (m, 1H), 7.76 (d, J=8.8 Hz, 1H), 7.58-7.54 (m, 1H), 7.33-7.27 (m, 4H), 7.23-7.18 (m, 1H), 6.63-6.56 (m, 1H), 5.66 (d, J=15.2 Hz, 1H), 4.37 (d, J=5.9 Hz, 2H), 4.10 (s, 3H), 3.63-3.55 (m, 4H), 3.27 (d, J=6.4 Hz, 2H), 2.33-2.19 (m, 8H), 1.65-1.56 (m, 2H); LCMS (ESI) m/z: 476.7 [M+$H^+$].

N-Benzyl-4-(N-(1-methyl-1H-indazol-5-yl)acrylamido)tetrahydro-2H-pyran-4-carboxamide B11. $^1$H NMR (400 MHz, DMSO-$d_6$) δ 8.24 (t, J=5.9 Hz, 1H), 8.12 (d, J=0.6 Hz, 1H), 7.92 (d, J=1.7 Hz, 1H), 7.74 (d, J=8.8 Hz, 1H), 7.55 (dd, J=8.8, 1.9 Hz, 1H), 7.33-7.27 (m, 4H), 7.23-7.18 (m, 1H), 6.08 (dd, J=16.8, 2.4 Hz, 1H), 5.70 (dd, J=16.8, 10.3 Hz, 1H), 5.42 (dd, J=10.3, 2.4 Hz, 1H), 4.37 (d, J=5.9 Hz, 2H), 4.09 (s, 3H), 3.67-3.53 (m, 4H), 2.29-2.18 (m, 2H), 1.66-1.57 (m, 2H).

4-(N-(Benzo[d][1,3]dioxol-5-yl)-2-chloroacetamido)-N-benzyltetrahydro-2H-pyran-4-carboxamide C19. $^1$H NMR (400 MHz, DMSO-$d_6$) δ 8.14 (t, J=6.0 Hz, 1H), 7.30-7.28 (m, 5H), 7.23-7.20 (m, 1H), 7.07 (dd, J=4.0, 8.0 Hz, 1H), 7.00 (d, J=8.0 Hz, 1H), 6.13 (d, J=4.0 Hz, 1H), 4.39-4.30 (m, 2H), 3.95-3.87 (m, 2H), 3.68-3.50 (m, 4H), 2.20 (d, J=12.0 Hz, 1H), 2.06 (d, J=12.0 Hz, 1H), 1.65-1.52 (m, 2H); LCMS (ESI) m/z: 431.1 [M+$H^+$].

1-(2-Chloro-N-(3-chloro-4-methoxyphenyl)acetamido)-4,4-difluoro-N-phenethyl-cyclohexane-1-carboxamide C20. $^1$H NMR (400 MHz, DMSO-$d_6$) δ 7.80-7.75 (m, 2H), 7.50 (dd, J=4.0, 8.0 Hz, 1H), 7.31-7.17 (m, 6H), 3.92 (s, 3H), 3.86 (s, 2H), 3.35 (d, J=4.0 Hz, 2H), 2.74 (t, J=6.0 Hz, 1H), 2.31-2.07 (m, 2H), 1.93-1.78 (m, 4H), 1.60-1.54 (m, 1H), 1.38 (t, J=12.0 Hz, 1H); LCMS (ESI) m/z: 439.4 [M+$H^+$].

N-Benzyl-4-(2-chloro-N-(1-methyl-1H-indazol-5-yl)acetamido)tetrahydro-2H-pyran-4-carboxamide C21. $^1$H NMR (400 MHz, DMSO-$d_6$) δ 8.27 (t, J=6.0 Hz, 1H), 8.14 (s, 1H), 8.04 (s, 1H), 7.75 (d, J=12.0 Hz, 1H), 7.63 (d, J=8.0 Hz, 1H), 7.34-7.29 (m, 4H), 7.25-7.20 (m, 1H), 4.39 (d, J=4.0 Hz, 2H), 4.09 (s, 3H), 3.89-3.76 (m, 2H), 3.60-3.54 (m, 4H), 2.16 (d, J=12.0 Hz, 2H), 1.71-1.63 (m, 2H); LCMS (ESI) m/z: 441.9 [M+H$^+$].

4-(2-Chloro-N-(1-methyl-1H-indazol-5-yl)acetamido)-N-phenethyltetrahydro-2H-pyran-4-carboxamide C22. $^1$H NMR (400 MHz, DMSO-$d_6$) δ 8.14 (s, 1H), 7.93 (d, J=4.0 Hz, 1H), 7.76-7.71 (m, 2H), 7.56-7.53 (m, 1H), 7.32-7.18 (m, 5H), 4.09 (s, 1H), 3.86-3.73 (m, 2H), 3.50-3.45 (m, 4H), 3.41-3.36 (m, 2H), 2.78 (t, J=8.0 Hz, 2H), 2.04 (d, J=16.0 Hz, 2H), 1.54-1.48 (m, 2H); LCMS (ESI) m/z: 455.9 [M+H$^+$].

N-Benzyl-4-(2-bromo-N-(1-methyl-1H-indazol-5-yl)propanamido)tetrahydro-2H-pyran-4-carboxamide C23. $^1$H NMR (400 MHz, DMSO-$d_6$) δ 8.18-8.13 (m, 2H), 8.06 (dd, J=8.1, 1.5 Hz, 1H), 7.76 (d, J=8.9 Hz, 1H), 7.68-7.62 (m, 1H), 7.34-7.27 (m, 4H), 7.22 (d, J=6.9 Hz, 1H), 4.43-4.33 (m, 2H), 4.10 (s, 3H), 4.07-3.88 (m, 1H), 3.68-3.49 (m, 4H), 2.32 (dd, J=10.9, 8.6 Hz, 1H), 2.05 (dd, J=14.3, 3.8 Hz, 1H), 1.67-1.59 (m, 1H), 1.55-1.52 (m, 3H), 1.24 (s, 1H).

N-Benzyl-4-(2-chloro-N-(1-methyl-1H-indazol-5-yl)propanamido)tetrahydro-2H-pyran-4-carboxamide C24. $^1$H NMR (400 MHz, DMSO-$d_6$) δ 8.20-8.15 (m, 2H), 8.05 (dd, J=36.0, 1.5 Hz, 1H), 7.77 (d, J=8.4 Hz, 1H), 7.64 (ddd, J=32.5, 8.9, 1.9 Hz, 1H), 7.34-7.28 (m, 4H), 7.24-7.20 (m, 1H), 4.40-4.36 (m, 2H), 4.10 (s, 3H), 4.07-3.92 (m, 1H), 3.71-3.49 (m, 4H), 2.33 (d, J=12.9 Hz, 1H), 2.10-2.00 (m, 1H), 1.71-1.58 (m, 1H), 1.52-1.44 (m, 1H), 1.40-1.36 (m, 3H).

N-Benzyl-4-(2-chloro-N-(3-chloro-4-methoxyphenyl)acetamido)tetrahydro-2H-pyran-4-carboxamide C25. $^1$H NMR (400 MHz, DMSO-$d_6$) δ 8.23 (t, J=5.9 Hz, 1H), 7.85 (d, J=2.5 Hz, 1H), 7.55 (dd, J=8.8, 2.6 Hz, 1H), 7.31-7.19 (m, 6H), 4.40-4.31 (m, 2H), 3.93-3.85 (m, 5H), 3.70-3.48 (m, 4H), 2.25 (d, J=13.1 Hz, 1H), 2.00 (d, J=13.2 Hz, 1H), 1.67-1.59 (m, 1H), 1.52-1.45 (m, 1H); LCMS (ESI) m/z: 452.4 [M+H$^+$].

4-(2-Chloro-N-(3-chloro-4-methoxyphenyl)acetamido)-N-phenethyltetrahydro-2H-pyran-4-carboxamide C26. $^1$H NMR (400 MHz, DMSO-$d_6$) δ 7.79-7.67 (m, 2H), 7.49 (dd, J=8.7, 2.6 Hz, 1H), 7.32-7.16 (m, 6H), 3.92 (s, 3H), 3.85 (s, 2H), 3.66-3.34 (m, 6H), 2.75 (t, J=7.3 Hz, 2H), 2.14 (d, J=13.4 Hz, 1H), 1.85 (d, J=13.0 Hz, 1H), 1.60-1.49 (m, 1H), 1.46-1.35 (m, 1H); LCMS (ESI) m/z: 466.4 [M+H$^+$].

N-Benzyl-1-(2-chloro-N-(3-chloro-4-methoxyphenyl)acetamido)-4,4-difluoro-cyclohexane-1-carboxamide C27. $^1$H NMR (400 MHz, DMSO-$d_6$) δ 8.28 (t, J=4.0 Hz, 1H), 7.92 (d, J=4.0 Hz, 1H), 7.56 (d, J=8.0 Hz, 1H), 7.30-7.20 (m, 6H), 4.34 (dd, J=8.0, 4.0 Hz, 2H), 3.92 (s, 3H), 3.89 (s, 2H), 2.41-2.23 (m, 2H), 2.09-1.87 (m, 4H), 1.50-1.44 (m, 2H); LCMS (ESI) m/z: 485.4 [M+H$^+$].

4-(N-(Benzo[c][1,2,5]thiadiazol-4-yl)-2-chloroacetamido)-N-benzyltetrahydro-2H-pyran-4-carboxamide C28. $^1$H NMR (400 MHz, DMSO-$d_6$) δ 8.70 (t, J=4.0 Hz, 1H), 8.25 (d, J=8.0 Hz, 1H), 8.02 (d, J=8.0 Hz, 1H), 7.86-7.82 (m, 1H), 7.37-7.30 (m, 4H), 7.27-7.23 (m, 1H), 4.47 (d, J=8.0 Hz, 2H), 4.00 (d, J=12.0 Hz, 1H), 3.83-3.77 (m, 1H), 3.69 (d, J=16.0 Hz, 1H), 3.60-3.52 (m, 2H), 3.48-3.43 (m, 1H), 2.46 (s, 1H), 1.87 (d, J=12.0 Hz, 1H), 1.71-1.55 (m, 2H); LCMS (ESI) m/z: 444.9 [M+H$^+$].

4-(N-(Benzo[c][1,2,5]thiadiazol-4-yl)-2-chloroacetamido)-N-phenethyltetrahydro-2H-pyran-4-carboxamide C29. $^1$H NMR (400 MHz, DMSO-$d_6$) δ 8.24 (dd, J=8.0, 4.0 Hz, 1H), 8.20 (t, J=4.0 Hz, 1H), 7.93 (dd, J=8.0, 4.0 Hz, 1H), 7.84-7.80 (m, 1H), 7.28-7.23 (m, 4H), 7.19-7.15 (m, 1H), 3.96 (d, J=16.0 Hz, 1H), 3.87-3.82 (m, 1H), 3.63-3.57 (m, 3H), 3.55-3.47 (m, 1H), 3.43-3.40 (m, 1H), 3.29-3.25 (m, 2H), 2.88-2.74 (m, 2H), 1.61-1.54 (m, 1H), 1.45-1.41 (m, 2H); LCMS (ESI) m/z: 458.9 [M+H$^+$].

N-Benzyl-4-(N-(1-methyl-1H-indazol-5-yl)oxirane-2-carboxamido)tetrahydro-2H-pyran-4-carboxamide C30. $^1$H NMR (400 MHz, DMSO-$d_6$) δ 8.25 (t, J=6.0 Hz, 1H), 8.20 (s, 1H), 7.76 (d, J=8.0 Hz, 2H), 7.36-7.29 (m, 3H), 7.24-7.21 (m, 2H), 4.33 (d, J=4.0 Hz, 2H), 4.08 (s, 3H), 3.88-3.76 (m, 2H), 3.59-3.54 (m, 4H), 2.13 (d, J=12.0 Hz, 4H), 1.71-1.65 (m, 2H); LCMS (ESI) m/z: 435.5 [M+H$^+$].

N-Benzyl-4-(2,2-difluoro-N-(1-methyl-1H-indazol-5-yl)acetamido)tetrahydro-2H-pyran-4-carboxamide D1. $^1$H NMR (400 MHz, DMSO-$d_6$) δ 8.38 (t, J=6.0 Hz, 1H), 8.17 (d, J=4.0 Hz, 1H), 8.05 (s, 1H), 7.77 (d, J=8.0 Hz, 1H), 7.65 (d, J=8.0 Hz, 1H), 7.32-7.28 (m, 4H), 7.25-7.20 (m, 1H), 5.76 (t, J=8.0 Hz, 1H), 4.39 (d, J=4.0 Hz, 2H), 4.10 (s, 3H), 3.63-3.52 (m, 4H), 2.19 (t, J=14.0 Hz, 2H), 1.68-1.57 (m, 2H); LCMS (ESI) m/z: 443.2 [M+H$^+$].

N-Benzyl-3-(N-(1-methyl-1H-indazol-5-yl)acetamido)tetrahydro-2H-pyran-3-carboxamide D2. $^1$H NMR (400 MHz, DMSO-$d_6$) δ 8.19 (t, J=6.0 Hz, 1H), 7.76-7.68 (m, 4H), 7.53-7.47 (m, 3H), 4.51 (d, J=8.0 Hz, 2H), 3.60-3.54 (m, 5H), 3.43 (s, 3H), 2.21 (s, 3H), 2.16-2.07 (m, 2H), 1.60-1.55 (m, 2H); LCMS (ESI) m/z: 407.2 [M+H$^+$].

N-Benzyl-4-(2-hydroxy-N-(1-methyl-1H-indazol-5-yl)acetamido)tetrahydro-2H-pyran-4-carboxamide D3. $^1$H NMR (400 MHz, DMSO-$d_6$) δ 8.26 (t, J=6.0 Hz, 1H), 8.12 (s, 1H), 8.01 (s, 1H), 7.72 (d, J=12.0 Hz, 1H), 7.61-7.59 (m, 1H), 7.31 (d, J=8.0 Hz, 4H), 7.24-7.20 (m, 1H), 4.48 (t, J=4.0 Hz, 2H), 4.37 (s, 2H), 4.09 (s, 3H), 3.60-3.39 (m, 6H), 2.19-2.15 (m, 2H), 1.69-1.63 (m, 2H).

N-Benzyl-4-(3-chloro-N-(1-methyl-1H-indazol-5-yl)propanamido)tetrahydro-2H-pyran-4-carboxamide D5. $^1$H NMR (400 MHz, DMSO-$d_6$) δ 8.17 (t, J=6.0 Hz, 1H), 8.14 (d, J=0.8 Hz, 1H), 7.98 (d, J=1.5 Hz, 1H), 7.76 (d, J=8.9 Hz, 1H), 7.58 (dd, J=8.8, 1.9 Hz, 1H), 7.33-7.28 (m, 4H), 7.24-7.20 (m, 1H), 4.37 (d, J=5.9 Hz, 2H), 4.09 (s, 3H), 3.66-3.56 (m, 6H), 2.39-2.15 (m, 4H), 1.65-1.55 (m, 2H).

N-Benzyl-4-(3-bromo-N-(1-methyl-1H-indazol-5-yl)propanamido)tetrahydro-2H-pyran-4-carboxamide D6. $^1$H NMR (400 MHz, DMSO-$d_6$) δ 8.17 (t, J=6.0 Hz, 1H), 8.14 (d, J=0.8 Hz, 1H), 7.98 (d, J=1.5 Hz, 1H), 7.76 (d, J=8.9 Hz, 1H), 7.57 (dd, J=8.8, 1.9 Hz, 1H), 7.33-7.30 (m, 4H), 7.24-7.20 (m, 1H), 4.37 (d, J=5.9 Hz, 2H), 4.09 (s, 3H), 3.60-3.53 (m, 4H), 3.48 (t, J=6.8 Hz, 2H), 2.48-2.32 (m, 2H), 2.18 (t, J=12.8 Hz, 2H), 1.65-1.56 (m, 2H).

N-Benzyl-4-(N-(3-chlorophenyl)-2-cyanoacetamido)tetrahydro-2H-pyran-4-carboxamide D7. $^1$H NMR (400 MHz, DMSO-$d_6$) δ 8.30 (t, J=5.9 Hz, 1H), 7.81 (t, J=2.0 Hz, 1H), 7.59-7.53 (m, 3H), 7.33-7.29 (m, 4H), 7.25-7.20 (m, 1H), 4.37 (dd, J=5.9, 1.9 Hz, 2H), 3.67-3.50 (m, 4H), 3.45 (d, J=2.3 Hz, 2H), 2.25 (d, J=13.4 Hz, 1H), 2.04 (d, J=13.6 Hz, 1H), 1.66-1.59 (m, 1H), 1.52-1.45 (m, 1H); LCMS (ESI) m/z: 412.5 [M+H$^+$].

Example B1

Cell Proliferation Assay

The activity of a test compound was determined in a cell proliferation assay using the hepatocellular carcinoma cell line Hub-7. Cells (4,000 cells per well) were seeded in a 96-well tissue culture plate. After incubated overnight, a test compound was added at predetermined concentrations, starting with 10 μM and followed by 3-fold serial dilution. After the cells were incubated for 24 h, cell viability was determined using a CELL-TITER GLO® assay. The CELL-TITER GLO® reagent (50 μL) was added to each well and the luminescence was measured by a multimode microplate reader after a brief period of shaking. $EC_{50}$ values were determined for the test compound. The results are summarized in Table 1, wherein A represents a value no greater than 100 nM, B represents a value greater than 100 nM but no greater than 500 nM, C represents a value greater than 500 nM but no greater than 2 μM, D represents a value greater than 2 μM but no greater than 10 μM; and E represents a value greater than 10 μM. In the assay, ML-162 was used as a control and determined to have an $EC_{50}$ of 138 nM.

TABLE 1

Inhibition of Cell Proliferation

| Cmpd. | $EC_{50}$ |
|---|---|
| A2 | E |
| A3 | A |
| A4 | B |
| A5 | B |
| A6 | D |
| A7 | B |
| A8 | A |
| A9 | D |
| A10 | E |
| A11 | E |
| A12 | E |
| A13 | D |
| A14 | A |
| A15 | D |
| A16 | D |
| A17 | E |
| A18 | C |
| A20 | B |
| A21 | B |
| A22 | D |
| A23 | D |
| A24 | E |
| A25 | E |
| A26 | D |
| A27 | D |
| A28 | B |
| A29 | C |
| A32 | A |
| A33 | A |
| A34 | A |
| A35 | A |
| A36 | C |
| A37 | A |
| A38 | B |
| A39 | D |
| A40 | A |
| A41 | A |
| A42 | D |
| A43 | B |
| A44 | D |
| A45 | D |
| A46 | B |
| A47 | E |
| A48 | A |
| A49 | A |
| A50 | E |
| A52 | A |
| A53 | A |
| A54 | A |
| A55 | B |
| A56 | D |
| A57 | A |
| A58 | D |
| A59 | B |
| A60 | A |
| A61 | A |
| A62 | E |
| A63 | D |
| A64 | D |
| A65 | A |
| A66 | A |
| A67 | C |
| A68 | E |
| A69 | A |

TABLE 1-continued

Inhibition of Cell Proliferation

| Cmpd. | $EC_{50}$ |
|---|---|
| A70 | C |
| A71 | D |
| A72 | B |
| A73 | A |
| A74 | A |
| A75 | A |
| A76 | A |
| A77 | B |
| A78 | C |
| A79 | A |
| A80 | A |
| A81 | B |
| A82 | A |
| A83 | B |
| A84 | B |
| A85 | A |
| A86 | B |
| A87 | A |
| A88 | A |
| A89 | A |
| A90 | A |
| A91 | A |
| A92 | B |
| A93 | A |
| A94 | A |
| A95 | B |
| A96 | A |
| A97 | B |
| A98 | B |
| A99 | A |
| A100 | A |
| A101 | A |
| A102 | D |
| A103 | A |
| A104 | A |
| A105 | B |
| A106 | B |
| A107 | A |
| A108 | A |
| A109 | B |
| A110 | B |
| A111 | B |
| A114 | A |
| A115 | A |
| A116 | B |
| A117 | E |
| A118 | D |
| A119 | A |
| A120 | A |
| A121 | A |
| A122 | A |
| A123 | A |
| A124 | C |
| A125 | E |
| A126 | D |
| A127 | E |
| A129 | E |
| A130 | E |
| A131 | E |
| A132 | E |
| A133 | E |
| A134 | A |
| A135 | B |
| A136 | B |
| A137 | E |
| A138 | A |
| A139 | A |
| A140 | B |
| A141 | A |
| A142 | A |
| A143 | A |
| A144 | A |
| A145 | A |
| A146 | A |
| A147 | B |
| A148 | A |

TABLE 1-continued

| Inhibition of Cell Proliferation | |
|---|---|
| Cmpd. | $EC_{50}$ |
| A149 | A |
| A150 | B |
| A151 | B |
| A152 | D |
| A153 | A |
| A154 | C |
| A155 | B |
| A156 | C |
| A157 | A |
| A158 | D |
| A159 | C |
| A160 | A |
| A161 | A |
| A162 | A |
| A163 | C |
| A164 | A |
| A165 | B |
| A166 | B |
| A167 | B |
| A168 | C |
| A169 | E |
| A170 | E |
| A171 | D |
| A172 | A |
| A173 | A |
| A174 | A |
| A175 | A |
| A176 | A |
| A177 | A |
| A178 | A |
| A179 | A |
| A180 | A |
| A181 | A |
| A182 | A |
| A183 | D |
| A184 | B |
| A185 | B |
| A186 | D |
| A187 | B |
| A188 | B |
| A189 | B |
| A190 | C |
| A191 | C |
| A192 | E |
| A193 | B |
| A194 | D |
| A195 | A |
| B2 | E |
| B3 | E |
| B4 | E |
| B5 | E |
| B6 | E |
| B7 | E |
| B8 | E |
| B9 | E |
| B10 | E |
| B11 | E |
| C1 | E |
| C2 | D |
| C3 | B |
| C4 | C |
| C5 | B |
| C6 | C |
| C7 | B |
| C8 | D |
| C9 | D |
| C10 | B |
| C11 | D |
| C12 | D |
| C13 | D |
| C14 | C |
| C15 | B |
| C16 | C |
| C17 | C |
| C18 | D |
| C19 | D |

TABLE 1-continued

| Inhibition of Cell Proliferation | |
|---|---|
| Cmpd. | $EC_{50}$ |
| C20 | B |
| C21 | C |
| C22 | C |
| C24 | E |
| C25 | B |
| C26 | A |
| C27 | A |
| C28 | B |
| C29 | C |
| C30 | E |
| D1 | E |
| D2 | E |
| D3 | E |
| D4 | E |
| D5 | E |
| D6 | E |
| D7 | E |
| ML-162 | B |

The anti-proliferation activity of compound 80 was tested in the presence of an ferroptosis inhibitor, ferrostatin-1 (1 μM) or liproxstatin-1 (1 μM). The results are summarized in Table 2.

TABLE 2

| Inhibition of Cell Proliferation in the Presence of a Ferroptosis Inhibitor | | | |
|---|---|---|---|
| | $EC_{50}$ | | |
| Cmpd. | No Ferroptosis inhibitor | Ferrostatin-1 | Liproxstatin-1 |
| A80 | A | E | E |

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A compound of Formula (XVIII):

(XVIII)

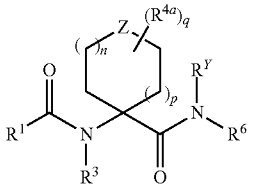

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof, wherein:

$R^1$ is

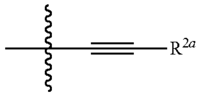

wherein $R^{2a}$ is hydrogen or deuterium;

$R^3$ is $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl;

$R^6$ is hydrogen, deuterium, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl;

$R^Y$ is hydrogen, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl;

Z is a bond, —NH—, —$NR^{4a}$—, —O—, —S—, —S(O)—, or —$S(O)_2$—;

n and p are each independently an integer of 0, 1, 2, or 3;

q is an integer of 0, 1, 2, 3, 4, 5, or 6; and each $R^{4a}$ is independently (a) deuterium, cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —$C(O)R^{1a}$, —$C(O)OR^{1a}$, —$C(O)NR^{1b}R^{1c}$, —$C(NR^{1a})NR^{1b}R^{1c}$, —$OR^{1a}$, —$OC(O)R^{1a}$, —$OC(O)OR^{1a}$, —$OC(O)NR^{1b}R^{1c}$, —$OC(NR^{1a})NR^{1b}R^{1c}$, —$OS(O)R^{1a}$, —$OS(O)_2R^{1a}$, —$OS(O)NR^{1b}R^{1c}$, —$OS(O)_2NR^{1b}R^{1c}$, —$NR^{1b}R^{1c}$, —$NR^{1a}C(O)R^{1d}$, —$NR^{1a}C(O)OR^{1d}$, —$NR^{1a}C(O)NR^{1b}R^{1c}$, —$NR^{1a}C(NR^{1d})NR^{1b}R^{1c}$, —$NR^{1a}S(O)R^{1d}$, —$NR^{1a}S(O)_2R^{1d}$, —$NR^{1a}S(O)NR^{1b}R^{1c}$, —$NR^{1a}S(O)_2NR^{1b}R^{1c}$, —$SR^{1a}$, —$S(O)R^{1a}$, —$S(O)_2R^{1a}$, —$S(O)NR^{1b}R^{1c}$, or —$S(O)_2NR^{1b}R^{1c}$; or when q is an integer of 2, 3, 4, 5, or 6, two $R^{4a}$ are linked together to form a bond, —$NR^{1a}$—, —O—, —S—, —S(O)—, —$S(O_2)$—, $C_{1-6}$ alkylene, $C_{1-6}$ heteroalkylene, $C_{2-6}$ alkenylene, or $C_{2-6}$ heteroalkenylene;

wherein each alkyl, alkylene, heteroalkylene, alkenyl, alkenylene, heteroalkenyl-ene, alkynyl, cycloalkyl, aryl, aralkyl, heteroaryl, and heterocyclyl is optionally substituted with one or more substituents Q, wherein each Q is independently selected from: (a) deuterium, cyano, halo, nitro, and oxo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more substituents $Q^a$; and (c) —$C(O)R^a$, —$C(O)OR^a$, —$C(O)NR^bR^c$, —$C(O)SR^a$, —$C(NR^a)NR^bR^c$, —$C(S)R^a$, —$C(S)OR^a$, —$C(S)NR^bR^c$, —$OR^a$, —$OC(O)R^a$, —$OC(O)OR^a$, —$OC(O)NR^bR^c$, —$OC(O)SR^a$, —$OC(NR^a)NR^bR^c$, —$OC(S)R^a$, —$OC(S)OR^a$, —$OC(S)NR^bR^c$, $OS(O)R^a$, —$OS(O)_2R^a$, —$OS(O)NR^bR^c$, —$OS(O)_2NR^bR^c$, —$NR^bR^c$, —$NR^aC(O)R^d$, —$NR^aC(O)OR^d$, —$NR^aC(O)NR^bR^c$, —$NR^aC(O)SR^d$, —$NR^aC(NR^d)NR^bR^c$, —$NR^aC(S)R^d$, —$NR^aC(S)OR^d$, —$NR^aC(S)NR^bR^c$, —$NR^aS(O)R^d$, —$NR^aS(O)_2R^d$, —$NR^aS(O)NR^bR^c$, —$NR^aS(O)_2NR^bR^c$, —$SR^a$, —$S(O)R^a$, —$S(O)_2R^a$, —$S(O)NR^bR^c$, and —$S(O)_2NR^bR^c$, wherein each $R^a$, $R^b$, $R^c$, and $R^d$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents $Q^a$; or (iii) $R^b$ and $R^c$ together with the N atom to which they are attached form heterocyclyl optionally substituted with one or more substituents $Q^a$;

wherein each $Q^a$ is independently selected from: (a) deuterium, cyano, halo, nitro, and oxo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —$C(O)R^e$, —$C(O)OR^e$, —$C(O)NR^fR^g$, —$C(O)SR^e$, —$C(NR^e)NR^fR^g$, —$C(S)R^e$, —$C(S)OR^e$, —$C(S)NR^fR^g$, —$OR^e$, —$OC(O)R^e$, —$OC(O)OR^e$, —$OC(O)NR^fR^g$, —$OC(O)SR^e$, —$OC(NR^e)NR^fR^g$, —$OC(S)R^e$, —$OC(S)OR^e$, —$OC(S)NR^fR^g$, —$OS(O)R^e$, —$OS(O)_2R^e$, —$OS(O)NR^fR^g$, —$OS(O)_2NR^fR^g$, —$NR^fR^g$, —$NR^eC(O)R^h$, —$NR^eC(O)OR^f$, —$NR^eC(O)NR^fR^g$, —$NR^eC(O)SR^f$, —$NR^eC(NR^h)NR^fR^g$, —$NR^eC(S)R^h$, —$NR^eC(S)OR^f$, —$NR^eC(S)NR^fR^g$, —$NR^eS(O)R^h$, —$NR^eS(O)_2R^h$, —$NR^eS(O)NR^fR^g$, —$NR^eS(O)_2NR^fR^g$, —$SR^e$, —$S(O)R^e$, —$S(O)_2R^e$, —$S(O)NR^fR^g$, and —$S(O)_2NR^fR^g$; wherein each $R^e$, $R^f$, $R^g$, and $R^h$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

2. The compound of claim 1, wherein Z is a bond or —O—.

3. The compound of claim 1, wherein n is an integer of 1 or 2.

4. The compound of claim 1, wherein p is an integer of 1 or 2.

5. The compound of claim 1, wherein $R^{2a}$ is hydrogen.

6. The compound of claim 1, wherein $R^6$ is $C_{1-6}$ alkyl, $C_{3-10}$ cycloalkyl, or $C_{7-15}$ aralkyl, each optionally substituted with one or more substituents Q.

7. The compound of claim 6, wherein $R^6$ is $C_{1-6}$ alkyl or $C_{7-15}$ aralkyl, each optionally substituted with one or more substituents Q.

8. The compound of claim 6, wherein $R^6$ is tert-butyl, cyclopropylmethyl, oxetan-3-ylmethyl, (tetrahydropyran-4-yl)methyl, hydroxycarbonylmethyl, ethoxycarbonylmethyl, 2-hydroxyethylaminocarbonylmethyl, phenylaminocarbonylmethyl, benzylaminocarbonylmethyl, 2-cyanobenzylaminocarbonylmethyl, 2-chlorobenzylamino-carbonylmethyl, 2-hydroxybenzylaminocarbonylmethyl, 3-hydroxypiperid-1-ylcarbonylmethyl, 3-(hydroxymethyl)piperid-1-ylcarbonylmethyl, 3-methoxycarbonylpiperid-1-ylcarbonylmethyl, 4-methylphenylsulfonylmethyl, benzyl, 2-cyanobenzyl, 4-cyanobenzyl, 3-chlorobenzyl, 2-fluorobenzyl, 4-fluorobenzyl, or 2-phenylethyl.

9. The compound of claim 1, wherein $R^Y$ is hydrogen.

10. A compound of:

A79

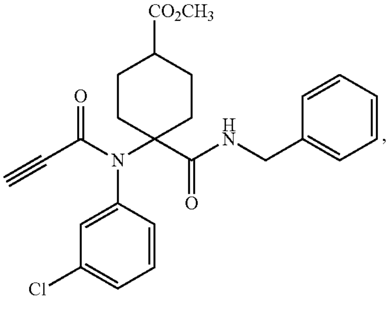,

-continued
A80
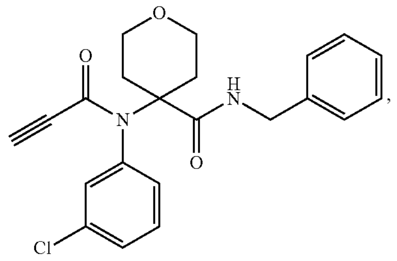
A86
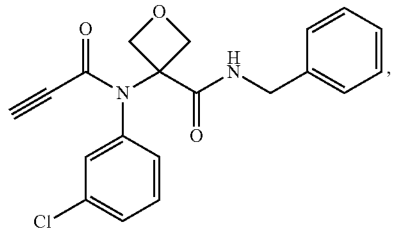
A101
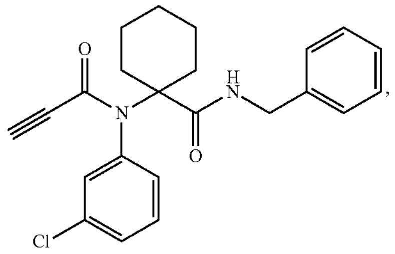
A103
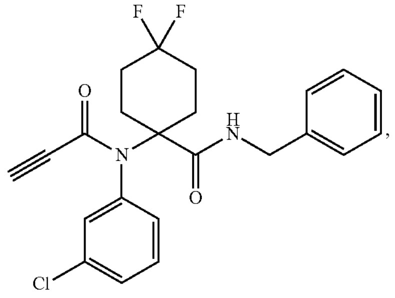
A108
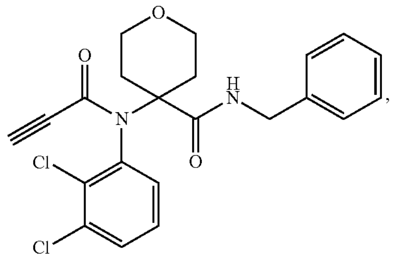
A109
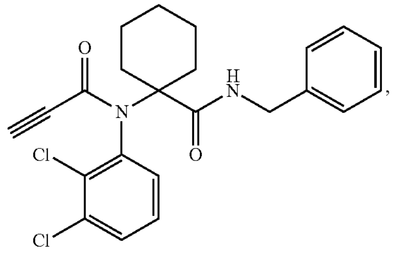
-continued
A110
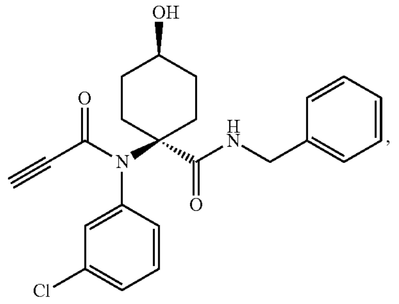
A111
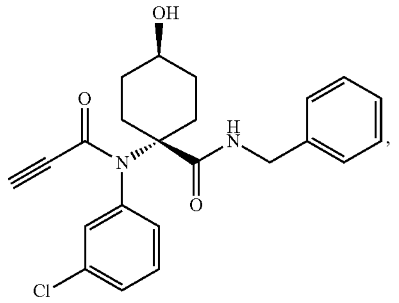
A135
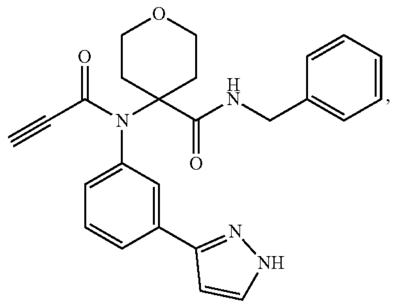
A136
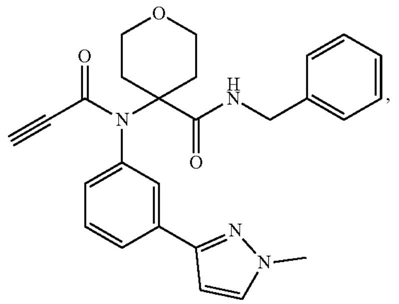
A137
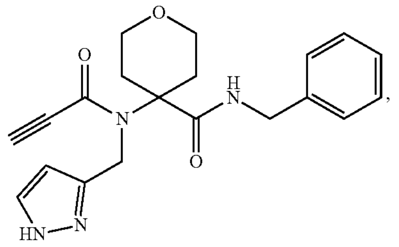

-continued
A138
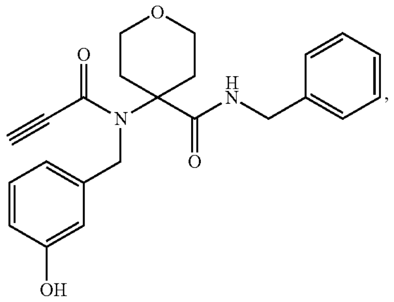
A139
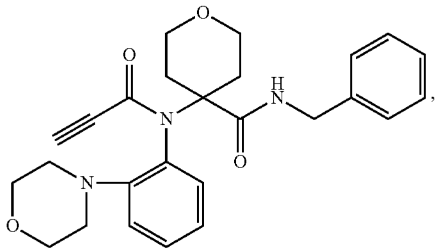
A140
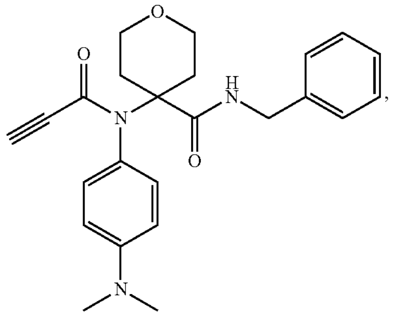
A141
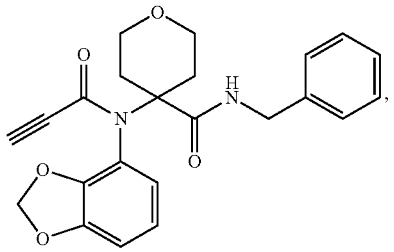
A144
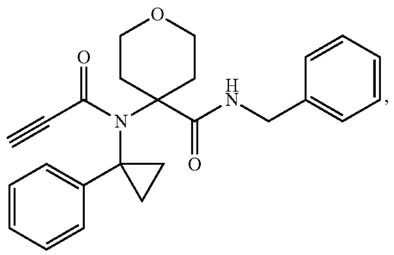
-continued
A148
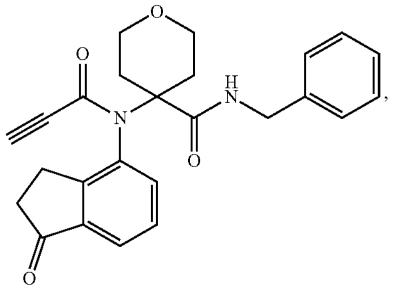
A149
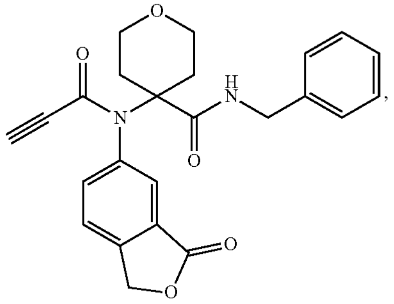
A150
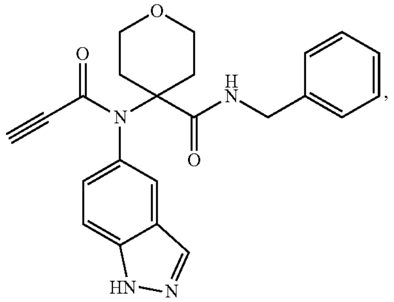
A151
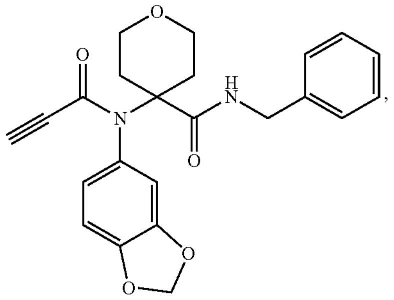
A152
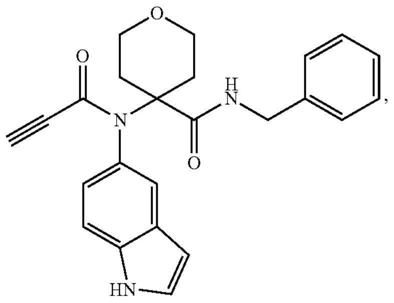

-continued
A153
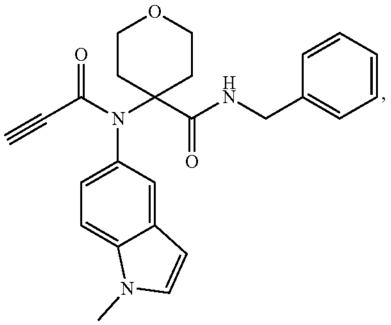
A154
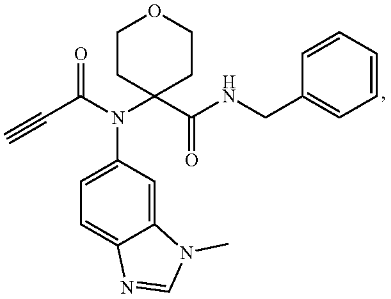
A155
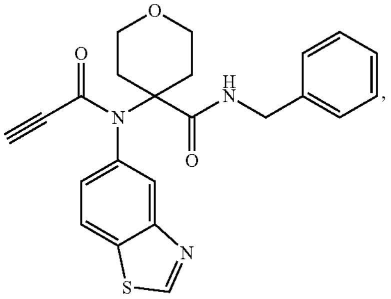
A156
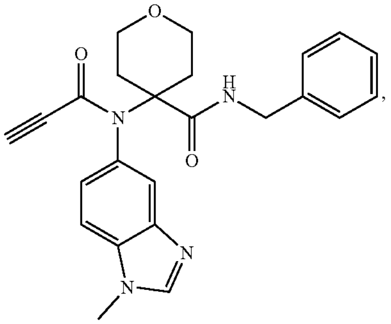
A157
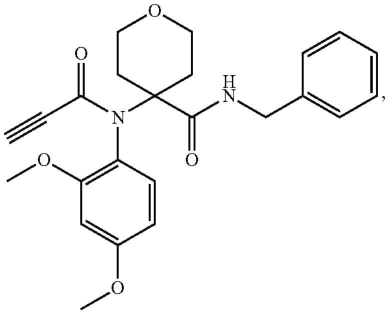
-continued
A159
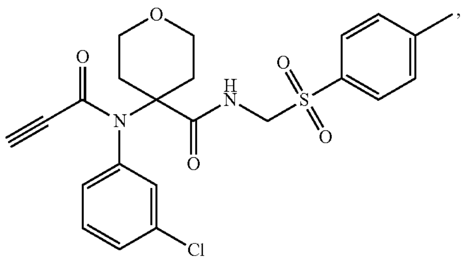
A161
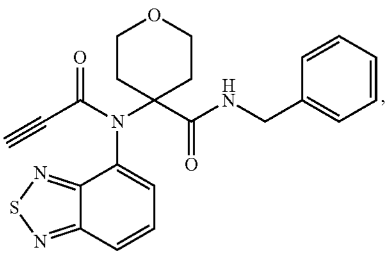
A162
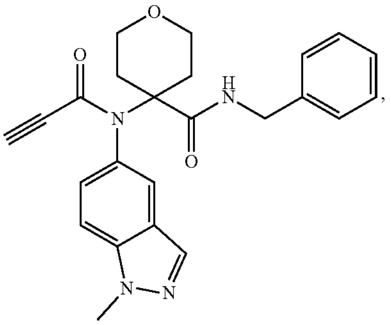
A163
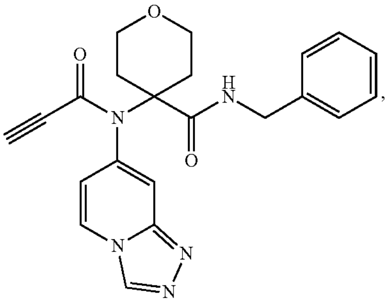
A164
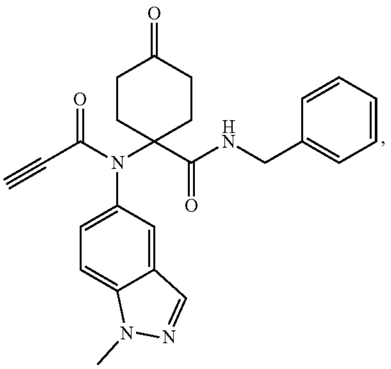

-continued
A165
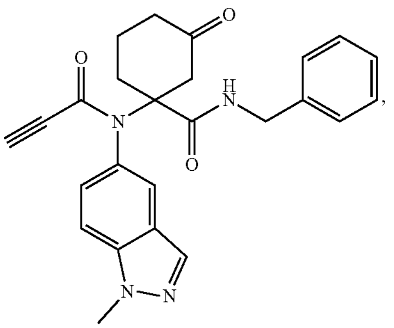
A166
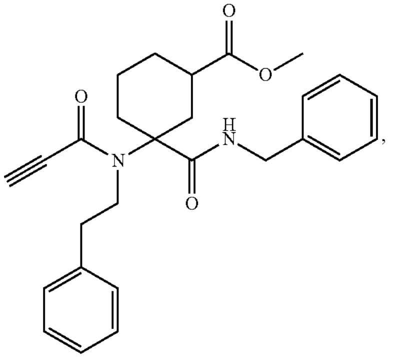
A167
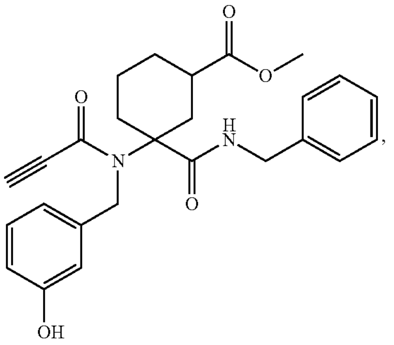
A168
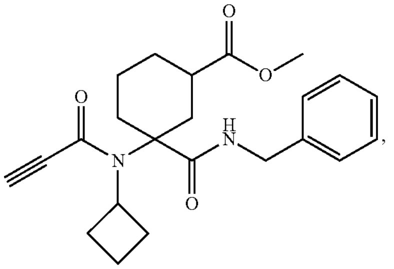
-continued
A169
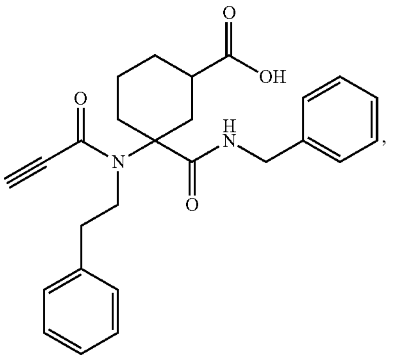
A170
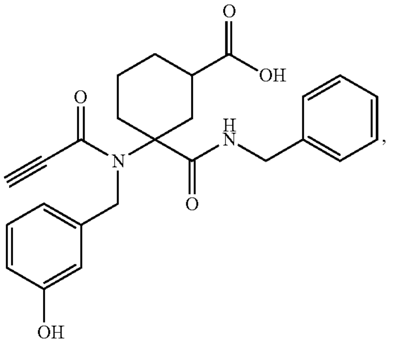
A171
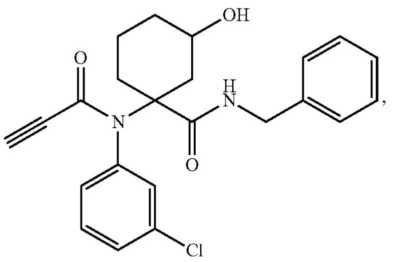
A172
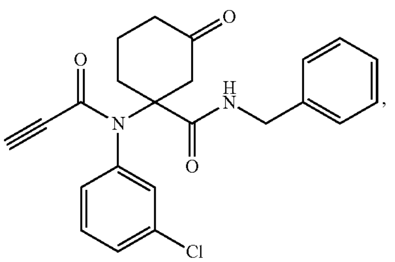
A173
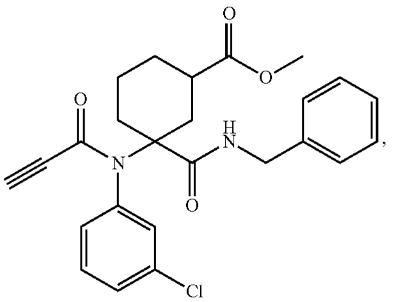

-continued
A174
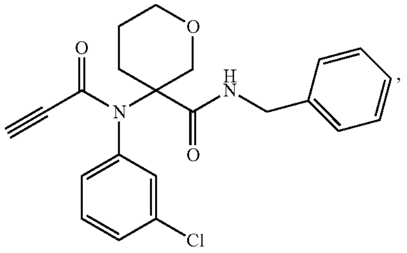
A175
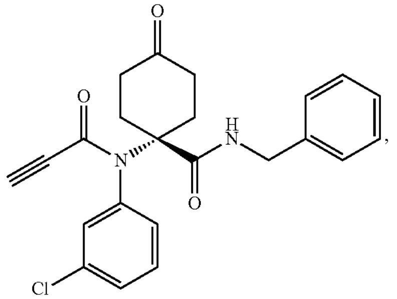
A176
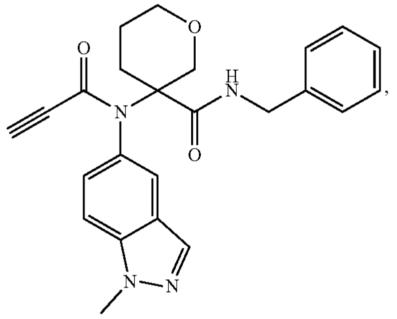
A177
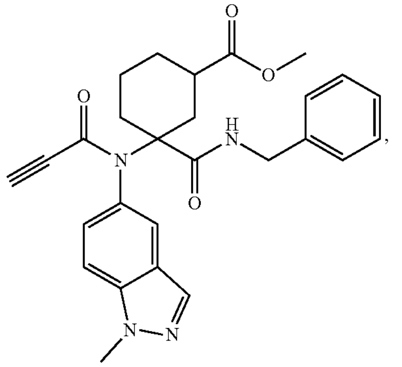
A182
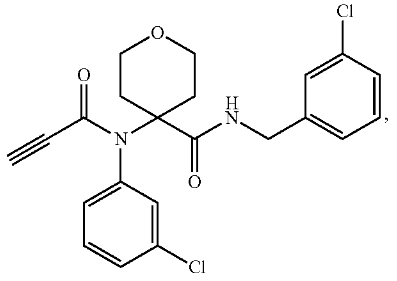
-continued
A183
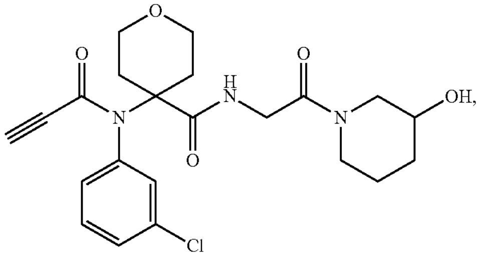
A184
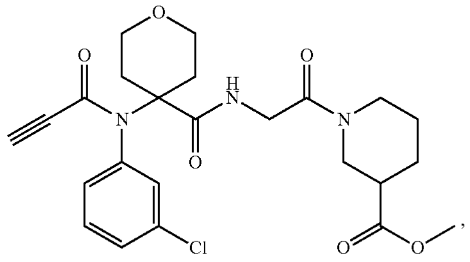
A185
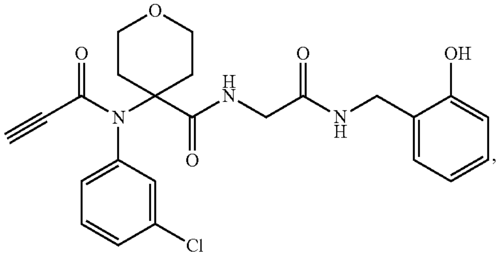
A186
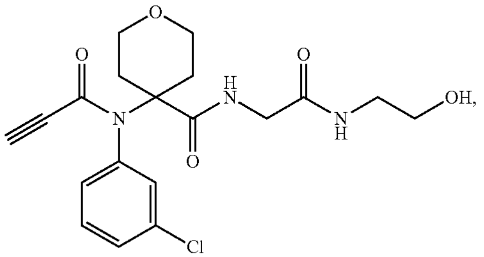
A187
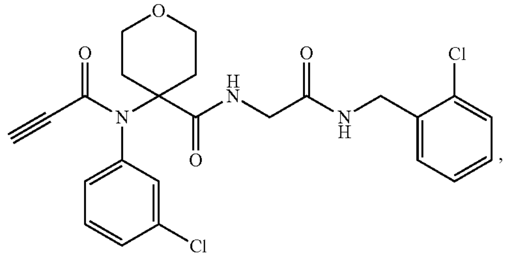

-continued
A188
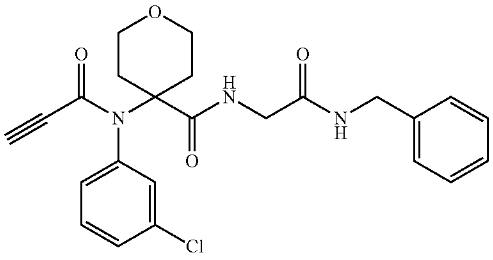,
A189
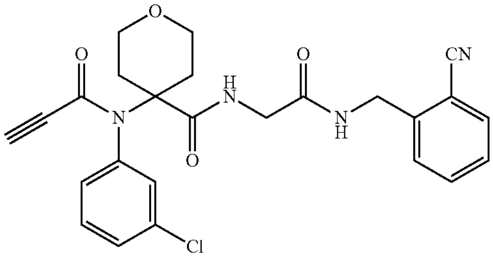,
A191
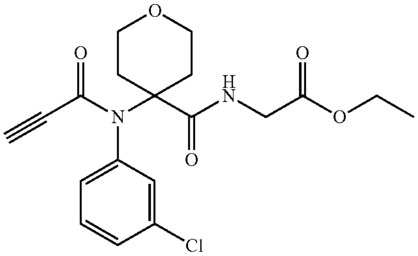,
A192
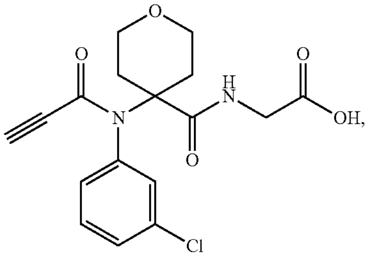
A193
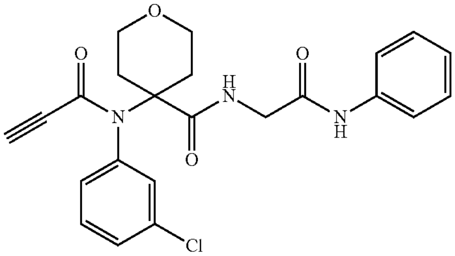,
-continued
A194
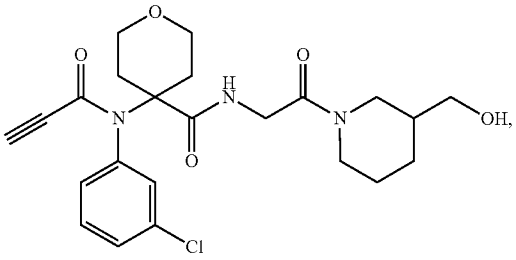
A195
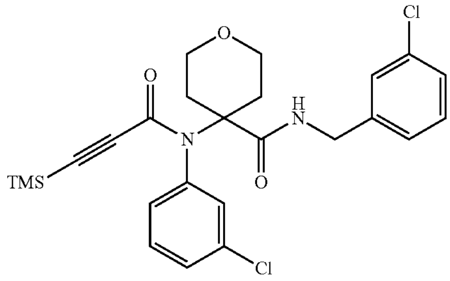,
C19
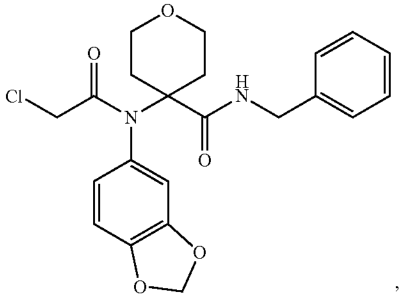,
C20
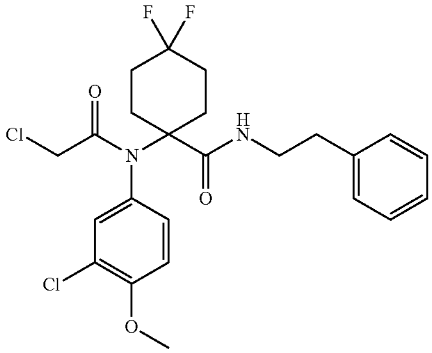,
C21
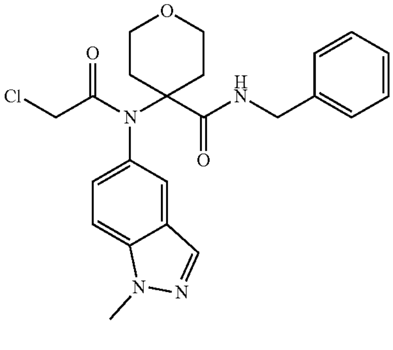, -continued
C22
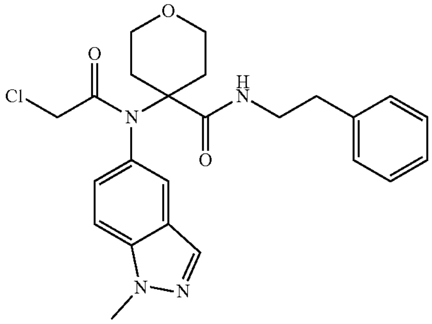
,
C23
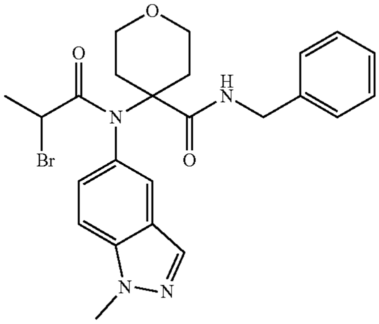
,
C24
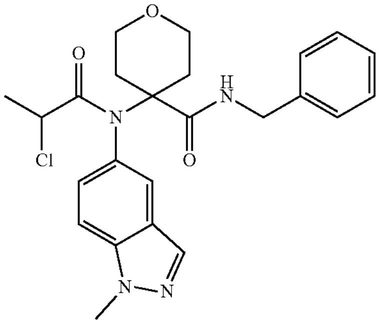
,
C25
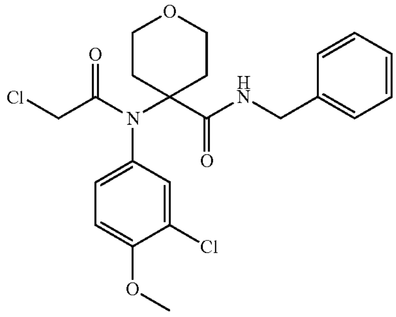
,
C26
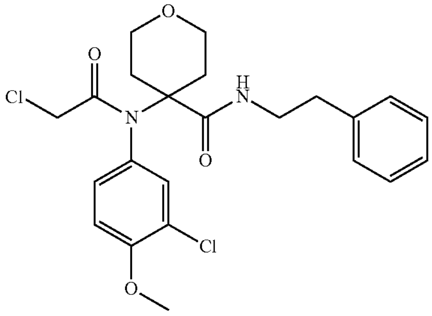
,
-continued
C27
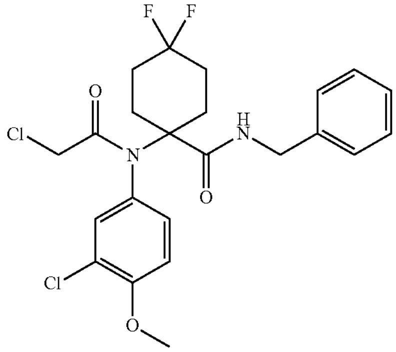
,
C28
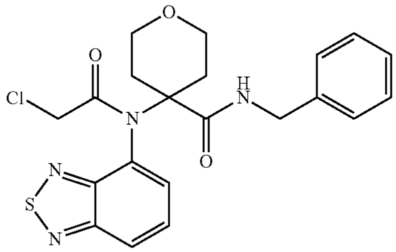
,
C29
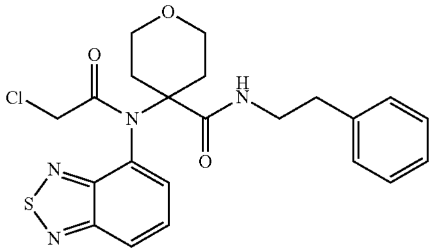
,
C30
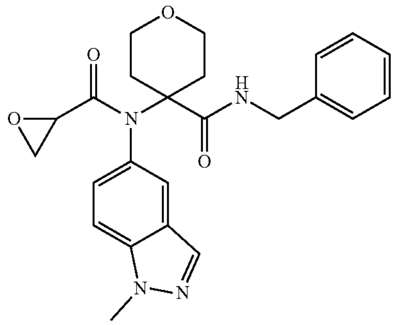
,
D1
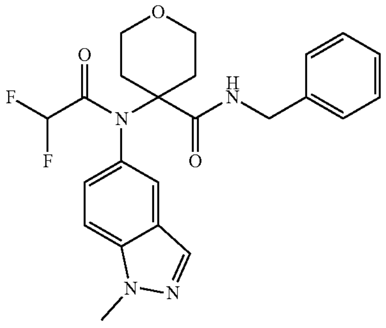
, -continued

D2

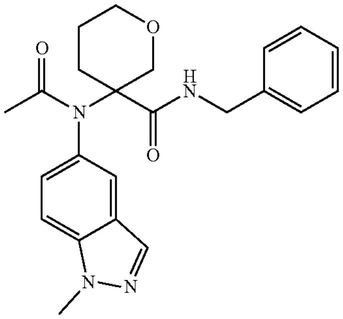

,

D3

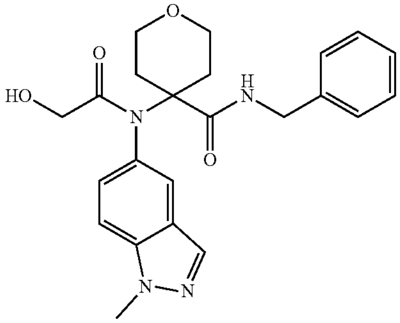

,

D5

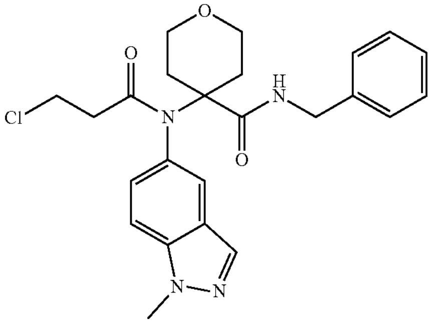

,

-continued

D6

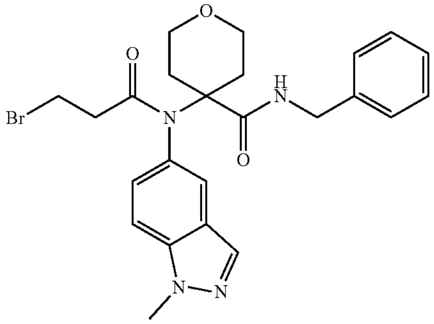

, or

D7

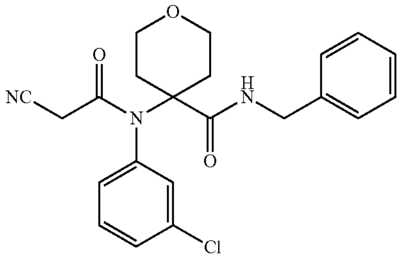

;

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, or hydrate thereof.

11. A pharmaceutical composition comprising the compound of claim 1, or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, or hydrate thereof, and a pharmaceutically acceptable excipient.

* * * * *